US012595290B2

(12) United States Patent (10) Patent No.: US 12,595,290 B2
Schmitt et al. (45) Date of Patent: Apr. 7, 2026

(54) T CELL RECEPTORS SPECIFIC FOR MESOTHELIN AND THEIR USE IN IMMUNOTHERAPY

(71) Applicants: FRED HUTCHINSON CANCER CENTER, Seattle, WA (US); JUNO THERAPEUTICS, INC., Seattle, WA (US)

(72) Inventors: Thomas M. Schmitt, Seattle, WA (US); Aude G. Chapuis, Seattle, WA (US); Philip D. Greenberg, Mercer Island, WA (US)

(73) Assignees: FRED HUTCHINSON CANCER CENTER, Seattle, WA (US); JUNO THERAPEUTICS, INC., Seattle, WA (US)

( * ) Notice: Subject to any disclaimer, the term of this patent is extended or adjusted under 35 U.S.C. 154(b) by 1262 days.

(21) Appl. No.: 17/291,985

(22) PCT Filed: Nov. 8, 2019

(86) PCT No.: PCT/US2019/060570
§ 371 (c)(1),
(2) Date: May 6, 2021

(87) PCT Pub. No.: WO2020/097530
PCT Pub. Date: May 14, 2020

(65) Prior Publication Data
US 2022/0009992 A1 Jan. 13, 2022

Related U.S. Application Data

(60) Provisional application No. 62/758,397, filed on Nov. 9, 2018.

(51) Int. Cl.
| | |
|---|---|
| *C07K 14/725* | (2006.01) |
| *A61K 40/11* | (2025.01) |
| *A61K 40/32* | (2025.01) |
| *A61K 40/42* | (2025.01) |
| *A61K 45/06* | (2006.01) |
| *A61P 35/00* | (2006.01) |
| *C12N 5/0783* | (2010.01) |
| *C12N 15/86* | (2006.01) |

(52) U.S. Cl.
CPC .......... *C07K 14/7051* (2013.01); *A61K 40/11* (2025.01); *A61K 40/32* (2025.01); *A61K 40/4255* (2025.01); *A61K 45/06* (2013.01); *A61P 35/00* (2018.01); *C12N 5/0636* (2013.01); *C12N 15/86* (2013.01); *A61K 2239/49* (2023.05); *C07K 2319/00* (2013.01)

(58) Field of Classification Search
CPC ............ C07K 14/7051; C07K 2319/00; A61K 40/11; A61K 40/32; A61K 40/4255; A61P 35/00; C12N 5/0636; C12N 2510/00
See application file for complete search history.

(56) References Cited

U.S. PATENT DOCUMENTS

| | | | |
|---|---|---|---|
| 5,283,173 | A | 2/1994 | Fields et al. |
| 5,420,032 | A | 5/1995 | Marshall et al. |
| 5,468,614 | A | 11/1995 | Fields et al. |
| 6,833,252 | B1 | 12/2004 | Dujon et al. |
| 8,119,772 | B2 | 2/2012 | Yang et al. |
| 8,697,359 | B1 | 4/2014 | Zhang |
| 9,574,000 | B2 | 2/2017 | Langermann et al. |
| 2004/0002092 | A1 | 1/2004 | Arnould et al. |
| 2004/0087025 | A1 | 5/2004 | June et al. |
| 2006/0078552 | A1 | 4/2006 | Arnould et al. |
| 2006/0153826 | A1 | 7/2006 | Arnould et al. |
| 2006/0206949 | A1 | 9/2006 | Arnould et al. |
| 2007/0117128 | A1 | 5/2007 | Smith et al. |
| 2011/0189141 | A1 | 8/2011 | Kieback et al. |
| 2011/0243972 | A1 | 10/2011 | Jaffee |
| 2011/0301073 | A1 | 12/2011 | Gregory et al. |
| 2014/0068797 | A1 | 3/2014 | Doudna et al. |
| 2014/0186843 | A1 | 7/2014 | Zhang et al. |

FOREIGN PATENT DOCUMENTS

| | | | |
|---|---|---|---|
| WO | WO 2010084158 | A1 | 7/2010 |
| WO | WO 2013025779 | A1 | 2/2013 |
| WO | WO 2015071474 | A2 | 5/2015 |
| WO | WO 2016040724 | A1 | 3/2016 |

(Continued)

OTHER PUBLICATIONS

Rossjohn et al, T Cell Antigen Receptor Recognition of Antigen-Presenting Molecules.Annu. Rev. Immunol. 2015. 33:169-200 (Year: 2015).*
Song et al.Broad TCR repertoire and diverse structural solutions for recognition of an immunodominant CD8+ T cell epitope.nature structural & molecular biology vol. 24 No. 4 Apr. 2017. (Year: 2017).*
Altschul et al., "Gapped BLAST and PSI-BLAST: a new generation of protein database search programs," *Nucleic Acids Research* 25(17):3389-3402, 1997.
Arbabi-Ghahroudi, "Camelid Single-Domain Antibodies: Historical Perspective and Future Outlook," *Frontiers in Immunology* 8(1589), Nov. 20, 2017. (8 pages).
Argast et al., "I-Ppol and I-Crel Homing Site Sequence Degeneracy Determined by Random Mutagenesis and Sequential in Vitro Enrichment," *J. Mol. Biol.* 280:345-353, 1998.

(Continued)

*Primary Examiner* — Janet L Andres
*Assistant Examiner* — Brian Hartnett
(74) *Attorney, Agent, or Firm* — Seed IP Law Group LLP

(57) ABSTRACT

Binding proteins specific for Msln20-28 or Msln530-538 peptides are provided herein. Polynucleotides encoding the binding proteins, as well as compositions and recombinant host cells comprising the binding proteins or polynucleotides are also provided. The compositions and recombinant host cells may be used to treat a subject having mesothelioma, pancreatic cancer, ovarian cancer, lung cancer, a cancer wherein an Msln20-28 peptide is expressed on a tumor cell of the cancer, or a cancer wherein an Msln530-538 peptide is expressed on a tumor cell of the cancer.

38 Claims, 23 Drawing Sheets
Specification includes a Sequence Listing.

(56)                    References Cited

FOREIGN PATENT DOCUMENTS

| WO | WO 2016054638 A1 | 4/2016 | |
| WO | WO 2016134333 A1 | 8/2016 | |
| WO | WO 2017021526 A1 | 2/2017 | |
| WO | WO-2017112944 A1 * | 6/2017 | ............. A61K 35/12 |
| WO | WO 2017192924 A1 | 11/2017 | |
| WO | WO 2018058002 A1 | 3/2018 | |
| WO | WO 2018129270 A1 | 7/2018 | |

OTHER PUBLICATIONS

Ashouri et al., "Endogenous Nur77 is a specific indicator of antigen receptor signaling in human T and B cells," *J. Immunol.* 198(2):657-668, Jan. 15, 2017. (28 pages).

Ashworth et al., "Computational redesign of endonuclease DNA binding and cleavage specificity," *Nature* 441(7093):656-659, Jun. 1, 2006. (11 pages).

Belfort et al., "Homing endonucleases: keeping the house in order," *Nucleic Acids Research* 25(17):3379-3388, 1997.

Betts et al., "The Functional Profile of Primary Human Antiviral CD8⁺ T Cell Effector Activity Is Dictated by Cognate Peptide Concentration," *The Journal of Immunology* 172:6407-6417, 2004. (13 pages).

Borst et al., "The T3 Complex on Human T Lymphocytes Involves Four Structurally Distinct Glycoproteins," *The Journal of Biological Chemistry* 258(8):5135-5141, 1983.

Cawthon et al., "Peptide Requirement for CTL Activation Reflects the Sensitivity to CD3 Engagement: Correlation with CD8ab Versus CD8aa Expression," *The Journal of Immunology* 167:2577-2584, 2001. (9 pages).

Chapuis et al., "Abstract LB-136: IL-21-derived melanoma-reactive CTL combined with anti-CTLA4 persist, acquire central memory characteristics, and mediate tumor regression in patients with metastatic melanoma," *Cancer Res.* 72(8 Suppl):LB-136, Apr. 2012. (Abstract only) (4 pages).

Chapuis et al., "Transferred melanoma-specific CD8⁺ T cells persist, mediate tumor regression, and acquire central memory phenotype," *PNAS* 109(12):4592-4597, Mar. 20, 2012.

Chapuis et al., "Transferred WT1-reactive CD8⁺ T cells can mediate antileukemic activity and persist in post-transplant patients," *Sci. Transl. Med.* 5(174):174ra27, Feb. 27, 2013. (25 pages).

Chen et al., "Fusion protein linkers: Property, design and functionality," *Advanced Drug Delivery Reviews* 65:1357-1369, 2013.

Chevalier et al., "Design, Activity, and Structure of a Highly Specific Artificial Endonuclease," *Molecular Cell* 10:895-905, Oct. 2002.

Chothia, et al., "The outline structure of the T-cell ab receptor," *The EMBO Journal* 7(12):3745-3755, 1988.

Cohen et al., "Enhanced Antitumor Activity of T Cells Engineered to Express T-Cell Receptors with a Second Disulfide Bond," *Cancer Res.* 67(8):3898-3903, Apr. 15, 2007. (7 pages).

Dangaj et al., "Novel Recombinant Human B7-H4 Antibodies Overcome Tumoral Immune Escape to Potentiate T-Cell Antitumor Responses," *Cancer Res.* 73(15):4820-4829, Aug. 1, 2013. (11 pages).

Database Geneseq, "Sequence 17 from Patent WO2017112944," XP-002798113, retrieved from EBI accession No. EPOP:LP835765, Apr. 27, 2018. (1 page).

Database Geneseq, "Sequence 54 from Patent WO2017089768," XP-002798116, retrieved from EBI accession No. EPOP:MS816951, Jun. 30, 2017. (1 page).

Database Geneseq, "T cell receptor (TCR) beta chain variable domain, SEQ ID 15," XP-002798114, retrieved from EBI accession No. GSP:BEA52192, Aug. 24, 2017. (1 page).

Database Geneseq, "Transgene construction related TCR construct encoding gene SEQ 59," XP-002798115, retrieved from EBI accession No. GSN:BFE48571, May 17, 2018. (1 page).

Desjarlais et al., "Use of a zinc-finger consensus sequence framework and specificity rules to design specific DNA binding proteins," *Proc. Natl. Acad. Sci. USA* 90:2256-2260, Mar. 1993.

Di Stasi et al., "Inducible Apoptosis as a Safety Switch for Adoptive Cell Therapy," *N. Engl. J. Med.* 365(18):1673-1683, Nov. 3, 2011. (16 pages).

Dossett et al., "Adoptive Immunotherapy of Disseminated Leukemia With TCR-transduced, CD8⁺ T Cells Expressing a Known Endogenous TCR," *Molecular Therapy* 17(4):742-749, Apr. 2009.

Dujon et al., "Mobile introns: definition of terms and recommended nomenclature," *Gene* 82:115-118, 1989.

Dunbar et al., "ANARCI: antigen receptor numbering and receptor classification," *Bioinformatics* 32(2):298-300, 2016.

Engels et al., "Retroviral Vectors for High-Level Transgene Expression in T Lymphocytes," *Human Gene Therapy* 14:1155-1168, Aug. 10, 2003.

Epinat et al., "A novel engineered meganuclease induces homologous recombination in yeast and mammalian cells," *Nucleic Acids Research* 31(11):2952-2962, 2003.

Eyquem et al., "Targeting a CAR to the TRAC locus with CRISPR/Cas9 enhances tumour rejection," *Nature* 543:113-117, Mar. 2, 2017. (19 pages).

Fehse et al., "CD34 Splice Variant: An Attractive Marker for Selection of Gene-Modified Cells," *Molecular Therapy* 1(5):448-456, May 2000.

Frecha et al., "Advances in the Field of Lentivector-based Transduction of T and B Lymphocytes for Gene Therapy," *Molecular Therapy* 18(10):1748-1757, Oct. 2010.

Geurts et al., "Gene Transfer into Genomes of Human Cells by the Sleeping Beauty Transposon System," *Molecular Therapy* 8(1):108-117, Jul. 2003.

Gimble et al., "Substrate Recognition and Induced DNA Distortion by the PI-Scel Endonuclease, an Enzyme Generated by Protein Splicing," *J. Mol. Biol.* 263:163-180, 1996.

Green et al., "Mitochondria and Apoptosis," *Science* 281:1309-1312, Aug. 28, 1998.

Harris et al., "Adoptive T Cell Therapies: A Comparison of T Cell Receptors and Chimeric Antigen Receptors," *Trends in Pharmacological Scienecs* 37(3):220-230, Mar. 2016.

Ho et al., "In vitro methods for generating CD8⁺ T-cell clones for immunotherapy from the naïve repertoire," *Journal of Immunological Methods* 310:40-52, 2006.

International Search Report and Written Opinion, mailed Jun. 25, 2020, for International Patent Application No. PCT/US2019/060570. (17 pages).

Jasin, "Genetic manipulation of genomes with rare-cutting endonucleases," *TIG* 12(6):224-228, Jun. 1996.

Jinek et al., "A Programmable Dual-RNA-Guided DNA Endonuclease in Adaptive Bacterial Immunity," *Science* 337:816-821, Aug. 17, 2012.

Jores et al., "Resolution of hypervariable regions in T-cell receptor Beta chains by a modified Wu-Kabat index of amino acid diversity," *Proc. Natl. Acad. Sci. USA* 87:9138-9142, Dec. 1990.

Kieback et al., "A safeguard eliminates T cell receptor gene-modified autoreactive T cells after adoptive transfer," *PNAS* 105(2):623-628, Jan. 15, 2008.

Kreiter et al., "Mutant MHC class II epitopes drive therapeutic immune responses to cancer," *Nature* 520:692-696, Apr. 30, 2015. (17 pages).

Krisky et al., "Development of herpes simplex virus replication-defective multigene vectors for combination gene therapy applications," *Gene Therapy* 5:1517-1530, 1998.

Kuball et al., "Facilitating matched pairing and expression of TCR chains introduced into human T cells," *Blood* 109(6):2331-2338, Mar. 15, 2007. (17 pages).

Langenkamp et al., "T cell priming by dendritic cells: thresholds for proliferation, differentiation and death and intraclonal functional diversification," *Eur. J. Immunol.* 32:2046-2054, 2002.

Larkin et al., "Clustal W and Clustal X version 2.0," *Bioinformatics* 23(21):2947-2948, 2007.

Leen et al., "Improving T Cell Therapy for Cancer" *Annu. Rev. Immunol.* 25:243-265, 2007. (26 pages).

(56)          References Cited

OTHER PUBLICATIONS

Lefranc et al., "IMGT unique numbering for immunoglobulin and T cell receptor variable domains and Ig superfamily V-like domains," *Developmental and Comparative Immunology* 27:55-77, 2003.
Liebl et al., "Transfer of *Brevibacterium divaricatum* DSM 20297ᵀ*Brevibacterium flavum*' DSM 20411, '*Brevibacterium lactofermentum*' DSM 20412 and DSM 1412, and *Corynebacterium lilium* DSM 20137ᵀ to *Corynebacterium glutamicum* and Their Distinction by rRNA Gene Restriction Patterns," *International Journal of Systematic Bacteriology* 41(2):255-260, Apr. 1991.
Liu et al., "Selective inhibition of IDO1 effectively regulates mediators of antitumor immunity," *Blood* 115(17):3520-3530, Apr. 29, 2010. (12 pages).
Mautino et al., "Abstract 491: NLG919, a novel indoleamine-2,3-dioxygenase (IDO)-pathway inhibitor drug candidate for cancer therapy," *Cancer Res.* 73(8 Suppl):Abstract nr 491, Apr. 2013. (4 pages).
Mavilio et al., "Peripheral Blood Lymphocytes as Target Cells of Retroviral Vector-Mediated Gene Transfer," *Blood* 83(7):1988-1997, Apr. 1, 1994. (11 pages).
Mátés et al., "Molecular evolution of a novel hyperactive Sleeping Beauty transposase enables robust stable gene transfer in vertebrates," *Nature Genetics* 41:753-761, May 3, 2009. (33 pages).
Penix et al., "Two Essential Regulatory Elements in the Human Interferon γ Promoter Confer Activation Specific Expression in T Cells," *The Journal of Experimental Medicine* 178:1483-1496, Nov. 1993.
Perler et al., "Protein splicing elements: inteins and exteins—a definition of terms and recommended nomenclature," *Nucleic Acids Research* 22(7):1125-1127, 1994.
Pfeifer et al., "Gene Therapy: Promises and Problems," *Annu. Rev. Genomics Hum. Genet.* 2:177-211, 2001. (37 pages).
Philip et al., "A highly compact epitope-based marker/suicide gene for easier and safer T-cell therapy," *Blood* 124(8):1277-1287, Aug. 21, 2014. (12 pages).
Porteus et al., "Gene targeting using zinc finger nucleases," *Nature Biotechnology* 23(8):967-973, Aug. 2005.
Pâques et al., "Meganucleases and DNA Double-Strand Break-Induced Recombination: Perspectives for Gene Therapy," *Current Gene Therapy* 7(1):49-66, 2007.
Ren et al., "Multiplex Genome Editing to Generate Universal CAR T Cells Resistant to PD1 Inhibition," Clin. Cancer Res. 23(9):2255-2266, May 1, 2017. (13 pages).
Robbins et al., "Tumor Regression in Patients With Metastatic Synovial Cell Sarcoma and Melanoma Using Genetically Engineered Lymphocytes Reactive With NY-ESO-1," *Journal of Clinical Oncology* 29(7):917-924, Mar. 1, 2011.
Robins et al., "Comprehensive assessment of T-cell receptor β-chain diversity in αβ T cells," *Blood* 114(19):4099-4107, Nov. 5, 2009.
Robins et al., "Overlap and Effective Size of the Human CD8+ T Cell Receptor Repertoire," *Science Translational Medicine* 2(47):47ra64, Sep. 1, 2010. (9 pages).
Robins et al., "Ultra-sensitive detection of rare T cell clones," *J. Immunol. Methods* 375:14-19, Jan. 31, 2012. (9 pages).
Sadelain et al., "The basic principles of chimeric antigen receptor (CAR) design," *Cancer Discov.* 3(4):388-398, Apr. 2013. (21 pages).
Scatchard, "The Attractions of Proteins for Small Molecules and Ions," *Annals New York Academy of Sciences* 51(4):660-672, May 1949.
Schmitt et al., "Abstract A51: High-throughput method identifies rare, high-affinity, thymus-vetted T cell receptors (TCRs) for clinical translation," *Cancer Immunol. Res.* 6(9 Suppl): Abstract nr A51, Sep. 2018. (4 pages).
Schmitt et al., "T Cell Receptor Gene Therapy for Cancer," *Human Gene Therapy* 20:1240-1248, Nov. 2009.
Scholten et al., "Codon modification of T cell receptors allows enhanced functional expression in transgenic human T cells," *Clinical Immunology* 119:135-145, 2006.

Stone et al., "A novel T cell receptor single-chain signaling complex mediates antigen-specific T cell activity and tumor control," *Cancer Immunol. Immunother.* 63:1163-1176, 2014.
Stone et al., "Role of T cell receptor affinity in the efficacy and specificity of adoptive T cell therapies," *Frontiers in Immunology* 4(244), Aug. 21, 2013. (16 pages).
Straathof et al., "An inducible caspase 9 safety switch for T-cell therapy," *Blood* 105(11):4247-4254, Jun. 1, 2005. (20 pages).
Stromnes et al., "Re-adapting T cells for cancer therapy: from mouse models to clinical trials," *Immunol Rev.* 257(1):145-164, Jan. 2014. (34 pages).
Stromnes et al., "T Cells Engineered against a Native Antigen Can Surmount Immunologic and Physical Barriers to Treat Pancreatic Ductal Adenocarcinoma," *Cancer Cell* 28:638-652, Nov. 9, 2015. (16 pages).
Sussman et al., "Isolation and Characterization of New Homing Endonuclease Specificities at Individual Target Site Positions," *J. Mol. Biol.* 342:31-41, 2004.
Terentis et al., "The Selenazal Drug Ebselen Potently Inhibits Indoleamine 2,3-Dioxygenase by Targeting Enzyme Cysteine Residues," *Biochemistry* 49(3):591-600, 2010.
Thompson et al., "cis-Acting Sequences Required for Inducible Interleukin-2 Enhancer Function Bind a Novel Ets-Related Protein, Elf-1," *Molecular and Cellular Biology* 12(3):1043-1053, Mar. 1992.
Till et al., "Adoptive immunotherapy for indolent non-Hodgkin lymphoma and mantle cell lymphoma using genetically modified autologous CD20-specific T cells," *Blood* 112(6):2261-2271, Sep. 15, 2008. (25 pages).
Todd et al., "Transcription of the Interleukin 4 Gene Is Regulated by Multiple Promoter Elements," *J. Exp. Med.* 177:1663-1674, Jun. 1993.
Van Rosmalen et al., "Tuning the Flexibility of Glycine-Serine Linkers To Allow Rational Design of Multidomain Proteins," *Biochemistry* 56:6565-6574, Nov. 23, 2017.
Verhoeyen et al., "Lentiviral Vector Gene Transfer into Human T Cells," *Methods in Molecular Biology, Methods and Protocols* 506:97-114, 2009.
Viola et al., "T Cell Activation Determined by T Cell Receptor Number and Tunable Thresholds," *Science* 273:104-106, Jul. 5, 1996.
Wälchli et al., "A Practical Approach to T-Cell Receptor Cloning and Expression," *PLoS ONE* 6(11):e27930, Nov. 21, 2011. (11 pages).
Walseng et al., "A TCR-based Chimeric Antigen Receptor," *Scientific Reports* 7:10713, 2017. (10 pages).
Walseng et al., "Soluble T-Cell Receptors Produced in Human Cells for Targeted Delivery," *PLoS ONE* 10(4):e0119559, Apr. 13, 2015. (15 pages).
Wang et al., "A transgene-encoded cell surface polypeptide for selection, in vivo tracking, and ablation of engineered cells," *Blood* 118(5):1255-1263, Aug. 4, 2011. (10 pages).
Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, Aug. 2007. (16 pages).
Warren et al., "Exhaustive T-cell repertoire sequencing of human peripheral blood samples reveals signatures of antigen selection and a directly measured repertoire size of at least 1 million clonotypes," *Genome Research* 21:790-797, 2011. (9 pages).
Wolfe et al., "Analysis of Zinc Fingers Optimized via Phage Display: Evaluating the Utility of a Recognition Code," *J. Mol. Biol.* 285:1917-1934, 1999.
Xie et al., "sgRNAcas9: A Software Package for Designing CRISPR sgRNA and Evaluating Potential Off-Target Cleavage Sites," *PLoS ONE* 9(6):e100448, Jun. 23, 2014. (9 pages).
Zhao et al., "Primary Human Lymphocytes Transduced with NY-ESO-1 Antigen-Specific TCR Genes Recognize and Kill Diverse Human Tumor Cell Lines," *The Journal of Immunology* 174:4415-4423, 2005.
Zhou et al., "Improving the Safety of T Cell Therapies using an Inducible Caspase-9 Gene," *Exp. Hematol.* 44(11):1013-1019, Nov. 2016. (14 pages).

(56) References Cited

OTHER PUBLICATIONS

Zoete et al., "Structure-based, rational design of T cell receptors,"
*Frontiers in Immunology* 4(268), Sep. 12, 2013. (19 pages).

* cited by examiner

FIG. 5A

Meso530 TCRs

530-B11

% IFNg Positive log[peptide], µM

530-B9
530-A11
530-B11

Meso20 TCRs

20-B3

% IFNg Positive log[peptide], µM

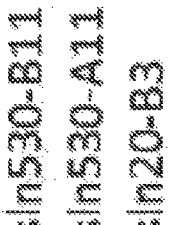
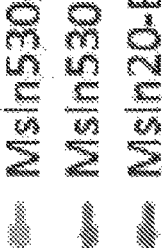
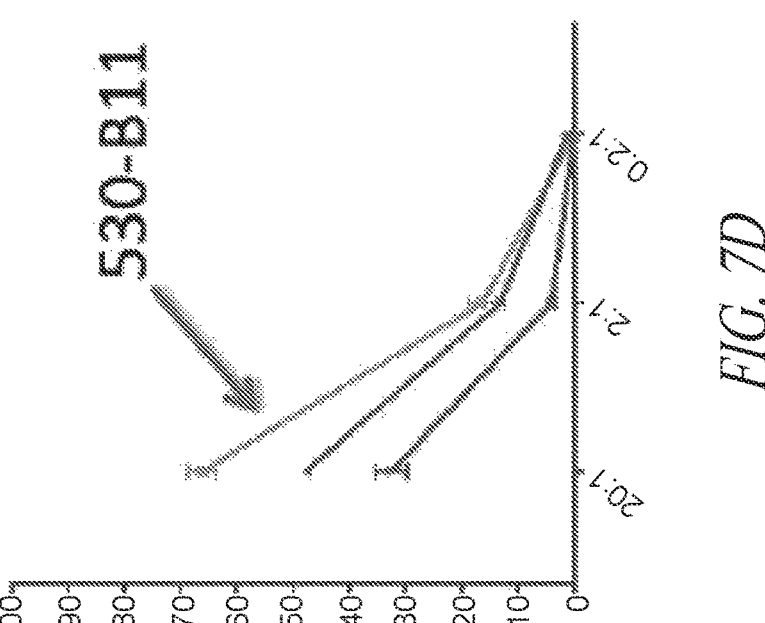
*FIG. 7D*
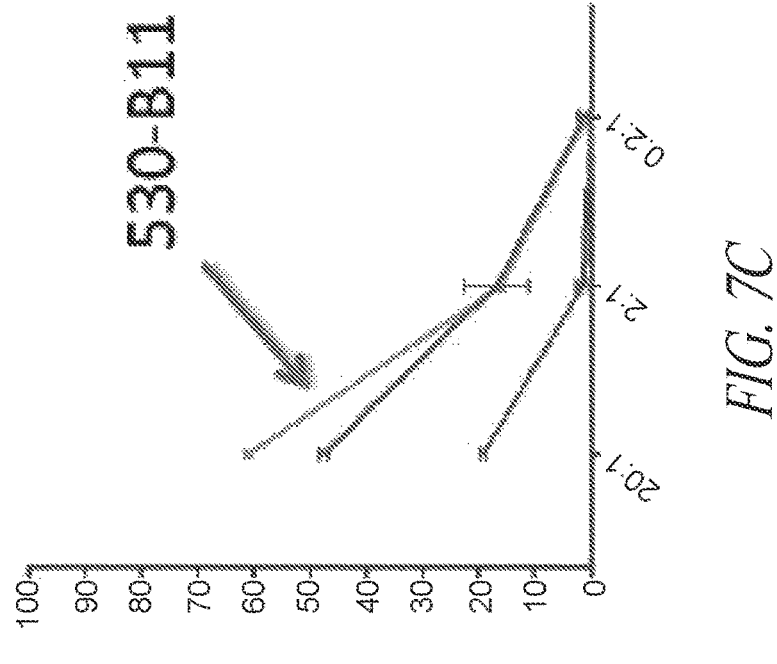
*FIG. 7C*

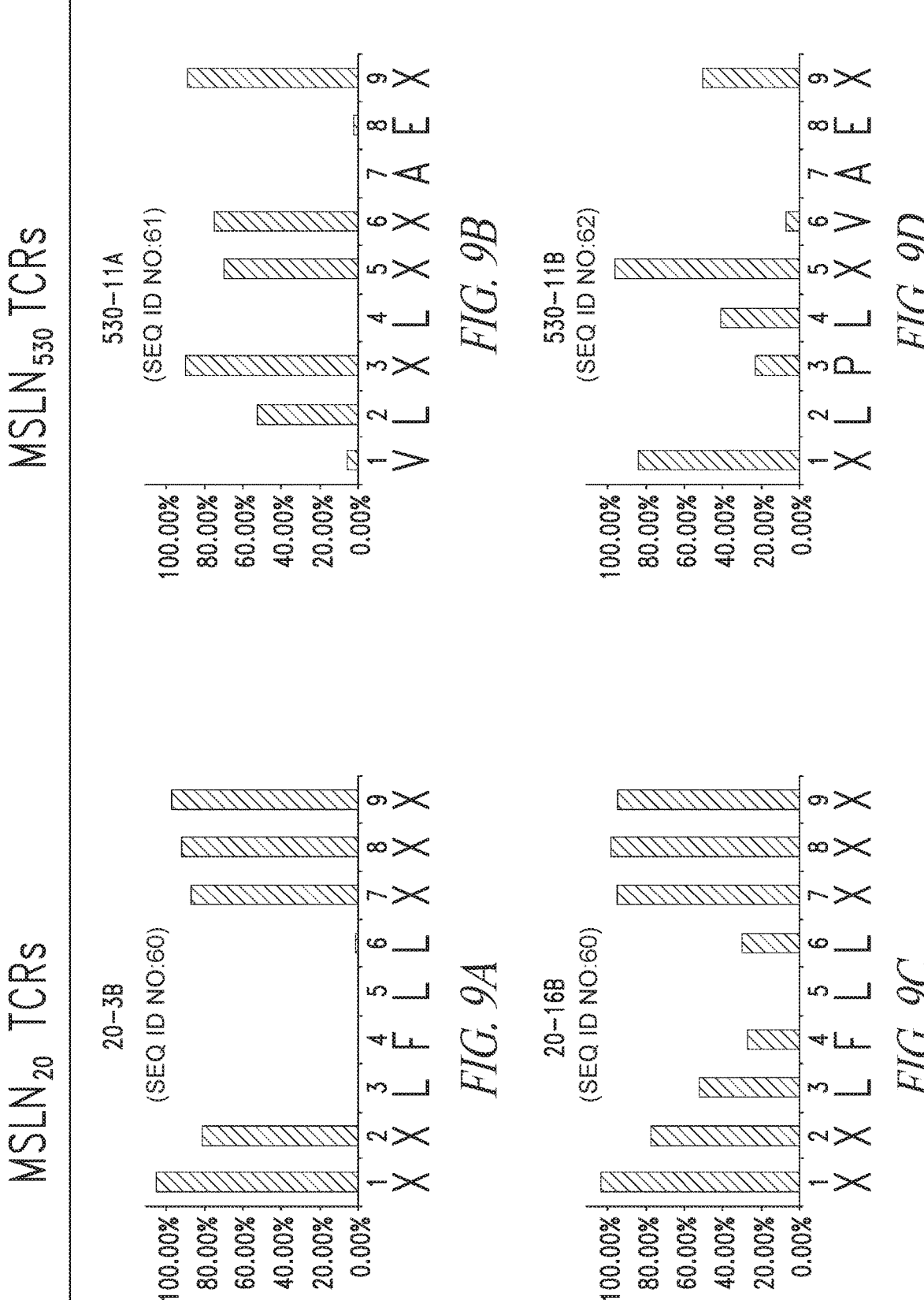

MsIn530 (SEQ ID NO:32)
Epitope = VLPLTVAEV

TCR: 530-A11 (SEQ ID NO:61)
Search string = V-L-x-L-x-A-E-x

| 53011A: V-L-x-L-x-A-E-x | | Peptide | SITHPATHI (>15) | PanMHCnet score (SB=<0.5; WB=<2) | IEDB (<1%) |
|---|---|---|---|---|---|
| MSLN | (SEQ ID NO:32) | VLPLTVAEV | 29 | 0.2335 | 1 |
| EHF | (SEQ ID NO:63) | VILLSLAEI | 29 | 0.5991 | 0.8 |
| YN010 | (SEQ ID NO:64) | VLALWEAEV | 27 | 0.2128 | 0.5 |
| MLEC | (SEQ ID NO:65) | VLVLKFAEV | 26 | 0.2994 | 0.9 |
| CHPF2 | (SEQ ID NO:66) | VLPLLVAEA | 24 | 0.6854 | 2.4 |
| ULK1 | (SEQ ID NO:67) | VLYLKVAEL | 31 | 0.78503 | 0.9 |
| OR2J2 | (SEQ ID NO:68) | VLALGIAEC | 23 | 0.9438 | 4.7 |
| DNHD1 | (SEQ ID NO:69) | VLEILLAEL | 29 | 1.0951 | 3.1 |
| AL1L1 | (SEQ ID NO:70) | VLELITEAEL | 24 | 1.1985 | 8.3 |
| GALP | (SEQ ID NO:71) | VLLLSLAET | 25 | 1.7861 | 3.3 |
| OR2J1 | (SEQ ID NO:72) | VLALGTAEC | 21 | 1.8786 | 3.3 |
| ADPRH | (SEQ ID NO:73) | VMHLATAEA | 19 | 1.9817 | 4.3 |

MsIn530 (SEQ ID NO:32)
Epitope = VLPLTVAEV

TCR: 530-B11 (SEQ ID NO:62)
Search string = X-L-P-L-X-V-A-E-X

| | | Peptide | SITHPATHI (>15) | PanMHCnet score (SB=<0.5; WB=<2) | IEDB (<1%) |
|---|---|---|---|---|---|
| MSLN | (SEQ ID NO:32) | VLPLTVAEV | 29 | 0.2335 | 1 |
| CHPF2 | (SEQ ID NO:74) | VLPLIVAEA | 24 | 0.6854 | 2.4 |
| LRCH3 | (SEQ ID NO:75) | dLPLRVAEI | 25 | 6.861 | 8.11 |
| IN80B | (SEQ ID NO:76) | MLPLPVAEG | 19 | 8.3672 | 13 |
| CEAM3 | (SEQ ID NO:77) | SMPLSVAEG | 18 | 17.1852 | 16 |

Potential cross-reacting peptide      Did not meet recommended cut-off criteria

*FIG. 10*

| | peptide #1 | peptide #2 | peptide #3 | peptide #4 | peptide #5 | peptide #6 | peptide #7 | peptide #8 | peptide #9 | peptide #10 | peptide #11 | peptide #12 | peptide wt | peptide max |
|---|---|---|---|---|---|---|---|---|---|---|---|---|---|---|
| Meso530-11A | 2.08 | 42.8 | 0.68 | 53.7 | 21.5 | 0.66 | 2.42 | 0.45 | 0.28 | 0.1 | 0.2 | 0.077 | 46.6 | 76.6 |
| Meso530-11B | 0.37 | 1.48 | 0.86 | 0.98 | 2.14 | 0.95 | 0.82 | 0.37 | 0.26 | 19 | 0.24 | 0.14 | 76 | 91.5 |

Legend:
— Peptide#9
--- Peptide#10*
—•— Peptide#11
— — Peptide#12
—•—•— WT

○ −7
▲ −10.3

More than 3-log difference in EC50 (~3000x more peptide required for same response)

| Initials (Prot.) | HLA-A | HLA-B | HLA-Cw |
|---|---|---|---|
| DAH #2 (956) | A1,A2 | B7,B15 | C1,C7 |
| DMJ (1334) | A2,A2 | B44,B44 | C5,C7 |
| FGA (1334) | A2,A30 | B7,B44 | C7,C7 |
| GWB (956) | A2,A11 | B15,B44 | C3,C5 |
| JAS (956) | A1,A68 | B44,B55 | C3,C5 |
| JRL #2 (956) | A1,A2 | B8,B55 | C3,C7 |
| JWP (TN) | A2,A33 | B7,B15 | C3,C7 |
| SING (ND) | A24,A32 | B35,B40 | C2,C4 |
*FIG. 12A*
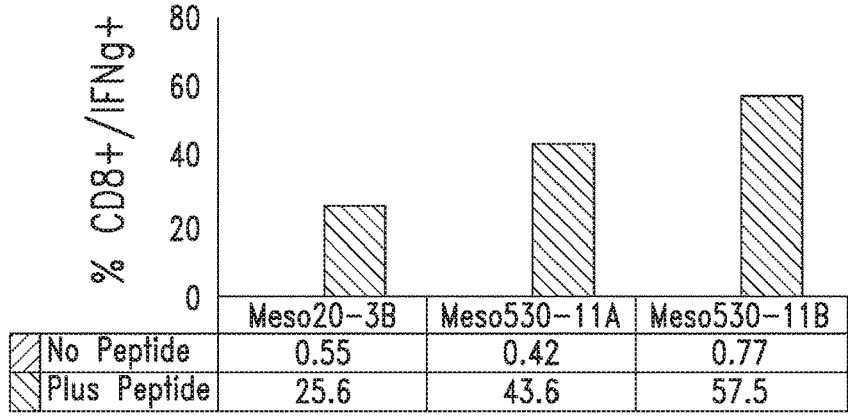
JWP (TN) LCL Cell Line
| | Meso20-3B | Meso530-11A | Meso530-11B |
|---|---|---|---|
| No Peptide | 0.55 | 0.42 | 0.77 |
| Plus Peptide | 25.6 | 43.6 | 57.5 |
*FIG. 12B*
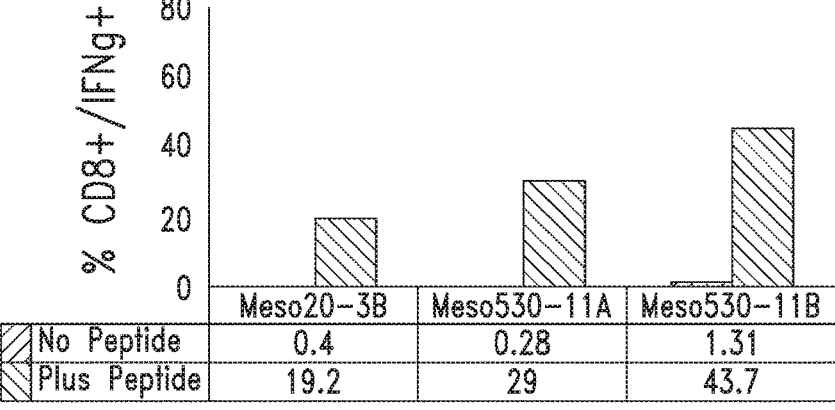
SING (ND) LCL Cell Line
| | Meso20-3B | Meso530-11A | Meso530-11B |
|---|---|---|---|
| No Peptide | 0.4 | 0.28 | 1.31 |
| Plus Peptide | 19.2 | 29 | 43.7 |
*FIG. 12C*

DAH#2 (956) LCL Cell Line

| | Meso20-3B | Meso530-11A | Meso530-11B |
|---|---|---|---|
| No Peptide | 1.15 | 0.89 | 1.01 |
| Plus Peptide | 33.2 | 43 | 65.4 |

DMJ (1334) LCL Cell Line

| | Meso20-3B | Meso530-11A | Meso530-11B |
|---|---|---|---|
| No Peptide | 0.45 | 0.38 | 1.01 |
| Plus Peptide | 33.9 | 43.1 | 58.1 |

FGA (1334) LCL Cell Line

| | Meso20-3B | Meso530-11A | Meso530-11B |
|---|---|---|---|
| No Peptide | 0.32 | 0.46 | 0.89 |
| Plus Peptide | 29.9 | 41.6 | 60.4 |

GWB (956) LCL Cell Line

| | Meso20-3B | Meso530-11A | Meso530-11B |
|---|---|---|---|
| No Peptide | 0.48 | 0.58 | 0.48 |
| Plus Peptide | 26.4 | 40.8 | 58.2 |

JAS (956) LCL Cell Line

| | Meso20-3B | Meso530-11A | Meso530-11B |
|---|---|---|---|
| No Peptide | 0.35 | 0.28 | 0.94 |
| Plus Peptide | 17.8 | 32 | 49 |

JRL#2 (956) LCL Cell Line

| | Meso20-3B | Meso530-11A | Meso530-11B |
|---|---|---|---|
| No Peptide | 0.038 | 0.25 | 1.08 |
| Plus Peptide | 34.2 | 44.1 | 63.5 |

| Initials (Prot.) | HLA-A | HLA-B | HLA-Cw |
|---|---|---|---|
| FAH | A3, A68 | B13:02:01, B40 | C2, C6:02:01 |
| CLP | A2, A3 | B40, B51 | C3, C15 |
| JOG | A3, A29 | B40, B44 | C3, C16 |
| MS | A11, A11 | B13:01:01, B15 | C4, C12 |
| GIM | A2, A30 | B7, B13:02:01 | C6:02:01, C7 |
| MDS | A1, A24 | B7, B57 | C6:02:01, C7 |
| PAJ | A1, A3 | B8, B49 | C7, C7 |

*FIG. 13A*

SEQUENCE LISTING

<160> NUMBER OF SEQ ID NOS: 123

<210> SEQ ID NO 1
<211> LENGTH: 939
<212> TYPE: DNA
<213> ORGANISM: Artificial Sequence
<220> FEATURE:
<223> OTHER INFORMATION: Synthetic sequence Meso20-3B WT- TCR beta

<400> SEQUENCE: 1

```
atgggctcct ggaccctctg ctgtgtgtcc ctttgcatcc tggtagcaaa gcacacagat      60
gctggagtta tccagtcacc ccggcacgag gtgacagaga tgggacaaga agtgactctg     120
agatgtaaac caatttcagg acacgactac cttttctggt acagacagac catgatgcgg     180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gttttactag cgggagctac     360
gagcagtact tcgggccggg caccaggctc acggtcacag aggacctgaa aaacgtgttc     420
ccacccgagg tcgctgtgtt tgagccatca gaagcagaga tctcccacac ccaaaaggcc     480
acactggtgt gcctggccac aggcttctac cccgaccacg tggagctgag ctggtgggtg     540
aatgggaagg aggtgcacag tggggtcagc acagaccccg agccctcaa ggagcagccc      600 gccctcaatg actccagata ctgcctgagc agccgcctga gggtctcggc caccttctgg     660 cagaacccc gcaaccactt ccgctgtcaa gtccagttct acgggctctc ggagaatgac      720
gagtggaccc aggatagggc caaacctgtc acccagatcg tcagcgccga ggcctggggt     780
```
agagcagact gtggcttcac ctccgagtct taccagcaag gggtcctgtc tgccaccatc          840
ctctatgaga tcttgctagg gaaggccacc ttgtatgccg tgctggtcag tgccctcgtg          900
ctgatggcca tggtcaagag aaaggattcc agaggctag                                939

<210> SEQ ID NO 2
<211> LENGTH: 950
<212> TYPE: DNA
<213> ORGANISM: Artificial Sequence
<220> FEATURE:
<223> OTHER INFORMATION: Synthetic sequence Meso20-3B Codon optimized
      -TCR beta

<400> SEQUENCE: 2
ggcgcgccac catgggaagc tggacactgt gttgcgttag cctgtgtatc ctggtggcca           60
aacacacaga tgctggagtg attcagagcc ctagacacga ggtgacagag atgggacagg          120
aagtgacact gagatgtaag cccattagcg acacgacta cctgttctgg tacaggcaga          180
ccatgatgag aggactggaa ctgctgatct acttcaacaa caacgtgccc atcgacgata          240
gcggcatgcc tgaggacaga tttagcgcca agatgcctaa tgccagcttt tctaccctga          300
agatccagcc ctctgagccc agagattctg ccgtgtactt ttgtgccagc agctttacat          360
ctggctctta tgagcagtac ttcggcccag gcacaaggct gacagtgaca gaggacctga          420
agaacgtgtt cccccagag gtggccgtgt cgagcctag cgaggccgag atcagccaca          480
cccagaaagc caccctcgtg tgcctggcca ccggctttta ccccgaccac gtggaactgt          540
cttggtgggt caacggcaaa gaggtgcaca cgggcgtctg caccgacccc cagccctga          600 aagagcagcc cgccctgaac gacagccggt actgtctgag cagcagactg agagtgtccg          660
ccaccttctg gcagaacccc cggaaccact tcagatgcca ggtgcagttc tacggcctga          720
gcgagaacga cgagtggacc caggaccggg ccaagcccgt gacccagatc gtgtctgctg          780
aggcctgggg cagagccgat tgcggcttca ccagcgagag ctaccagcag ggcgtgctga          840
gcgccaccat cctgtacgag atcctgctgg gcaaggccac cctgtacgcc gtgctggtgt          900
ccgccctggt gctgatggcc atggtcaagc ggaaggacag ccggggctga                     950

<210> SEQ ID NO 3
<211> LENGTH: 801
<212> TYPE: DNA
<213> ORGANISM: Artificial Sequence
<220> FEATURE:
<223> OTHER INFORMATION: Synthetic sequence Meso20-3B WT-TCR alpha

<400> SEQUENCE: 3
atgtggggag ctttccttct ctatgtttcc atgaagatgg gaggcactgc aggacaaagc           60
cttgagcagc cctctgaagt gacagctgtg gaaggagcca ttgtccagat aaactgcacg          120
taccagacat ctgggttta tgggctgtcc tggtaccagc aacatgatgg cggagcaccc          180
acatttcttt cttacaatgc tctggatggt ttggaggaga caggtcgttt ttcttcattc          240
cttagtcgct ctgatagtta tggttacctc cttctacagg agctccagat gaaagactct          300
gcctcttact tctgcgctgt gaatgatgct tccaagataa tctttggatc agggaccaga          360
ctcagcatcc ggccaaatat ccagaaccct gaccctgccg tgtaccagct gagagactct          420
aaatccagtg acaagtctgt ctgcctattc accgattttg attctcaaac aaatgtgtca          480
caaagtaagg attctgatgt gtatatcaca gacaaaactg tgctagacat gaggtctatg          540
gacttcaaga gcaacagtgc tgtggcctgg agcaacaaat ctgactttgc atgtgcaaac          600

-continued

```
gccttcaaca acagcattat tccagaagac accttcttcc ccagcccaga aagttcctgt      660
gatgtcaagc tggtcgagaa aagctttgaa acagatacga acctaaactt tcaaaacctg      720
tcagtgattg ggttccgaat cctcctcctg aaagtggccg ggtttaatct gctcatgacg      780
ctgcggctgt ggtccagctg a                                                801
```

<210> SEQ ID NO 4
<211> LENGTH: 801
<212> TYPE: DNA
<213> ORGANISM: Artificial Sequence
<220> FEATURE:
<223> OTHER INFORMATION: Synthetic sequence Meso20-3B Codon optimized
      -TCR alpha

<400> SEQUENCE: 4

```
atgtggggcg cttttcttct gtatgtgagc atgaagatgg cggaacagc tggacagtct       60 ctggaacagc ctagcgaggt tacagctgtt gaaggagcta ttgtgcagat caactgcacc      120
taccagacaa gcggcttcta cggcctgagc tggtatcaac agcacgatgg aggagctcct      180
acatttctga gctataatgc cctggatggc ctggaggaga caggcagatt tagcagcttc      240
ctgagcagat ctgactctta cggatatctg ctgctgcagg agctgcagat gaaggatagc      300
gccagctact tttgtgccgt gaatgatgcc tctaagatca tcttcggcag cggcaccaga      360
ctgagcatca ggcccaatat ccagaatcca gatcctgctg tgtaccagct gcgggacagc      420
aagagcagcg acaagagcgt gtgcctgttc accgacttcg acagccagac caacgtgtcc      480
cagagcaagg acagcgacgt gtacatcacc gataagtgcg tgctggacat gcggagcatg      540
gacttcaaga gcaacagcgc cgtggcctgg tccaacaaga gcgacttcgc ctgcgccaac      600
gccttcaaca acagcattat ccccgaggac acattcttcc caagcccga gagcagctgc       660 gacgtgaagc tggtggaaaa gagcttcgag acagacacca acctgaactt ccagaacctc      720
agcgtgatcg gcttccggat cctgctgctg aaggtggccg gcttcaacct gctgatgacc      780
ctgcggctgt ggtccagctg a                                                801
```

<210> SEQ ID NO 5
<211> LENGTH: 1820
<212> TYPE: DNA
<213> ORGANISM: Artificial Sequence
<220> FEATURE:
<223> OTHER INFORMATION: Synthetic sequence Meso20-3B CO-TCR beta-P2A-
      TCR alpha

<400> SEQUENCE: 5

```
ggcgcgccac catgggaagc tggacactgt gttgcgttag cctgtgtatc ctggtggcca       60
aacacacaga tgctggagtg attcagagcc ctagacacga ggtgacagag atgggacagg      120
aagtgacact gagatgtaag cccattagcg gacacgacta cctgttctgg tacaggcaga      180
ccatgatgag aggactggaa ctgctgatct acttcaacaa caacgtgccc atcgacgata      240
gcggcatgcc tgaggacaga tttagcgcca agatgcctaa tgccagcttt tctaccctga      300
agatccagcc ctctgagccc agagattctg ccgtgtactt ttgtgccagc agctttacat      360
ctggctctta tgagcagtac ttcggcccag gcacaaggct gacagtgaca gaggacctga      420
agaacgtgtt cccccagag gtggccgtgt tcgagcctag cgaggccgag atcagccaca      480
cccagaaagc caccctcgtg tgcctggcca ccggctttta ccccgaccac gtggaactgt      540
cttggtgggt caacggcaaa gaggtgcaca gcggcgtctg caccgacccc cagccctga       600 aagagcagcc cgccctgaac gacagccggt actgtctgag cagcagactg agagtgtccg      660
```

-continued

```
ccaccttctg gcagaacccc cggaaccact tcagatgcca ggtgcagttc tacggcctga        720
gcgagaacga cgagtggacc caggaccggg ccaagcccgt gacccagatc gtgtctgctg        780
aggcctgggg cagagccgat tgcggcttca ccagcgagag ctaccagcag ggcgtgctga        840
gcgccaccat cctgtacgag atcctgctgg gcaaggccac cctgtacgcc gtgctggtgt        900
ccgccctggt gctgatggcc atggtcaagc ggaaggacag ccggggcggt tccggagcca        960
cgaacttctc tctgttaaag caagcaggag acgtggaaga aaaccccggt cccatgtggg       1020
gcgcttttct tctgtatgtg agcatgaaga tgggcggaac agctggacag tctctggaac       1080
agcctagcga ggttacagct gttgaaggag ctattgtgca gatcaactgc acctaccaga       1140
caagcggctt ctacggcctg agctggtatc aacagcacga tggaggagct cctacatttc       1200
tgagctataa tgccctggat ggcctggagg agacaggcag atttagcagc ttcctgagca       1260
gatctgactc ttacggatat ctgctgctgc aggagctgca gatgaaggat agcgccagct       1320
acttttgtgc cgtgaatgat gcctctaaga tcatcttcgg cagcggcacc agactgagca       1380
tcaggcccaa tatccagaat ccagatcctg ctgtgtacca gctgcgggac agcaagagca       1440
gcgacaagag cgtgtgcctg ttcaccgact tcgacagcca gaccaacgtg tcccagagca       1500
aggacagcga cgtgtacatc accgataagt gcgtgctgga catgcggagc atggacttca       1560
agagcaacag cgccgtggcc tggtccaaca gagcgacttc gcctgcgcc aacgccttca       1620 acaacagcat tatccccgag gacacattct tcccaagccc cgagagcagc tgcgacgtga       1680
agctggtgga aaagagcttc gagacagaca ccaacctgaa cttccagaac ctcagcgtga       1740
tcggcttccg gatcctgctg ctgaaggtgg ccggcttcaa cctgctgatg accctgcggc       1800
tgtggtccag ctgagtcgac                                                    1820
```

<210> SEQ ID NO 6
<211> LENGTH: 312
<212> TYPE: PRT
<213> ORGANISM: Artificial Sequence
<220> FEATURE:
<223> OTHER INFORMATION: Synthetic sequence Meso20-3B Protein TCRbeta -
    with signal peptide

<400> SEQUENCE: 6

```
Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Phe Thr Ser Gly Ser Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140
```

-continued

```
Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
                180                 185                 190

Pro Gln Pro Leu Lys Glu Gln Pro Ala Leu Asn Asp Ser Arg Tyr Cys
                195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
                275                 280                 285

Ala Thr Leu Tyr Ala Val Leu Val Ser Ala Leu Val Leu Met Ala Met
        290                 295                 300

Val Lys Arg Lys Asp Ser Arg Gly
305                 310

<210> SEQ ID NO 7
<211> LENGTH: 266
<212> TYPE: PRT
<213> ORGANISM: Artificial Sequence
<220> FEATURE:
<223> OTHER INFORMATION: Synthetic sequence Meso20-3B Protein TCRalpha -
      with signal peptide

<400> SEQUENCE: 7

Met Trp Gly Ala Phe Leu Leu Tyr Val Ser Met Lys Met Gly Gly Thr
1               5                   10                  15

Ala Gly Gln Ser Leu Glu Gln Pro Ser Glu Val Thr Ala Val Glu Gly
                20                  25                  30

Ala Ile Val Gln Ile Asn Cys Thr Tyr Gln Thr Ser Gly Phe Tyr Gly
                35                  40                  45

Leu Ser Trp Tyr Gln Gln His Asp Gly Gly Ala Pro Thr Phe Leu Ser
        50                  55                  60

Tyr Asn Ala Leu Asp Gly Leu Glu Glu Thr Gly Arg Phe Ser Ser Phe
65                  70                  75                  80

Leu Ser Arg Ser Asp Ser Tyr Gly Tyr Leu Leu Leu Gln Glu Leu Gln
                85                  90                  95

Met Lys Asp Ser Ala Ser Tyr Phe Cys Ala Val Asn Asp Ala Ser Lys
                100                 105                 110

Ile Ile Phe Gly Ser Gly Thr Arg Leu Ser Ile Arg Pro Asn Ile Gln
                115                 120                 125

Asn Pro Asp Pro Ala Val Tyr Gln Leu Arg Asp Ser Lys Ser Ser Asp
        130                 135                 140

Lys Ser Val Cys Leu Phe Thr Asp Phe Asp Ser Gln Thr Asn Val Ser
145                 150                 155                 160

Gln Ser Lys Asp Ser Asp Val Tyr Ile Thr Asp Lys Cys Val Leu Asp
                165                 170                 175

Met Arg Ser Met Asp Phe Lys Ser Asn Ser Ala Val Ala Trp Ser Asn
                180                 185                 190
```

```
Lys Ser Asp Phe Ala Cys Ala Asn Ala Phe Asn Asn Ser Ile Ile Pro
        195             200             205

Glu Asp Thr Phe Phe Pro Ser Pro Glu Ser Ser Cys Asp Val Lys Leu
    210             215             220

Val Glu Lys Ser Phe Glu Thr Asp Thr Asn Leu Asn Phe Gln Asn Leu
225             230             235             240

Ser Val Ile Gly Phe Arg Ile Leu Leu Leu Lys Val Ala Gly Phe Asn
            245             250             255

Leu Leu Met Thr Leu Arg Leu Trp Ser Ser
        260             265
```

```
<210> SEQ ID NO 8
<211> LENGTH: 600
<212> TYPE: PRT
<213> ORGANISM: Artificial Sequence
<220> FEATURE:
<223> OTHER INFORMATION: Synthetic sequence Meso20-3B Protein CO-TCR
      beta-P2A-TCR alpha

<400> SEQUENCE: 8

Met Gly Ser Trp Thr Leu Cys Cys Val Ser Leu Cys Ile Leu Val Ala
1               5               10              15

Lys His Thr Asp Ala Gly Val Ile Gln Ser Pro Arg His Glu Val Thr
            20              25              30

Glu Met Gly Gln Glu Val Thr Leu Arg Cys Lys Pro Ile Ser Gly His
        35              40              45

Asp Tyr Leu Phe Trp Tyr Arg Gln Thr Met Met Arg Gly Leu Glu Leu
    50              55              60

Leu Ile Tyr Phe Asn Asn Asn Val Pro Ile Asp Asp Ser Gly Met Pro
65              70              75              80

Glu Asp Arg Phe Ser Ala Lys Met Pro Asn Ala Ser Phe Ser Thr Leu
            85              90              95

Lys Ile Gln Pro Ser Glu Pro Arg Asp Ser Ala Val Tyr Phe Cys Ala
        100             105             110

Ser Ser Phe Thr Ser Gly Ser Tyr Glu Gln Tyr Phe Gly Pro Gly Thr
        115             120             125

Arg Leu Thr Val Thr Glu Asp Leu Lys Asn Val Phe Pro Pro Glu Val
    130             135             140

Ala Val Phe Glu Pro Ser Glu Ala Glu Ile Ser His Thr Gln Lys Ala
145             150             155             160

Thr Leu Val Cys Leu Ala Thr Gly Phe Tyr Pro Asp His Val Glu Leu
            165             170             175

Ser Trp Trp Val Asn Gly Lys Glu Val His Ser Gly Val Cys Thr Asp
            180             185             190

Pro Gln Pro Leu Lys Glu Gln Pro Ala Leu Asn Asp Ser Arg Tyr Cys
        195             200             205

Leu Ser Ser Arg Leu Arg Val Ser Ala Thr Phe Trp Gln Asn Pro Arg
        210             215             220

Asn His Phe Arg Cys Gln Val Gln Phe Tyr Gly Leu Ser Glu Asn Asp
225             230             235             240

Glu Trp Thr Gln Asp Arg Ala Lys Pro Val Thr Gln Ile Val Ser Ala
            245             250             255

Glu Ala Trp Gly Arg Ala Asp Cys Gly Phe Thr Ser Glu Ser Tyr Gln
        260             265             270

Gln Gly Val Leu Ser Ala Thr Ile Leu Tyr Glu Ile Leu Leu Gly Lys
```

-continued

```
              275                 280                 285
Ala Thr Leu Tyr Ala Val Leu Val Ser Ala Leu Val Leu Met Ala Met
    290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Trp
                325                 330                 335

Gly Ala Phe Leu Leu Tyr Val Ser Met Lys Met Gly Gly Thr Ala Gly
            340                 345                 350

Gln Ser Leu Glu Gln Pro Ser Glu Val Thr Ala Val Glu Gly Ala Ile
            355                 360                 365

Val Gln Ile Asn Cys Thr Tyr Gln Thr Ser Gly Phe Tyr Gly Leu Ser
    370                 375                 380

Trp Tyr Gln Gln His Asp Gly Gly Ala Pro Thr Phe Leu Ser Tyr Asn
385                 390                 395                 400

Ala Leu Asp Gly Leu Glu Glu Thr Gly Arg Phe Ser Ser Phe Leu Ser
                405                 410                 415

Arg Ser Asp Ser Tyr Gly Tyr Leu Leu Leu Gln Glu Leu Gln Met Lys
                420                 425                 430

Asp Ser Ala Ser Tyr Phe Cys Ala Val Asn Asp Ala Ser Lys Ile Ile
            435                 440                 445

Phe Gly Ser Gly Thr Arg Leu Ser Ile Arg Pro Asn Ile Gln Asn Pro
    450                 455                 460

Asp Pro Ala Val Tyr Gln Leu Arg Asp Ser Lys Ser Ser Asp Lys Ser
465                 470                 475                 480

Val Cys Leu Phe Thr Asp Phe Asp Ser Gln Thr Asn Val Ser Gln Ser
                485                 490                 495

Lys Asp Ser Asp Val Tyr Ile Thr Asp Lys Cys Val Leu Asp Met Arg
                500                 505                 510

Ser Met Asp Phe Lys Ser Asn Ser Ala Val Ala Trp Ser Asn Lys Ser
            515                 520                 525

Asp Phe Ala Cys Ala Asn Ala Phe Asn Asn Ser Ile Ile Pro Glu Asp
    530                 535                 540

Thr Phe Phe Pro Ser Pro Glu Ser Ser Cys Asp Val Lys Leu Val Glu
545                 550                 555                 560

Lys Ser Phe Glu Thr Asp Thr Asn Leu Asn Phe Gln Asn Leu Ser Val
                565                 570                 575

Ile Gly Phe Arg Ile Leu Leu Leu Lys Val Ala Gly Phe Asn Leu Leu
            580                 585                 590

Met Thr Leu Arg Leu Trp Ser Ser
            595                 600
```

```
<210> SEQ ID NO 9
<211> LENGTH: 939
<212> TYPE: DNA
<213> ORGANISM: Artificial Sequence
<220> FEATURE:
<223> OTHER INFORMATION: Synthetic sequence Meso20-16B - WT-TCR beta

<400> SEQUENCE: 9
atggactcct ggaccttctg ctgtgtgtcc ctttgcatcc tggtagcgaa gcatacagat        60
gctggagtta tccagtcacc ccgccatgag gtgacagaga tgggacaaga agtgactctg       120
agatgtaaac caattttcagg ccacaactcc ctttttctggt acagacagac catgatgcgg       180
ggactggagt tgctcatttta cttttaacaac aacgttccga tagatgattc agggatgccc       240
```

```
gaggatcgat tctcagctaa gatgcctaat gcatcattct ccactctgaa gatccagccc      300
tcagaaccca gggactcagc tgtgtacttc tgtgccagca gttcgcctga caggctgggc      360
gagcagtact tcgggccggg caccaggctc acggtcacag aggacctgaa aaacgtgttc      420
ccacccgagg tcgctgtgtt tgagccatca gaagcagaga tctcccacac ccaaaaggcc      480
acactggtgt gcctggccac aggcttctac cccgaccacg tggagctgag ctggtgggtg      540
aatgggaagg aggtgcacag tggggtcagc acagaccccg cagcccctcaa ggagcagccc      600 gccctcaatg actccagata ctgcctgagc agccgcctga gggtctcggc caccttctgg      660 cagaacccc gcaaccactt ccgctgtcaa gtccagttct acgggctctc ggagaatgac      720
gagtggaccc aggatagggc caaacctgtc acccagatcg tcagcgccga ggcctggggt      780
agagcagact gtggcttcac ctccgagtct taccagcaag gggtcctgtc tgccaccatc      840
ctctatgaga tcttgctagg gaaggccacc ttgtatgccg tgctggtcag tgccctcgtg      900
ctgatggcca tggtcaagag aaaggattcc agaggctag                            939
```

```
<210> SEQ ID NO 10
<211> LENGTH: 939
<212> TYPE: DNA
<213> ORGANISM: Artificial Sequence
<220> FEATURE:
<223> OTHER INFORMATION: Synthetic sequence Meso20-16B - CO-TCRbeta

<400> SEQUENCE: 10
```

```
atggatagct ggaccttctg ttgcgtgagc ctgtgtatcc tggtggccaa acacacagat       60
gctggagtga ttcagagccc tagacatgag gtgaccgaaa tgggacagga ggtgacactg      120
agatgtaagc ccatttctgg ccacaacagc ctgttctggt acagacagac catgatgagg      180
ggactggaac tgctgatcta cttcaacaac aacgtgccca tcgacgatag cggcatgcct      240
gaggacagat ttagcgccaa gatgcctaat gccagctttt ctaccctgaa gatccagccc      300
tctgagccca gagattctgc cgtgtacttt tgtgccagct cttctcctga tagactggga      360
gagcagtact ttggccctgg cacaagactg acagtgacag aggacctgaa gaacgtgttc      420 ccccagagg tggccgtgtt cgagcctagc gaggccgaga tcagccacac ccagaaagcc      480
accctcgtgt gcctggccac cggctttttac cccgaccacg tggaactgtc ttggtgggtc      540
aacggcaaag aggtgcacag cggcgtctgc accgacccc agcccctgaa agagcagccc      600
gccctgaacg acagccggta ctgtctgagc agcagactga gagtgtccgc caccttctgg      660 cagaacccc ggaaccactt cagatgccag gtgcagttct acgggcctgag cgagaacgac      720 gagtggaccc aggaccgggc caagcccgtg acccagatcg tgtctgctga ggcctggggc      780
agagccgatt gcggcttcac cagcgagagc taccagcagg gcgtgctgag cgccaccatc      840
ctgtacgaga tcctgctggg caaggccacc ctgtacgccg tgctggtgtc cgccctggtg      900
ctgatggcca tggtcaagcg gaaggacagc cggggctga                            939
```

```
<210> SEQ ID NO 11
<211> LENGTH: 819
<212> TYPE: DNA
<213> ORGANISM: Artificial Sequence
<220> FEATURE:
<223> OTHER INFORMATION: Synthetic sequence Meso20-16B - WT-TCR alpha

<400> SEQUENCE: 11
```

```
atgatgaaat ccttgagagt tttactggtg atcctgtggc ttcagttaag ctgggtttgg       60
```

-continued

```
agccaacaga aggaggtgga gcaggatcct ggaccactca gtgttccaga gggagccatt        120
gtttctctca actgcactta cagcaacagt gcttttcaat acttcatgtg gtacagacag        180
tattccagaa aaggccctga gttgctgatg tacacatact ccagtggtaa caaagaagat        240
ggaaggttta cagcacaggt cgataaatcc agcaagtata tctccttgtt catcagagac        300
tcacagccca gtgattcagc cacctacctc tgtgcaggag ggggaaacac acctcttgtc        360
tttggaaagg cacaagact ttctgtgatt gcaaatatcc agaaccctga ccctgccgtg        420
taccagctga gagactctaa atccagtgac aagtctgtct gcctattcac cgattttgat        480
tctcaaacaa atgtgtcaca aagtaaggat tctgatgtgt atatcacaga caaaactgtg        540
ctagacatga ggtctatgga cttcaagagc aacagtgctg tggcctggag caacaaatct        600
gactttgcat gtgcaaacgc cttcaacaac agcattattc agaagacac cttcttcccc         660 agcccagaaa gttcctgtga tgtcaagctg gtcgagaaaa gctttgaaac agatacgaac        720
ctaaactttc aaaacctgtc agtgattggg ttccgaatcc tcctcctgaa agtggccggg        780
tttaatctgc tcatgacgct gcggctgtgg tccagctga                                819
```

```
<210> SEQ ID NO 12
<211> LENGTH: 819
<212> TYPE: DNA
<213> ORGANISM: Artificial Sequence
<220> FEATURE:
<223> OTHER INFORMATION: Synthetic sequence Meso20-16B - CO-TCR alpha

<400> SEQUENCE: 12
```

```
atgatgaaga gcctgcgagt cctcctggtg attctgtggt tacagctgtc ttgggtgtgg        60
tctcagcaga aagaagtgga gcaggatcct ggacctctgt ctgtgcctga aggagctatt        120
gtgagcctga attgcaccta cagcaatagc gccttccagt acttcatgtg gtaccggcag        180
tacagcagaa agggccctga actgctgatg tacacctact ctagcggcaa taaggaagat        240
ggccggttta cagctcaggt ggacaagagc agcaagtaca tcagcctgtt catcagggat        300
tctcagccta gcgattctgc cacctacctg tgtgctggag cggaaatac acctctggtt          360 tttggaaaag caccagact gtctgtgatc gccaacatcc agaacccccga ccctgctgtg        420 taccagctgc gggacagcaa gagcagcgac aagagcgtgt gcctgttcac cgacttcgac        480
agccagacca acgtgtccca gagcaaggac agcgacgtgt acatcaccga taagtgcgtg        540
ctggacatgc ggagcatgga cttcaagagc aacagcgccg tggcctggtc caacaagagc        600
gacttcgcct gcgccaacgc cttcaacaac agcattatcc ccgaggacac attcttccca        660
agccccgaga gcagctgcga cgtgaagctg gtggaaaaga gcttcgagac agacaccaac        720
ctgaacttcc agaacctcag cgtgatcggc ttccggatcc tgctgctgaa ggtggccggc        780
ttcaacctgc tgatgaccct gcggctgtgg tccagctga                                819
```

```
<210> SEQ ID NO 13
<211> LENGTH: 1838
<212> TYPE: DNA
<213> ORGANISM: Artificial Sequence
<220> FEATURE:
<223> OTHER INFORMATION: Synthetic sequence Meso20-16B - CO-TCR beta-
      P2A-TCR alpha

<400> SEQUENCE: 13
```

```
ggcgcgccac catggatagc tggaccttct gttgcgtgag cctgtgtatc ctggtggcca        60
aacacacaga tgctggagtg attcagagcc ctagacatga ggtgaccgaa atgggacagg        120
```

-continued

```
aggtgacact gagatgtaag cccatttctg gccacaacag cctgttctgg tacagacaga    180
ccatgatgag gggactggaa ctgctgatct acttcaacaa caacgtgccc atcgacgata    240
gcggcatgcc tgaggacaga tttagcgcca agatgcctaa tgccagcttt tctaccctga    300
agatccagcc ctctgagccc agagattctg ccgtgtactt ttgtgccagc tcttctcctg    360
atagactggg agagcagtac tttggccctg gcacaagact gacagtgaca gaggacctga    420
agaacgtgtt cccccagag gtggccgtgt cgagcctag cgaggccgag atcagccaca    480
cccagaaagc caccctcgtg tgcctggcca ccggcttttta ccccgaccac gtggaactgt    540
cttggtgggt caacggcaaa gaggtgcaca gcggcgtctg caccgacccc cagcccctga    600
aagagcagcc cgccctgaac gacagccggt actgtctgag cagcagactg agagtgtccg    660
ccaccttctg gcagaacccc cggaaccact tcagatgcca ggtgcagttc tacggcctga    720
gcgagaacga cgagtggacc caggaccggg ccaagcccgt gacccagatc gtgtctgctg    780
aggcctgggg cagagccgat tgcggcttca ccagcgagag ctaccagcag ggcgtgctga    840
gcgccaccat cctgtacgag atcctgctgg gcaaggccac cctgtacgcc gtgctggtgt    900
ccgccctggt gctgatggcc atggtcaagc ggaaggacag ccggggcggt tccggagcca    960
cgaacttctc tctgttaaag caagcaggag acgtggaaga aaaccccggt cccatgatga   1020
agagcctgcg agtcctcctg gtgattctgt ggttacagct gtcttgggtg tggtctcagc   1080
agaaagaagt ggagcaggat cctggacctc tgtctgtgcc tgaaggagct attgtgagcc   1140
tgaattgcac ctacagcaat agcgccttcc agtacttcat gtggtaccgg cagtacagca   1200
gaaagggccc tgaactgctg atgtacacct actctagcgg caataaggaa gatggccggt   1260
ttacagctca ggtggacaag agcagcaagt acatcagcct gttcatcagg gattctcagc   1320
ctagcgattc tgccacctac ctgtgtgctg gaggcggaaa tacacctctg gttttttggaa   1380 aaggcaccag actgtctgtg atcgccaaca tccagaaccc cgaccctgct gtgtaccagc   1440
tgcgggacac caagagcagc gacaagagcg tgtgcctgtt caccgacttc gacagccaga   1500
ccaacgtgtc ccagagcaag gacagcgacg tgtacatcac cgataagtgc gtgctggaca   1560
tgcggagcat ggacttcaag agcaacagcg ccgtggcctg gtccaacaag agcgacttcg   1620
cctgcgccaa cgccttcaac aacagcatta tccccgagga cacattcttc ccaagcccg    1680 agagcagctg cgacgtgaag ctggtggaaa gagcttcga gacagacacc aacctgaact   1740
tccagaacct cagcgtgatc ggcttccgga tcctgctgct gaaggtggcc ggcttcaacc   1800
tgctgatgac cctgcggctg tggtccagct gagtcgac                          1838
```

```
<210> SEQ ID NO 14
<211> LENGTH: 312
<212> TYPE: PRT
<213> ORGANISM: Artificial Sequence
<220> FEATURE:
<223> OTHER INFORMATION: Synthetic sequence Meso20-16B - Protein TCR
      beta - with signal peptide

<400> SEQUENCE: 14

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
```

```
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                    85                  90                  95

Lys Ile Gln Pro Ser Glu Pro Arg Asp Ser Ala Val Tyr Phe Cys Ala
                100                 105                 110

Ser Ser Ser Pro Asp Arg Leu Gly Glu Gln Tyr Phe Gly Pro Gly Thr
            115                 120                 125

Arg Leu Thr Val Thr Glu Asp Leu Lys Asn Val Phe Pro Pro Glu Val
            130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
            210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
            290                 295                 300

Val Lys Arg Lys Asp Ser Arg Gly
305                 310
```

```
<210> SEQ ID NO 15
<211> LENGTH: 272
<212> TYPE: PRT
<213> ORGANISM: Artificial Sequence
<220> FEATURE:
<223> OTHER INFORMATION: Synthetic sequence Meso20-16B - Protein TCR
      alpha - with signal peptide

<400> SEQUENCE: 15
```

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95
```

-continued

```
Phe Ile Arg Asp Ser Gln Pro Ser Asp Ser Ala Thr Tyr Leu Cys Ala
            100                 105                 110

Gly Gly Gly Asn Thr Pro Leu Val Phe Gly Lys Gly Thr Arg Leu Ser
            115                 120                 125

Val Ile Ala Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 16
<211> LENGTH: 606
<212> TYPE: PRT
<213> ORGANISM: Artificial Sequence
<220> FEATURE:
<223> OTHER INFORMATION: Synthetic sequence Meso20-16B - Protein TCR
      beta-P2A-TCR alpha

<400> SEQUENCE: 16

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
            85                  90                  95

Lys Ile Gln Pro Ser Glu Pro Arg Asp Ser Ala Val Tyr Phe Cys Ala
            100                 105                 110

Ser Ser Ser Pro Asp Arg Leu Gly Glu Gln Tyr Phe Gly Pro Gly Thr
            115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190
```

-continued

```
Pro Gln Pro Leu Lys Glu Gln Pro Ala Leu Asn Asp Ser Arg Tyr Cys
        195             200             205

Leu Ser Ser Arg Leu Arg Val Ser Ala Thr Phe Trp Gln Asn Pro Arg
        210             215             220

Asn His Phe Arg Cys Gln Val Gln Phe Tyr Gly Leu Ser Glu Asn Asp
225             230             235             240

Glu Trp Thr Gln Asp Arg Ala Lys Pro Val Thr Gln Ile Val Ser Ala
            245             250             255

Glu Ala Trp Gly Arg Ala Asp Cys Gly Phe Thr Ser Glu Ser Tyr Gln
            260             265             270

Gln Gly Val Leu Ser Ala Thr Ile Leu Tyr Glu Ile Leu Leu Gly Lys
            275             280             285

Ala Thr Leu Tyr Ala Val Leu Val Ser Ala Leu Val Leu Met Ala Met
        290             295             300

Val Lys Arg Lys Asp Ser Arg Gly Gly Ser Gly Ala Thr Asn Phe Ser
305             310             315             320

Leu Leu Lys Gln Ala Gly Asp Val Glu Glu Asn Pro Gly Pro Met Met
            325             330             335

Lys Ser Leu Arg Val Leu Leu Val Ile Leu Trp Leu Gln Leu Ser Trp
            340             345             350

Val Trp Ser Gln Gln Lys Glu Val Glu Gln Asp Pro Gly Pro Leu Ser
            355             360             365

Val Pro Glu Gly Ala Ile Val Ser Leu Asn Cys Thr Tyr Ser Asn Ser
        370             375             380

Ala Phe Gln Tyr Phe Met Trp Tyr Arg Gln Tyr Ser Arg Lys Gly Pro
385             390             395             400

Glu Leu Leu Met Tyr Thr Tyr Ser Ser Gly Asn Lys Glu Asp Gly Arg
            405             410             415

Phe Thr Ala Gln Val Asp Lys Ser Ser Lys Tyr Ile Ser Leu Phe Ile
            420             425             430

Arg Asp Ser Gln Pro Ser Asp Ser Ala Thr Tyr Leu Cys Ala Gly Gly
        435             440             445

Gly Asn Thr Pro Leu Val Phe Gly Lys Gly Thr Arg Leu Ser Val Ile
        450             455             460

Ala Asn Ile Gln Asn Pro Asp Pro Ala Val Tyr Gln Leu Arg Asp Ser
465             470             475             480

Lys Ser Ser Asp Lys Ser Val Cys Leu Phe Thr Asp Phe Asp Ser Gln
            485             490             495

Thr Asn Val Ser Gln Ser Lys Asp Ser Asp Val Tyr Ile Thr Asp Lys
            500             505             510

Cys Val Leu Asp Met Arg Ser Met Asp Phe Lys Ser Asn Ser Ala Val
            515             520             525

Ala Trp Ser Asn Lys Ser Asp Phe Ala Cys Ala Asn Ala Phe Asn Asn
        530             535             540

Ser Ile Ile Pro Glu Asp Thr Phe Phe Pro Ser Pro Glu Ser Ser Cys
545             550             555             560

Asp Val Lys Leu Val Glu Lys Ser Phe Glu Thr Asp Thr Asn Leu Asn
            565             570             575

Phe Gln Asn Leu Ser Val Ile Gly Phe Arg Ile Leu Leu Leu Lys Val
            580             585             590

Ala Gly Phe Asn Leu Leu Met Thr Leu Arg Leu Trp Ser Ser
        595             600             605
```

-continued

<210> SEQ ID NO 17
<211> LENGTH: 930
<212> TYPE: DNA
<213> ORGANISM: Artificial Sequence
<220> FEATURE:
<223> OTHER INFORMATION: Synthetic sequence Meso530-11A WT-TCR beta

<400> SEQUENCE: 17

```
atgggctgca ggctgctctg ctgtgcggtt ctctgtctcc tgggagcagt tcccatagac      60
actgaagtta cccagacacc aaaacacctg gtcatgggaa tgacaaataa gaagtctttg     120
aaatgtgaac aacatatggg gcacagggct atgtattggt acaagcagaa agctaagaag     180
ccaccggagc tcatgtttgt ctacagctat gagaaactct ctataaatga aagtgtgcca     240
agtcgcttct cacctgaatg ccccaacagc tctctcttaa accttcacct acacgccctg     300
cagccagaag actcagccct gtatctctgc gccagcagcc acgggtccct gaacactgaa     360
gctttctttg acaaggcac agactcaca gttgtagagg acctgaacaa ggtgttccca     420
cccgaggtcg ctgtgtttga gccatcagaa gcagagatct cccacaccca aaaggccaca     480
ctggtgtgcc tggccacagg cttcttcccc gaccacgtgg agctgagctg gtgggtgaat     540
gggaaggagg tgcacagtgg ggtcagcacg gacccgcagc ccctcaagga gcagcccgcc     600
ctcaatgact ccagatactg cctgagcagc cgcctgaggg tctcggccac cttctggcag     660 aaccccgca accacttccg ctgtcaagtc cagttctacg ggctctcgga gaatgacgag     720
tggacccagg atagggccaa acccgtcacc cagatcgtca gcgccgaggc ctggggtaga     780
gcagactgtg gctttacctc ggtgtcctac cagcaagggg tcctgtctgc caccatcctc     840
tatgagatcc tgctagggaa ggccacccctg tatgctgtgc tggtcagcgc ccttgtgttg     900
atggccatgg tcaagagaaa ggatttctga                                    930
```

<210> SEQ ID NO 18
<211> LENGTH: 930
<212> TYPE: DNA
<213> ORGANISM: Artificial Sequence
<220> FEATURE:
<223> OTHER INFORMATION: Synthetic sequence Meso530-11A CO-TCR beta

<400> SEQUENCE: 18

```
atgggctgta gactgctgtg ttgtgctgtg ctttgtctgc ttggagctgt gcctatcgat      60
acagaggtga cccagacacc taagcatctg gtgatgggca tgaccaacaa gaagagcctg     120
aagtgtgaac agcacatggg ccataggggcc atgtactggt acaagcagaa ggccaagaaa     180
cctcctgagc tgatgttcgt gtacagctac gagaagctga gcatcaacga gagcgtgccc     240
agcagatttt ctcctgagtg ccctaatagc tctctgctga atctgcacct gcatgctctg     300
cagcctgagg attctgctct gtacctgtgt gcttcttctc acggatctct gaatacagag     360
gccttcttcg ccagggcac aagactgaca gtggttgagg atctgaacaa ggtgttcccc     420
ccagaggtgg ccgtgttcga gccttctgag gccgagatct cccacaccca gaaagccacc     480
ctcgtgtgcc tggccaccgg ctttttcccc gaccacgtgg aactgtcttg gtgggtcaac     540
ggcaaagagg tgcactccgg cgtgtgcacc gatccccagc ctctgaaaga acagcccgcc     600
ctgaacgaca gccggtactg cctgagcagc agactgagag tgtccgccac cttctggcag     660 aaccccgga accacttcag atgccaggtg cagttctacg gcctgagcga gaacgacgag     720
tggacccagg acagagccaa gcccgtgaca cagatcgtgt ctgccgaagc ctggggcaga     780
gccgattgcg gctttacctc cgtgtcctat cagcagggcg tgctgagcgc cacaatcctg     840
```

-continued

```
tacgagatcc tgctgggcaa ggccaccctg tacgccgtgc tggtgtctgc cctggtgctg      900
atggccatgg tcaagcggaa ggacttctga                                       930

<210> SEQ ID NO 19
<211> LENGTH: 831
<212> TYPE: DNA
<213> ORGANISM: Artificial Sequence
<220> FEATURE:
<223> OTHER INFORMATION: Synthetic sequence Meso530-11A WT-TCR alpha

<400> SEQUENCE: 19
atgaagacat tgctggatt ttcgttcctg tttttgtggc tgcagctgga ctgtatgagt        60
agaggagagg atgtggagca gagtctttc ctgagtgtcc gagagggaga cagctccgtt      120
ataaactgca cttacacaga cagctcctcc acctacttat actggtataa gcaagaacct      180
ggagcaggtc tccagttgct gacgtatatt ttttcaaata tggacatgaa acaagaccaa      240
agactcactt tctattgaa taaaaaggat aaacatctgt ctctgcgcat tgcagacacc       300
cagactgggg actcagctat ctacttctgt gcagagaccc cggggtatgg tggtgctaca      360
aacaagctca tctttggaac tggcactctg cttgctgtcc agccaaatat ccagaaccct      420
gaccctgccg tgtaccagct gagagactct aaatccagtg acaagtctgt ctgcctattc      480
accgattttg attctcaaac aaatgtgtca caaagtaagg attctgatgt gtatatcaca      540
gacaaaactg tgctagacat gaggtctatg gacttcaaga gcaacagtgc tgtggcctgg      600
agcaacaaat ctgactttgc atgtgcaaac gccttcaaca acagcattat tccagaagac      660
accttcttcc ccagcccaga aagttcctgt gatgtcaagc tggtcgagaa aagctttgaa      720
acagatacga acctaaactt tcaaaacctg tcagtgattg ggttccgaat cctcctcctg      780
aaagtggccg ggtttaatct gctcatgacg ctgcggctgt ggtccagctg a               831

<210> SEQ ID NO 20
<211> LENGTH: 831
<212> TYPE: DNA
<213> ORGANISM: Artificial Sequence
<220> FEATURE:
<223> OTHER INFORMATION: Synthetic sequence Meso530-11A CO-TCR alpha

<400> SEQUENCE: 20
atgaagacct tgccggctt cagcttcctg tttctgtggc tgcagctgga ttgtatgagc        60
agaggcgaag atgtggaaca gagcctgttc ctgagcgtta gagagggcga tagctctgtg      120
atcaattgca cctacaccga tagcagcagc acctacctgt actggtacaa gcaggagcct      180
ggagctggat tacagctgct gacatacatc ttcagcaaca tggacatgaa gcaggaccag      240
aggctgaccg tgctgctgaa caagaaggac aagcacctgt ctctgagaat tgccgataca      300
cagacaggcg atagcgccat ctacttctgt gccgagacac tggctatgg aggagctacc      360 aataagctga ttttcggcac aggcacactg ttagctgtgc agcccaacat ccagaatccc      420
gatcctgctg tgtaccagct gcgggacagc aagagcagcg acaagagcgt gtgcctgttc      480
accgacttcg acagccagac caacgtgtcc cagagcaagg acagcgacgt gtacatcacc      540
gataagtgcg tgctggacat gcggagcatg gacttcaaga gcaacagcgc cgtggcctgg      600
tccaacaaga gcgacttcgc ctgcgccaac gccttcaaca acagcattat ccccgaggac      660
acattcttcc caagccccga gagcagctgc gacgtgaagc tggtggaaaa gagcttcgag      720
acagacacca acctgaactt ccagaacctc agcgtgatcg gcttccggat cctgctgctg      780
```

-continued

```
aaggtggccg gcttcaacct gctgatgacc ctgcggctgt ggtccagctg a          831
```

<210> SEQ ID NO 21
<211> LENGTH: 1841
<212> TYPE: DNA
<213> ORGANISM: Artificial Sequence
<220> FEATURE:
<223> OTHER INFORMATION: Synthetic sequence Meso530-11A CO-TCR beta-P2A-
       TCR alpha

<400> SEQUENCE: 21

```
ggcgcgccac catgggctgt agactgctgt gttgtgctgt gctttgtctg cttggagctg          60
tgcctatcga tacagaggtg acccagacac ctaagcatct ggtgatgggc atgaccaaca          120
agaagagcct gaagtgtgaa cagcacatgg ccatagggc catgtactgg tacaagcaga          180
aggccaagaa acctcctgag ctgatgttcg tgtacagcta cgagaagctg agcatcaacg          240
agagcgtgcc cagcagattt tctcctgagt gccctaatag ctctctgctg aatctgcacc          300
tgcatgctct gcagcctgag gattctgctc tgtacctgtg tgcttcttct cacggatctc          360
tgaatacaga ggccttcttc ggccagggca agactgac agtggttgag atctgaaca          420 aggtgttccc cccagaggtg gccgtgttcg agccttctga ggccgagatc tcccacaccc          480
agaaagccac cctcgtgtgc ctggccaccg gcttttttccc cgaccacgtg gaactgtctt          540
ggtgggtcaa cggcaaagag gtgcactccg gcgtgtgcac cgatccccag cctctgaaag          600
aacagcccgc cctgaacgac agccggtact gcctgagcag cagactgaga gtgtccgcca          660
ccttctggca gaaccccgg aaccacttca gatgccaggt gcagttctac ggcctgagcg          720
agaacgacga gtggacccag gacagagcca agcccgtgac acagatcgtg tctgccgaag          780
cctggggcag agccgattgc ggctttacct ccgtgtccta tcagcagggc gtgctgagcg          840
ccacaatcct gtacgagatc ctgctgggca aggccaccct gtacgccgtg ctggtgtctg          900
ccctggtgct gatggccatg gtcaagcgga aggacttcgg ttccggagcc acgaacttct          960
ctctgttaaa gcaagcagga gacgtggaag aaaaccccgg tcccatgaag acctttgccg          1020
gcttcagctt cctgtttctg tggctgcagc tggattgtat gagcagaggc gaagatgtgg          1080
aacagagcct gttcctgagc gttagagagg gcgatagctc tgtgatcaat tgcacctaca          1140
ccgatagcag cagcacctac ctgtactggt acaagcagga gcctggagct ggattacagc          1200
tgctgacata catcttcagc aacatggaca tgaagcagga ccagaggctg accgtgctgc          1260
tgaacaagaa ggacaagcac ctgtctctga gaattgccga tacacagaca ggcgatagcg          1320
ccatctactt ctgtgccgag acacctggct atggaggagc taccaataag ctgattttcg          1380
gcacaggcac actgttagct gtgcagccca acatccagaa tcccgatcct gctgtgtacc          1440
agctgcggga cagcaagagc agcgacaaga gcgtgtgcct gttcaccgac ttcgacagcc          1500
agaccaacgt gtcccagagc aaggacagcg acgtgtacat caccgataag tgcgtgctgg          1560
acatgcggag catggacttc aagagcaaca gcgccgtggc ctggtccaac aagagcgact          1620
tcgcctgcgc caacgccttc aacaacagca ttatccccga ggacacattc ttcccaagcc          1680
ccgagagcag ctgcgacgtg aagctggtgg aaaagagctt cgagacagac accaacctga          1740
acttccagaa cctcagcgtg atcggcttcc ggatcctgct gctgaaggtg gccggcttca          1800
acctgctgat gaccctgcgg ctgtggtcca gctgagtcga c          1841
```

<210> SEQ ID NO 22
<211> LENGTH: 309
<212> TYPE: PRT

<213> ORGANISM: Artificial Sequence
<220> FEATURE:
<223> OTHER INFORMATION: Synthetic sequence Meso530-11A Protein CO-TCR
      beta - with signal peptide

<400> SEQUENCE: 22

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
                20                  25                  30

Gly Met Thr Asn Lys Lys Ser Leu Lys Cys Glu Gln His Met Gly His
            35                  40                  45

Arg Ala Met Tyr Trp Tyr Lys Gln Lys Ala Lys Lys Pro Pro Glu Leu
        50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser His Gly Ser Leu Asn Thr Glu Ala Phe Phe Gly Gln Gly Thr Arg
            115                 120                 125

Leu Thr Val Val Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 23
<211> LENGTH: 276
<212> TYPE: PRT
<213> ORGANISM: Artificial Sequence
<220> FEATURE:
<223> OTHER INFORMATION: Synthetic sequence Meso530-11A Protein CO-TCR
      alpha - with signal peptide

<400> SEQUENCE: 23

Met Lys Thr Phe Ala Gly Phe Ser Phe Leu Phe Leu Trp Leu Gln Leu

```
1              5               10              15

Asp Cys Met Ser Arg Gly Glu Asp Val Glu Gln Ser Leu Phe Leu Ser
            20              25              30

Val Arg Glu Gly Asp Ser Ser Val Ile Asn Cys Thr Tyr Thr Asp Ser
            35              40              45

Ser Ser Thr Tyr Leu Tyr Trp Tyr Lys Gln Glu Pro Gly Ala Gly Leu
    50              55              60

Gln Leu Leu Thr Tyr Ile Phe Ser Asn Met Asp Met Lys Gln Asp Gln
65              70              75              80

Arg Leu Thr Val Leu Leu Asn Lys Lys Asp Lys His Leu Ser Leu Arg
            85              90              95

Ile Ala Asp Thr Gln Thr Gly Asp Ser Ala Ile Tyr Phe Cys Ala Glu
            100             105             110

Thr Pro Gly Tyr Gly Gly Ala Thr Asn Lys Leu Ile Phe Gly Thr Gly
            115             120             125

Thr Leu Leu Ala Val Gln Pro Asn Ile Gln Asn Pro Asp Pro Ala Val
    130             135             140

Tyr Gln Leu Arg Asp Ser Lys Ser Ser Asp Lys Ser Val Cys Leu Phe
145             150             155             160

Thr Asp Phe Asp Ser Gln Thr Asn Val Ser Gln Ser Lys Asp Ser Asp
            165             170             175

Val Tyr Ile Thr Asp Lys Cys Val Leu Asp Met Arg Ser Met Asp Phe
            180             185             190

Lys Ser Asn Ser Ala Val Ala Trp Ser Asn Lys Ser Asp Phe Ala Cys
            195             200             205

Ala Asn Ala Phe Asn Asn Ser Ile Ile Pro Glu Asp Thr Phe Phe Pro
    210             215             220

Ser Pro Glu Ser Ser Cys Asp Val Lys Leu Val Glu Lys Ser Phe Glu
225             230             235             240

Thr Asp Thr Asn Leu Asn Phe Gln Asn Leu Ser Val Ile Gly Phe Arg
            245             250             255

Ile Leu Leu Leu Lys Val Ala Gly Phe Asn Leu Leu Met Thr Leu Arg
            260             265             270

Leu Trp Ser Ser
        275
```

```
<210> SEQ ID NO 24
<211> LENGTH: 607
<212> TYPE: PRT
<213> ORGANISM: Artificial Sequence
<220> FEATURE:
<223> OTHER INFORMATION: Synthetic sequence Meso530-11A Protein
      Vbeta-P2A-Valpha

<400> SEQUENCE: 24
```

```
Met Gly Cys Arg Leu Leu Cys Cys Ala Val Leu Cys Leu Leu Gly Ala
1              5               10              15

Val Pro Ile Asp Thr Glu Val Thr Gln Thr Pro Lys His Leu Val Met
            20              25              30

Gly Met Thr Asn Lys Lys Ser Leu Lys Cys Glu Gln His Met Gly His
            35              40              45

Arg Ala Met Tyr Trp Tyr Lys Gln Lys Ala Lys Lys Pro Pro Glu Leu
    50              55              60

Met Phe Val Tyr Ser Tyr Glu Lys Leu Ser Ile Asn Glu Ser Val Pro
65              70              75              80
```

-continued

```
Ser Arg Phe Ser Pro Glu Cys Pro Asn Ser Ser Leu Leu Asn Leu His
             85                  90                  95

Leu His Ala Leu Gln Pro Glu Asp Ser Ala Leu Tyr Leu Cys Ala Ser
            100                 105                 110

Ser His Gly Ser Leu Asn Thr Glu Ala Phe Phe Gly Gln Gly Thr Arg
            115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Lys Thr Phe Ala
                325                 330                 335

Gly Phe Ser Phe Leu Phe Leu Trp Leu Gln Leu Asp Cys Met Ser Arg
            340                 345                 350

Gly Glu Asp Val Glu Gln Ser Leu Phe Leu Ser Val Arg Glu Gly Asp
            355                 360                 365

Ser Ser Val Ile Asn Cys Thr Tyr Thr Asp Ser Ser Ser Thr Tyr Leu
    370                 375                 380

Tyr Trp Tyr Lys Gln Glu Pro Gly Ala Gly Leu Gln Leu Leu Thr Tyr
385                 390                 395                 400

Ile Phe Ser Asn Met Asp Met Lys Gln Asp Gln Arg Leu Thr Val Leu
                405                 410                 415

Leu Asn Lys Lys Asp Lys His Leu Ser Leu Arg Ile Ala Asp Thr Gln
            420                 425                 430

Thr Gly Asp Ser Ala Ile Tyr Phe Cys Ala Glu Thr Pro Gly Tyr Gly
            435                 440                 445

Gly Ala Thr Asn Lys Leu Ile Phe Gly Thr Gly Thr Leu Leu Ala Val
            450                 455                 460

Gln Pro Asn Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
                485                 490                 495

Gln Thr Asn Val Ser Gln Ser Lys Asp Ser Asp Val Tyr Ile Thr Asp
```

-continued

```
              500              505              510
Lys Cys Val Leu Asp Met Arg Ser Met Asp Phe Lys Ser Asn Ser Ala
         515              520              525

Val Ala Trp Ser Asn Lys Ser Asp Phe Ala Cys Ala Asn Ala Phe Asn
     530              535              540

Asn Ser Ile Ile Pro Glu Asp Thr Phe Phe Pro Ser Pro Glu Ser Ser
545              550              555              560

Cys Asp Val Lys Leu Val Glu Lys Ser Phe Glu Thr Asp Thr Asn Leu
             565              570              575

Asn Phe Gln Asn Leu Ser Val Ile Gly Phe Arg Ile Leu Leu Leu Lys
             580              585              590

Val Ala Gly Phe Asn Leu Leu Met Thr Leu Arg Leu Trp Ser Ser
             595              600              605
```

<210> SEQ ID NO 25
<211> LENGTH: 939
<212> TYPE: DNA
<213> ORGANISM: Artificial Sequence
<220> FEATURE:
<223> OTHER INFORMATION: Synthetic sequence Meso530-11B CO-TCR beta

<400> SEQUENCE: 25

```
atgggacctg gactgttatg ttgggttctg ctgtgtctgc ttggagctgg atctgtggaa      60
acaggcgtta cacagtcccc tacacacctg atcaagacaa gaggacagca ggtgaccctg     120
agatgttcta gccagtctgg ccacaataca gtgagctggt atcagcaggc tttaggacag     180 ggacccccagt tcatcttcca gtactaccgg gaggaagaga atggcagagg caattttcca     240
cccagattta gcggcctgca gttccccaat tacagcagcg agctgaacgt gaatgccctt     300
gaactggacg attctgctct gtacctgtgt gccagctctt ttgctggcgg aagaagcgat     360
acccagtatt ttggacctgg aaccagactg acagtgctgg aggacctgaa gaacgtgttc     420
cccccagagg tggccgtgtt cgagcctagc gaggccgaga tcagccacac ccagaaagcc     480
accctcgtgt gcctggccac cggctttttac cccgaccacg tggaactgtc ttggtgggtc     540
aacggcaaag aggtgcacag cggcgtctgc accgaccccc agcccctgaa agagcagccc     600
gccctgaacg acagccggta ctgtctgagc agcagactga gagtgtccgc caccttctgg     660 cagaacccccc ggaaccactt cagatgccag gtgcagttct acggcctgag cgagaacgac     720
gagtggaccc aggaccgggc caagcccgtg acccagatcg tgtctgctga ggcctggggc     780
agagccgatt gcggcttcac cagcgagagc taccagcagg gcgtgctgag cgccaccatc     840
ctgtacgaga tcctgctggg caaggccacc ctgtacgccg tgctggtgtc cgccctggtg     900
ctgatggcca tggtcaagcg gaaggacagc cggggctga                            939
```

<210> SEQ ID NO 26
<211> LENGTH: 831
<212> TYPE: DNA
<213> ORGANISM: Artificial Sequence
<220> FEATURE:
<223> OTHER INFORMATION: Synthetic sequence Meso530-11B CO-TCR alpha

<400> SEQUENCE: 26

```
atggagacac tgctgggact actgattctg tggctgcaac tgcaatgggt gagcagcaaa      60
caggaggtta cccagattcc tgctgctctg tctgttcctg aaggcgagaa tctggtgctg     120
aactgcagct tcacagatag cgccatctac aacctgcagt ggttcagaca ggatcctgga     180
aaaggcctga caagcctgct gctgattcag agctctcaga gagagcagac atctggaaga     240
```

-continued

```
ctgaatgcta gcctggacaa gtctagcggc agaagcaccc tgtatattgc cgcctctcaa      300
cctggagatt ctgccacata cctgtgtgct gttaggctgc tgtttgccca aggaggaagc      360
gagaaactgg tgtttggaaa gggcacaaag ctgaccgtga atccctacat ccagaaccct      420
gatcctgccg tgtaccagct gcgggacagc aagagcagcg acaagagcgt gtgcctgttc      480
accgacttcg acagccagac caacgtgtcc cagagcaagg acagcgacgt gtacatcacc      540
gataagtgcg tgctggacat gcggagcatg gacttcaaga gcaacagcgc cgtggcctgg      600
tccaacaaga gcgacttcgc ctgcgccaac gccttcaaca acagcattat ccccgaggac      660
acattcttcc caagccccga gagcagctgc gacgtgaagc tggtggaaaa gagcttcgag      720
acagacacca acctgaactt ccagaacctc agcgtgatcg gcttccggat cctgctgctg      780
aaggtggccg gcttcaacct gctgatgacc ctgcggctgt ggtccagctg a              831
```

<210> SEQ ID NO 27
<211> LENGTH: 1843
<212> TYPE: DNA
<213> ORGANISM: Artificial Sequence
<220> FEATURE:
<223> OTHER INFORMATION: Synthetic sequence Meso530-11B -TCR beta-P2A-
      TCR alpha

<400> SEQUENCE: 27

```
caccatggga cctggactgt tatgttgggt tctgctgtgt ctgcttggag ctggatctgt       60
ggaaacaggc gttacacagt cccctacaca cctgatcaag acaagaggac agcaggtgac      120
cctgagatgt tctagccagt ctggccacaa tacagtgagc tggtatcagc aggctttagg      180
acagggaccc cagttcatct tccagtacta ccgggaggaa gagaatggca gaggcaattt      240
tccacccaga tttagcggcc tgcagttccc caattacagc agcgagctga cgtgaatgc       300 ccttgaactg gacgattctg ctctgtacct gtgtgccagc tcttttgctg gcggaagaag      360
cgatacccag tattttggac ctggaaccag actgacagtg ctggaggacc tgaagaacgt      420
gttcccccca gaggtggccg tgttcgagcc tagcgaggcc gagatcagcc acacccagaa      480 agccacccctc gtgtgcctgg ccaccggctt ttaccccgac cacgtggaac tgtcttggtg      540
ggtcaacggc aaagaggtgc acagcggcgt ctgcaccgac ccccagcccc tgaaagagca      600
gcccgccctg aacgacagcc ggtactgtct gagcagcaga ctgagagtgt ccgccacctt      660
ctggcagaac ccccggaacc acttcagatg ccaggtgcag ttctacggcc tgagcgagaa      720
cgacgagtgg acccaggacc gggccaagcc cgtgacccag atcgtgtctg ctgaggcctg      780
gggcagagcc gattgcggct tcaccagcga gagctaccag cagggcgtgc tgagcgccac      840
catcctgtac gagatcctgc tgggcaaggc caccctgtac gccgtgctgg tgtccgccct      900
ggtgctgatg gccatggtca gcggaagga cagccggggc ggttccggag ccacgaactt      960
ctctctgtta aagcaagcag gagacgtgga agaaaccccc ggtcccatgg agacactgct     1020
gggactactg attctgtggc tgcaactgca atgggtgagc agcaaacagg aggttaccca     1080
gattcctgct gctctgtctg ttcctgaagg cgagaatctg gtgctgaact gcagcttcac     1140
agatagcgcc atctacaacc tgcagtggtt cagacaggat cctggaaaag cctgacaag      1200 cctgctgctg attcagagct ctcagagaga gcagacatct ggaagactga atgctagcct     1260
ggacaagtct agcggcagaa gcaccctgta tattgccgcc tctcaacctg agattctgc      1320 cacatacctg tgtgctgtta ggctgctgtt tgcccaagga ggaagcgaga aactggtgtt     1380
tggaaagggc acaaagctga ccgtgaatcc ctacatccag aaccctgatc ctgccgtgta     1440
```

-continued

```
ccagctgcgg gacagcaaga gcagcgacaa gagcgtgtgc ctgttcaccg acttcgacag    1500
ccagaccaac gtgtcccaga gcaaggacag cgacgtgtac atcaccgata agtgcgtgct    1560
ggacatgcgg agcatggact tcaagagcaa cagcgccgtg gcctggtcca acaagagcga    1620
cttcgcctgc gccaacgcct tcaacaacag cattatcccc gaggacacat tcttcccaag    1680
ccccgagagc agctgcgacg tgaagctggt ggaaaagagc ttcgagacag acaccaacct    1740
gaacttccag aacctcagcg tgatcggctt ccggatcctg ctgctgaagg tggccggctt    1800
caacctgctg atgaccctgc ggctgtggtc cagctgagtc gac    1843
```

<210> SEQ ID NO 28
<211> LENGTH: 312
<212> TYPE: PRT
<213> ORGANISM: Artificial Sequence
<220> FEATURE:
<223> OTHER INFORMATION: Synthetic sequence Meso530-11B Protein CO-TCR
      beta - with signal peptide

<400> SEQUENCE: 28

```
Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
                20                  25                  30

Thr Arg Gly Gln Gln Val Thr Leu Arg Cys Ser Ser Gln Ser Gly His
            35                  40                  45

Asn Thr Val Ser Trp Tyr Gln Gln Ala Leu Gly Gln Gly Pro Gln Phe
        50                  55                  60

Ile Phe Gln Tyr Tyr Arg Glu Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Phe Ala Gly Gly Arg Ser Asp Thr Gln Tyr Phe Gly Pro Gly Thr
        115                 120                 125

Arg Leu Thr Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285
```

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 29
<211> LENGTH: 276
<212> TYPE: PRT
<213> ORGANISM: Artificial Sequence
<220> FEATURE:
<223> OTHER INFORMATION: Synthetic sequence Meso530-11B Protein CO-TCR
      alpha - with signal peptide

<400> SEQUENCE: 29

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Leu Leu Phe Ala Gln Gly Gly Ser Glu Lys Leu Val Phe Gly Lys Gly
        115                 120                 125

Thr Lys Leu Thr Val Asn Pro Tyr Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Cys Val Leu Asp Met Arg Ser Met Asp Phe
                180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
        260                 265                 270

Leu Trp Ser Ser
        275

<210> SEQ ID NO 30
<211> LENGTH: 610
<212> TYPE: PRT
<213> ORGANISM: Artificial Sequence
<220> FEATURE:
<223> OTHER INFORMATION: Synthetic sequence Meso530-11B Protein CO-TCR -continued

```
    beta-P2A-TCR alpha

<400> SEQUENCE: 30

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
                20                  25                  30

Thr Arg Gly Gln Gln Val Thr Leu Arg Cys Ser Ser Gln Ser Gly His
            35                  40                  45

Asn Thr Val Ser Trp Tyr Gln Gln Ala Leu Gly Gln Gly Pro Gln Phe
        50                  55                  60

Ile Phe Gln Tyr Tyr Arg Glu Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
                100                 105                 110

Ser Phe Ala Gly Gly Arg Ser Asp Thr Gln Tyr Phe Gly Pro Gly Thr
            115                 120                 125

Arg Leu Thr Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
        290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Glu
            325                 330                 335

Thr Leu Leu Gly Leu Leu Ile Leu Trp Leu Gln Leu Gln Trp Val Ser
            340                 345                 350

Ser Lys Gln Glu Val Thr Gln Ile Pro Ala Ala Leu Ser Val Pro Glu
            355                 360                 365

Gly Glu Asn Leu Val Leu Asn Cys Ser Phe Thr Asp Ser Ala Ile Tyr
        370                 375                 380

Asn Leu Gln Trp Phe Arg Gln Asp Pro Gly Lys Gly Leu Thr Ser Leu
385                 390                 395                 400
```

```
Leu Leu Ile Gln Ser Ser Gln Arg Glu Gln Thr Ser Gly Arg Leu Asn
            405             410             415

Ala Ser Leu Asp Lys Ser Ser Gly Arg Ser Thr Leu Tyr Ile Ala Ala
            420             425             430

Ser Gln Pro Gly Asp Ser Ala Thr Tyr Leu Cys Ala Val Arg Leu Leu
            435             440             445

Phe Ala Gln Gly Gly Ser Glu Lys Leu Val Phe Gly Lys Gly Thr Lys
    450             455             460

Leu Thr Val Asn Pro Tyr Ile Gln Asn Pro Asp Pro Ala Val Tyr Gln
465             470             475             480

Leu Arg Asp Ser Lys Ser Ser Asp Lys Ser Val Cys Leu Phe Thr Asp
            485             490             495

Phe Asp Ser Gln Thr Asn Val Ser Gln Ser Lys Asp Ser Asp Val Tyr
            500             505             510

Ile Thr Asp Lys Cys Val Leu Asp Met Arg Ser Met Asp Phe Lys Ser
            515             520             525

Asn Ser Ala Val Ala Trp Ser Asn Lys Ser Asp Phe Ala Cys Ala Asn
    530             535             540

Ala Phe Asn Asn Ser Ile Ile Pro Glu Asp Thr Phe Phe Pro Ser Pro
545             550             555             560

Glu Ser Ser Cys Asp Val Lys Leu Val Glu Lys Ser Phe Glu Thr Asp
            565             570             575

Thr Asn Leu Asn Phe Gln Asn Leu Ser Val Ile Gly Phe Arg Ile Leu
            580             585             590

Leu Leu Lys Val Ala Gly Phe Asn Leu Leu Met Thr Leu Arg Leu Trp
            595             600             605

Ser Ser
    610
```

<210> SEQ ID NO 31
<211> LENGTH: 9
<212> TYPE: PRT
<213> ORGANISM: Artificial Sequence
<220> FEATURE:
<223> OTHER INFORMATION: Synthetic sequence Msln20-28

<400> SEQUENCE: 31

```
Ser Leu Leu Phe Leu Leu Phe Ser Leu
1               5
```

<210> SEQ ID NO 32
<211> LENGTH: 9
<212> TYPE: PRT
<213> ORGANISM: Artificial Sequence
<220> FEATURE:
<223> OTHER INFORMATION: Synthetic sequence Msln530-538

<400> SEQUENCE: 32

```
Val Leu Pro Leu Thr Val Ala Glu Val
1               5
```

<210> SEQ ID NO 33
<211> LENGTH: 11
<212> TYPE: PRT
<213> ORGANISM: Artificial Sequence
<220> FEATURE:
<223> OTHER INFORMATION: Synthetic sequence Meso20-3B CDR3 alpha

<400> SEQUENCE: 33

```
Cys Ala Val Asn Asp Ala Ser Lys Ile Ile Phe
```

-continued

```
1                5                10
```

```
<210> SEQ ID NO 34
<211> LENGTH: 14
<212> TYPE: PRT
<213> ORGANISM: Artificial Sequence
<220> FEATURE:
<223> OTHER INFORMATION: Synthetic sequence Meso20-3B CDR3 beta

<400> SEQUENCE: 34

Cys Ala Ser Ser Phe Thr Ser Gly Ser Tyr Glu Gln Tyr Phe
1                5                10

<210> SEQ ID NO 35
<211> LENGTH: 11
<212> TYPE: PRT
<213> ORGANISM: Artificial Sequence
<220> FEATURE:
<223> OTHER INFORMATION: Synthetic sequence Meso20-16B CDR3 alpha

<400> SEQUENCE: 35

Cys Ala Gly Gly Gly Asn Thr Pro Leu Val Phe
1                5                10

<210> SEQ ID NO 36
<211> LENGTH: 14
<212> TYPE: PRT
<213> ORGANISM: Artificial Sequence
<220> FEATURE:
<223> OTHER INFORMATION: Synthetic sequence Meso20-16B CDR3 beta

<400> SEQUENCE: 36

Cys Ala Ser Ser Ser Pro Asp Arg Leu Gly Glu Gln Tyr Phe
1                5                10

<210> SEQ ID NO 37
<211> LENGTH: 16
<212> TYPE: PRT
<213> ORGANISM: Artificial Sequence
<220> FEATURE:
<223> OTHER INFORMATION: Synthetic sequence Meso530-11A CDR3 alpha

<400> SEQUENCE: 37

Cys Ala Glu Thr Pro Gly Tyr Gly Gly Ala Thr Asn Lys Leu Ile Phe
1                5                10                15

<210> SEQ ID NO 38
<211> LENGTH: 14
<212> TYPE: PRT
<213> ORGANISM: Artificial Sequence
<220> FEATURE:
<223> OTHER INFORMATION: Synthetic sequence Meso530-11A CDR3 beta

<400> SEQUENCE: 38

Cys Ala Ser Ser His Gly Ser Leu Asn Thr Glu Ala Phe Phe
1                5                10

<210> SEQ ID NO 39
<211> LENGTH: 17
<212> TYPE: PRT
<213> ORGANISM: Artificial Sequence
<220> FEATURE:
<223> OTHER INFORMATION: Synthetic sequence Meso530-11B CDR3 alpha

<400> SEQUENCE: 39

Cys Ala Val Arg Leu Leu Phe Ala Gln Gly Gly Ser Glu Lys Leu Val
1                5                10                15
```

-continued

Phe

<210> SEQ ID NO 40
<211> LENGTH: 15
<212> TYPE: PRT
<213> ORGANISM: Artificial Sequence
<220> FEATURE:
<223> OTHER INFORMATION: Synthetic sequence Meso530-11B CDR3 beta

<400> SEQUENCE: 40

Cys Ala Ser Ser Phe Ala Gly Gly Arg Ser Asp Thr Gln Tyr Phe
1               5                   10                  15

<210> SEQ ID NO 41
<211> LENGTH: 66
<212> TYPE: DNA
<213> ORGANISM: Artificial Sequence
<220> FEATURE:
<223> OTHER INFORMATION: Synthetic sequence Porcine teschovirus
      self-cleaving peptide P2A-1

<400> SEQUENCE: 41
ggaagtggag ctacgaattt ttctttatta aaacaagcag gagatgttga ggagaatccc     60
ggtcca                                                                66

<210> SEQ ID NO 42
<211> LENGTH: 63
<212> TYPE: DNA
<213> ORGANISM: Artificial Sequence
<220> FEATURE:
<223> OTHER INFORMATION: Synthetic sequence Porcine teschovirus
      self-cleaving peptide P2A-2

<400> SEQUENCE: 42
agcggcgcca ccaacttcag cctgctgaaa caggccggcg acgtggaaga gaaccctggc     60
cct                                                                   63

<210> SEQ ID NO 43
<211> LENGTH: 65
<212> TYPE: DNA
<213> ORGANISM: Artificial Sequence
<220> FEATURE:
<223> OTHER INFORMATION: Synthetic sequence Porcine teschovirus
      self-cleaving peptide P2A-3

<400> SEQUENCE: 43
gaagcggcgc cacaaatttc agcctgctga agcaggccgg cgacgtggaa gagaaccctg     60
gccct                                                                 65

<210> SEQ ID NO 44
<211> LENGTH: 66
<212> TYPE: DNA
<213> ORGANISM: Artificial Sequence
<220> FEATURE:
<223> OTHER INFORMATION: Synthetic sequence Porcine teschovirus
      self-cleaving peptide P2A-4

<400> SEQUENCE: 44
ggctccggcg ccaccaactt ttcactgctg aaacaggctg gggatgtgga agaaaatccc     60
ggccca                                                                66

<210> SEQ ID NO 45
<211> LENGTH: 66

<212> TYPE: DNA
<213> ORGANISM: Artificial Sequence
<220> FEATURE:
<223> OTHER INFORMATION: Synthetic sequence Porcine teschovirus
      self-cleaving peptide P2A-5

<400> SEQUENCE: 45
ggcagcggcg ccaccaactt tagcctgctg aaacaggctg gcgacgtgga agagaacccc      60
ggacct                                                                66

<210> SEQ ID NO 46
<211> LENGTH: 66
<212> TYPE: DNA
<213> ORGANISM: Artificial Sequence
<220> FEATURE:
<223> OTHER INFORMATION: Synthetic sequence Porcine teschovirus
      self-cleaving peptide P2A-6

<400> SEQUENCE: 46
ggctctggcg ccaccaactt tagcctgctg aaacaggctg gcgacgtgga agagaacccc      60
ggacct                                                                66

<210> SEQ ID NO 47
<211> LENGTH: 63
<212> TYPE: DNA
<213> ORGANISM: Artificial Sequence
<220> FEATURE:
<223> OTHER INFORMATION: Synthetic sequence Thoseaasigna virus 2A T2A

<400> SEQUENCE: 47
ggaagcggag agggcagagg aagtctgcta acatgcggtg acgtcgagga gaatcctgga      60
cct                                                                   63

<210> SEQ ID NO 48
<211> LENGTH: 69
<212> TYPE: DNA
<213> ORGANISM: Artificial Sequence
<220> FEATURE:
<223> OTHER INFORMATION: Synthetic sequence Equine rhinitis A virus E2A

<400> SEQUENCE: 48
ggaagcggac agtgtactaa ttatgctctc ttgaaattgg ctggagatgt tgagagcaac      60
cctggacct                                                             69

<210> SEQ ID NO 49
<211> LENGTH: 75
<212> TYPE: DNA
<213> ORGANISM: Artificial Sequence
<220> FEATURE:
<223> OTHER INFORMATION: Synthetic sequence Foot-and-Mouth disease virus
      2 F2A

<400> SEQUENCE: 49
ggaagcggag tgaaacagac tttgaatttt gaccttctca agttggcggg agacgtggag      60
tccaaccctg gacct                                                      75

<210> SEQ ID NO 50
<211> LENGTH: 630
<212> TYPE: PRT
<213> ORGANISM: Artificial Sequence
<220> FEATURE:
<223> OTHER INFORMATION: Synthetic sequence human MSLN, isoform 1

<400> SEQUENCE: 50

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20              25                  30

Pro Ser Arg Thr Leu Ala Gly Glu Thr Gly Gln Glu Ala Ala Pro Leu
        35              40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415
```

```
Pro Gln Val Ala Thr Leu Ile Asp Arg Phe Val Lys Gly Arg Gly Gln
        420             425             430

Leu Asp Lys Asp Thr Leu Asp Thr Leu Thr Ala Phe Tyr Pro Gly Tyr
        435             440             445

Leu Cys Ser Leu Ser Pro Glu Glu Leu Ser Ser Val Pro Pro Ser Ser
    450             455             460

Ile Trp Ala Val Arg Pro Gln Asp Leu Asp Thr Cys Asp Pro Arg Gln
465             470             475             480

Leu Asp Val Leu Tyr Pro Lys Ala Arg Leu Ala Phe Gln Asn Met Asn
                485             490             495

Gly Ser Glu Tyr Phe Val Lys Ile Gln Ser Phe Leu Gly Gly Ala Pro
        500             505             510

Thr Glu Asp Leu Lys Ala Leu Ser Gln Gln Asn Val Ser Met Asp Leu
        515             520             525

Ala Thr Phe Met Lys Leu Arg Thr Asp Ala Val Leu Pro Leu Thr Val
    530             535             540

Ala Glu Val Gln Lys Leu Leu Gly Pro His Val Glu Gly Leu Lys Ala
545             550             555             560

Glu Glu Arg His Arg Pro Val Arg Asp Trp Ile Leu Arg Gln Arg Gln
        565             570             575

Asp Asp Leu Asp Thr Leu Gly Leu Gly Leu Gln Gly Gly Ile Pro Asn
        580             585             590

Gly Tyr Leu Val Leu Asp Leu Ser Met Gln Glu Ala Leu Ser Gly Thr
        595             600             605

Pro Cys Leu Leu Gly Pro Gly Pro Val Leu Thr Val Leu Ala Leu Leu
    610             615             620

Leu Ala Ser Thr Leu Ala
625             630
```

```
<210> SEQ ID NO 51
<211> LENGTH: 9
<212> TYPE: PRT
<213> ORGANISM: Artificial Sequence
<220> FEATURE:
<223> OTHER INFORMATION: Synthetic sequence Msln20-28 Ala variant 1

<400> SEQUENCE: 51

Ala Leu Leu Phe Leu Leu Phe Ser Leu
1               5
```

```
<210> SEQ ID NO 52
<211> LENGTH: 9
<212> TYPE: PRT
<213> ORGANISM: Artificial Sequence
<220> FEATURE:
<223> OTHER INFORMATION: Synthetic sequence Msln20-28 Ala variant 2

<400> SEQUENCE: 52

Ser Ala Leu Phe Leu Leu Phe Ser Leu
1               5
```

```
<210> SEQ ID NO 53
<211> LENGTH: 9
<212> TYPE: PRT
<213> ORGANISM: Artificial Sequence
<220> FEATURE:
<223> OTHER INFORMATION: Synthetic sequence Msln20-28 Ala variant 3

<400> SEQUENCE: 53

Ser Leu Ala Phe Leu Leu Phe Ser Leu
```

-continued

```
1               5
```

<210> SEQ ID NO 54
<211> LENGTH: 9
<212> TYPE: PRT
<213> ORGANISM: Artificial Sequence
<220> FEATURE:
<223> OTHER INFORMATION: Synthetic sequence Msln20-28 Ala variant 4

<400> SEQUENCE: 54

```
Ser Leu Leu Ala Leu Leu Phe Ser Leu
1               5
```

<210> SEQ ID NO 55
<211> LENGTH: 9
<212> TYPE: PRT
<213> ORGANISM: Artificial Sequence
<220> FEATURE:
<223> OTHER INFORMATION: Synthetic sequence Msln20-28 Ala variant 5

<400> SEQUENCE: 55

```
Ser Leu Leu Phe Ala Leu Phe Ser Leu
1               5
```

<210> SEQ ID NO 56
<211> LENGTH: 9
<212> TYPE: PRT
<213> ORGANISM: Artificial Sequence
<220> FEATURE:
<223> OTHER INFORMATION: Synthetic sequence Msln20-28 Ala variant 6

<400> SEQUENCE: 56

```
Ser Leu Leu Phe Leu Ala Phe Ser Leu
1               5
```

<210> SEQ ID NO 57
<211> LENGTH: 9
<212> TYPE: PRT
<213> ORGANISM: Artificial Sequence
<220> FEATURE:
<223> OTHER INFORMATION: Synthetic sequence Msln20-28 Ala variant 7

<400> SEQUENCE: 57

```
Ser Leu Leu Phe Leu Leu Ala Ser Leu
1               5
```

<210> SEQ ID NO 58
<211> LENGTH: 9
<212> TYPE: PRT
<213> ORGANISM: Artificial Sequence
<220> FEATURE:
<223> OTHER INFORMATION: Synthetic sequence Msln20-28 Ala variant 8

<400> SEQUENCE: 58

```
Ser Leu Leu Phe Leu Leu Phe Ala Leu
1               5
```

<210> SEQ ID NO 59
<211> LENGTH: 9
<212> TYPE: PRT
<213> ORGANISM: Artificial Sequence
<220> FEATURE:
<223> OTHER INFORMATION: Synthetic sequence Msln20-28 Ala variant 9

<400> SEQUENCE: 59

```
Ser Leu Leu Phe Leu Leu Phe Ser Ala
1               5
```

-continued

```
<210> SEQ ID NO 60
<211> LENGTH: 9
<212> TYPE: PRT
<213> ORGANISM: Artificial Sequence
<220> FEATURE:
<223> OTHER INFORMATION: Synthetic sequence Msln20-28 TCR epitope
      consensus sequence
<220> FEATURE:
<221> NAME/KEY: VARIANT
<222> LOCATION: 1,2,7,8,9
<223> OTHER INFORMATION: Xaa = any amino acid, optionally alanine

<400> SEQUENCE: 60

Xaa Xaa Leu Phe Leu Leu Xaa Xaa Xaa
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic sequence Msln530-538 TCR epitope
      consensus sequence 1
<220> FEATURE:
<221> NAME/KEY: VARIANT
<222> LOCATION: 3,5,6,9
<223> OTHER INFORMATION: Xaa = any amino acid, optionally alanine

<400> SEQUENCE: 61

Val Leu Xaa Leu Xaa Xaa Ala Glu Xaa
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic sequence Msln530-538 TCR epitope
      consensus sequence 2
<220> FEATURE:
<221> NAME/KEY: VARIANT
<222> LOCATION: 1,5,9
<223> OTHER INFORMATION: Xaa = any amino acid, optionally alanine

<400> SEQUENCE: 62

Xaa Leu Pro Leu Xaa Val Ala Glu Xaa
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic sequence EHF peptide

<400> SEQUENCE: 63

Val Leu Leu Leu Ser Leu Ala Glu Ile
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic sequence YN010 peptide

<400> SEQUENCE: 64

Val Leu Ala Leu Trp Glu Ala Glu Val
```

-continued

```
1              5
```

<210> SEQ ID NO 65
<211> LENGTH: 9
<212> TYPE: PRT
<213> ORGANISM: Artificial Sequence
<220> FEATURE:
<223> OTHER INFORMATION: Synthetic sequence MLEC peptide

<400> SEQUENCE: 65

Val Leu Val Leu Lys Phe Ala Glu Val
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic sequence CHPF2 peptide

<400> SEQUENCE: 66

Val Leu Pro Leu Leu Val Ala Glu Ala
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic sequence ULK1 peptide

<400> SEQUENCE: 67

Val Leu Tyr Leu Lys Val Ala Glu Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic sequenceOR2J2 peptide

<400> SEQUENCE: 68

Val Leu Ala Leu Gly Ile Ala Glu Cys
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic sequence  DNHD1 peptide

<400> SEQUENCE: 69

Val Leu Glu Leu Leu Leu Ala Glu Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic sequence AL1L1 peptide

<400> SEQUENCE: 70

Val Leu Glu Leu Thr Glu Ala Glu Leu
1               5

-continued

```
<210> SEQ ID NO 71
<211> LENGTH: 9
<212> TYPE: PRT
<213> ORGANISM: Artificial Sequence
<220> FEATURE:
<223> OTHER INFORMATION: Synthetic sequence GALP peptide

<400> SEQUENCE: 71

Val Leu Leu Leu Ser Leu Ala Glu Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic sequence OR2J1 peptide

<400> SEQUENCE: 72

Val Leu Ala Leu Gly Thr Ala Glu Cys
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic sequence ADPRH peptide

<400> SEQUENCE: 73

Val Met His Leu Ala Thr Ala Glu Ala
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic sequence CHPF2 peptide

<400> SEQUENCE: 74

Val Leu Pro Leu Ile Val Ala Glu Ala
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic sequence LRCH3 peptide

<400> SEQUENCE: 75

Asp Leu Pro Leu Arg Val Ala Glu Ile
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic sequence IN80B peptide

<400> SEQUENCE: 76

Met Leu Pro Leu Pro Val Ala Glu Gly
1               5
```

-continued

```
<210> SEQ ID NO 77
<211> LENGTH: 9
<212> TYPE: PRT
<213> ORGANISM: Artificial Sequence
<220> FEATURE:
<223> OTHER INFORMATION: Synthetic sequence CEAM3 peptide

<400> SEQUENCE: 77

Ser Met Pro Leu Ser Val Ala Glu Gly
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic sequence Meso20-3B CDR1 beta

<400> SEQUENCE: 78

Ser Gly His Asp Tyr
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic sequence Meso20-3B, Meso20-16B CDR2
      beta

<400> SEQUENCE: 79

Phe Asn Asn Asn Val Pro
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic sequence Meso20-3B CDR1 alpha

<400> SEQUENCE: 80

Thr Ser Gly Phe Tyr Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic sequence Meso20-3B CDR2 alpha v1

<400> SEQUENCE: 81

Asn Ala Leu Asp Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic sequenceMeso20-16B CDR1 beta

<400> SEQUENCE: 82

Ser Gly His Asn Ser
1               5
```

-continued

```
<210> SEQ ID NO 83
<211> LENGTH: 5
<212> TYPE: PRT
<213> ORGANISM: Artificial Sequence
<220> FEATURE:
<223> OTHER INFORMATION: Synthetic sequence Meso20-16B / Meso20-3B /
      Meso530 -11A / Meso530 -11B CDR1 beta consensus
<220> FEATURE:
<221> NAME/KEY: VARIANT
<222> LOCATION: 1
<223> OTHER INFORMATION: Xaa = M, S, or T
<220> FEATURE:
<221> NAME/KEY: VARIANT
<222> LOCATION: 4
<223> OTHER INFORMATION: Xaa = D, E, N, Q, R or K
<220> FEATURE:
<221> NAME/KEY: VARIANT
<222> LOCATION: 5
<223> OTHER INFORMATION: Xaa = Y, S, A, V, I, L, or T

<400> SEQUENCE: 83

Xaa Gly His Xaa Xaa
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic sequence Meso20-16B / Meso20-3B /
      Meso530 CDR2 beta consensus
<220> FEATURE:
<221> NAME/KEY: VARIANT
<222> LOCATION: 4
<223> OTHER INFORMATION: Xaa = D or N
<220> FEATURE:
<221> NAME/KEY: VARIANT
<222> LOCATION: 5
<223> OTHER INFORMATION: Xaa = Y, S, or T

<400> SEQUENCE: 84

Ser Gly His Xaa Xaa
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic sequence Meso20-16B CDR1 alpha

<400> SEQUENCE: 85

Asn Ser Ala Phe Gln Tyr
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic sequence Meso20-16B CDR2 alpha v1

<400> SEQUENCE: 86

Thr Tyr Ser Ser Gly
1               5

<210> SEQ ID NO 87
<211> LENGTH: 5
<212> TYPE: PRT
<213> ORGANISM: Artificial Sequence
```

<220> FEATURE:
<223> OTHER INFORMATION: Synthetic sequence Meso530-11A CDR1 beta

<400> SEQUENCE: 87

Met Gly His Arg Ala
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic sequence Meso530-11A CDR2 beta

<400> SEQUENCE: 88

Tyr Ser Tyr Glu Lys Leu
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic sequence Meso530-11A CDR1 alpha

<400> SEQUENCE: 89

Ser Ser Ser Thr Tyr Leu
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic sequence Meso530-11A CDR2 alpha

<400> SEQUENCE: 90

Ile Phe Ser Asn Met Asp Met
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic sequence Meso530-11B CDR1 beta

<400> SEQUENCE: 91

Ser Gly His Asn Thr
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic sequence Meso530-11B CDR2 beta

<400> SEQUENCE: 92

Tyr Tyr Arg Glu Glu Glu
1               5

<210> SEQ ID NO 93
<211> LENGTH: 6
<212> TYPE: PRT
<213> ORGANISM: Artificial Sequence
<220> FEATURE:

-continued

<223> OTHER INFORMATION: Synthetic sequence Meso530-11B CDR1 alpha

<400> SEQUENCE: 93

Asp Ser Ala Ile Tyr Asn
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic sequence Meso530-11B CDR2 alpha

<400> SEQUENCE: 94

Ile Gln Ser Ser Gln Arg Glu
1               5

<210> SEQ ID NO 95
<211> LENGTH: 114
<212> TYPE: PRT
<213> ORGANISM: Artificial Sequence
<220> FEATURE:
<223> OTHER INFORMATION: Synthetic sequence Meso20-3B V beta (mature)

<400> SEQUENCE: 95

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
                20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Phe
                85                  90                  95

Thr Ser Gly Ser Tyr Glu Gln Tyr Phe Gly Pro Gly Thr Arg Leu Thr
            100                 105                 110

Val Thr

<210> SEQ ID NO 96
<211> LENGTH: 108
<212> TYPE: PRT
<213> ORGANISM: Artificial Sequence
<220> FEATURE:
<223> OTHER INFORMATION: Synthetic sequence Meso20-3B V alpha (mature)

<400> SEQUENCE: 96

Gly Gln Ser Leu Glu Gln Pro Ser Glu Val Thr Ala Val Glu Gly Ala
1               5                   10                  15

Ile Val Gln Ile Asn Cys Thr Tyr Gln Thr Ser Gly Phe Tyr Gly Leu
                20                  25                  30

Ser Trp Tyr Gln Gln His Asp Gly Gly Ala Pro Thr Phe Leu Ser Tyr
        35                  40                  45

Asn Ala Leu Asp Gly Leu Glu Glu Thr Gly Arg Phe Ser Ser Phe Leu
    50                  55                  60

Ser Arg Ser Asp Ser Tyr Gly Tyr Leu Leu Leu Gln Glu Leu Gln Met
65                  70                  75                  80

Lys Asp Ser Ala Ser Tyr Phe Cys Ala Val Asn Asp Ala Ser Lys Ile

```
                    85              90              95

Ile Phe Gly Ser Gly Thr Arg Leu Ser Ile Arg Pro
                100             105
```

<210> SEQ ID NO 97
<211> LENGTH: 114
<212> TYPE: PRT
<213> ORGANISM: Artificial Sequence
<220> FEATURE:
<223> OTHER INFORMATION: Synthetic sequence Meso20-16B V beta (mature)

<400> SEQUENCE: 97

```
Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asn Ser Leu
                20                  25                  30

Phe Trp Tyr Arg Gln Thr Met Met Arg Gly Leu Glu Leu Leu Ile Tyr
            35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Ser
                85                  90                  95

Pro Asp Arg Leu Gly Glu Gln Tyr Phe Gly Pro Gly Thr Arg Leu Thr
            100                 105                 110

Val Thr
```

<210> SEQ ID NO 98
<211> LENGTH: 109
<212> TYPE: PRT
<213> ORGANISM: Artificial Sequence
<220> FEATURE:
<223> OTHER INFORMATION: Synthetic sequence Meso20-16B V alpha (mature)

<400> SEQUENCE: 98

```
Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
        50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Gly Gly Gly Asn Thr Pro
                85                  90                  95

Leu Val Phe Gly Lys Gly Thr Arg Leu Ser Val Ile Ala
            100                 105
```

<210> SEQ ID NO 99
<211> LENGTH: 113
<212> TYPE: PRT
<213> ORGANISM: Artificial Sequence
<220> FEATURE:
<223> OTHER INFORMATION: Synthetic sequence Meso530-11A V beta (mature)

<400> SEQUENCE: 99

```
Asp Thr Glu Val Thr Gln Thr Pro Lys His Leu Val Met Gly Met Thr
1               5                   10                  15

Asn Lys Lys Ser Leu Lys Cys Glu Gln His Met Gly His Arg Ala Met
                20                  25                  30

Tyr Trp Tyr Lys Gln Lys Ala Lys Lys Pro Pro Glu Leu Met Phe Val
            35                  40                  45

Tyr Ser Tyr Glu Lys Leu Ser Ile Asn Glu Ser Val Pro Ser Arg Phe
        50                  55                  60

Ser Pro Glu Cys Pro Asn Ser Ser Leu Leu Asn Leu His Leu His Ala
65                  70                  75                  80

Leu Gln Pro Glu Asp Ser Ala Leu Tyr Leu Cys Ala Ser Ser His Gly
                85                  90                  95

Ser Leu Asn Thr Glu Ala Phe Phe Gly Gln Gly Thr Arg Leu Thr Val
            100                 105                 110

Val
```

<210> SEQ ID NO 100
<211> LENGTH: 114
<212> TYPE: PRT
<213> ORGANISM: Artificial Sequence
<220> FEATURE:
<223> OTHER INFORMATION: Synthetic sequence Meso530-11A V alpha (mature)

<400> SEQUENCE: 100

```
Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
                20                  25                  30

Tyr Trp Tyr Lys Gln Glu Pro Gly Ala Gly Leu Gln Leu Leu Thr Tyr
            35                  40                  45

Ile Phe Ser Asn Met Asp Met Lys Gln Asp Gln Arg Leu Thr Val Leu
        50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Glu Thr Pro Gly Tyr Gly
                85                  90                  95

Gly Ala Thr Asn Lys Leu Ile Phe Gly Thr Gly Thr Leu Leu Ala Val
            100                 105                 110

Gln Pro
```

<210> SEQ ID NO 101
<211> LENGTH: 114
<212> TYPE: PRT
<213> ORGANISM: Artificial Sequence
<220> FEATURE:
<223> OTHER INFORMATION: Synthetic sequence Meso530-11B V beta (mature)

<400> SEQUENCE: 101

```
Glu Thr Gly Val Thr Gln Ser Pro Thr His Leu Ile Lys Thr Arg Gly
1               5                   10                  15

Gln Gln Val Thr Leu Arg Cys Ser Ser Gln Ser Gly His Asn Thr Val
                20                  25                  30

Ser Trp Tyr Gln Gln Ala Leu Gly Gln Gly Pro Gln Phe Ile Phe Gln
            35                  40                  45

Tyr Tyr Arg Glu Glu Glu Asn Gly Arg Gly Asn Phe Pro Pro Arg Phe
        50                  55                  60

Ser Gly Leu Gln Phe Pro Asn Tyr Ser Ser Glu Leu Asn Val Asn Ala
```

```
65                    70                    75                    80

Leu Glu Leu Asp Asp Ser Ala Leu Tyr Leu Cys Ala Ser Ser Phe Ala
                    85                    90                    95

Gly Gly Arg Ser Asp Thr Gln Tyr Phe Gly Pro Gly Thr Arg Leu Thr
                    100                   105                   110

Val Leu

<210> SEQ ID NO 102
<211> LENGTH: 116
<212> TYPE: PRT
<213> ORGANISM: Artificial Sequence
<220> FEATURE:
<223> OTHER INFORMATION: Synthetic sequence Meso530-11B V alpha (mature)

<400> SEQUENCE: 102

Lys Gln Glu Val Thr Gln Ile Pro Ala Ala Leu Ser Val Pro Glu Gly
1                   5                     10                    15

Glu Asn Leu Val Leu Asn Cys Ser Phe Thr Asp Ser Ala Ile Tyr Asn
                    20                    25                    30

Leu Gln Trp Phe Arg Gln Asp Pro Gly Lys Gly Leu Thr Ser Leu Leu
            35                    40                    45

Leu Ile Gln Ser Ser Gln Arg Glu Gln Thr Ser Gly Arg Leu Asn Ala
        50                    55                    60

Ser Leu Asp Lys Ser Ser Gly Arg Ser Thr Leu Tyr Ile Ala Ala Ser
65                    70                    75                    80

Gln Pro Gly Asp Ser Ala Thr Tyr Leu Cys Ala Val Arg Leu Leu Phe
                    85                    90                    95

Ala Gln Gly Gly Ser Glu Lys Leu Val Phe Gly Lys Gly Thr Lys Leu
                    100                   105                   110

Thr Val Asn Pro
        115

<210> SEQ ID NO 103
<211> LENGTH: 293
<212> TYPE: PRT
<213> ORGANISM: Artificial Sequence
<220> FEATURE:
<223> OTHER INFORMATION: Synthetic sequence Meso20-3B TCR beta (mature)

<400> SEQUENCE: 103

Asp Ala Gly Val Ile Gln Ser Pro Arg His Glu Val Thr Glu Met Gly
1                   5                     10                    15

Gln Glu Val Thr Leu Arg Cys Lys Pro Ile Ser Gly His Asp Tyr Leu
                    20                    25                    30

Phe Trp Tyr Arg Gln Thr Met Met Arg Gly Leu Glu Leu Leu Ile Tyr
            35                    40                    45

Phe Asn Asn Asn Val Pro Ile Asp Asp Ser Gly Met Pro Glu Asp Arg
        50                    55                    60

Phe Ser Ala Lys Met Pro Asn Ala Ser Phe Ser Thr Leu Lys Ile Gln
65                    70                    75                    80

Pro Ser Glu Pro Arg Asp Ser Ala Val Tyr Phe Cys Ala Ser Ser Phe
                    85                    90                    95

Thr Ser Gly Ser Tyr Glu Gln Tyr Phe Gly Pro Gly Thr Arg Leu Thr
                    100                   105                   110

Val Thr Glu Asp Leu Lys Asn Val Phe Pro Pro Glu Val Ala Val Phe
            115                   120                   125

Glu Pro Ser Glu Ala Glu Ile Ser His Thr Gln Lys Ala Thr Leu Val
```

-continued

```
        130             135              140

Cys Leu Ala Thr Gly Phe Tyr Pro Asp His Val Glu Leu Ser Trp Trp
145                 150              155                 160

Val Asn Gly Lys Glu Val His Ser Gly Val Cys Thr Asp Pro Gln Pro
                165             170              175

Leu Lys Glu Gln Pro Ala Leu Asn Asp Ser Arg Tyr Cys Leu Ser Ser
                180             185              190

Arg Leu Arg Val Ser Ala Thr Phe Trp Gln Asn Pro Arg Asn His Phe
            195             200              205

Arg Cys Gln Val Gln Phe Tyr Gly Leu Ser Glu Asn Asp Glu Trp Thr
    210             215              220

Gln Asp Arg Ala Lys Pro Val Thr Gln Ile Val Ser Ala Glu Ala Trp
225                 230              235                 240

Gly Arg Ala Asp Cys Gly Phe Thr Ser Glu Ser Tyr Gln Gln Gly Val
                245             250              255

Leu Ser Ala Thr Ile Leu Tyr Glu Ile Leu Leu Gly Lys Ala Thr Leu
                260             265              270

Tyr Ala Val Leu Val Ser Ala Leu Val Leu Met Ala Met Val Lys Arg
            275             280              285

Lys Asp Ser Arg Gly
    290
```

<210> SEQ ID NO 104
<211> LENGTH: 249
<212> TYPE: PRT
<213> ORGANISM: Artificial Sequence
<220> FEATURE:
<223> OTHER INFORMATION: Synthetic sequence Meso20-3B TCR alpha
      (mature) - Cys mod

<400> SEQUENCE: 104

```
Gly Gln Ser Leu Glu Gln Pro Ser Glu Val Thr Ala Val Glu Gly Ala
1               5               10              15

Ile Val Gln Ile Asn Cys Thr Tyr Gln Thr Ser Gly Phe Tyr Gly Leu
                20              25              30

Ser Trp Tyr Gln Gln His Asp Gly Gly Ala Pro Thr Phe Leu Ser Tyr
            35              40              45

Asn Ala Leu Asp Gly Leu Glu Glu Thr Gly Arg Phe Ser Ser Phe Leu
    50              55              60

Ser Arg Ser Asp Ser Tyr Gly Tyr Leu Leu Leu Gln Glu Leu Gln Met
65              70              75              80

Lys Asp Ser Ala Ser Tyr Phe Cys Ala Val Asn Asp Ala Ser Lys Ile
                85              90              95

Ile Phe Gly Ser Gly Thr Arg Leu Ser Ile Arg Pro Asn Ile Gln Asn
            100             105             110

Pro Asp Pro Ala Val Tyr Gln Leu Arg Asp Ser Lys Ser Ser Asp Lys
        115             120             125

Ser Val Cys Leu Phe Thr Asp Phe Asp Ser Gln Thr Asn Val Ser Gln
    130             135             140

Ser Lys Asp Ser Asp Val Tyr Ile Thr Asp Lys Cys Val Leu Asp Met
145             150             155             160

Arg Ser Met Asp Phe Lys Ser Asn Ser Ala Val Ala Trp Ser Asn Lys
                165             170             175

Ser Asp Phe Ala Cys Ala Asn Ala Phe Asn Asn Ser Ile Ile Pro Glu
                180             185             190
```

```
Asp Thr Phe Phe Pro Ser Pro Glu Ser Ser Cys Asp Val Lys Leu Val
        195                 200                 205

Glu Lys Ser Phe Glu Thr Asp Thr Asn Leu Asn Phe Gln Asn Leu Ser
        210                 215                 220

Val Ile Gly Phe Arg Ile Leu Leu Leu Lys Val Ala Gly Phe Asn Leu
225                 230                 235                 240

Leu Met Thr Leu Arg Leu Trp Ser Ser
                245

<210> SEQ ID NO 105
<211> LENGTH: 293
<212> TYPE: PRT
<213> ORGANISM: Artificial Sequence
<220> FEATURE:
<223> OTHER INFORMATION: Synthetic sequence Meso20-16B TCR beta
      (mature) - Cys mod

<400> SEQUENCE: 105

Asp Ala Gly Val Ile Gln Ser Pro Arg His Glu Val Thr Glu Met Gly
1                   5                   10                  15

Gln Glu Val Thr Leu Arg Cys Lys Pro Ile Ser Gly His Asn Ser Leu
                20                  25                  30

Phe Trp Tyr Arg Gln Thr Met Met Arg Gly Leu Glu Leu Leu Ile Tyr
                35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Ser
                85                  90                  95

Pro Asp Arg Leu Gly Glu Gln Tyr Phe Gly Pro Gly Thr Arg Leu Thr
                100                 105                 110

Val Thr Glu Asp Leu Lys Asn Val Phe Pro Pro Glu Val Ala Val Phe
                115                 120                 125

Glu Pro Ser Glu Ala Glu Ile Ser His Thr Gln Lys Ala Thr Leu Val
        130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Cys Leu Ser Ser
                180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
        210                 215                 220

Gln Asp Arg Ala Lys Pro Val Thr Gln Ile Val Ser Ala Glu Ala Trp
225                 230                 235                 240

Gly Arg Ala Asp Cys Gly Phe Thr Ser Glu Ser Tyr Gln Gln Gly Val
                245                 250                 255

Leu Ser Ala Thr Ile Leu Tyr Glu Ile Leu Leu Gly Lys Ala Thr Leu
                260                 265                 270

Tyr Ala Val Leu Val Ser Ala Leu Val Leu Met Ala Met Val Lys Arg
                275                 280                 285

Lys Asp Ser Arg Gly
        290
```

```
<210> SEQ ID NO 106
<211> LENGTH: 250
<212> TYPE: PRT
<213> ORGANISM: Artificial Sequence
<220> FEATURE:
<223> OTHER INFORMATION: Synthetic sequence Meso20-16B TCR alpha
      (mature) - Cys mod

<400> SEQUENCE: 106

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Gly Gly Gly Asn Thr Pro
                85                  90                  95

Leu Val Phe Gly Lys Gly Thr Arg Leu Ser Val Ile Ala Asn Ile Gln
            100                 105                 110

Asn Pro Asp Pro Ala Val Tyr Gln Leu Arg Asp Ser Lys Ser Ser Asp
            115                 120                 125

Lys Ser Val Cys Leu Phe Thr Asp Phe Asp Ser Gln Thr Asn Val Ser
    130                 135                 140

Gln Ser Lys Asp Ser Asp Val Tyr Ile Thr Asp Lys Cys Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser Cys Asp Val Lys Leu
            195                 200                 205

Val Glu Lys Ser Phe Glu Thr Asp Thr Asn Leu Asn Phe Gln Asn Leu
    210                 215                 220

Ser Val Ile Gly Phe Arg Ile Leu Leu Leu Lys Val Ala Gly Phe Asn
225                 230                 235                 240

Leu Leu Met Thr Leu Arg Leu Trp Ser Ser
                245                 250

<210> SEQ ID NO 107
<211> LENGTH: 290
<212> TYPE: PRT
<213> ORGANISM: Artificial Sequence
<220> FEATURE:
<223> OTHER INFORMATION: Synthetic sequence Meso530-11A TCR beta
      (mature) - Cys mod

<400> SEQUENCE: 107

Asp Thr Glu Val Thr Gln Thr Pro Lys His Leu Val Met Gly Met Thr
1               5                   10                  15

Asn Lys Lys Ser Leu Lys Cys Glu Gln His Met Gly His Arg Ala Met
            20                  25                  30

Tyr Trp Tyr Lys Gln Lys Ala Lys Lys Pro Pro Glu Leu Met Phe Val
        35                  40                  45
```

```
Tyr Ser Tyr Glu Lys Leu Ser Ile Asn Glu Ser Val Pro Ser Arg Phe
    50              55              60

Ser Pro Glu Cys Pro Asn Ser Ser Leu Leu Asn Leu His Leu His Ala
65              70              75              80

Leu Gln Pro Glu Asp Ser Ala Leu Tyr Leu Cys Ala Ser Ser His Gly
                85              90              95

Ser Leu Asn Thr Glu Ala Phe Phe Gly Gln Gly Thr Arg Leu Thr Val
            100             105             110

Val Glu Asp Leu Asn Lys Val Phe Pro Pro Glu Val Ala Val Phe Glu
        115             120             125

Pro Ser Glu Ala Glu Ile Ser His Thr Gln Lys Ala Thr Leu Val Cys
    130             135             140

Leu Ala Thr Gly Phe Phe Pro Asp His Val Glu Leu Ser Trp Trp Val
145             150             155             160

Asn Gly Lys Glu Val His Ser Gly Val Cys Thr Asp Pro Gln Pro Leu
            165             170             175

Lys Glu Gln Pro Ala Leu Asn Asp Ser Arg Tyr Cys Leu Ser Ser Arg
            180             185             190

Leu Arg Val Ser Ala Thr Phe Trp Gln Asn Pro Arg Asn His Phe Arg
        195             200             205

Cys Gln Val Gln Phe Tyr Gly Leu Ser Glu Asn Asp Glu Trp Thr Gln
    210             215             220

Asp Arg Ala Lys Pro Val Thr Gln Ile Val Ser Ala Glu Ala Trp Gly
225             230             235             240

Arg Ala Asp Cys Gly Phe Thr Ser Val Ser Tyr Gln Gln Gly Val Leu
            245             250             255

Ser Ala Thr Ile Leu Tyr Glu Ile Leu Leu Gly Lys Ala Thr Leu Tyr
            260             265             270

Ala Val Leu Val Ser Ala Leu Val Leu Met Ala Met Val Lys Arg Lys
        275             280             285

Asp Phe
    290
```

```
<210> SEQ ID NO 108
<211> LENGTH: 255
<212> TYPE: PRT
<213> ORGANISM: Artificial Sequence
<220> FEATURE:
<223> OTHER INFORMATION: Synthetic sequence Meso530-11A TCR alpha
      (mature) - Cys mod

<400> SEQUENCE: 108
```

```
Gly Glu Asp Val Glu Gln Ser Leu Phe Leu Ser Val Arg Glu Gly Asp
1               5               10              15

Ser Ser Val Ile Asn Cys Thr Tyr Thr Asp Ser Ser Ser Thr Tyr Leu
            20              25              30

Tyr Trp Tyr Lys Gln Glu Pro Gly Ala Gly Leu Gln Leu Leu Thr Tyr
        35              40              45

Ile Phe Ser Asn Met Asp Met Lys Gln Asp Gln Arg Leu Thr Val Leu
    50              55              60

Leu Asn Lys Lys Asp Lys His Leu Ser Leu Arg Ile Ala Asp Thr Gln
65              70              75              80

Thr Gly Asp Ser Ala Ile Tyr Phe Cys Ala Glu Thr Pro Gly Tyr Gly
                85              90              95

Gly Ala Thr Asn Lys Leu Ile Phe Gly Thr Gly Thr Leu Leu Ala Val
```

-continued

```
                100                 105                 110

Gln Pro Asn Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
                180                 185                 190

Asn Ser Ile Ile Pro Glu Asp Thr Phe Phe Pro Ser Pro Glu Ser Ser
            195                 200                 205

Cys Asp Val Lys Leu Val Glu Lys Ser Phe Glu Thr Asp Thr Asn Leu
        210                 215                 220

Asn Phe Gln Asn Leu Ser Val Ile Gly Phe Arg Ile Leu Leu Leu Lys
225                 230                 235                 240

Val Ala Gly Phe Asn Leu Leu Met Thr Leu Arg Leu Trp Ser Ser
                245                 250                 255

<210> SEQ ID NO 109
<211> LENGTH: 293
<212> TYPE: PRT
<213> ORGANISM: Artificial Sequence
<220> FEATURE:
<223> OTHER INFORMATION: Synthetic sequence Meso530-11B TCR beta
      (mature) - Cys mod

<400> SEQUENCE: 109

Glu Thr Gly Val Thr Gln Ser Pro Thr His Leu Ile Lys Thr Arg Gly
1               5                   10                  15

Gln Gln Val Thr Leu Arg Cys Ser Ser Gln Ser Gly His Asn Thr Val
                20                  25                  30

Ser Trp Tyr Gln Gln Ala Leu Gly Gln Gly Pro Gln Phe Ile Phe Gln
            35                  40                  45

Tyr Tyr Arg Glu Glu Glu Asn Gly Arg Gly Asn Phe Pro Pro Arg Phe
    50                  55                  60

Ser Gly Leu Gln Phe Pro Asn Tyr Ser Ser Glu Leu Asn Val Asn Ala
65                  70                  75                  80

Leu Glu Leu Asp Asp Ser Ala Leu Tyr Leu Cys Ala Ser Ser Phe Ala
                85                  90                  95

Gly Gly Arg Ser Asp Thr Gln Tyr Phe Gly Pro Gly Thr Arg Leu Thr
                100                 105                 110

Val Leu Glu Asp Leu Lys Asn Val Phe Pro Pro Glu Val Ala Val Phe
            115                 120                 125

Glu Pro Ser Glu Ala Glu Ile Ser His Thr Gln Lys Ala Thr Leu Val
        130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Cys Leu Ser Ser
                180                 185                 190

Arg Leu Arg Val Ser Ala Thr Phe Trp Gln Asn Pro Arg Asn His Phe
                195                 200                 205
```

-continued

```
Arg Cys Gln Val Gln Phe Tyr Gly Leu Ser Glu Asn Asp Glu Trp Thr
    210             215             220

Gln Asp Arg Ala Lys Pro Val Thr Gln Ile Val Ser Ala Glu Ala Trp
225             230             235             240

Gly Arg Ala Asp Cys Gly Phe Thr Ser Glu Ser Tyr Gln Gln Gly Val
                245             250             255

Leu Ser Ala Thr Ile Leu Tyr Glu Ile Leu Leu Gly Lys Ala Thr Leu
                260             265             270

Tyr Ala Val Leu Val Ser Ala Leu Val Leu Met Ala Met Val Lys Arg
                275             280             285

Lys Asp Ser Arg Gly
    290
```

```
<210> SEQ ID NO 110
<211> LENGTH: 257
<212> TYPE: PRT
<213> ORGANISM: Artificial Sequence
<220> FEATURE:
<223> OTHER INFORMATION: Synthetic sequence Meso530-11B TCR alpha
      (mature) - Cys mod

<400> SEQUENCE: 110
```

```
Lys Gln Glu Val Thr Gln Ile Pro Ala Ala Leu Ser Val Pro Glu Gly
1               5               10              15

Glu Asn Leu Val Leu Asn Cys Ser Phe Thr Asp Ser Ala Ile Tyr Asn
                20              25              30

Leu Gln Trp Phe Arg Gln Asp Pro Gly Lys Gly Leu Thr Ser Leu Leu
                35              40              45

Leu Ile Gln Ser Ser Gln Arg Glu Gln Thr Ser Gly Arg Leu Asn Ala
    50              55              60

Ser Leu Asp Lys Ser Ser Gly Arg Ser Thr Leu Tyr Ile Ala Ala Ser
65              70              75              80

Gln Pro Gly Asp Ser Ala Thr Tyr Leu Cys Ala Val Arg Leu Leu Phe
                85              90              95

Ala Gln Gly Gly Ser Glu Lys Leu Val Phe Gly Lys Gly Thr Lys Leu
                100             105             110

Thr Val Asn Pro Tyr Ile Gln Asn Pro Asp Pro Ala Val Tyr Gln Leu
                115             120             125

Arg Asp Ser Lys Ser Ser Asp Lys Ser Val Cys Leu Phe Thr Asp Phe
    130             135             140

Asp Ser Gln Thr Asn Val Ser Gln Ser Lys Asp Ser Asp Val Tyr Ile
145             150             155             160

Thr Asp Lys Cys Val Leu Asp Met Arg Ser Met Asp Phe Lys Ser Asn
                165             170             175

Ser Ala Val Ala Trp Ser Asn Lys Ser Asp Phe Ala Cys Ala Asn Ala
                180             185             190

Phe Asn Asn Ser Ile Ile Pro Glu Asp Thr Phe Phe Pro Ser Pro Glu
                195             200             205

Ser Ser Cys Asp Val Lys Leu Val Glu Lys Ser Phe Glu Thr Asp Thr
    210             215             220

Asn Leu Asn Phe Gln Asn Leu Ser Val Ile Gly Phe Arg Ile Leu Leu
225             230             235             240

Leu Lys Val Ala Gly Phe Asn Leu Leu Met Thr Leu Arg Leu Trp Ser
                245             250             255

Ser
```

-continued

<210> SEQ ID NO 111
<211> LENGTH: 831
<212> TYPE: DNA
<213> ORGANISM: Artificial Sequence
<220> FEATURE:
<223> OTHER INFORMATION: Synthetic sequence Meso530-11B WT TCR alpha

<400> SEQUENCE: 111
atggagaccc tcttgggcct gcttatcctt tggctgcagc tgcaatgggt gagcagcaaa      60
caggaggtga cgcagattcc tgcagctctg agtgtcccag aaggagaaaa cttggttctc     120
aactgcagtt tcactgatag cgctatttac aacctccagt ggtttaggca ggaccctggg     180
aaaggtctca catctctgtt gcttattcag tcaagtcaga gagagcaaac aagtggaaga     240
cttaatgcct cgctggataa atcatcagga cgtagtactt tatacattgc agcttctcag     300
cctggtgact cagccaccta cctctgtgct gtgaggctat tattcgctca gggcggatct     360
gaaaagctgg tctttggaaa gggaacgaaa ctgacagtaa acccatatat ccagaaccct     420
gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca acagcattat tccagaagac     660
accttcttcc ccagcccaga aagttcctgt gatgtcaagc tggtcgagaa aagctttgaa     720
acagatacga acctaaactt tcaaaacctg tcagtgattg ggttccgaat cctcctcctg     780
aaagtggccg ggtttaatct gctcatgacg ctgcggctgt ggtccagctg a               831

<210> SEQ ID NO 112
<211> LENGTH: 939
<212> TYPE: DNA
<213> ORGANISM: Artificial Sequence
<220> FEATURE:
<223> OTHER INFORMATION: Synthetic sequence Meso530-11B WT TCR beta

<400> SEQUENCE: 112
atgggccctg ggctcctctg ctgggtgctg ctttgtctcc tgggagcagg ctcagtggag      60
actggagtca cccaaagtcc cacacacctg atcaaaacga gaggacagca agtgactctg     120
agatgctctt ctcagtctgg gcacaacact gtgtcctggt accaacaggc cctgggtcag     180 gggcccagt ttatctttca gtattatagg gaggaagaga tggcagagg aaacttccct     240 cctagattct caggtctcca gttccctaat tatagctctg agctgaatgt gaacgccttg     300
gagctggacg actcggccct gtatctctgt gccagcagct cgcgggggg gcgatcagat     360 acgcagtatt ttggcccagg cacccggctg acagtgctcg aggacctgaa aaacgtgttc     420
ccacccgagg tcgctgtgtt tgagccatca gaagcagaga tctcccacac ccaaaaggcc     480
acactggtgt gcctggccac aggcttctac cccgaccacg tggagctgag ctggtgggtg     540
aatgggaagg aggtgcacag tggggtcagc acagacccgc agcccctcaa ggagcagccc     600
gccctcaatg actccagata ctgcctgagc agccgcctga gggtctcggc caccttctgg     660 cagaacccc gcaaccactt ccgctgtcaa gtccagttct acgggctctc ggagaatgac     720
gagtggaccc aggatagggc caaacctgtc acccagatcg tcagcgccga ggcctggggt     780
agagcagact gtggcttcac ctccgagtct taccagcaag gggtcctgtc tgccaccatc     840
ctctatgaga tcttgctagg gaaggccacc ttgtatgccg tgctggtcag tgccctcgtg     900
ctgatggcca tggtcaagag aaaggattcc agaggctag                             939

```
<210> SEQ ID NO 113
<211> LENGTH: 22
<212> TYPE: PRT
<213> ORGANISM: Artificial Sequence
<220> FEATURE:
<223> OTHER INFORMATION: Synthetic sequence Porcine teschovirus
      self-cleaving peptide P2A-1

<400> SEQUENCE: 113

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 114
<211> LENGTH: 21
<212> TYPE: PRT
<213> ORGANISM: Artificial Sequence
<220> FEATURE:
<223> OTHER INFORMATION: Synthetic sequence Porcine teschovirus
      self-cleaving peptide P2A-2

<400> SEQUENCE: 114

Ser Gly Ala Thr Asn Phe Ser Leu Leu Lys Gln Ala Gly Asp Val Glu
1               5                   10                  15

Glu Asn Pro Gly Pro
            20

<210> SEQ ID NO 115
<211> LENGTH: 21
<212> TYPE: PRT
<213> ORGANISM: Artificial Sequence
<220> FEATURE:
<223> OTHER INFORMATION: Synthetic sequence Thoseaasigna virus 2A T2A

<400> SEQUENCE: 115

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 116
<211> LENGTH: 23
<212> TYPE: PRT
<213> ORGANISM: Artificial Sequence
<220> FEATURE:
<223> OTHER INFORMATION: Synthetic sequence Equine rhinitis A virus E2A

<400> SEQUENCE: 116

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 117
<211> LENGTH: 25
<212> TYPE: PRT
<213> ORGANISM: Artificial Sequence
<220> FEATURE:
<223> OTHER INFORMATION: Synthetic sequence Foot-and-Mouth disease virus
      2 F2A

<400> SEQUENCE: 117

Gly Ser Gly Val Lys Gln Thr Leu Asn Phe Asp Leu Leu Lys Leu Ala
```

```
1               5               10              15

Gly Asp Val Glu Ser Asn Pro Gly Pro
            20              25
```

```
<210> SEQ ID NO 118
<211> LENGTH: 6
<212> TYPE: PRT
<213> ORGANISM: Artificial Sequence
<220> FEATURE:
<223> OTHER INFORMATION: Synthetic sequence - Meso20-3B CDR2 alpha v2

<400> SEQUENCE: 118

Asn Ala Leu Asp Gly Leu
1               5
```

```
<210> SEQ ID NO 119
<211> LENGTH: 6
<212> TYPE: PRT
<213> ORGANISM: Artificial Sequence
<220> FEATURE:
<223> OTHER INFORMATION: Synthetic sequence - Meso20-16B CDR2 alpha v2

<400> SEQUENCE: 119

Thr Tyr Ser Ser Gly Asn
1               5
```

```
<210> SEQ ID NO 120
<211> LENGTH: 1833
<212> TYPE: DNA
<213> ORGANISM: Artificial Sequence
<220> FEATURE:
<223> OTHER INFORMATION: Synthetic sequence - Meso530-11B
      CO-Beta-P2A-Alpha: (alternate optimization)

<400> SEQUENCE: 120
atgggacctg gattgctttg ttgggtgctg ctgtgtctgc tcggagccgg atctgtggaa       60
acaggcgtga cacagagccc cacacacctg atcaagacca gaggccagca agtgaccctg      120
agatgcagct ctcagagcgg ccacaatacc gtgtcctggt atcagcaggc cctcggacag      180
ggccctcagt tcatcttcca gtactacaga gaggaagaga acggcagagg caacttccca      240
cctagattca gcggcctgca gttccccaac tacagcagcg agctgaacgt gaacgccctg      300
gaactggatg acagcgccct gtacctgtgc gccagttctt ttgccggcgg aagaagcgac      360
acccagtact ttggacctgg caccagactg accgtgctgg aagatctgaa gaacgtgttc      420
ccacctgagg tggccgtgtt cgagccttct gaggccgaga tcagccacac acagaaagcc      480
acactcgtgt gtctggccac cggcttctat cccgatcacg tggaactgtc ttggtgggtc      540
aacggcaaag aggtgcacag cggcgtctgt accgatcctc agcctctgaa agagcagccc      600
gctctgaacg acagcagata ctgcctgagc agcagactga gagtgtccgc caccttctgg      660
cagaacccca gaaaccactt cagatgccag gtgcagttct acggcctgag cgagaacgat      720
gagtggaccc aggatagagc caagcctgtg actcagatcg tgtctgccga gcctgggggc      780
agagccgatt gtggctttac cagcgagtct taccagcagg gcgtgctgtc tgccaccatc      840
ctgtatgaga tcctgctggg caaagccact ctgtacgccg tgctggtttc tgccctggtg      900
ctgatggcca tggtcaagcg gaaggatagc agaggcggaa gcggcgccac aaacttctca      960
ctgctgaaac aggccggcga cgtggaagag aatcccggac ctatggaaac actgctggga     1020
ctgctgatcc tgtggctgca gcttcagtgg gtgtccagca gcaagaagt gacccagatt     1080 cctgccgcac tgtctgtgcc tgagggcgag aatctggtcc tgaactgctc cttcaccgac     1140
```

-continued

```
agcgccatct acaacctgca gtggttcaga caggaccccg gcaagggact gacaagcctg    1200
ctgctgattc agagcagcca gagagagcag accagcggca gactgaatgc cagcctggat    1260
aagtcctccg gcagaagcac cctgtatatc gccgcttctc agcctggcga tagcgccaca    1320
tatctgtgtg ccgtgcggct gctgtttgcc caaggcggat ctgagaagct ggtgttcggc    1380
aagggcacca agctgacagt gaacccctac attcagaacc ccgatcctgc cgtgtaccag    1440
ctgagagaca gcaagagcag cgacaagagc gtgtgcctgt tcaccgactt cgacagccag    1500
accaacgtgt cccagagcaa ggacagcgac gtgtacatca ccgataagtg cgtgctggac    1560
atgcggagca tggacttcaa gagcaacagc gccgtggcct ggtccaacaa gagcgatttc    1620
gcctgcgcca acgccttcaa caacagcatt atccccgagg acacattctt cccaagtcct    1680
gagtccagct gcgacgtgaa actggtggaa aagagcttcg agacagacac caacctgaac    1740
ttccagaacc tgagcgtgat cggcttccgg atcctgctcc tgaaagtggc cggcttcaac    1800
ctgctgatga ccctgcgact gtggtccagc taa                                 1833
```

```
<210> SEQ ID NO 121
<211> LENGTH: 9
<212> TYPE: PRT
<213> ORGANISM: Artificial Sequence
<220> FEATURE:
<223> OTHER INFORMATION: Synthetic sequence - Meganuclease sequence

<400> SEQUENCE: 121

Leu Ala Gly Leu Ile Asp Ala Asp Gly
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic sequence - Meganuclease sequence

<400> SEQUENCE: 122

Gly Ile Tyr Tyr Ile Gly
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic sequence - Meganuclease sequence
<220> FEATURE:
<221> NAME/KEY: VARIANT
<222> LOCATION: 3
<223> OTHER INFORMATION: Xaa = D or E
<220> FEATURE:
<221> NAME/KEY: VARIANT
<222> LOCATION: 4
<223> OTHER INFORMATION: Xaa = any amino acid

<400> SEQUENCE: 123

Pro Asp Xaa Xaa Lys
1               5
```

T CELL RECEPTORS SPECIFIC FOR MESOTHELIN AND THEIR USE IN IMMUNOTHERAPY

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_475USPC_SEQUENCE_LISTING.txt. The text file is 115 KB, was created on May 6, 2021, and is being submitted electronically via EFS-Web.

TECHNICAL FIELD

The present disclosure relates to the field of biomedicine and, specifically, to methods and compositions useful for use in treating diseases or disorders in which cells express mesothelin, such as in cancer therapy. In particular, embodiments of the present disclosure relate to methods and compositions of TCRs with high affinity against tumor-associated antigen mesothelin, T cells expressing such high affinity antigen specific TCRs, nucleic acids encoding the same, and methods of use for carrying out cellular immunotherapy including engineered T cells.

BACKGROUND

Adoptive transfer of tumor-specific T-cells is an appealing strategy to eliminate existing tumors and requires the establishment of a robust population of antigen-specific T cells in vivo to eliminate existing tumor and prevent recurrences (see Stromnes, et al., Immunol. Rev. 257: 145, 2014). Although transfer of tumor-specific $CD8^+$ cytotoxic T lymphocytes (CTLs) is safe and can mediate direct anti-tumor activity in select patients (see Chapuis et al., Cancer Res. 72:LB-136, 2012; Chapuis et al., Sci. Transl. Med. 5: 174ra127, 2013; and Chapuis et al., Proc. Natl. Acad. Sci. U.S.A. 09:4592, 2012), the variability in the avidity of the CTLs isolated from each patient or donor limits the anti-tumor efficacy in clinical trials (see Chapuis et al., 2013). Since TCR affinity is an important determinant of CTL avidity (see Zoete et al., Frontiers Immunol. 4:26%, 2013), strategies have been developed to redirect the antigen specificity of donor or patient T cells using high affinity $TCR\alpha/\beta$ genes isolated from a well-characterized T cell clone specific for a tumor-specific antigen (see Stromnes et al., Immunol. Rev. 257: 145, 2014 and Robbins et al., J. Clin. Oncol. 29:917, 2011).

Such high affinity self/tumor-reactive T cells are rare, since T cells that express self/tumor-reactive TCRs are subject to central and peripheral tolerance (see Stone and Kranz, Frontiers Immunol. 4:244, 2013), with relative TCR affinities varying widely between donors. Therefore, many matched donors must be screened to identify a sufficiently high-affinity tumor-specific T cell clone from which a $TCR\alpha/\beta$ gene therapy construct can be generated. For example, isolation of a naturally elicited Wilms' Tumor antigen 1 (WT1)-specific TCR with high functional avidity for a single HLA-allele required screening of hundreds of WT-specific T cell lines representing thousands of individual T cell clones from the peripheral repertoires of greater than 75 normal donors, a very time and labor intensive process (see Chapuis et al., 2013; Schmitt et al., Hum. Gene Ther. 20:1240, 2009; and Ho et al., J. Immunol. Methods 310:40, 2006).

There is a need for alternative antigen-specific immunotherapies directed against various cancers, such as solid tumors. Presently disclosed embodiments address these needs and provide other related advantages.

BRIEF DESCRIPTION OF THE DRAWINGS

The embodiments disclosed herein will become more fully apparent from the following description and appended claims, taken in conjunction with the accompanying drawings.

FIGS. 5A-5C show functional evaluation of TCRs heterologously expressed in primary $CD8^+$ T cells. CD8+ T cells were purified from donor PBMCs and lentivirally transduced with each TCR. After 8 days, cells that sorted high for tetramer-positive were further sorted and further expanded for 8-10 days.

FIGS. 7A-7D show specific lysis of two representative Msln-positive tumor cell lines ((A, B) MDA-MB-468 and (C, D) MDA-MB-231) by CD8+ T cells transduced with the indicated $Msln_{530}$-specific TCR or with a $Msln_{20}$-specific TCR and in the presence or absence of exogenous IFN-$\gamma$.

FIGS. 9A-9D show results from alanine mutagenesis scanning experiments using TCRs specific for $Msln_{20}$ (SEQ ID NO:31) or $Msln_{530}$ (SEQ ID NO:32). The x-axis shows the percent of IFN-γ+ T cells in response to each alanine-substituted peptide. The y-axis shows the sequence of the tested peptide, wherein an X indicates that this residue is not required for TCR specificity, as indicated by near normal functional activity as compared to the wild-type peptide.

FIG. 10 shows human peptides (SEQ ID NOs: 63-77) that were investigated for potential cross-reactivity with the target $Msln_{530}$ peptide (SEQ ID NO:32), based on the specificity of the TCR as determined by alanine scanning experiments. The genes encoding the indicated peptides are shown at the left of the table. Consensus sequences containing the essential residues identified by alanine scanning were input into prediction algorithms, as described in Example 8.

FIGS. 12A-12I depict experiments investigating the potential for alloreactivity of T cells expressing an exemplary Msln-specific TCR of the present disclosure (Meso20-3B, Meso530-11A, or Meso530-11B) by targeting diverse donor-derived lymphoblastoid cell lines (LCLs) in the presence of absence of wild-type peptide.

FIGS. 13A-13H depict additional analysis of alloreactivity by targeting diverse donor-derived LCLs to assess no cross-reactivity to other HLA subtypes, as described in Example 10. As indicated for cell lines FAH and GIM, Meso530-11B indicates potential reactivity in the presence of peptide (as highlighted in the table) for non HLA-A2 alleles.

DETAILED DESCRIPTION

Figure 1A:
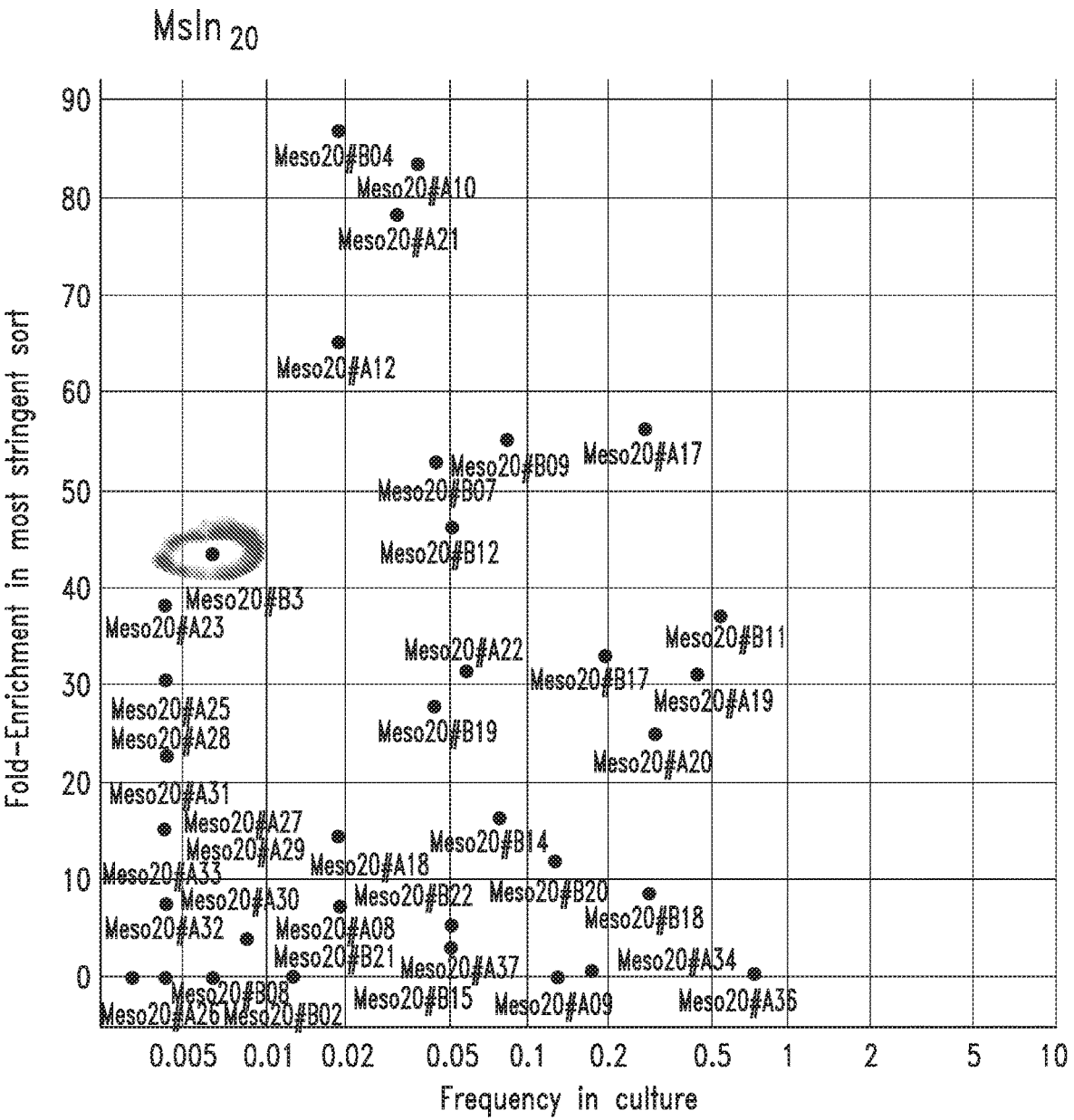
FIG. 1A depicts identification and selection of TCRs specific for $Msln_{20}$ (SEQ ID NO:31) based on the fold-enrichment of TCRs to peptide:HLA tetramer binding. A TCR selected for further studies is circled.

In some aspects, the present disclosure provides binding proteins that comprise a TCR alpha chain variable domain (Vα) and a TCR beta chain variable domain (Vβ) and are capable of specifically binding to a $Msln_{20-28}$ or $Msln_{530-538}$ epitope and/or peptide ($Msln_{20-28}$ (SLLFLLFSL; SEQ ID NO: 31)) and $Msln_{530-538}$ (SEQ ID NO:32 (VLPLTVAEV)) are also referred to herein as $Msln_{20}$ and $M_{530}$, respectively); e.g., in a peptide:HLA complex. In any of the presently disclosed embodiments, a Msln-specific binding protein is capable of binding to a Msln peptide:HLA complex, wherein the Msln peptide comprises the amino acid sequence set forth in SEQ ID NO:31 or 32 and wherein the HLA is or comprises HLA-A2, such as HLA-A*02:01.

In certain embodiments, a Msln-specific $_{20-28}$-specific binding protein comprises: (a) a TCR Vα comprising a CDR3 amino acid sequence as set forth in SEQ ID NO:33 or 35, and a TCR Vβ, wherein optionally the TCR Vβ has at least about 85% (i.e., at least about 85%, 86%, 87%, 89% 90%, 91%, 92%, 93%, 94%, 95%, 96%, 97%, 98%, 99%, or more) identity to the amino acid sequence set forth in SEQ ID NO:95 or 97; (b) a TCR Vβ comprising a CDR3 amino acid sequence as set forth in SEQ ID NO:34 or 36, and (b) a TCR Vα, wherein optionally the TCR Vα has at least about 85% (i.e., at least about 85%, 86%, 87%, 88%, 89%, 90%, 91%, 92%, 93%, 94%, 95%, 96%, 97%, 98%, 99%, or more) identity to the amino acid sequence set forth in SEQ ID NO:96 or 98; or (c) a TCR Vα comprising a CDR3 amino acid sequence as set forth in SEQ ID NO:33 or 35, wherein optionally the TCR Vα has at least about 85% identity to the amino acid sequence set forth in SEQ ID NO:96 or 98 and a TCR Vβ comprising a CDR3 amino acid sequence as set forth in SEQ ID NO:34 or 36, wherein optionally the TCR Vβ has at least about 85% identity to the amino acid sequence set forth in SEQ ID NO:95 or 97.

Unless specifically indicated otherwise, as used herein, a sequence identity of "at least about" an indicated percentage includes the indicated percentage ±20% thereof, and every integer and non-integer percentage above the specific percentage. Accordingly, "at least about 85%" identity to the referenced sequence (e.g., any one of SEQ ID NOs:1-123) includes about 85%, 86%, 87%, 89%, 90%, 91%, 92%, 93%, 94%, 95%, 96%, 97%, 98%, 99%, or 100% identity to the referenced sequence, and also includes all non-integer percentages in between two integer percentages (e.g., 92.5%, 99.1%, etc.).

In certain embodiments, a $Msln_{20-28}$-specific binding protein comprises a CDR3α amino acid sequence as set forth in SEQ ID NO:33 and a CDR3β amino acid sequence as set forth in SEQ ID NO:34. In further embodiments, the binding protein comprises a CDR1α amino acid sequence as set forth SEQ ID NO:80, a CDR2α amino acid sequence as set forth in SEQ ID NO:81 or 118, a CDR1β amino acid sequence as set forth in any one of SEQ ID NOs:78, 82, 83, or 84, and a CDR2β amino acid sequence as set forth in SEQ ID NO:79. In certain embodiments, the Vα comprises an amino acid sequence having at least about 85% identity to the amino acid sequence set forth in SEQ ID NO:96, and/or the Vβ comprises an amino acid sequence having at least about 85% identity to the amino acid sequence set forth in SEQ ID NO:95, wherein optionally there are no changes in CDR1α, CDR2α, CDR1β, and/or CDR2β.

In certain embodiments, the $Msln_{20-28}$-specific binding protein comprises (i) a TCR Vβ comprising (a) an amino acid sequence having at least about 85% identity to an amino acid sequence encoded by TRBV12-4*01 (e.g., to a TRBV12-4*01-encoded amino acid sequence that is at least about 10, 15, 20, 25, 30, 35, 40, 45, 50, 55, 60, 65, 70, 75, 80, 85, 90, 95, 100, 105, or 108 contiguous amino acids in length); and/or (b) an amino acid sequence having at least about 85% identity an amino acid sequence encoded by TRBJ2-7*01 (e.g., to a TRBJ2-7*01-encoded amino acid sequence that is at least about 5, 6, 7, 8, 9, 10, 11, 12, 13, or 14 amino acids long); and/or (ii) TCR Vα comprising (a) an amino acid sequence having at least about 85% identity to an amino acid sequence encoded by TRAV1-1*01 (e.g., to a TRAV1-1*01-encoded amino acid sequence that is at least about 10, 15, 20, 25, 30, 35, 40, 45, 50, 55, 60, 65, 70, 75, 80, 85, 90, 95, 100, 105, or 107 contiguous amino acids in length) and/or (b) an amino acid sequence having at least about 85% identity to an amino acid sequence encoded by TRAJ3*01 (e.g., to a TRAJ3*01-encoded amino acid sequence that is at least about 5, 6, 7, 8, 9, 10, 11, 12, 13, 14, 15, 16, 17, 18, 19, or 20 amino acids long).

In any of the presently disclosed embodiments, a TCR Vβ may include an amino acid sequence that is at least about 85% identical to an amino acid sequence encoded by TRBD1*01 or TRBD2*02.

Amino acid sequences encoded by these and other TCR genes are known and can be found at, for example, imgt.org, which provides gene tables and nucleotide and amino acid sequences for human TRAV, TRBV, TRAJ, TRBJ, TRBD, TRAC, and TRBD alleles.

In certain embodiments, a $Msln_{20-28}$-specific binding protein comprises a CDR3α amino acid sequence as set forth in SEQ ID NO:36 and a CDR3β amino acid sequence as set forth in SEQ ID NO:35. In some embodiments, the binding protein further comprises a CDR1α amino acid sequence as set forth SEQ ID NO:85, a CDR2α amino acid sequence as set forth in SEQ ID NO:86 or 119, a CDR1β amino acid sequence as set forth in any one of SEQ ID NOs: 82, 83, or 84, and a CDR2β amino acid sequence as set forth in SEQ ID NO:79. In certain embodiments, the Vα comprises an amino acid sequence having at least about 85% identity to the amino acid sequence set forth in SEQ ID NO:98, and/or the Vβ comprises an amino acid sequence having at least about 85% identity to the amino acid sequence set forth in SEQ ID NO:97, wherein there are optionally no changes in CDR1α, CDR2α, CDR1β, and/or CDR2β.

In certain embodiments, the $Msln_{20-28}$-specific binding protein comprises a TCR Vα comprising (a) an amino acid sequence having at least about 85% identity to an amino acid sequence encoded by TRAV12-3*01 (e.g., to a TRAV12-3*01-encoded amino acid sequence that is at least about 10, 15, 20, 25, 30, 35, 40, 45, 50, 55, 60, 65, 70, 75, 80, 85, 90, 95, 100, 105, or 108 contiguous amino acids in length) and/or (b) an amino acid sequence having at least about 85% identity to an amino acid sequence encoded by TRA29*01 (e.g., to a TRAJ29*01-encoded amino acid sequence that is at least about 5, 6, 7, 8, 9, 10, 11, 12, 13, 14, 15, 16, 17, 18, or 19 amino acids long).

In certain embodiments, alanine mutagenesis of any one or more of residues 1, 2, 7, 8, or 9 of SEQ ID NO:31 does not abrogate or does not substantially impair binding by a $Msln_{20-28}$-specific binding protein. In certain embodiments, a $Msln_{20-28}$-specific binding protein is capable of binding to a peptide comprising or consisting of the consensus amino acid sequence set forth in SEQ ID NO:60; e.g., in a peptide:HLA complex as disclosed herein.

In certain embodiments, a $Msln_{530-538}$-specific binding protein comprises: (a) a TCR Vα comprising a CDR3 amino acid sequence as set forth in SEQ ID NO:37 or 39, and a TCR Vβ, wherein the TCR Vβ optionally has at least about 85% identity to the amino acid sequence set forth in SEQ ID NO:99 or 101; (b) a TCR Vβ comprising a CDR3 amino acid sequence as set forth in SEQ ID NO:34 or 36, and (b) a TCR Vα, wherein the TCR Vα optionally has at least about 85% identity to the amino acid sequence set forth in SEQ ID NO:100 or 102; or (c) a TCR Vα comprising a CDR3 amino acid sequence as set forth in SEQ ID NO:37 or 39 and a TCR Vβ comprising a CDR3 amino acid sequence as set forth in SEQ ID NO:38 or 40.

In certain embodiments, a $Msln_{530-538}$-specific binding protein comprises a CDR3α amino acid sequence as set forth in SEQ ID NO:37 and a CDR3β amino acid sequence as set forth in SEQ ID NO:38. In some embodiments, the binding protein further comprises a CDR1α amino acid sequence as set forth SEQ ID NO:89, a CDR2α amino acid sequence as set forth in SEQ ID NO:90, a CDR1β amino acid sequence as set forth in any one of SEQ ID NOs: 83 or 87, and a CDR2β amino acid sequence as set forth in SEQ ID NO:88. In certain embodiments, the Vα comprises an amino acid sequence having at least about 85% identity to the amino acid sequence set forth in SEQ ID NO:100, and/or the Vβ comprises an amino acid sequence having at least about 85% identity to the amino acid sequence set forth in SEQ ID NO:99, wherein optionally there are no changes in CDR1α, CDR2α, CDR1β, and/or CDR2β.

In certain embodiments, a $Msln_{530-538}$-specific binding protein comprises a CDR3α amino acid sequence as set forth in SEQ ID NO:39 and a CDR3β amino acid sequence as set forth in SEQ ID NO:40. In some embodiments, the binding protein further comprises a CDR1α amino acid sequence as set forth SEQ ID NO:93, a CDR2α amino acid sequence as set forth in SEQ ID NO:94, a CDR1β amino acid sequence as set forth in any one of SEQ ID NOs: 83, 84, or 91, and a CDR2β amino acid sequence as set forth in SEQ ID NO:92. In certain embodiments, the Vα comprises an amino acid sequence having at least about 85% identity to the amino acid sequence set forth in SEQ ID NO:102, and/or the Vβ comprises an amino acid sequence having at least about 85% identity to the amino acid sequence set forth in SEQ ID NO:101, wherein there are optionally no changes in CDR1α, CDR2α, CDR1β, and/or CDR2β.

In certain embodiments, the $Msln_{530-538}$-specific binding protein comprises a TCR Vβ comprising an amino acid sequence having at least about 85% identity to an amino acid sequence encoded by TRBJ2-3*01 (e.g., to a TRBJ2-3*01-encoded amino acid sequence that is at least about 4, 5, 6, 7, 8, 9, 10, 11, 12, 13, 14, 15, or 15 contiguous amino acids in length).

In certain embodiments, alanine mutagenesis of any one or more of residues 3, 5, 6, or 9 of SEQ ID NO:32 does not abrogate or does not substantially impair binding by a $Msln_{530-538}$-specific binding protein. In certain embodiments, a $Msln_{530-538}$-specific binding protein is capable of binding to a peptide comprising or consisting of the consensus amino acid sequence set forth in SEQ ID NO:61; e.g., in a peptide:HLA complex as disclosed herein.

In certain embodiments, alanine mutagenesis of any one or more of residues 1, 5, or 9 of SEQ ID NO:32 does not abrogate or does not substantially impair binding by a $Msln_{530-538}$-specific binding protein. In certain embodiments, a $Msln_{530-538}$-specific binding protein is capable of binding to a peptide comprising or consisting of the consensus amino acid sequence set forth in SEQ ID NO:62; e.g., in a peptide:HLA complex as disclosed herein.

In certain embodiments, a $Msln_{530-538}$-specific binding protein of the present disclosure does not bind, or does not specifically bind relative to $Msln_{530-538}$, to a peptide:HLA complex wherein the peptide comprises or consists of the amino acid sequence set forth in any one or more of SEQ ID NOs:63, 64, 65, 66, 67, 68, 69, 70, 71, 72, 73, 74, 75, 76, and 77, and wherein the HLA optionally comprises an HLA-A2, such as HLA-A:02*01.

In any of the presently disclosed embodiments, a Msln-specific binding protein (i.e., $Msln_{20-28}$-specific binding protein, $Msln_{530-538}$-specific binding protein) is capable of binding to a Msln peptide:HLA complex as disclosed herein in the absence of, or independent of, CD8. In certain embodiments, a binding protein (e.g., when expressed on the cell surface of a human T cell) has a Msln peptide EC50 of about 9 μM, about 8 μM, about 7 μM, about 6 μM, about 5 μM, about 4 μM, about 3 μM, about 2 μM, about 1 μM, about 0.9 μM, about 0.8 μM, about 0.7 μM, about 0.6 μM, about 0.5 μM, about 0.4 μM, about 0.3 μM, about 0.2 μM, or less.

Msln-specific binding proteins are non-alloreactive against various human HLA types in the absence of a Msln peptide antigen. In certain embodiments, an immune cell (e.g., a T cell) expressing a Msln-specific binding protein of this disclosure does not produce IFN-γ and/or does not exhibit activation (e.g., CD8 expression, CD3 expression, Nur77 expression) and/or cytotoxic activity (e.g., specific killing, production and release of a perforin and/or a granzyme) when contacted with a cell expressing: (i) HLA-C6: 02:01; (ii) HLA-B13:01:01 without HLA-B13:02:01; (iii) HLA-A3; (iv) HLA-A29; (v) HLA-B40; (vi) HLA-B44; (vii) HLA-C3; (viii) HLA-C16; (ix) HLA-A1; (x) HLA-24; (xi) HLA-B7; (xii) HLA-B57; (xiii) HLA-C7; (xiv) HLA-A11; (xv) HLA-B15; (xvi) HLA-C4; (xvii) HLA-C12; (xviii) HLA-B8; (xix) HLA-B49; (xx) HLA-B51; (xxi) HLA-C15; (xxii) HLA-A30; (xxiii) HLA-A68; (xxiv) HLA-C2; (xxv) HLA-A32; (xxvi) HLA-A33; (xxvii) HLA-B55; (xxviii) HLA-C1; (xxvix) HLA-C5; (xxix) HLA-B8; (xxx) HLA-B35; or (xxxi) any combination of (i)-(xxx), when in the absence of a Msln peptide as provided herein.

Compositions and recombinant host cells (e.g., immune cells, such as a T cell) including, encoding, and/or expressing the binding proteins are also provided. In any of the presently disclosed embodiments, a binding protein is capable of expression on a cell surface by a host T cell. In any of the presently disclosed embodiments, binding by a Msln-specific binding protein that is expressed on the surface of an immune cell (e.g., a T cell) to a Msln peptide:HLA complex activates the immune cell, wherein activation is optionally determined by Nur77 expression and/or activity.

The presently disclosed binding proteins are highly sensitive for a cognate Mlsn peptide antigen. In certain embodiments, Nur77 expression is increased when the immune cell is in the presence of about $10^{-2}$ μM peptide, about $10^{-1}$ μM peptide, about 1 μM peptide, or about $10^1$ μM peptide, wherein the peptide is optionally presented by an antigen presenting cell; i.e., in a peptide:HLA complex.

In another aspect, polynucleotides are provided that encode a mesothelin-specific binding protein as described herein. In certain embodiments, a binding protein-encoding polynucleotide comprises a polynucleotide having at least about 50% sequence identity (i.e., at least about 50%, 55%, 60%, 65%, 70%, 75%, 80%, 85%, 86%, 87%, 89% 90%, 91%, 92%, 93%, 94%, 95%, 96%, 97%, 98%, 99%, or more) to the polynucleotide sequence set forth in any one of SEQ ID NOS: 1-5, 9-13, 17-21, 25-27, and 120. Vectors that contain a polynucleotide are also provided.

Presently disclosed binding proteins, and recombinant host cells, and related compositions may be used to treat a subject having a disease or disorder associated with mesothelin expression and/or activity, such as for example, a cancer. In certain embodiments, the cancer is a solid cancer. In certain embodiments, the solid cancer is or comprises biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer. In certain embodiments, the presently disclosed compositions and recombinant host cells may be used to treat a cancer wherein an $Msln_{20-28}$ peptide is expressed on a tumor cell of the cancer, or a cancer wherein an $Msln_{530-538}$ peptide is expressed on a tumor cell of the cancer, such as, for example, mesothelioma, pancreatic cancer, ovarian cancer, or lung cancer.

Also provided herein are polynucleotides that encode a binding protein as provided herein, vectors that comprise a binding-protein-encoding polynucleotide, and host cells that comprise a vector.

Prior to setting forth this disclosure in more detail, it may be helpful to an understanding thereof to provide definitions of certain terms to be used herein. Unless specifically defined otherwise, the technical terms, as used herein, have their normal meaning as understood in the art. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, is to be understood to include any integer within the recited range, unless otherwise indicated. "About," as used herein, when referring to a measurable value, range, or structure, is meant to encompass variations of ±20%, ±10%, ±5%, ±1%, or ±0.1% from the specified value, unless otherwise indicated.

It should be understood that the terms "a" and "an" as used herein refer to "one or more" of the enumerated components. The use of the alternative (e.g., "or") should be understood to mean any one, all, or any combination of the alternatives. As used herein, the terms "include," "have," and "comprise" are used synonymously, which terms and variants thereof are intended to be construed as non-limiting.

"Optional" or "optionally" means that the subsequently described element, component, event, or circumstance may or may not occur, and that the description includes instances in which the element, component, event, or circumstance occurs and instances in which they do not.

In addition, it should be understood that the individual constructs, or groups of constructs, derived from the various combinations of the structures and subunits described herein, are disclosed by the present application to the same extent as if each construct or group of constructs was set forth individually. Thus, selection of particular structures or particular subunits is within the scope of the present disclosure.

The term "consisting essentially of" is not equivalent to "comprising" and refers to the specified materials or steps of a claim, or to those that do not materially affect the basic characteristics of a claimed subject matter. For example, a protein domain, region, or module (e.g., a binding domain, hinge region, or linker) or a protein (which may have one or more domains, regions, or modules) "consists essentially of"

a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company. Variant proteins, peptides, polypeptides, and amino acid sequences of the present disclosure can, in certain embodiments, comprise one or more conservative substitutions relative to a reference amino acid sequence.

As used herein, "protein" or "polypeptide" refers to a polymer of amino acid residues. Proteins apply to naturally occurring amino acid polymers, as well as to amino acid polymers in which one or more amino acid residue is an artificial chemical mimetic of a corresponding naturally occurring amino acid and non-naturally occurring amino acid polymers.

As used herein, "fusion protein" refers to a protein that, in a single chain, has at least two distinct domains or motifs, wherein the domains or motifs are not naturally found together (e.g., in the specified arrangement, order, or number, or at all) in a protein. In certain embodiments, a fusion protein comprises at least two distinct domains or motifs that are not naturally found together in a single peptide or polypeptide. A polynucleotide encoding a fusion protein may be constructed using PCR, recombinantly engineered, or the like, or such fusion proteins can be synthesized. A fusion protein may further contain other components, such as a tag, a linker, or a transduction marker. In certain embodiments, a fusion protein expressed or produced by a host cell (e.g., a T cell) locates to the cell surface, where the fusion protein is anchored to the cell membrane (e.g., via a transmembrane domain) and comprises an extracellular portion or component (e.g., containing a binding domain and, in certain embodiments, a linker, a spacer, or both) and an intracellular portion or component.

"Junction amino acids" or "junction amino acid residues" refer to one or more (e.g., about 2-10) amino acid residues between two adjacent motifs, regions, or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

"Nucleic acid molecule" or "polynucleotide" refers to a polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid molecules include polyribonucleic acid (RNA), polydeoxyribonucleic acid (DNA), which includes cDNA, genomic DNA, and synthetic DNA, either of which may be single or double-stranded. If single-stranded, the nucleic acid molecule may be the coding strand or non-coding (anti-sense strand). A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

Variants of nucleic acid molecules of this disclosure are also contemplated. Variant nucleic acid molecules are at least 70%, 75%, 80%, 85%, 90%, and are preferably 95%, 96%, 97%, 98%, 99%, or 99.9% identical a nucleic acid molecule of a defined or reference polynucleotide as described herein, or that hybridize to a polynucleotide under stringent hybridization conditions of 0.015 M sodium chloride, 0.0015 M sodium citrate at about 65-68° C. or 0.015 M sodium chloride, 0.0015 M sodium citrate, and 50% formamide at about 42° C. Nucleic acid molecule variants retain the capacity to encode a fusion protein or a binding domain thereof having a functionality described herein, such as specifically binding a target molecule.

"Percent sequence identity" refers to a relationship between two or more sequences, as determined by comparing the sequences. Preferred methods to determine sequence identity are designed to give the best match between the sequences being compared. For example, the sequences are aligned for optimal comparison purposes (e.g., gaps can be introduced in one or both of a first and a second amino acid or nucleic acid sequence for optimal alignment). Further, non-homologous sequences may be disregarded for comparison purposes. The percent sequence identity referenced herein is calculated over the length of the reference sequence, unless indicated otherwise. Methods to determine sequence identity and similarity can be found in publicly available computer programs. Sequence alignments and percent identity calculations may be performed using a BLAST program (e.g., BLAST 2.0, BLASTP, BLASTN, or BLASTX). The mathematical algorithm used in the BLAST programs can be found in Altschul et al., Nucleic Acids Res. 25:3389-3402, 1997. Within the context of this disclosure, it will be understood that where sequence analysis software is used for analysis, the results of the analysis are based on the "default values" of the program referenced. "Default values" mean any set of values or parameters which originally load with the software when first initialized.

As understood in the art, "similarity" between two polypeptides is determined by comparing the amino acid sequence and conserved amino acid substitutes thereto of the polypeptide to the sequence of a second polypeptide (e.g., using GENEWORKS™, Align, Clustal™, the BLAST algorithm, or the like). In certain embodiments, the BLAST algorithm is preferred.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region ("leader and trailer") as well as intervening sequences (introns) between individual coding segments (exons).

In some contexts, the term "variant" as used herein, refers to at least one fragment of the full length sequence referred to, more specifically one or more amino acid or nucleic acid sequence which is, relative to the full-length sequence, truncated at one or both termini by one or more amino acids. Such a fragment includes or encodes for a peptide having at least 6, 7, 8, 10, 12, 15, 20, 25, 50, 75, 100, 150, or 200 successive amino acids of the original sequence or a variant thereof. The total length of the variant may be at least 6, 7, 8, 9, 10, 11, 12, 20, 25, 30, 40, 50, 60, 70, 80, 90, 100, or more amino acids.

In some embodiments, the term "variant" relates not only to at least one fragment, but also to a polypeptide or a fragment thereof including amino acid sequences that are at least 40%, 50%, 60%, 70%, 75%, 80%, 85%, 90%, 91%, 92%, 93%, 94%, 95%, 96%, 97%, 98%, 99%, or 99.5% identical to the reference amino acid sequence referred to or the fragment thereof, wherein amino acids other than those essential for the biological activity or the fold or structure of the polypeptide are deleted or substituted, one or more such essential amino acids are replaced in a conservative manner, and/or amino acids are added such that the biological activity of the polypeptide is preserved. The state of the art includes various methods that may be used to align two given nucleic acid or amino acid sequences and to calculate the degree of identity (see, e.g., Arthur Lesk (2008), Introduction to bioinformatics, Oxford University Press, 2008, 3rd edition). In some embodiments, the Clustal W software can be used using default settings (Larkin, M. A., et al. (2007). Clustal W and Clustal X version 2.0. Bioinformatics, 23, 2947-2948).

In certain embodiments, variants may, in addition, include chemical modifications, for example, isotopic labels or covalent modifications such as glycosylation, phosphorylation, acetylation, decarboxylation, citrullination, hydroxylation and the like. Methods for modifying polypeptides are known and in general will be employed so as not to abolish or substantially diminish a desired activity of the polypeptide.

In an embodiment, the term "variant" of a nucleic acid molecule includes nucleic acids the complementary strand of which hybridizes, for example, under stringent conditions, to the reference or wild type nucleic acid. Stringency of hybridization reactions is readily determinable by one of ordinary skill in the art, and in general is an empirical calculation dependent on probe length, washing temperature, and salt concentration. In general, longer probes require higher temperatures for proper annealing, while shorter probes less so. Hybridization generally depends on the ability of denatured DNA to reanneal to complementary strands present in an environment below their melting temperature: the higher the degree of desired homology between the probe and hybridizable sequence, the higher the relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In an embodiment, stringent conditions are applied for any hybridization, i.e., hybridization occurs only if the probe is 70% or more identical to the target sequence. Probes having a lower degree of identity with respect to the target sequence may hybridize, but such hybrids are unstable and will be removed in a washing step under stringent conditions, for example, lowering the concentration of salt to 2×SSC or, optionally and subsequently, to 0.5×SSC, while the temperature is, for example, about 50° C.-68° C., about 52° C.-68° C., about 54° C.-68° C., about 56° C.-68° C., about 58° C.-68° C., about 60° C.-68° C., about 62° C.-68° C., about 64° C.-68° C., or about 66° C.-68° C. In an embodiment, the temperature is about 64° C.-68° C. or about 66° C.-68° C. It is possible to adjust the concentration of salt to 0.2×SSC or even 0.1×SSC. Nucleic acid sequences having a degree of identity with respect to the reference or wild type sequence of at least 70%, 80%, 85%, 90%, 91%, 92%, 93%, 94%, 95%, 96%, 97%, 98%, 99%, or 99.5% may be isolated. In an embodiment, the term variant of a nucleic acid sequence, as used herein, refers to any nucleic acid sequence that encodes the same amino acid sequence and variants thereof as the reference nucleic acid sequence, in line with the degeneracy of the genetic code.

A "functional variant" refers to a polypeptide or polynucleotide that is structurally similar or substantially structurally similar to a parent or reference compound of this disclosure, but differs, in some contexts slightly, in composition (e.g., one base, atom or functional group is different, added, or removed; or one or more amino acids are mutated, inserted, or deleted), such that the polypeptide or encoded polypeptide is capable of performing at least one function of the encoded parent polypeptide with at least 50% efficiency, preferably at least 55%, 60%, 70%, 75%, 80%, 85%, 90%, 95%, 96%, 97%, 98%, 99%, 99.9%, or 100% level of activity of the parent polypeptide. In other words, a functional variant of a polypeptide or encoded polypeptide of this disclosure has "similar binding," "similar affinity" or "similar activity" when the functional variant displays no more than a 50% reduction in performance in a selected assay as compared to the parent or reference polypeptide, such as an assay for measuring binding affinity (e.g., Biacore® or tetramer staining measuring an association (Ka) or a dissociation (KD) constant), avidity, or activation of a host cell. As used herein, a "functional portion" or "functional fragment" refers to a polypeptide or polynucleotide that comprises only a domain, motif, portion or fragment of a parent or reference compound, and the polypeptide or encoded polypeptide retains at least 50% activity associated with the domain, portion or fragment of the parent or reference compound, preferably at least 55%, 60%, 70%, 75%, 80%, 85%, 90%, 95%, 96%, 97%, 98%, 99%, 99.9%, or 100% level of activity of the parent polypeptide, or provides a biological benefit (e.g., effector function).

A "functional portion" or "functional fragment" of a polypeptide or encoded polypeptide of this disclosure has "similar binding" or "similar activity" when the functional portion or fragment displays no more than a 50% reduction in performance in a selected assay as compared to the parent or reference polypeptide (preferably no more than 20% or 10%, or no more than a log difference as compared to the parent or reference with regard to affinity), such as an assay for measuring binding affinity or measuring effector function (e.g., cytokine release). In certain embodiments, a functional portion refers to a "signaling portion" of an effector molecule, effector domain, costimulatory molecule, or costimulatory domain.

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, or TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%).

As used herein, "heterologous" or "non-endogenous" or "exogenous" refers to any gene, protein, compound, nucleic acid molecule, or activity that is not native to a host cell or a subject, or any gene, protein, compound, nucleic acid molecule, or activity native to a host cell or a subject that has been altered. Heterologous, non-endogenous, or exogenous includes genes, proteins, compounds, or nucleic acid molecules that have been mutated or otherwise altered such that the structure, activity, or both is different as between the native and altered genes, proteins, compounds, or nucleic acid molecules. In certain embodiments, heterologous, non-endogenous, or exogenous genes, proteins, or nucleic acid molecules (e.g., receptors, ligands, etc.) may not be endogenous to a host cell or a subject, but instead nucleic acids encoding such genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). It will be appreciated that in the case of a host cell that comprises a heterologous polynucleotide, the polynucleotide is "heterologous" to progeny of the host cell, whether or not the progeny were themselves manipulated (e.g., transduced) to contain the polynucleotide.

The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

As used herein, the term "endogenous" or "native" refers to a polynucleotide, gene, protein, compound, molecule, or activity that is normally present in a host cell or a subject.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof. An expressed nucleic acid molecule is typically operably linked to an expression control sequence (e.g., a promoter).

The term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

The term "introduced" in the context of inserting a nucleic acid molecule into a cell, means "transfection", or "transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA). As used herein, the term "engineered," "recombinant" or "non-natural" or "modified" refers to an organism, microorganism, cell, nucleic acid molecule, or vector that includes at least one genetic alteration or has been modified by introduction of an exogenous nucleic acid molecule, wherein such alterations or modifications are introduced by genetic engineering (i.e., human intervention). Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a polynucleotide, gene or operon; e.g., such that expression of an endogenous nucleic acid molecule or gene is controlled, deregulated, or constitutive, where such alterations or modifications may be introduced by genetic engineering. Genetic alterations may include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When two or more heterologous nucleic acid molecules are introduced into a host cell, it is understood that the two or more heterologous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

The term "construct" refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Vectors of the present disclosure also include transposon systems (e.g., Sleeping Beauty, see, e.g., Geurts et al., Mol. Ther. 8:108, 2003: Mates et al., Nat. Genet. 41:753, 2009). Exemplary vectors are those capable of autonomous replication (episomal vector), capable of delivering a polynucleotide to a cell genome (e.g., viral vector), or capable of expressing nucleic acid molecules to which they are linked (expression vectors).

As used herein, the term "host" refers to a cell (e.g., an immune system cell as described herein) or microorganism targeted for genetic modification with a heterologous nucleic acid molecule to produce a polypeptide of interest. In certain embodiments, a host cell may optionally already possess or be modified to include other genetic modifications that confer desired properties related or unrelated to, e.g., biosynthesis of the heterologous protein (e.g., inclusion of a detectable marker; deleted, altered or truncated endogenous TCR; or increased co-stimulatory factor expression).

A "binding domain" (also referred to as a "binding region" or "binding moiety"), as used herein, refers to a molecule, such as a peptide, oligopeptide, polypeptide, or protein that possesses the ability to specifically and non-covalently associate, unite, or combine with a target molecule (e.g., $Msln_{20-28}$ peptide (SEQ ID NO:31) or $Msln_{530-538}$ peptide (SEQ ID NO:32), in certain embodiments, in a complex with an HLA molecule). A binding domain includes any naturally occurring, synthetic, semisynthetic, or recombinantly produced binding partner for a biological molecule or other target of interest. In some embodiments, the binding domain is an antigen-binding domain, such as an antibody or TCR or functional binding domain or antigen-binding fragment thereof. Exemplary binding domains include single chain antibody variable regions (e.g., single domain antibodies, sFv, scFv, and Fab), receptor ectodomains (e.g., TNF-$\alpha$), ligands (e.g., cytokines and chemokines), antigen-binding regions of TCRs, such as single chain TCRs (scTCRs), synthetic polypeptides selected for the specific ability to bind to a biological molecule, aptamers, or single domain antibodies (e.g., camelid or fish derived single domain antibodies; see, e.g., Arbabi-Ghahroudi M (2017) Front. Immunol. 8:1589).

The term "variable region" or "variable domain" refers to the domain of a TCR $\alpha$-chain or $\beta$-chain (or $\gamma$-chain and $\delta$-chain for $\gamma\delta$ TCRs), or of an antibody heavy or light chain, that is involved in binding to antigen (i.e., contains amino acids and/or other structures that contact antigen and result in binding). The variable domains of the $\alpha$-chain and $\beta$-chain (V$\alpha$ and V$\beta$, respectively) of a native TCR generally have similar structures, with each domain comprising four generally conserved framework regions (FRs) and three CDRs. Variable domains of antibody heavy ($V_H$) and light ($V_L$) chains each also generally comprise four generally conserved framework regions (FRs) and three CDRs. In both TCRs and antibodies, framework regions separate CDRs and CDRs are situated between framework regions (i.e., in primary structure).

The variable domains of the $\alpha$-chain and $\beta$-chain (V$\alpha$ and V$\beta$, respectively) of a native TCR generally have similar structures, with each domain comprising four framework regions (FRs) and three CDRs. The V$\alpha$ domain is encoded by two separate DNA segments, the variable gene segment and the joining gene segment (V-J); the V$\beta$ domain is encoded by three 5 separate DNA segments, the variable gene segment, the diversity gene segment, and the joining gene segment (V-D-J). Human TCR V, D, and J alleles, including the nucleotide and encoded amino acid sequences thereof, are known in the art. A single V$\alpha$ or V$\beta$ domain may be sufficient to confer antigen-binding specificity. Furthermore, TCRs that bind a particular antigen may be isolated using a V$\alpha$ or V$\beta$ domain from a TCR that binds the antigen to screen a library of complementary V$\alpha$ or V$\beta$ domains, respectively.

The terms "complementarity determining region," and "CDR," are synonymous with "hypervariable region" or "HVR," and are known in the art to refer to sequences of amino acids within TCR or antibody variable regions, which, in general, confer antigen specificity and/or binding affinity and are separated from one another in primary structure by framework sequence. In some cases, framework amino acids can also contribute to binding, e.g., may also contact the antigen or antigen-containing molecule. In general, there are three CDRs in each variable region (i.e., three CDRs in each of the TCRα-chain and β-chain variable regions; 3 CDRs in each of the antibody heavy chain and light chain variable regions). In the case of TCRs, CDR3 is thought to be the main CDR responsible for recognizing processed antigen. CDR1 and CDR2 mainly, or in some cases exclusively, interact with the MHC. Variable domain sequences can be aligned to a numbering scheme (e.g., Kabat, EU, International Immunogenetics Information System (IMGT) and Aho), which can allow equivalent residue positions to be annotated and for different molecules to be compared using Antigen receptor Numbering And Receptor Classification (ANARCI) software tool (2016, Bioinformatics 15:298-300). In certain embodments herein, CDRs are numbered according to the IMGT numbering system.

As used herein, "specifically binds" refers to an association or union of a binding domain, or of a protein comprising the same, to a target molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample. Binding domains (or fusion proteins thereof) may be classified as "high affinity" binding domains (or fusion proteins thereof) or "low affinity" binding domains (or fusion proteins thereof). "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding domains refer to those binding domains with a $K_a$ of up to $10^7$ $M^{-1}$, up to $10^6$ $M^{-1}$, or up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a $K_a$ (equilibrium association constant) for the target antigen that is higher than the wild type binding domain, or due to a $K_d$ for the target antigen that is less than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as western blot, ELISA, and BIACORE® analysis (see also, e.g., Scatchard, et al., Ann. N. Y. Acad. Sci. 57:660, 1949; and U.S. Pat. Nos. 5,283,173, 5,468,614, or the equivalent).

Assays for assessing affinity or apparent affinity or relative affinity are known. In certain examples, apparent affinity for a TCR is measured by assessing binding to various concentrations of tetramers, for example, by flow cytometry using labeled tetramers. In some examples, apparent $K_d$ of a TCR is measured using 2-fold dilutions of labeled tetramers (i.e., peptide:MHC tetramers) at a range of concentrations, followed by determination of binding curves by non-linear regression, apparent $K_d$ being determined as the concentration of ligand that yielded half-maximal binding. In certain embodiments, a $Msln_{20-28}$- or $Msln_{530-538}$-specific binding protein includes a $Msln_{20-28}$- or $Msln_{530-538}$-specific immunoglobulin superfamily binding protein or binding portion thereof, respectively.

"MHC-peptide tetramer staining" refers to an assay used to detect antigen-specific T cells, which features a tetramer of MHC molecules, each including an identical peptide having an amino acid sequence that is cognate (e.g., identical or related to) at least one epitope (e.g., $Msln_{20-28}$ or $Msln_{530-538}$), wherein the complex is capable of binding TCRs specific for the cognate epitope. Each of the MHC molecules may be tagged with a biotin molecule. Biotinylated MHC/peptides are tetramer zed by the addition of streptavidin, which can be fluorescently labeled. The tetramer may be detected by flow cytometry via the fluorescent label. In certain embodiments, an MHC-peptide tetramer assay is used to detect or select enhanced affinity TCRs of the instant disclosure. Levels of cytokines may be determined according to methods described herein and practiced in the art, including for example, ELISA, ELISpot, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation, and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

"Antigen" or "Ag" as used herein refers to an immunogenic molecule that provokes an immune response. This immune response may involve antibody production, activation of specific immunologically-competent cells (e.g., T cells), or both. An antigen (immunogenic molecule) may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be chemically synthesized or produced by cells that have been modified or genetically engineered to express an antigen.

The term "epitope" or "antigenic epitope" includes any molecule, structure, amino acid sequence or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

"$Msln_{20-28}$" and "$Msln_{20-28}$ peptide," and "Msln20 peptide" as used herein, refer to a peptide comprising or consisting of mesothelin amino acids 20-28 of SEQ ID NO:50 (human mesothelin, isoform 1); i.e., SLLFLLFSL (SEQ ID NO:31), which peptide can associate with HLA-A*201.

"$Msln_{530-538}$" and "$Msln_{530-538}$ peptide," "Msln530 peptide" as used herein, refer to a peptide comprising or consisting of mesothelin amino acids 530-538 of SEQ ID NO:50; e.g., VLPLTVAEV (SEQ ID NO:32), which peptide can associate with HLA-A*201.

The term "$Msln_{20-28}$-specific binding protein" refers to a protein or polypeptide that specifically binds to and/or that is specific for and/or that has or confers high avidity for a $Msln_{20-28}$ peptide. In some embodiments, a protein or polypeptide binds to $Msln_{20-28}$, such as a $Msln_{20-28}$ peptide complexed with an MEW or HLA molecule, e.g., on a cell surface, with a, or at least about a, particular affinity. A $Msln_{20-28}$-specific binding protein may bind to a $Msln_{20-28}$ peptide, a variant thereof, or a fragment thereof. For example, the $Msln_{20-28}$-specific binding protein may bind to an amino acid sequence of SEQ ID NO:31 (SLLFLLFSL), or an amino acid sequence having at least 90%, 91%, 92%, 93%, 94%, 95%, 96%, 97%, 98%, or 99% sequence identity to SEQ ID NO:31. In certain embodiments, a $Msln_{20-28}$-specific binding protein binds a $Msln_{20-28}$-peptide:HLA complex (or $Msln_{20-28}$-derived peptide:MHC complex) with an affinity that is about the same as, at least about the same as, or is greater than at or about the affinity exhibited by an exemplary $Msln_{20-28}$-specific binding protein provided herein, such as any of the $Msln_{20-28}$-specific TCRs provided herein, for example, as measured by the same assay. In certain embodiments, a $Msln_{20-28}$-specific binding protein can bind to an $Msln_{20-28}$ epitope as provided herein; e.g., a consensus epitope sequence according to SEQ ID NO:60. As disclosed herein, a Msln-specific binding protein does not bind, or does not substantially bind, to a non-Msln human protein or peptide having high sequence homology or identity to SEQ ID NO:60.

The term "$Msln_{530-538}$-specific binding protein" refers to a protein or polypeptide that specifically binds to and/or that is specific for and/or that has or confers high avidity for a $Msln_{530-538}$ peptide. In some embodiments, a protein or polypeptide binds to $Msln_{530-538}$, such as a $Msln_{530-538}$ peptide is complexed with an MEW or HLA molecule, e.g., on a cell surface, with a, or at least about a, particular affinity. A $Msln_{530-538}$-specific binding protein may bind to a $Msln_{530-538}$ peptide, a variant thereof, or a fragment thereof. For example, the $Msln_{530-538}$-specific binding protein may bind to an amino acid sequence of SEQ ID NO:32 (VLPLTVAEV), or an amino acid sequence having at least 90%, 91%, 92%, 93%, 94%, 95%, 96%, 97%, 98%, or 99% sequence identity to SEQ ID NO:32. In certain embodiments, a $Msln_{530-538}$-specific binding protein binds a $Msln_{530-538}$-peptide:HLA complex (or $Msln_{530-538}$-derived peptide:MHC complex) with an affinity that is about the same as, at least about the same as, or is greater than at or about the affinity exhibited by an exemplary $Msln_{530-538}$ specific binding protein provided herein, such as any of the $Msln_{530-538}$-specific TCRs provided herein, for example, as measured by the same assay. In certain embodiments, a $Msln_{530-538}$-specific binding protein can bind to an $Msln_{530-538}$ epitope as provided herein; e.g., a consensus epitope sequence according to SEQ ID NO:61 or 62. As disclosed herein, a Msln-specific binding protein does not bind, or does not substantially bind, to a non-Msln human protein or peptide having high sequence homology or identity to SEQ ID NO:61 or 62.

A target molecule, which is specifically bound by a binding domain of the present disclosure, may be found on or in association with a cell of interest ("target cell"). Exemplary target cells include a cancer cell, a cell associated with an autoimmune disease or disorder or with an inflammatory disease or disorder, and an infectious organism or cell (e.g., bacteria, virus, or virus-infected cell). A cell of an infectious organism, such as a mammalian parasite, is also contemplated as a target cell.

The term "functional avidity" refers to a biological measure or activation threshold of an in vitro immune cell (e.g., T cell, NK cell, NK-T cell) response to a given concentration of a ligand, wherein the biological measures can include cytokine production (e.g., IFNγ production, IL-2 production, etc.), cytotoxic activity, and proliferation. For example, T cells that biologically (immunologically) respond in vitro to a low antigen dose by producing cytokines, being cytotoxic, or proliferating are considered to have high functional avidity, while T cells having lower functional avidity require higher amounts of antigen before an immune response, similar to the high-avidity T cells, is elicited. It will be understood that functional avidity is different from affinity and avidity. Affinity refers to the strength of any given bond between a binding protein and its antigen/ligand. Some binding proteins are multivalent and bind to multiple antigens—in this case, the strength of the overall connection is the avidity.

Numerous correlations exist between the functional avidity and the effectiveness of an immune response. Some ex vivo studies have shown that distinct T cell functions (e.g., proliferation, cytokines production, etc.) can be triggered at different thresholds (see, e.g., Betts et al., J. Immunol. 172:6407, 2004; Langenkamp et al., Eur. J. Immunol. 32:2046, 2002). Factors that affect functional avidity include (a) the affinity of a TCR for the pMHC-complex, that is, the strength of the interaction between the TCR and pMHC (Cawthon et al., J. Immunol. 167:2577, 2001), (b) expression levels of the TCR and the CD4 or CD8 co receptors, and (c) the distribution and composition of signaling molecules (Viola and Lanzavecchia, Science 273:104, 1996), as well as expression levels of molecules that attenuate T cell function and TCR signaling.

The concentration of antigen needed to induce a half-maximum response between the baseline and maximum response after a specified exposure time is referred to as the "half maximal effective concentration" or "EC50". The EC50 value is generally presented as a molar (moles/liter) amount, but it is often converted into a logarithmic value as follows—log 10(EC50). For example, if the EC50 equals 1 μM ($10^{-6}$ M), the log 10 (EC50) value is −6. Another value used is pEC50, which is defined as the negative logarithm of the EC50 (−log 10 (EC50)). In the above example, the EC50 equaling 1 μM has a pEC50 value of 6. In certain embodiments, the functional avidity of the binding proteins of this disclosure will be a measure of its ability to promote IFNγ production by T cells, which can be measured using assays described herein. "High functional avidity" TCRs or binding domains thereof refer to those TCRs or binding domains thereof having a EC50 of at least $10^{-4}$ M, at least about $10^{-5}$ M, or at least about $10^{-6}$ M.

In certain embodiments, mesothelin-specific binding proteins or domains as described herein may expressed by a host T cell and can be functionally characterized according to any of a large number of art accepted methodologies for assaying T cell activity, including determination of T cell binding, activation or induction and also including determination of T cell responses that are antigen-specific. In certain embodiments, the binding protein is capable of promoting an antigen-specific T cell response against human mesothelin in a class I HLA-restricted manner. In further embodiments, the class I HLA-restricted response is transporter-associated with antigen processing (TAP)-independent. In certain embodiments, the antigen-specific T cell response comprises at least one of a CD4+ helper T lymphocyte (Th) response and a CD8+ cytotoxic T lymphocyte (CTL) response. In related embodiments, the CTL response is directed against a mesothelin-overexpressing cell. Further examples of methodologies for assaying T cell activity include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (Immunology Methods Manual: The Comprehensive Sourcebook of Techniques, 1998). See also Current Protocols in Immunology; Weir, Handbook of Experimental Immunology, Blackwell Scientific, Boston, MA (1986); Mishell and Shigii (eds.) Selected Methods in Cellular Immunology, Freeman Publishing, San Francisco, CA (1979); Green and Reed, Science 281:1309 (1998) and references cited therein).

As used herein, an "immune system cell" refers to any cell of the immune system that originates from a hematopoietic stem cell in the bone marrow, which gives rise to two major lineages, a myeloid progenitor cell (which gives rise to myeloid cells such as monocytes, macrophages, dendritic cells, megakaryocytes, and granulocytes) and a lymphoid progenitor cell (which gives rise to lymphoid cells such as T cells, B cells, and natural killer (NK) cells). Exemplary immune system cells include a CD4+ T cell, a CD8+ T cell, a CD4− CD8− double negative T cell, a γδ T cell, a regulatory T cell, a stem cell memory T cell, a natural killer cell (e.g., a NK cell or a NK-T cell), a B cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

A "T cell" or "T lymphocyte" is an immune system cell that matures in the thymus and produces TCRs. T cells can be naïve (not exposed to antigen; increased expression of CD62L, CCR7, CD28, CD3, CD127, and CD45RA, and decreased expression of CD45RO as compared to $TC_M$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells (TEM, decreased expression of CD62L, CCR7, CD28, CD45RA, and increased expression of CD127 as compared to naïve T cells or $TC_M$).

Effector T cells ($T_E$) refer to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as CD4+ CD25+ (Foxp3+) regulatory T cells and Treg17 cells, as well as Tr1, Th3, CD8+CD28−, and Qa-1 restricted T cells.

Helper T cells ($T_H$) are CD4+ cells that influence the activity of other immune cells by releasing cytokines. CD4+ T cells can activate and suppress an adaptive immune response, and which of those two functions is induced will depend on presence of other cells and signals. T cells can be collected using known techniques, and the various subpopulations or combinations thereof can be enriched or depleted by known techniques, such as by affinity binding to antibodies, flow cytometry, or immunomagnetic selection.

"Cells of T cell lineage" refer to cells that show at least one phenotypic characteristic of a T cell, or a precursor or progenitor thereof that distinguishes the cells from other lymphoid cells, and cells of the erythroid or myeloid lineages. Such phenotypic characteristics can include expression of one or more proteins specific for T cells (e.g., CD3+, CD4+, CD8+), or a physiological, morphological, functional, or immunological feature specific for a T cell. For example, cells of the T cell lineage may be progenitor or precursor cells committed to the T cell lineage; CD25+ immature and inactivated T cells; cells that have undergone CD4 or CD8 linage commitment; thymocyte progenitor cells that are CD4+CD8+ double positive; single positive CD4+ or CD8+; TCRαβ or TCR γδ; or mature and functional or activated T cells.

A "hematopoietic progenitor cell" is a cell derived from hematopoietic stem cells (HSCs) or fetal tissue that is capable of further differentiation into mature cell types (e.g., cells of the T cell lineage). In certain embodiments, $CD24^{lo}$ Lin− CD117+ hematopoietic progenitor cells are useful. As defined herein, hematopoietic progenitor cells may include embryonic stem cells, which are capable of further differentiation to cells of the T cell lineage. Hematopoietic progenitor cells may be from various animal species, including human, mouse, rat, or other mammals. A "thymocyte progenitor cell" or "thymocyte" is a hematopoietic progenitor cell present in the thymus.

"Hematopoietic stem cells" or "HSCs" refer to undifferentiated hematopoietic cells that are capable of self-renewal either in vivo, essentially unlimited propagation in vitro, and capable of differentiation to other cell types including cells of the T cell lineage. HSCs may be isolated, for example, but not limited to, from fetal liver, bone marrow, and cord blood.

"Embryonic stem cells," "ES cells," or "ESCs" refer to undifferentiated embryonic stem cells that have the ability to integrate into and become part of the germ line of a developing embryo. Embryonic stem cells are capable of differentiating into hematopoietic progenitor cells and any tissue or organ. Embryonic stem cells that are suitable for use herein include cells from the J1 ES cell line, 129J ES cell line, murine stem cell line D3 (American Type Culture Collection), the R1 or E14K cell lines derived from 129/Sv mice, cell lines derived from Balb/c and C57Bl/6 mice, and human embryonic stem cells (e.g., from WICELL® Research Institute, WI; or ES cell International, Melbourne, Australia).

The term "T cell receptor" (TCR) refers to an immunoglobulin superfamily member (having a variable binding domain, a constant domain, a transmembrane region, and a short cytoplasmic tail; see, e.g., Janeway, et al., Immunobiology: The Immune System in Health and Disease, 3$^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain and β-chain) contain two immunoglobulin domains, a variable domain (e.g., α-chain variable domain or $V_α$, β-chain variable domain or $V_β$; typically amino acids 1 to 116 based on Kabat numbering (Kabat, et al., "Sequences of Proteins of Immunological Interest," US Dept. Health and Human Services, Public Health Service National Institutes of Health, 1991, 5$^{th}$ ed.)) at the N-terminus, and one constant domain (e.g., α-chain constant domain or $C_α$, typically amino acids 117 to 259 based on Kabat, β-chain constant domain or $C_β$, typically amino acids 117 to 295 based on Kabat) adjacent to the cell membrane. Also like immunoglobulins, the variable domains contain complementary determining regions (CDRs) separated by framework regions (FRs) (see, e.g., Jores, et al., Proc. Nat'l Acad. Sci. U.S.A. 57:9138, 1990; Chothia, et al., EMBO J. 7:3745, 1988; see also Lefranc, et al., Dev. Comp. Immunol. 27:55, 2003). In certain embodiments, a TCR is found on the surface of T cells (or T lymphocytes) and associates with the CD3 complex. The source of a TCR as used in the present disclosure may be from various animal species, such as a human, mouse, rat, cat, dog, goat, horse, or other mammal.

"CD3" is a multi-protein complex of six chains (see, Borst J, et al., J Biol Chem, 258(8):5135-41, 1983 and Janeway, et al., p. 172 and 178, 1999 supra). In mammals, the complex includes a CD3γ chain, a CD3δ chain, two CD3ε chains, and a homodimer of CD3ζ chains. The CD3γ, CD3δ, and CD3ε chains are related cell surface proteins of the immunoglobulin superfamily containing a single immunoglobulin domain. The transmembrane regions of the CD3γ, CD3δ, and CD3ε chains are negatively charged, which is a characteristic that is thought to allow these chains to associate with positively charged regions of TCR chains. The intracellular tails of the CD3γ, CD3δ, and CD3ε chains each contain a single conserved motif known as an immunoreceptor tyrosine-based activation motif or ITAM, whereas each CD3ζ chain has three. Without being bound by any one theory, it is believed the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCR chain.

A "component of a TCR complex," as used herein, refers to a TCR chain (i.e., TCRα, TCRβ, TCRγ, or TCRδ), a CD3 chain (i.e., CD3γ, CD3δ, CD3ε, or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Major histocompatibility complex" (MHC) refers to glycoproteins that deliver peptide antigens to a cell surface. MHC class I molecules are heterodimers having a membrane spanning a chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by CD8+ T cells. MHC class II molecules deliver peptides originating in the vesicular system to the cell surface, where they are recognized by CD4+ T cells. Human MHC is referred to as human leukocyte antigen (HLA).

Mesothelin-Specific Binding Proteins

In certain aspects, the present disclosure provides binding proteins that are capable of specifically binding to a mesothelin peptide antigen as described herein (e.g., a peptide comprising, consisting, or consisting essentially of the amino acid sequence set forth in SEQ ID NO:31 or SEQ ID NO:32). Binding proteins herein include a TCR alpha chain variable domain (Vα) and a TCR beta chain variable domain (Vβ). In any of the presently disclosed embodiments, a mesothelin-specific binding protein is capable of specifically binding to a mesothelin peptide:HLA complex, such as a mesothelin peptide:HLA-A*02:01 complex.

In certain embodiments, a Msln-530-538-specific binding protein is provided that comprises: (a) a TCR Vα comprising a CDR3 amino acid sequence as set forth in SEQ ID NO:37 or 39, and a TCR Vβ, wherein the TCR Vβ optionally comprises an amino acid sequence having at least about 85% (i.e., at least about 86%, 85%, 88%, 89% 90%, 91%, 92%, 93%, 94%, 95%, 96%, 97%, 98%, 99%, or more) identity to the amino acid sequence set forth in SEQ ID NO:99 or 101; (b) a TCR Vβ comprising a CDR3 amino acid sequence as set forth in SEQ ID NO:38 or 40, and (b) a TCR Vα, wherein the TCR Vα optionally comprises an amino acid sequence having at least about 85% (i.e., at least about 86%, 85%, 88%, 89% 90%, 91%, 92%, 93%, 94%, 95%, 96%, 97%, 98%, 99%, or more) identity to the amino acid sequence set forth in SEQ ID NO:100 or 102; or (c) a TCR Vα comprising a CDR3 amino acid sequence as set forth in SEQ ID NO:37 or 39, wherein the TCR Vα optionally comprises an amino acid sequence having at least about 85% identity to the amino acid sequence set forth in SEQ ID NO:100 or 102, and a TCR Vβ comprising a CDR3 amino acid sequence as set forth in SEQ ID NO:38 or 40, wherein the TCR Vβ optionally comprises an amino acid sequence having at least about 85% identity to the amino acid sequence set forth in SEQ ID NO:99 or 101.

In any of the embodiments described herein, an encoded polypeptide of this disclosure (e.g., TCR variable domain or TCR chain) can comprise a "signal peptide" (also known as a leader sequence, leader peptide, or transit peptide). Signal peptides target newly synthesized polypeptides to an appropriate location inside or outside the cell. A signal peptide may be removed from the polypeptide during or once localization or secretion is completed. Polypeptides that have a signal peptide are referred to herein as a "pre-protein" and polypeptides having their signal peptide removed are referred to herein as "mature" proteins or polypeptides. Representative signal peptides include those amino acid sequences from position 1 to position 19 any one of SEQ ID NOs: 6, 14, 22, 28, or 29; from position 1 to 17 of SEQ ID NO: 7; from position 1 to 22 of SEQ ID NO: 15; from position 1 to 21 of SEQ ID NO: 23. Exemplary mature polypeptide sequences are provided in SEQ ID NOs:95-119.

In any of the presently disclosed embodiments, a Msln530-538-specific binding protein can comprise a TCR Vα comprising an amino acid sequence having at least about 85% identity to the amino acid sequence set forth in SEQ ID NO:100 or 102 and/or a TCR Vβ comprising an amino acid sequence having at least about 85% identity to the amino acid sequence set forth in SEQ ID NO:99 or 101. In certain embodiments, a binding protein comprises a variant of a referenced TCR variable domain sequence, provided that at least three or four of the CDRs of the binding protein have no change in sequence according to a referenced TCR variable domain sequence, wherein the CDRs that do have sequence changes have only up to two amino acid substitutions, up to a contiguous five amino acid deletion, or a combination thereof.

In certain embodiments, a Msln530-538-specific binding protein comprises a CDR3α amino acid sequence as set forth in SEQ ID NO:39 and a CDR3β amino acid sequence as set forth in SEQ ID NO:40. In some embodiments, the binding protein further comprises a CDR1α amino acid sequence as set forth SEQ ID NO:93, a CDR2α amino acid sequence as set forth in SEQ ID NO:94, a CDR1β amino acid sequence as set forth in any one of SEQ ID NOs: 83, 84, or 91, and/or a CDR2β amino acid sequence as set forth in SEQ ID NO:92. In further embodiments, the Vα comprises an amino acid sequence having at least about 85% identity to the amino acid sequence set forth in SEQ ID NO:102, and/or the Vβ comprises an amino acid sequence having at least about 85% identity to the amino acid sequence set forth in SEQ ID NO:101, wherein there are optionally no changes in CDR1α, CDR2α, CDR1β, and/or CDR2β.

In certain embodiments, the $Msln_{530-538}$-specific binding protein comprises a TCR Vβ comprising an amino acid sequence having at least about 85% identity to an amino acid sequence encoded by TRBJ2-3*01 (e.g., to a TRBJ2-3*01-encoded amino acid sequence that is at least about 4, 5, 6, 7, 8, 9, 10, 11, 12, 13, 14, 15, or 15 contiguous amino acids in length), and/or an amino acid sequence having at least about 85% identity to an amino acid sequence encoded by TRAV21*01 or TRAV21*02 (e.g., to a TRAV21*01 or TRAV21*02-encoded sequence that is at least about 10, 15, 20, 25, 30, 35, 40, 45, 50, 55, 60, 65, 70, 75, 80, 85, 90, 95, 100, 105, or 107 amino acids in length), and/or an amino acid sequence having at least about 85% identity to an amino acid sequence encoded by TRBV5-4*01 (e.g., to a TRBV5-4*01-encoded sequence that is at least about 10, 15, 20, 25, 30, 35, 40, 45, 50, 55, 60, 65, 70, 75, 80, 85, 90, 95, 100, 105, or 108 amino acids in length), and/or an amino acid sequence having at least about 85% identity to an amino acid sequence encoded by TRAJ57*01 (e.g., to a TRAJ57*01-encoded sequence that is at least about 5, 6, 7, 8, 9, 10, 11, 12, 13, 14, 15, 16, 17, 18, 19, or 20 amino acids in length).

In certain embodiments, a $Msln_{530-538}$-specific binding protein comprises a TCR Vα comprising or consisting of the amino acid sequence set forth in SEQ ID NO:102 and a TCR Vβ comprising or consisting of the amino acid sequence set forth in SEQ ID NO:101.

In other embodiments, a $Msln_{530-538}$-specific binding protein comprises a CDR3α amino acid sequence as set forth in SEQ ID NO:37 and a CDR3β amino acid sequence as set forth in SEQ ID NO:38. In some embodiments, the binding protein further comprises a CDR1α amino acid sequence as set forth SEQ ID NO:89, a CDR2α amino acid sequence as set forth in SEQ ID NO:90, a CDR1β amino acid sequence as set forth in any one of SEQ ID NOs: 83 or 87, and a CDR2β amino acid sequence as set forth in SEQ ID NO:88. In certain embodiments, the Vα comprises an amino acid sequence having at least about 85% identity to the amino acid sequence set forth in SEQ ID NO:100, and/or the Vβ comprises an amino acid sequence having at least about 85% identity to the amino acid sequence set forth in SEQ ID NO:99, wherein there are optionally no changes in CDR1α, CDR2α, CDR1β, and/or CDR2β.

In certain embodiments, a $Msln_{530-538}$-specific binding protein comprises an amino acid sequence having at least about 85% identity to an amino acid sequence encoded by TRAV4-1*01 (e.g., to a TRAV4-1*01-encoded sequence that is at least about 10, 15, 20, 25, 30, 35, 40, 45, 50, 55, 60, 65, 70, 75, 80, 85, 90, 95, 100, 105, or 108 amino acids in length), and/or an amino acid sequence having at least about 85% identity to an amino acid sequence encoded by TRAJ18*01 (e.g., to a TRAJ18*01-encoded sequence that is at least about 5, 6, 7, 8, 9, 10, 11, 12, 13, 14, 15, 16, 17, 18, 19, 20, or 21 amino acids in length) and/or an amino acid sequence having at least about 85% identity to an amino acid sequence encoded by TRBJ1-1*01 (e.g., to a TRBJ1-1*01-encoded sequence that is at least about 5, 6, 7, 8, 9, 10, 11, 12, 13, 14, or 15 amino acids in length), and/or an amino acid sequence having at least about 85% identity to an amino acid sequence encoded by TRBJ2-3*01 (e.g., to a TRBJ2-3*01-encoded sequence that is at least about 5, 6, 7, 8, 9, 10, 11, 12, 13, 14, 15, or 16 amino acids in length).

In certain embodiments, a $Msln_{530-538}$-specific binding protein comprises a TCR Vα comprising or consisting of the amino acid sequence set forth in SEQ ID NO:100 and a TCR Vβ comprising or consisting of the amino acid sequence set forth in SEQ ID NO:99.

In certain embodiments, alanine mutagenesis of any one or more of residues 3, 5, 6, or 9 of SEQ ID NO:32 does not abrogate or does not substantially impair binding by a $Msln_{530-538}$-specific binding protein. In certain embodiments, a $Msln_{530-538}$-specific binding protein is capable of binding to a peptide comprising or consisting of the consensus amino acid sequence set forth in SEQ ID NO:61; e.g., in a peptide:HLA complex as disclosed herein.

In certain embodiments, alanine mutagenesis of any one or more of residues 1, 5, or 9 of SEQ ID NO:32 does not abrogate or does not substantially impair binding by a $Msln_{530-538}$-specific binding protein. In certain embodiments, a $Msln_{530-538}$-specific binding protein is capable of binding to a peptide comprising or consisting of the consensus amino acid sequence set forth in SEQ ID NO:62; e.g., in a peptide:HLA complex as disclosed herein.

Presently disclosed Msln-specific binding proteins advantageously present low to no risk of alloreactivity against non-Msln targets; e.g., that are expressed in healthy tissue. Briefly, the present disclosure shows that Msln-specific binding proteins do not react, or do not substantially react, with human proteins with sequence homology to a Msln peptide antigen as provided herein. Thus, the binding proteins are highly specific for Msln peptide antigens.

For example, in certain embodiments, a $Msln_{530-538}$-specific binding protein of the present disclosure does not bind, or does not specifically bind relative to binding to $Msln_{530-538}$, to a peptide:HLA complex wherein the peptide comprises or consists of the amino acid sequence set forth in any one or more of SEQ ID NOs:63, 64, 65, 66, 67, 68, 69, 70, 71, 72, 73, 74, 75, 76, and 77, and wherein the HLA optionally comprises an HLA-A2, such as HLA-A:02*01.

In certain embodiments, a $Msln_{20-28}$-specific binding protein is provided that comprises: (a) a TCR Vα comprising a CDR3 amino acid sequence as set forth in SEQ ID NO:33 or 35, and a TCR Vβ, wherein the TCR Vβ optionally has at least about 85% (i.e., at least about 85%, 86%, 87%, 88%, 89% 90%, 91%, 92%, 93%, 94%, 95%, 96%, 97%, 98%, 99%, or more) identity to the amino acid sequence set forth in SEQ ID NO:95 or 97; (b) a TCR Vβ comprising a CDR3 amino acid sequence as set forth in SEQ ID NO:34 or 36, and (b) a TCR Vα, wherein the TCR Vα optionally has at least about 85% identity to the amino acid sequence set forth in SEQ ID NO:96 or 98; or (c) a TCR Vα comprising a CDR3 amino acid sequence as set forth in SEQ ID NO:33 or 35 and a TCR Vβ comprising a CDR3 amino acid sequence as set forth in SEQ ID NO:34 or 36, wherein the TCR Vα optionally comprises an amino acid sequence having at least about 85% identity to the amino acid sequence set forth in SEQ ID NO:95 or 97, and wherein the TCR Vβ optionally comprises an amino acid sequence having at least about 85% identity to the amino acid sequence set forth in SEQ ID NO:96 or 98.

In any of the presently disclosed embodiments, a $Msln_{20-28}$-specific binding protein can comprise a TCR Vα comprising an amino acid sequence having at least about 85% identity to the amino acid sequence set forth in SEQ ID NO:96 or 98 and/or a TCR Vβ comprising an amino acid sequence having at least about 85% identity to the amino acid sequence set forth in SEQ ID NO:95 or 97. In certain embodiments, a binding protein comprises a variant of a referenced TCR variable domain sequence, provided that at least three or four of the CDRs of the binding protein have no change in sequence according to a referenced TCR variable domain sequence, wherein the CDRs that do have sequence changes have only up to two amino acid substitutions, up to a contiguous five amino acid deletion, or a combination thereof.

In certain embodiments, a $Msln_{20-28}$-specific binding protein specific binding protein comprises a CDR3α amino acid sequence as set forth in SEQ ID NO:33 and a CDR3β amino acid sequence as set forth in SEQ ID NO:34. In some embodiments, the binding protein further comprises a CDR1α amino acid sequence as set forth SEQ ID NO:80, a CDR2α amino acid sequence as set forth in SEQ ID NO:81 or 118, a CDR1β amino acid sequence as set forth in any one of SEQ ID NOs: 78, 83, or 84, and a CDR2β amino acid sequence as set forth in SEQ ID NO:79. In certain embodiments, the Vα comprises an amino acid sequence having at least about 85% identity to the amino acid sequence set forth in SEQ ID NO:96, and/or the Vβ comprises an amino acid sequence having at least about 85% identity to the amino acid sequence set forth in SEQ ID NO:95, wherein there are optionally no changes in CDR1α, CDR2α, CDR1β, and/or CDR2β.

In certain embodiments, the $Msln_{20-28}$-specific binding protein comprises (i) a TCR Vβ comprising (a) an amino acid sequence having at least about 85% identity (i.e., at least about 85%, 86%, 87%, 88%, 89% 90%, 91%, 92%, 93%, 94%, 95%, 96%, 97%, 98%, 99%, or more) to an amino acid sequence encoded by TRBV12-4*01 (e.g., to a TRBV12-4*01-encoded amino acid sequence that is at least about 10, 15, 20, 25, 30, 35, 40, 45, 50, 55, 60, 65, 70, 75, 80, 85, 90, 95, 100, 105, or 108 contiguous amino acids in length); and/or (b) an amino acid sequence having at least about 85% identity an amino acid sequence encoded by TRBJ2-7*01 (e.g., to a TRBJ2-7*01-encoded amino acid sequence that is at least about 5, 6, 7, 8, 9, 10, 11, 12, 13, or 14 amino acids long); and/or (ii) TCR Vα comprising (a) an amino acid sequence having at least about 85% identity to an amino acid sequence encoded by TRAV1-1*01 (e.g., to a TRAV1-1*01-encoded amino acid sequence that is at least about 10, 15, 20, 25, 30, 35, 40, 45, 50, 55, 60, 65, 70, 75, 80, 85, 90, 95, 100, 105, or 107 contiguous amino acids in length) and/or (b) an amino acid sequence having at least about 85% identity to an amino acid sequence encoded by TRAJ3*01 (e.g., to a TRAJ3*01-encoded amino acid sequence that is at least about 5, 6, 7, 8, 9, 10, 11, 12, 13, 14, 15, 16, 17, 18, 19, or 20 amino acids long), and/or (c) r an amino acid sequence having at least about 85% identity to an amino acid sequence encoded by TRBJ2-3*01 (e.g., to a TRBJ2-3*01-encoded sequence that is at least about 5, 6, 7, 8, 9, 10, 11, 12, 13, 14, 15, or 16 amino acids in length).

In certain embodiments, a $Msln_{20-28}$-specific binding protein comprises a TCR Vα comprising or consisting of the amino acid sequence set forth in SEQ ID NO:96, and a TCR Vβ comprising or consisting of the amino acid sequence set forth in SEQ ID NO:95.

In certain embodiments, a $Msln_{20-28}$-specific binding protein a CDR3α amino acid sequence as set forth in SEQ ID NO:35 and a CDR3β amino acid sequence as set forth in SEQ ID NO:36. In some embodiments, the binding protein further comprises a CDR1α amino acid sequence as set forth SEQ ID NO:85, a CDR2α amino acid sequence as set forth in SEQ ID NO:86 or 119, a CDR1β amino acid sequence as set forth in any one of SEQ ID NOs:82, 83, or 84, and a CDR2β amino acid sequence as set forth in SEQ ID NO:79. In certain embodiments, the Vα comprises an amino acid sequence having at least about 85% identity to the amino acid sequence set forth in SEQ ID NO:98, and/or the Vβ comprises an amino acid sequence having at least about 85% identity to the amino acid sequence set forth in SEQ ID NO:97, wherein there are optionally no changes in CDR1α, CDR2α, CDR1β, and/or CDR2β.

In certain embodiments, the $Msln_{20-28}$-specific binding protein comprises a TCR Vα comprising (a) an amino acid sequence having at least about 85% identity to an amino acid sequence encoded by TRAV12-3*01 (e.g., to a TRAV12-3*01-encoded amino acid sequence that is at least about 10, 15, 20, 25, 30, 35, 40, 45, 50, 55, 60, 65, 70, 75, 80, 85, 90, 95, 100, 105, or 108 contiguous amino acids in length) and/or (b) an amino acid sequence having at least about 85% identity to an amino acid sequence encoded by TRAJ29*01 (e.g., to a TRAJ29*01-encoded amino acid sequence that is at least about 5, 6, 7, 8, 9, 10, 11, 12, 13, 14, 15, 16, 17, 18, or 19 amino acids long), and/or (c) and/or an amino acid sequence having at least about 85% identity to an amino acid sequence encoded by TRBJ2-3*01 (e.g., to a TRBJ2-3*01-encoded sequence that is at least about 5, 6, 7, 8, 9, 10, 11, 12, 13, 14, 15, or 16 amino acids in length).

In certain embodiments, a $Msln_{20-28}$-specific binding protein comprises a TCR Vα comprising or consisting of the amino acid sequence set forth in SEQ ID NO:98 and a TCR Vβ comprising or consisting of the amino acid sequence set forth in SEQ ID NO:97.

In certain embodiments, alanine mutagenesis of any one or more of residues 1, 2, 7, 8, or 9 of SEQ ID NO:31 does not abrogate or does not substantially impair binding by a $Msln_{20-28}$-specific binding protein. In certain embodiments, a $Msln_{20-28}$-specific binding protein is capable of binding to a peptide comprising or consisting of the consensus amino acid sequence set forth in SEQ ID NO:60; e.g., in a peptide:HLA complex as disclosed herein.

In any of the presently disclosed embodiments, a Msln-specific binding protein is capable of binding to a Msln peptide:HLA complex, wherein the Msln peptide comprises the amino acid sequence set forth in SEQ ID NO:31 or 32 and wherein the HLA is or comprises HLA-A2, such as HLA-A*02:01.

In any of the presently disclosed embodiments, an immune cell (e.g., a T cell) expressing a Msln-specific binding protein of this disclosure does not produce IFN-γ and/or does not exhibit activation (e.g., CD8 expression, CD3 expression, Nur77 expression) and/or cytotoxic activity (e.g., specific killing, production and release of a perforin and/or a granzyme) when contacted with a cell expressing: (i) HLA-C6:02:01; (ii) HLA-B13:01:01 without HLA-B13: 02:01; (iii) HLA-A3; (iv) HLA-A29; (v) HLA-B40; (vi) HLA-B44; (vii) HLA-C3; (viii) HLA-C16; (ix) HLA-A1; (x) HLA-24; (xi) HLA-B7; (xii) HLA-B57; (xiii) HLA-C7; (xiv) HLA-A11; (xv) HLA-B15; (xvi) HLA-C4; (xvii) HLA-C12; (xviii) HLA-B8; (xix) HLA-B49; (xx) HLA-B51; (xxi) HLA-C15; (xxii) HLA-A30; (xxiii) HLA-A68; (xxiv) HLA-C2; (xxv) HLA-A32; (xxvi) HLA-A33; (xxvii) HLA-B55; (xxviii) HLA-C1; (xxvix) HLA-05; (xxix) HLA-B8; (xxx) HLA-B35; or (xxxi) any combination of (i)-(xxx), when in the absence of a Msln peptide as provided herein.

In any of the presently disclosed embodiments, a Msln-specific binding protein, when expressed on the surface of a host cell, is capable of binding to a Msln peptide:HLA complex as disclosed herein in the absence of, or independent of, CD8.

In certain embodiments, a binding protein according to the present disclosure has a Msln peptide EC50 of about 9 μM, about 8 μM, about 7 μM, about 6 μM, about 5 μM, about 4 μM, about 3 μM, about 2 μM, about 1 μM, about 0.9 μM, about 0.8 μM, about 0.7 μM, about 0.6 μM, about 0.5 μM, about 0.4 μM, about 0.3 μM, about 0.2 μM, or less.

In any of the presently disclosed embodiments, a Msln-specific binding protein is capable of more efficiently associating with a CD3 protein, and/or has increased expression at a cell surface relative to an endogenous TCR, when the Msln-specific binding protein is expressed in a host T cell or NK-T cell.

In certain embodiments, the binding protein is a TCR, a single chain TCR (scTCR), or a CAR.

In some embodiments, the binding protein is a TCR. In certain embodiments, the binding protein comprises a TCR Vβ, a TCR CP, a TCR Vα, and a TCR Cα, wherein the Vβ and the Cβ together comprise a TCR β chain (TCRβ), and wherein the Vα and the Cα together comprise a TCR α chain (TCRα), and wherein the TCRβ and the TCRα are capable of associating to form a dimer. In further embodiments, a TCR Cβ comprises a cysteine amino acid in place of a native serine at amino acid position 57 (e.g., GV(S→C)TD) and a TCR Cα comprises a cysteine amino acid in place of a native threonine at amino acid position 48 (e.g., DK(T→C)VL; see. e.g., Cohen et al., Cancer Res. 67(8): 3898-3903 (2007)).

In further embodiments, a Msln-specific binding protein is a TCR comprising a TCRβ and a TCRα, wherein the TCRβ and the TCRα respectively comprise an amino acid sequence having at least about 85%, 90%, 91%, 92%, 93%, 94%, 95%, 96%, 97%, 98%, 99% identity, or more, to the amino acid sequences set forth in SEQ ID NOs: (i) 103 or 6 (TCRβ) and 104 or 7 (TCRα); (ii) 105 or 14 (TCRβ) and 106 or 15 (TCRα); (iii) 107 or 22 (TCRβ) and 108 or 23 (TCRα); or (iv) 109 or 28 (TCRβ) and 110 or 29 (TCRα).

In certain embodiments, the binding protein is a soluble TCR, optionally including or coupled to a cytotoxic and/or detectable element or agent. (see, e.g., Walseng et al., *PLoS One* doi:10.1371/journal.pone.0119559 (2015)). Methods useful for isolating and purifying recombinantly produced soluble TCR, by way of example, may include obtaining supernatants from suitable host cell/vector systems that secrete the recombinant soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In some embodiments, two or more distinct polypeptide domains or sequences are connected by a linker (e.g., a TCRVα and a TCRVβ in the context of a scTCR or a CAR). A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, about four to about 20 amino acids, about eight to about 15 amino acids, about 15 to about 25 amino acids, or another suitable number of amino acids. In general, a linker is preferably chemically inert, flexible, and non-immunogenic or minimally immunogenic. Linker sequences can be repeated so as to achieve a desired length to, for example, facilitate a desired protein interaction by or between linked domains. Exemplary linkers (including glycine-serine linkers) and properties of linkers are discussed in, for example, Chen et al., *Adv. Drug Deliv Rev,* 65(10):1357-1369 (2013), and in van Rosmalen et al., *Biochemistry* 56(60):6565-6574 (2017), which linker amino acid sequences and design properties are incorporated herein by reference.

In particular embodiments, a Msln-specific binding protein is or comprises a scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker).

In certain embodiments, a Msln-specific binding protein is or comprises a CAR. "Chimeric antigen receptor" (CAR) refers to a fusion protein of the present disclosure engineered to contain two or more naturally occurring (or engineered) amino acid sequences linked together in a way that does not occur naturally or does not occur naturally in a host cell, which fusion protein can function as a receptor when present on a surface of a cell. CARs of the present disclosure include an extracellular portion comprising an antigen-binding domain (e.g., obtained or derived from an immunoglobulin or immunoglobulin-like molecule, such as a scFv or scTCR derived from an antibody or TCR specific for a cancer antigen, or an antigen-binding domain derived or obtained from a killer immunoreceptor from an NK cell, or from another protein (natural, recombinant, or synthetic) that has, or is engineered to possess, the ability to specifically bind to an antigen) linked to a transmembrane domain and one or more intracellular signaling domains (optionally containing co-stimulatory domain(s)) (see, e.g., Sadelain et al., *Cancer Discov.,* 3(4):388 (2013); see also Harris and Kranz, *Trends Pharmacol. Sci.,* 37(3):220 (2016); Stone et al., *Cancer Immunol. Immunother.,* 63(11):1163 (2014)). In certain embodiments, a binding protein comprises a CAR comprising an antigen-specific TCR binding domain (see, e.g., Walseng et al., *Scientific Reports* 7:10713, 2017; the TCR CAR constructs and methods of which are hereby incorporated by reference in their entirety).

Polynucleotides, Vectors, and Host Cells

Also provided herein are polynucleotides that encode a Msln-specific binding protein, or a portion thereof, (e.g., TCR variable domain) of this disclosure. It will be appreciated by those of ordinary skill in the art that, due to the degeneracy of the genetic code, there are numerous nucleotide sequences that encode a binding protein or portion thereof, as described herein. Some such polynucleotides can bear limited or minimal sequence identity to the nucleotide sequence of a native, original, or identified polynucleotide sequence. Nonetheless, polynucleotides that vary due to differences in codon usage are expressly contemplated by the present disclosure.

In certain embodiments, sequences that have been codon-optimized for expression in a host cell, such as a mammalian cell, are specifically contemplated. Codon optimization can be performed using known techniques and tools, e.g., using the GenScript® OptimumGene™ tool. Codon-optimized sequences include sequences that are at least partially codon-optimized (i.e., one or more codon is optimized for expression in the host cell) and those that are fully codon-optimized. Codon optimization for expression in certain immune host cells is described in, for example, Scholten et al., Clin. Immunol. 119:135, 2006.

Exemplary polynucleotide sequences encoding TCR chains of the present disclosure are provided in SEQ ID NOs:1-4, 9-12, 17-20, 25, and 26. Accordingly, in certain embodiments, a polynucleotide encoding a Msln-specific binding protein comprises a polynucleotide having at least about 50% (i.e., at least about 50%, 55%, 60%, 65% 70%, 75%, 80%, 85%, 86%, 87%, 89% 90%, 91%, 92%, 93%, 94%, 95%, 96%, 97%, 98%, 99%, or more) identity to the polynucleotide sequence set forth in any one of SEQ ID NOs:1-4, 9-12, 17-20, 25, and 26.

In certain embodiments, a TCRα chain-encoding polynucleotide and a TCRβ chain-encoding polynucleotide are provided that have at least about 50% identity to the polynucleotide sequences set forth in SEQ ID NOs: (i) 1 and 3, respectively; (ii) 2 and 4, respectively; (iii) 9 and 11, respectively; (iv) 10 and 12, respectively; (v) 17 and 19, respectively; (vi) 18 and 20, respectively; or (vii) 25 and 26, respectively.

In certain embodiments, a polynucleotide encoding two or more components or portions of a binding protein or TCR of the present disclosure comprises the two or more coding sequences operatively associated in a single open reading frame. Such an arrangement can advantageously allow coordinated expression of desired gene products, such as, for example, contemporaneous expression of alpha and beta chains of a TCR, such that they are produced in about a 1:1 ratio. In certain embodiments, two or more substituent gene products of a binding protein of this disclosure, such as a TCR (e.g., alpha and beta chains), are expressed as separate molecules and associate post-translationally. In further embodiments, two or more substituent gene products of a binding protein of this disclosure are expressed as a single peptide with the parts separated by a cleavable or removable segment.

For instance, self-cleaving peptides (also referred to as "ribosomal skip elements") are useful for expression of separable polypeptides encoded by a single polynucleotide or vector are known in the art and include, for example, a P2A peptide encoded by a polynucleotide having the nucleotide sequence shown in any one of SEQ ID NOS:41-46, a Thoseaasigna virus 2A (T2A) peptide, such as a peptide encoded by a polynucleotide having the nucleotide sequence shown in SEQ ID NO:47, an Equine rhinitis A virus (ERAV) 2A (E2A) peptide, such as a peptide encoded by a polynucleotide having the nucleotide sequence shown in SEQ ID NO:48, and a Foot-and-Mouth disease virus 2A (F2A) peptide, such as a peptide encoded by a polynucleotide having the nucleotide sequence shown in SEQ ID NO:49. Exemplary amino acid sequences of self-cleaving peptides are provided in SEQ ID NOs:113-117.

Exemplary polynucleotides encoding a Msln-specific TCR of the present disclosure, wherein a polynucleotide encoding a self-cleaving peptide is disposed between a polynucleotide encoding a TCRβ chain and a polynucleotide encoding a TCRα chain, include those that encode an amino acid sequence as set forth in any one of SEQ ID NOs:8, 16, 24, and 30. Exemplary such polynucleotides have a polynucleotide sequence as set forth in any one of SEQ ID NOs:5, 13, 21, 27, and 120; in certain embodiments, a polynucleotide is provided that has at least about 50% identity to the polynucleotide sequence as set forth in any one of SEQ ID NOs:5, 13, 21, 27, and 120.

In further embodiments, a binding protein is expressed as part of a transgene construct that encodes, and/or a host immune cell containing the binding-protein-encoding polynucleotide can further encode: one or more additional accessory protein, such as a safety switch protein; a tag, a selection marker; a CD8 co receptor β chain; a CD8 co-receptor α chain or both; or any combination thereof. Polynucleotides and transgene constructs useful for encoding and expressing binding proteins and accessory components (e.g., one or more of a safety switch protein, a selection marker, CD8 co-receptor β-chain, or a CD8 co-receptor α-chain) are described in published PCT application no. WO 2018/058002, the polynucleotides, transgene constructs, and accessory components, including the nucleotide and amino acid sequences thereof, of which are hereby incorporated by reference. It will be understood that any or all of a binding protein of the present disclosure, a safety switch protein, a tag, a selection marker, a CD8 co-receptor β chain, or a CD8 co-receptor α-chain may be encoded by a single nucleic acid molecule or may be encoded by polynucleotide sequences that are, or are present on, separate nucleic acid molecules.

Exemplary safety switch proteins include, for example, a truncated EGF receptor polypeptide (huEGFRt) that is devoid of extracellular N terminal ligand binding domains and intracellular receptor tyrosine kinase activity, but that retains its native amino acid sequence, has type I transmembrane cell surface localization, and has a conformationally intact binding epitope for pharmaceutical-grade anti-EGFR monoclonal antibody, cetuximab (Erbitux) tEGF receptor (tEGFr; Wang et al., Blood 118:1255-1263, 2011); a caspase polypeptide (e.g., iCasp9; Straathof et al., Blood 105:4247-4254, 2005; Di Stasi et al., N. Engl. J. Med. 365:1673-1683, 2011; Zhou and Brenner, Exp. Hematol. pii:S0301-472X (16)30513-6. doi:10.1016/j.exphem.2016.07.011), RQR8 (Philip et al., Blood 124:1277-1287, 2014); a 10-amino-acid tag derived from the human c-myc protein (Myc) (Kieback et al., Proc. Natl. Acad. Sci. USA 105:623-628, 2008); and a marker/safety switch polypeptide, such as RQR (CD20+ CD34; Philip et al., 2014).

Other accessory components useful for recombinant host cells of the present disclosure comprise a tag or selection marker that allows the cells to be identified, sorted, isolated, enriched, or tracked. For example, marked cells having desired characteristics (e.g., an antigen-specific TCR and a safety switch protein) can be sorted away from unmarked cells in a sample and more efficiently activated and expanded for inclusion in a product of desired purity.

As used herein, the term "selection marker" comprises a nucleic acid construct (and the encoded gene product) that confers an identifiable change to a cell permitting detection and positive selection of immune cells transduced with a polynucleotide comprising a selection marker. RQR is a selection marker that comprises a major extracellular loop of CD20 and two minimal CD34 binding sites. In some embodiments, an RQR-encoding polynucleotide comprises a polynucleotide that encodes the 16-amino-acid CD34 minimal epitope. In some embodiments, the CD34 minimal epitope is incorporated at the amino terminal position of a CD8 co-receptor stalk domain (Q8). In further embodiments, the CD34 minimal binding site sequence can be combined with a target epitope for CD20 to form a compact marker/suicide gene for T cells (RQR8) (Philip et al., 2014, incorporated by reference herein). This construct allows for the selection of immune cells expressing the construct, with for example, CD34 specific antibody bound to magnetic beads (Miltenyi) and that utilizes clinically accepted pharmaceutical antibody, rituximab, that allows for the selective deletion of a transgene expressing engineered T cell (Philip et al., 2014).

Further exemplary selection markers also include several truncated type I transmembrane proteins normally not expressed on T cells: the truncated low-affinity nerve growth factor, truncated CD19, and truncated CD34 (see for example, Di Stasi et al., N. Engl. J. Med. 365:1673-1683, 2011; Mavilio et al., Blood 83:1988-1997, 1994; Fehse et al., Mol. Ther. 1:448-456, 2000; each incorporated herein in their entirety). A useful feature of CD19 and CD34 is the availability of the off-the-shelf Miltenyi CliniMACs™ selection system that can target these markers for clinical-grade sorting. However, CD19 and CD34 are relatively large surface proteins that may tax the vector packaging capacity and transcriptional efficiency of an integrating vector. Surface markers containing the extracellular, non-signaling domains or various proteins (e.g., CD19, CD34, LNGFR) also can be employed. Any selection marker may be employed and should be acceptable for Good Manufacturing Practices. In certain embodiments, selection markers are expressed with a polynucleotide that encodes a gene product of interest (e.g., a binding protein of the present disclosure, such as a TCR or CAR). Further examples of selection markers include, for example, reporters such as GFP, EGFP, β-gal or chloramphenicol acetyltransferase (CAT). In certain embodiments, a selection marker, such as, for example, CD34 is expressed by a cell and the CD34 can be used to select enrich for, or isolate (e.g., by immunomagnetic selection) the transduced cells of interest for use in the methods described herein. As used herein, a CD34 marker is distinguished from an anti-CD34 antibody, or, for example, a scFv, TCR, or other antigen recognition moiety that binds to CD34.

In certain embodiments, a selection marker comprises an RQR polypeptide, a truncated low-affinity nerve growth factor (tNGFR), a truncated CD19 (tCD19), a truncated CD34 (tCD34), or any combination thereof.

In practicing various embodiments of the present disclosure, standard techniques may be used for recombinant DNA, peptide, and oligonucleotide synthesis; immunoassays; tissue culture; and transformation (e.g., electroporation and lipofection). Enzymatic reactions and purification techniques may be performed according to manufacturer's specifications or as commonly accomplished in the art or as described herein. These and related techniques and procedures may be generally performed according to conventional methods well-known in the art and as described in various general and more specific references in microbiology, molecular biology, biochemistry, molecular genetics, cell biology, virology, and immunology techniques that are cited and discussed throughout the present specification (see, e.g., Sambrook, et al, Molecular Cloning: A Laboratory Manual, 3d ed., Cold Spring Harbor Laboratory Press, Cold Spring Harbor, N.Y.; Current Protocols in Molecular Biology (John Wiley and Sons, updated July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford Univ. Press USA, 1985); Current Protocols in Immunology (Edited by: John E. Coligan, Ada M. Kruisbeek, David H. Margulies, Ethan M. Shevach, Warren Strober 2001 John Wiley & Sons, NY, NY); Real-Time PCR: Current Technology and Applications, Edited by Julie Logan, Kirstin Edwards and Nick Saunders, 2009, Caister Academic Press, Norfolk, UK; Anand, Techniques for the Analysis of Complex Genomes, (Academic Press, New York, 1992); Guthrie and Fink, Guide to Yeast Genetics and Molecular Biology (Academic Press, New York, 1991); Oligonucleotide Synthesis (N. Gait, Ed., 1984); Nucleic Acid Hybridization (B. Hames & S. Higgins, Eds., 1985); Transcription and Translation (B. Hames & S. Higgins, Eds., 1984); Animal Cell Culture (R. Freshney, Ed., 1986); Perbal, A Practical Guide to Molecular Cloning (1984); Next-Generation Genome Sequencing (Janitz, 2008 Wiley-VCH); PCR Protocols (Methods in Molecular Biology) (Park, Ed., 3rd Edition, 2010 Humana Press); Immobilized Cells And Enzymes (IRL Press, 1986); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Harlow and Lane, Antibodies, (Cold Spring Harbor Laboratory Press, Cold Spring Harbor, N.Y., 1998); Immunochemical Methods In Cell And Molecular Biology (Mayer and Walker, eds., Academic Press, London, 1987); Handbook Of Experimental Immunology, Volumes I-IV (D. M. Weir and CC Blackwell, eds., 1986); Roitt, Essential Immunology, 6th Edition, (Blackwell Scientific Publications, Oxford, 1988); Embryonic Stem Cells: Methods and Protocols (Methods in Molecular Biology) (Kurstad Turksen, Ed., 2002); Embryonic Stem Cell Protocols: Volume I: Isolation and Characterization (Methods in Molecular Biology) (Kurstad Turksen, Ed., 2006); Embryonic Stem Cell Protocols: Volume II: Differentiation Models (Methods in Molecular Biology) (Kurstad Turksen, Ed., 2006); Human Embryonic Stem Cell Protocols (Methods in Molecular Biology) (Kursad Turksen Ed., 2006); Mesenchymal Stem Cells: Methods and Protocols (Methods in Molecular Biology) (Darwin J. Prockop, Donald G. Phinney, and Bruce A. Bunnell Eds., 2008); Hematopoietic Stem Cell Protocols (Methods in Molecular Medicine) (Christopher A. Klug, and Craig T. Jordan Eds., 2001); and Hematopoietic Stem Cell Protocols (Methods in Molecular Biology) (Kevin D. Bunting Ed., 2008) Neural Stem Cells: Methods and Protocols (Methods in Molecular Biology) (Leslie P. Weiner Ed., 2008)).

Also provided are vectors that comprise a polynucleotide according to the present disclosure. Any suitable expression vector, including an exemplary expression vector as disclosed herein, may be used. Furthermore, the expression vector may be configured to or capable of delivering the polynucleotide to a host cell.

A typical vector may include a nucleic acid molecule capable of transporting another nucleic acid to which it has been linked, or which is capable of replication in a host organism. As discussed herein, some examples of vectors include plasmids, viral vectors, cosmids, and others.

Some vectors may be capable of autonomous replication in a host cell into which they are introduced (e.g., bacterial vectors having a bacterial origin of replication and episomal mammalian vectors), whereas other vectors may be integrated into the genome of a host cell upon introduction into the host cell and thereby replicate along with the host genome. Additionally, some vectors are capable of directing the expression of genes to which they are operatively linked (these vectors may be referred to as "expression vectors"). According to related embodiments, it is further understood that, if one or more agents (e.g., polynucleotides encoding a Msln-specific binding protein, or a variant thereof, as described herein) is co-administered to a subject, that each agent may reside in separate or the same vectors, and multiple vectors (each containing a different agent or the same agent) may be introduced to a cell or cell population or administered to a subject.

As used herein, "expression vector" refers to a DNA construct containing a nucleic acid molecule that is operably linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

In certain embodiments, a viral vector is used to introduce a non-endogenous nucleic acid sequence encoding a polypeptide specific for a target. A viral vector may be a retroviral vector or a lentiviral vector. A viral vector may also include nucleic acid sequences encoding transduction marker.

Viral vectors suitable for use with the compositions of the instant disclosure include those identified for human gene therapy applications (see Pfeifer and Verma, Ann. Rev. Genomics Hum. Genet. 2: 177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category.

Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, and cytomegalovirus), and poxvirus (e.g., vaccinia, fowlpox, and canarypox). Other viruses include, but are not limited to, Norwalk virus, togavirus, flavivirus, reoviruses, papovavirus, hepadnavirus, and hepatitis virus. Examples of retroviruses include avian leukosis-sarcoma, mammalian C-type, B-type viruses, D-type viruses, HTLV-BLV group, lentivirus, and spumavirus (Coffin, J. M., Retroviridae: The viruses and their replication, In Fundamental Virology, Third Edition, B. N. Fields, et al., Eds., Lippincott-Raven Publishers, Philadelphia, 1996).

"Retroviruses" are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses.

"Lentiviral vector," as used herein, refers to HIV-based lentiviral vectors for gene delivery, which can be integrative or non-integrative, have relatively large packaging capacity, and can transduce a range of different cell types. Lentiviral vectors are usually generated following transient transfection of three or more plasmids (packaging, envelope, and transfer) into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells. "Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV). Other examples include lentivirus vectors derived from HIV-2, FIV, equine infectious anemia virus, SIV, and Maedi-Visna virus (ovine lentivirus).

Methods of using retroviral and lentiviral viral vectors and packaging cells for transducing mammalian host cells with viral particles containing chimeric antigen receptor transgenes are known in the art and have been previous described, for example, in U.S. Pat. No. 8,119,772; Walchli, et al., PLoS One 6:327930, 2011; Zhao, et al., J. Immunol. 174:4415, 2005; Engels, et al., Hum. Gene Ther. 14: 1155, 2003; Frecha, et al., Mol. Ther. 75: 1748, 2010; and Verhoeyen, et al., Methods Mol. Biol. 506:91, 2009. Retroviral and lentiviral vector constructs and expression systems are also commercially available.

In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing TCR or CAR transgenes are known in the art and have been previous described, for example, in: U.S. Pat. No. 8,119,772; Walchli et al., PLoS One 6:327930, 2011; Zhao et al., J. Immunol. 174:4415, 2005; Engels et al., Hum. Gene Ther. 14:1155, 2003; Frecha et al., Mol. Ther. 18:1748, 2010; and Verhoeyen et al., Methods Mol. Biol. 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., Gene Ther. 5:1517, 1998).

Other vectors developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as Sleeping Beauty or other transposon vectors).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

In certain embodiments, the polynucleotide encoding a Msln-specific binding protein may be operatively linked to one or more certain elements of a vector. For example, polynucleotide sequences that are needed to effect the expression and processing of coding sequences to which they are ligated may be operatively linked. Expression control sequences may include appropriate transcription initiation, termination, promoter, and enhancer sequences; efficient RNA processing signals such as splicing and poly-adenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest. In some embodiments, a viral or plasmid vector further includes a transduction marker (e.g., green fluorescent protein, tEGFR, tCD19, tNGFR, etc.).

In certain embodiments, a vector is capable of delivering a polynucleotide construct to a host cell (e.g., a hematopoietic progenitor cell or a human immune system cell). In specific embodiments, a vector is capable of delivering a construct to human immune system cell, such as, for example, a CD4+ T cell, a CD8+ T cell, a CD4– CD8– double negative T cell, a γδ T cell, a natural killer cell, a dendritic cell, or any combination thereof. In further embodiments, a vector is capable of delivering a construct to a naïve T cell, a central memory T cell, a stem cell memory T cell, an effector memory T cell, or any combination thereof. In some embodiments, a vector that encodes a construct of the present disclosure may further comprise a polynucleotide that encodes a nuclease that can be used to perform a chromosomal knockout in a host cell (e.g., a CRISPR-Cas endonuclease or another endonuclease as disclosed herein) or that can be used to deliver a therapeutic transgene or portion thereof to a host cell in a gene therapy replacement or gene repair therapy. Alternatively, a nuclease used for a chromosomal knockout or a gene replacement or gene repair therapy can be delivered to a host cell independent of a vector that encodes a construct of this disclosure.

Construction of an expression vector that is used for recombinantly producing a Msln-specific binding protein can be accomplished by using any suitable molecular biology engineering techniques known in the art, including the use of restriction endonuclease digestion, ligation, transformation, plasmid purification, and DNA sequencing, for example as described in Sambrook, et al. (1989 and 2001 editions; Molecular Cloning: A Laboratory Manual, Cold Spring Harbor Laboratory Press, NY) and Ausubel, et al. (Current Protocols in Molecular Biology (2003)). To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the protein or peptide of interest.

In certain embodiments, nucleic acid molecules encoding a binding protein specific for a $Msln_{20-28}$ or $Msln_{530-538}$ peptide are used to transfect/transduce a host cell (e.g., T cells) for use in adoptive transfer therapy. Advances in TCR sequencing have been described (e.g., Robins, et al, 2009 Blood 114:4099; Robins, et al, 2010 Sci. Translat. Med. 2:47ra64, PMID: 20811043; Robins, et al. 2011 (Sep. 10) J. 1 mm. Meth. Epub ahead of print, PMID: 21945395; and Warren, et al., 2011 Genome Res. 21:790) and may be employed in the course of practicing the embodiments according to the present disclosure.

Similarly, methods for transfecting/transducing T cells with desired nucleic acids have been described (e.g., US 2004/0087025) as have adoptive transfer procedures using T cells of desired antigen-specificity (e.g., Schmitt, et al., Hum. Gen. 20: 1240, 2009; Dossett, et al., Mol. Ther. 77:742, 2009; Till et al, Blood 112:2261, 2008; Wang, et al., Hum. Gene Ther. 18:112, 2007; Kuball et al, Blood 109: 2331, 2007; US 2011/0243972; US 2011/0189141; and Leen, et al., Ann. Rev. Immunol. 25:243, 2007), such that adaptation of these methodologies to the presently disclosed embodiments is contemplated, based on the teachings herein, including those directed to binding proteins specific for a $Msln_{20-28}$ (SEQ ID NO:31) or $Msln_{530-538}$ (SEQ ID NO:32) peptide complexed with an HLA receptor.

The recombinant expression vectors may include, for example, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson, et al., Mol. Cell. Biol. 72:1043, (1992); Todd et al, J. Exp. Med. 177: 1663, (1993); and Penix, et al., J. Exp. Med. 775: 1483, (1993)).

Also provided are recombinant (e.g., modified) host cells that encode (e.g., comprise a heterologous polynucleotide encoding) and/or express a Msln-specific binding protein as disclosed herein. In some embodiments, the host cell may be a hematopoietic progenitor cell or an immune system cell as disclosed herein, such as a human immune system cell. In any of the presently disclosed embodiments, the immune system cell is a CD4+ T cell, a CD8+ T cell, a CD4– CD8– double negative T cell, a γδ T cell, a natural killer cell, a natural kill T cell, a macrophage, a dendritic cell, or any combination thereof. Additionally, the T cell may be a naïve T cell, a central memory T cell, an effector memory T cell, a stem cell memory T cell, or any combination thereof. In certain embodiments, the host cell is modified to comprise or contain the heterologous polynucleotide using a vector as disclosed herein.

The recombinant host cell may be allogeneic, syngeneic, or autologous (e.g., to a subject that receives the host cell for a therapy). In certain embodiments wherein the host cell encodes an endogenous TCR, the heterologous binding protein or TCR expressed by the T cell is capable of more efficiently associating with a CD3 protein as compared to an endogenous TCR. In some embodiments, the Msln-specific binding protein expressed by a host T cell is able to associate with the CD3 complex and shows functional surface expression and immune activity, e.g., production of cytokines and/or killing of antigen-expressing target cells. In certain embodiments, the Msln-specific binding protein may have higher cell surface expression as compared to an endogenous TCR.

In any of the presently disclosed embodiments, a host cell, such as a host immune cell, can comprise a chromosomal gene knockout of an endogenous immune cell protein, such as, for example, PD-1, TIM3, LAG3, CTLA4, TIGIT, an HLA component, or a TCR component, or any combination thereof. As used herein, the term "chromosomal gene knockout" refers to a genetic alteration or introduced inhibitory agent in a host cell that prevents (e.g., reduces, delays, suppresses, or abrogates) production, by the host cell, of a functionally active endogenous polypeptide product. Alterations resulting in a chromosomal gene knockout can include, for example, introduced nonsense mutations (including the formation of premature stop codons), missense mutations, gene deletion, and strand breaks, as well as the heterologous expression of inhibitory nucleic acid molecules that inhibit endogenous gene expression in the host cell.

A chromosomal gene knockout can be confirmed directly by DNA sequencing of the host immune cell following use of the knockout procedure or agent. Chromosomal gene knockouts can also be inferred from the absence of gene expression (e.g., the absence of an mRNA or polypeptide product encoded by the gene) following the knockout.

In certain embodiments, a chromosomal gene knock-out or gene knock-in is made by chromosomal editing of a host cell. Chromosomal editing can be performed using, for example, endonucleases. As used herein "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for a donor gene "knock-in", for target gene "knock-out", and optionally to inactivate a target gene through a donor gene knock in or target gene knock out event. NHEJ is an error-prone repair process that often results in changes to the DNA sequence at the site of the cleavage, e.g., a substitution, deletion, or addition of at least one nucleotide. NHEJ may be used to "knock-out" a target gene. Examples of endonucleases include zinc finger nucleases, TALE-nucleases, CRISPR-Cas nucleases, meganucleases, and megaTALs.

As used herein, a "zinc finger nuclease" (ZFN) refers to a fusion protein comprising a zinc finger DNA-binding domain fused to a non-specific DNA cleavage domain, such as a FokI endonuclease. Each zinc finger motif of about 30 amino acids binds to about 3 base pairs of DNA, and amino acids at certain residues can be changed to alter triplet sequence specificity (see, e.g., Desjarlais et al., Proc. Natl. Acad. Sci. 90:2256-2260, 1993; Wolfe et al., J. Mol. Biol. 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent 12th and 13th amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD (histine-aspartic acid) sequence at positions 12 and 13 of the TALE leads to the TALE binding to cytosine (C), NG (asparagine-glycine) binds to a T nucleotide, NI (asparagine-isoleucine) to A, NN (asparagine-asparagine) binds to a G or A nucleotide, and NG (asparagine-glycine) binds to a T nucleotide. Non-canonical (atypical) RVDs are also known (see, e.g., U.S. Patent Publication No. US 2011/0301073, which atypical RVDs are incorporated by reference herein in their entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., Science 337:816-21, 2012). Further, the region of the guide RNA complementary to the target site can be altered or programed to target a desired sequence (Xie et al., PLOS One 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; each of which is incorporated by reference). In certain embodiments, a gene knockout comprises an insertion, a deletion, a mutation or a combination thereof, and made using a CRISPR/Cas nuclease system.

Exemplary gRNA sequences and methods of using the same to knock out endogenous genes that encode immune cell proteins include those described in Ren et al., Clin. Cancer Res. 23(9):2255-2266 (2017), the gRNAs, CAS9 DNAs, vectors, and gene knockout techniques of which are hereby incorporated by reference in their entirety.

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG (SEQ ID NO:121), GIY-YIG (SEQ ID NO:122), HNH, His-Cys box and PD-(D/E)XK (SEQ ID NO:123). Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., Nucleic Acids Res. 25:3379-3388, 1997; Dujon et al., Gene 82:115-118, 1989; Perler et al., Nucleic Acids Res. 22:1125-1127, 1994; Jasin, Trends Genet. 12:224-228, 1996; Gimble et al., J. Mol. Biol. 263:163-180, 1996; Argast et al., J. Mol. Biol. 280:345-353, 1998).

In certain embodiments, naturally-occurring meganucleases may be used to promote site-specific genome modification of a target selected from PD-1, LAG3, TIM3, CTLA4, TIGIT, an HLA-encoding gene, or a TCR component-encoding gene.

In other embodiments, an engineered meganuclease having a novel binding specificity for a target gene is used for site-specific genome modification (see, e.g., Porteus et al., Nat. Biotechnol. 23:967-73, 2005; Sussman et al., J. Mol. Biol. 342:31-41, 2004; Epinat et al., Nucleic Acids Res. 31:2952-62, 2003; Chevalier et al., Molec. Cell 10:895-905, 2002; Ashworth et al., Nature 441:656-659, 2006; Paques et al., Curr. Gene Ther. 7:49-66, 2007; U.S. Patent Publication Nos. US 2007/0117128; US 2006/0206949; US 2006/0153826; US 2006/0078552; and US 2004/0002092). In further embodiments, a chromosomal gene knockout is generated using a homing endonuclease that has been modified with modular DNA binding domains of TALENs to make a fusion protein known as a megaTAL. MegaTALs can be utilized to not only knock-out one or more target genes, but to also introduce (knock in) heterologous or exogenous polynucleotides when used in combination with an exogenous donor template encoding a polypeptide of interest.

In certain embodiments, a chromosomal gene knockout comprises an inhibitory nucleic acid molecule that is introduced into a host cell (e.g., an immune cell) comprising a heterologous polynucleotide encoding an antigen-specific receptor that specifically binds to a tumor associated antigen, wherein the inhibitory nucleic acid molecule encodes a target-specific inhibitor and wherein the encoded target-specific inhibitor inhibits endogenous gene expression (i.e., of PD-1, TIM3, LAG3, CTLA4, TIGIT, an HLA component, or a TCR component, or any combination thereof) in the host immune cell.

In certain embodiments, a binding protein of interest may be knocked-in to a host cell; e.g., using any of the presently disclosed techniques or reagents useful for knocking a polynucleotide of interest into a host cell. In some embodiments, a polynucleotide encoding a binding protein is knocked-in to a host cell and does not integrate into an endogenous chromosome, such as in the cell nucleus. In some embodiments, a polynucleotide encoding a binding protein is knocked-in to a host cell at an endogenous gene locus, optionally disrupting a coding sequence of the endogenous locus. In certain embodiments, a polynucleotide encoding a binding protein is knocked-in to an endogenous TCR locus, thereby knocking-out endogenous TCR and knocking-in the protein of interest. See, e.g., Eyquem et al., Nature 543(7643):113-117 (2017).

In some embodiments, a polynucleotide encoding a mesothelin-specific binding protein (e.g., a polypeptide comprising, consisting, or consisting essentially of the amino acid sequence set forth in any one or more of SEQ ID Nos:6-8, 14-16, 22-24, 28-40, 78-110, 118, 119) is knocked-in to a host cell. Binding proteins herein include a TCR alpha chain variable domain (Vα) and a TCR beta chain variable domain (Vβ). In any of the presently disclosed embodiments, a mesothelin-specific binding protein is capable of specifically binding to a mesothelin peptide:HLA complex, such as a mesothelin peptide:HLA-A*02:01 complex.

In some embodiments, gene knock-in may be used to introduce a polynucleotide encoding a binding protein that is capable of specifically binding to a mesothelin peptide antigen as described herein (e.g., a peptide comprising, consisting, or consisting essentially of an amino acid sequence having at least about 85% (i.e., at least about 86%, 85%, 88%, 89% 90%, 91%, 92%, 93%, 94%, 95%, 96%, 97%, 98%, 99%, or more) identity to the amino acid sequence set forth in any one or more of SEQ ID Nos:6-8, 14-16, 22-24, 28-40, 78-110, 118, or 119).

In certain embodiments, a polynucleotide encoding a mesothelin-specific binding protein (e.g., a TCR) is knocked-in to a host cell, and the host cell further comprises a polynucleotide encoding a different binding protein. In some embodiments, the different binding protein is heterologous to the host cell. In other embodiments, the different binding protein is endogenous to the host cell. In certain embodiments, the polynucleotide encoding the different binding protein is knocked-in to the host cell. In certain embodiments, the different binding protein is a binding protein specific for a different antigen (e.g., a different Msln antigen, or an antigen from a different protein or target, such as, for example, BCMA, CA19-9, BRAF, CD3, CEACAM6, c-Met, EGFR, EGFRvIII, ErbB2, ErbB3, ErbB4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A (e.g., including MAGE-A1, MAGE-A3, and MAGE-A4), KRAS, HER2, NY-ESO-1, PSMA, RANK, ROR1, TNFRSF4, CD40, CD137, TWEAK-R, HLA, tumor- or pathogen-associated peptide bound to HLA, hTERT peptide bound to HLA, tyrosinase peptide bound to HLA, LTβR, LIFRβ, LRP5, MUC1, OSMRβ, TCRα, TCRβ, CD19, CD20, CD22, CD25, CD28, CD30, CD33, CD52, CD56, CD79a, CD79b, CD80, CD81, CD86, CD123, CD171, CD276, B7H4, TLR7, TLR9, PTCH1, WT-1, HA1-H, Robol, α-fetoprotein (AFP), Frizzled, OX40, PRAME, and SSX-2, or the like). For example, a host cell can comprise a knocked-in polynucleotide encoding a binding protein that specifically binds to a Msln antigen:HLA complex and a (e.g., knocked-in) polynucleotide encoding a binding protein (e.g., a TCR or a CAR) that specifically binds to a CA19-9 antigen.

In certain embodiments, a host immune cell encoding and/or expressing a Msln-specific binding protein of the present disclosure is capable of preferentially migrating to or localizing in vivo in a target tissue that expresses a cognate Msln antigen, such as a tumor, but is present at a statistically significant reduced amount in non-adjacent tissue of the same type. By way of illustration, a host immune cell may be present in a lung tumor (e.g., as determined using deep sequencing for the TCR V-region of the encoded binding protein), but is present at a lower level, or not at all, in tissue of the same lung that is not adjacent to the tumor. In some embodiments, non-adjacent tissue comprises or refers to tissue that is removed from a diseased or malignant tissue by at least 3 cm.

In certain embodiments, a host cell is enriched in a composition of cells, such as may be administered to a subject. As used herein, "enriched" or "depleted" with respect to amounts of cell types in a mixture refers to an increase in the number of the "enriched" type, a decrease in the number of the "depleted" cells, or both, in a mixture of cells resulting from one or more enriching or depleting processes or steps. Thus, depending upon the source of an original population of cells subjected to an enriching process, a mixture or composition may contain 30%, 35%, 40%, 45%, 50%, 55%, 60%, 65%, 70%, 75%, 80%, 85%, 90%, 91%, 92%, 93%, 94%, 95%, 96%, 97%, 98%, or 99% or more (in number or count) of the "enriched" cells. Cells subjected to a depleting process can result in a mixture or composition containing 50%, 45%, 40%, 35%, 30%, 25%, 20%, 15%, 10%, 9%, 8%, 7%, 6%, 5%, 4%, 3%, 2%, or 1% percent or less (in number or count) of the "depleted" cells. In certain embodiments, amounts of a certain cell type in a mixture will be enriched and amounts of a different cell type will be depleted, such as enriching for CD4+ cells while depleting CD8+ cells, or enriching for CD62L+ cells while depleting CD62L– cells, or combinations thereof.

Uses

In another aspect, the present disclosure provides methods treating a subject in need thereof (i.e., having or suspected of having a disease or disorder associated with a mesothelin antigen by administering to the subject an effective amount of a composition (e.g., binding protein, recombinant host cell, polynucleotide, vector, or related composition) as described herein. Also provided are such compositions for use in treating such a disease, or for the manufacture of a medicament for the treatment of such a disease. Such diseases include various forms of proliferative or hyperproliferative disorders, such as solid cancers and hematological malignancies.

"Treat" or "treatment" or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising a host cell expressing a binding protein of the present disclosure, and optionally an adjuvant, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease; stabilization of disease state; delay of disease progression; remission; survival; prolonged survival; or any combination thereof.

As used herein, the terms "adoptive immune therapy" or "adoptive immunotherapy" and "adoptive cell therapy" refer to administration of naturally occurring or genetically engineered, disease-antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

A "therapeutically effective amount" or "effective amount" of a binding protein or host cell of this disclosure, refers to an amount of binding proteins or host cells sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient or a cell expressing a single active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially or simultaneously. A combination may also be a cell expressing more than one active ingredient, such as two different binding proteins that specifically bind an antigen, or a fusion protein of the present disclosure.

As used herein, "statistically significant" refers to a p-value of 0.050 or less when calculated using the Student's t-test and indicates that it is unlikely that a particular event or result being measured has arisen by chance.

As used herein, "hyperproliferative disorder" refers to excessive growth or proliferation as compared to a normal or undiseased cell. Exemplary hyperproliferative disorders include tumors, cancers, neoplastic tissue, carcinoma, sarcoma, malignant cells, pre malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like). Certain diseases that involve abnormal or excessive growth that occurs more slowly than in the context of a hyperproliferative disease can be referred to as "proliferative diseases", and include certain tumors, cancers, neoplastic tissue, carcinoma, sarcoma, malignant cells, pre malignant cells, as well as non-neoplastic or non-malignant disorders.

Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer.

The presently disclosed binding proteins, host cells, polynucleotides, vectors, and compositions are useful to treat or manufacture a medicament for the treatment a cancer wherein a $Msln_{20-28}$ peptide is expressed on a tumor cell of the cancer, and/or wherein a $Msln_{530-538}$ peptide is expressed on a tumor cell of the cancer; exemplary cancers for treatment include mesothelioma, pancreatic cancer, ovarian cancer, and lung cancer.

In certain embodiments, the presently disclosed binding proteins, host cells, polynucleotides, vectors, and compositions are useful for treating and/or in the manufacture of a medicament for treating a cancer, such as a solid cancer or a hematological malignancy. In certain embodiments, the solid cancer is selected from or comprises biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

In certain embodiments, a cancer treatable according to the presently disclosed methods and uses comprises a carcinoma, a sarcoma, a glioma, a lymphoma, a leukemia, a myeloma, or any combination thereof. In certain embodiments, cancer comprises a cancer of the head or neck, melanoma, pancreatic cancer, cholangiocarcinoma, hepatocellular cancer, breast cancer including triple-negative breast cancer (TNBC), gastric cancer, non-small-cell lung cancer, prostate cancer, esophageal cancer, mesothelioma, small-cell lung cancer, colorectal cancer, glioblastoma, or any combination thereof. In certain embodiments, a cancer comprises Askin's tumor, sarcoma botryoides, chondrosarcoma, Ewing's sarcoma, PNET, malignant hemangioendothelioma, malignant schwannoma, osteosarcoma, alveolar soft part sarcoma, angiosarcoma, cystosarcoma phyllodes, dermatofibrosarcoma protuberans (DFSP), desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, undifferentiated pleomorphic sarcoma, malignant peripheral nerve sheath tumor (MPNST), neurofibrosarcoma, rhabdomyosarcoma, synovial sarcoma, undifferentiated pleomorphic sarcoma, squamous cell carcinoma, basal cell carcinoma, adenocarcinoma, linitis plastic, vipoma, cholangiocarcinoma, hepatocellular carcinoma, adenoid cystic carcinoma, renal cell carcinoma, Grawitz tumor, ependymoma, astrocytoma, oligodendroglioma, brainstem glioma, optice nerve glioma, a mixed glioma, Hodgkin's lymphoma, a B-cell lymphoma, non-Hodgkin's lymphoma (NHL), Burkitt's lymphoma, small lymphocytic lymphoma (SLL), diffuse large B-cell lymphoma, follicular lymphoma, immunoblastic large cell lymphoma, precursor B-lymphoblastic lymphoma, and mantle cell lymphoma, Waldenström's macroglobulinemia, CD37+ dendritic cell lymphoma, lymphoplasmacytic lymphoma, splenic marginal zone lymphoma, extra-nodal marginal zone B-cell lymphoma of mucosa-associated (MALT) lymphoid tissue, nodal marginal zone B-cell lymphoma, mediastinal (thymic) large B-cell lymphoma, intravascular large B-cell lymphoma, primary effusion lymphoma, adult T-cell lymphoma, extranodal NK/T-cell lymphoma, nasal type, enteropathy-associated T-cell lymphoma, hepatosplenic T-cell lymphoma, blastic NK cell lymphoma, Sezary syndrome, angioimmunoblastic T cell lymphoma, anaplastic large cell lymphoma, or any combination thereof.

In certain embodiments, the cancer comprises a solid tumor. In some embodiments, the solid tumor is a sarcoma or a carcinoma. In certain embodiments, the solid tumor is selected from: chondrosarcoma; fibrosarcoma (fibroblastic sarcoma); Dermatofibrosarcoma protuberans (DF SP); osteosarcoma; rhabdomyosarcoma; Ewing's sarcoma; a gastrointestinal stromal tumor; Leiomyosarcoma; angiosarcoma (vascular sarcoma); Kaposi's sarcoma; liposarcoma; pleomorphic sarcoma; or synovial sarcoma.

In certain embodiments, the solid tumor is selected from a lung carcinoma (e.g., Adenocarcinoma, Squamous Cell Carcinoma (Epidermoid Carcinoma); Squamous cell carcinoma; Adenocarcinoma; Adenosquamous carcinoma; anaplastic carcinoma; Large cell carcinoma; Small cell carcinoma; a breast carcinoma (e.g., Ductal Carcinoma in situ (non-invasive), Lobular carcinoma in situ (non-invasive), Invasive Ductal Carcinoma, Invasive lobular carcinoma, Non-invasive Carcinoma); a liver carcinoma (e.g., Hepatocellular Carcinoma, Cholangiocarcinomas or Bile Duct Cancer); Large-cell undifferentiated carcinoma, Bronchioalveolar carcinoma); an ovarian carcinoma (e.g., Surface epithelial-stromal tumor (Adenocarcinoma) or ovarian epithelial carcinoma (which includes serous tumor, endometrioid tumor and mucinous cystadenocarcinoma), Epidermoid (Squamous cell carcinoma), Embryonal carcinoma and choriocarcinoma (germ cell tumors)); a kidney carcinoma (e.g., Renal adenocarcinoma, hypernephroma, Transitional cell carcinoma (renal pelvis), Squamous cell carcinoma, Bellini duct carcinoma, Clear cell adenocarcinoma, Transitional cell carcinoma, Carcinoid tumor of the renal pelvis); an adrenal carcinoma (e.g., Adrenocortical carcinoma), a carcinoma of the testis (e.g., Germ cell carcinoma (Seminoma, Choriocarcinoma, Embryonal carcinoma, Teratocarcinoma), Serous carcinoma); Gastric carcinoma (e.g., Adenocarcinoma); an intestinal carcinoma (e.g., Adenocarcinoma of the duodenum); a colorectal carcinoma; or a skin carcinoma (e.g., Basal cell carcinoma, Squamous cell carcinoma). In certain embodiments, the solid tumor is an ovarian carcinoma, an ovarian epithelial carcinoma, a cervical adenocarcinoma or small cell carcinoma, a pancreatic carcinoma, a colorectal carcinoma (e.g., an adenocarcinoma or squamous cell carcinoma), a lung carcinoma, a breast ductal carcinoma, or an adenocarcinoma of the prostate.

In any of the presently disclosed embodiments, the host cell is an allogeneic cell, a syngeneic cell, or an autologous cell. Subjects that can be treated by the present invention are, in general, human and other primate subjects, such as monkeys and apes for veterinary medicine purposes. In any of the aforementioned embodiments, the subject may be a human subject. The subjects can be male or female and can be any suitable age, including infant, juvenile, adolescent, adult, and geriatric subjects. Cells according to the present disclosure may be administered in a manner appropriate to the disease, condition, or disorder to be treated as determined by persons skilled in the medical art. In any of the above embodiments, a cell comprising a fusion protein as described herein is administered intravenously, intraperitoneally, intratumorally, into the bone marrow, into a lymph node, or into the cerebrospinal fluid so as to encounter the tagged cells to be ablated. An appropriate dose, suitable duration, and frequency of administration of the compositions will be determined by such factors as a condition of the patient; size, type, and severity of the disease, condition, or disorder; the undesired type or level or activity of the tagged cells, the particular form of the active ingredient; and the method of administration.

In general, an appropriate dosage and treatment regimen provides the active molecules or cells in an amount sufficient to provide a benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine.

For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

In the case of an adoptive cell therapy, an effective dose is an amount of host cells encoding or expressing a Msln-specific binding protein used in adoptive transfer that is capable of producing a clinically desirable result (i.e., a sufficient amount to induce or enhance a specific T cell immune response against cells expressing an Msln-specific antigen response, e.g., a cytotoxic T cell response, in a statistically significant manner) in a treated human or non-human mammal. In particular embodiments, T cell is a naïve T cell, a central memory T cell, a stem cell memory T cell, an effector memory T cell, or any combination thereof.

Also contemplated are pharmaceutical compositions (compositions) that comprise a Msln-specific binding protein, host (i.e., modified) immune cell, polynucleotide, or vector as disclosed herein and a pharmaceutically acceptable carrier, diluents, or excipient. The term "pharmaceutically acceptable excipient or carrier" or "physiologically acceptable excipient or carrier" refer to biologically compatible vehicles, e.g., physiological saline, which are described in greater detail herein, that are suitable for administration to a human or other non-human mammalian subject and generally recognized as safe or not causing a serious adverse event. Suitable excipients include water, saline, dextrose, glycerol, or the like and combinations thereof. In embodiments, compositions comprising fusion proteins or host cells as disclosed herein further comprise a suitable infusion media. Suitable infusion media can be any isotonic medium formulation, typically normal saline, Normosol R (Abbott) or Plasma-Lyte A (Baxter), 5% dextrose in water, Ringer's lactate can be utilized. An infusion medium can be supplemented with human serum albumin or other human serum components.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity).

Also provided herein are unit doses that comprise an effective amount of a modified immune cell or of a composition comprising the modified immune cell. In certain embodiments, a unit dose comprises (i) a composition comprising at least about 30%, at least about 40%, at least about 50%, at least about 60%, at least about 70%, at least about 80%, at least about 85%, at least about 90%, or at least about 95% modified CD4+ T cells, combined with (ii) a composition comprising at least about 30%, at least about 40%, at least about 50%, at least about 60%, at least about 70%, at least about 80%, at least about 85%, at least about 90%, or at least about 95% modified CD8+ T cells, in about a 1:1 ratio, wherein the unit dose contains a reduced amount or substantially no naïve T cells (i.e., has less than about 50%, less than about 40%, less than about 30%, less than about 20%, less than about 10%, less than about 5%, or less then about 1% the population of naïve T cells present in a unit dose as compared to a patient sample having a comparable number of PBMCs).

In some embodiments, a unit dose comprises (i) a composition comprising at least about 50% modified CD4+ T cells, combined with (ii) a composition comprising at least about 50% modified CD8+ T cells, in about a 1:1 ratio, wherein the unit dose contains a reduced amount or substantially no naïve T cells. In further embodiments, a unit dose comprises (i) a composition comprising at least about 60% modified CD4+ T cells, combined with (ii) a composition comprising at least about 60% modified CD8+ T cells, in about a 1:1 ratio, wherein the unit dose contains a reduced amount or substantially no naïve T cells. In still further embodiments, a unit dose comprises (i) a composition comprising at least about 70% engineered CD4+ T cells, combined with (ii) a composition comprising at least about 70% engineered CD8+ T cells, in about a 1:1 ratio, wherein the unit dose contains a reduced amount or substantially no naïve T cells. In some embodiments, a unit dose comprises (i) a composition comprising at least about 80% modified CD4+ T cells, combined with (ii) a composition comprising at least about 80% modified CD8+ T cells, in about a 1:1 ratio, wherein the unit dose contains a reduced amount or substantially no naïve T cells. In some embodiments, a unit dose comprises (i) a composition comprising at least about 85% modified CD4+ T cells, combined with (ii) a composition comprising at least about 85% modified CD8+ T cells, in about a 1:1 ratio, wherein the unit dose contains a reduced amount or substantially no naïve T cells. In some embodiments, a unit dose comprises (i) a composition comprising at least about 90% modified CD4+ T cells, combined with (ii) a composition comprising at least about 90% modified CD8+ T cells, in about a 1:1 ratio, wherein the unit dose contains a reduced amount or substantially no naïve T cells.

The amount of cells in a composition or unit dose is at least one cell (for example, one recombinant CD8+ T cell subpopulation (e.g., optionally comprising memory and/or naïve CD8+ T cells); one recombinant CD4+ T cell subpopulation (e.g., optionally comprising memory and/or naïve CD4+ T cells)) or is more typically greater than $10^2$ cells, for example, up to $10^4$, up to $10^5$, up to $10^6$, up to $10^7$, up to $10^8$, up to $10^9$, or more than $10^{10}$ cells. In certain embodiments, the cells are administered in a range from about $10^4$ to about $10^{10}$ cells/m$^2$, preferably in a range of about $10^5$ to about $10^9$ cells/m$^2$. In some embodiments, an administered dose comprises up to about $3.3\times10^5$ cells/kg. In some embodiments, an administered dose comprises up to about $1\times10^6$ cells/kg. In some embodiments, an administered dose comprises up to about $3.3\times10^6$ cells/kg. In some embodiments, an administered dose comprises up to about $1\times10^7$ cells/kg. In certain embodiments, a recombinant host cell is administered to a subject at a dose comprising up to about $5\times10^4$ cells/kg, $5\times10^5$ cells/kg, $5\times10^6$ cells/kg, or up to about $5\times10^7$ cells/kg. In certain embodiments, a recombinant host cell is administered to a subject at a dose comprising at least about $5\times10^4$ cells/kg, $5\times10^5$ cells/kg, $5\times10^6$ cells/kg, or up to about $5\times10^7$ cells/kg. The number of cells will depend upon the ultimate use for which the composition is intended as well the type of cells included therein. For example, cells modified to express or encode a binding protein will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mls or less, 250 mls or less, or 100 mls or less. In embodiments, the density of the desired cells is typically greater than $10^4$ cells/ml and generally is greater than $10^7$ cells/ml, generally $10^8$ cells/ml or greater. The cells may be administered as a single infusion or in multiple infusions over a range of time. In certain embodiments, a clinically relevant number of cells can be apportioned into multiple infusions that cumulatively equal or exceed $10^6$, $10^7$, $10^8$, $10^9$, $10^{10}$, or $10^{11}$ cells. In certain embodiments, a unit dose of the cells can be co-administered with (e.g., simultaneously or contemporaneously with) hematopoietic stem cells from an allogeneic donor. In some embodiments, one or more of the cells comprised in the unit dose is autologous to the subject.

It will be appreciated that a unit dose, composition, or treatment regimen of the present disclosure may comprise a Msln-specific binding protein or recombinant host cell as described herein, and also comprise an (e.g., modified) immune cell expressing a binding protein specific for a different antigen (e.g., a different Msln antigen, or an antigen from a different protein or target, such as, for example, BCMA, CA19-9, BRAF, CD3, CEACAM6, c-Met, EGFR, EGFRvIII, ErbB2, ErbB3, ErbB4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A (e.g., including MAGE-A1, MAGE-A3, and MAGE-A4), KRAS, HER2, NY-ESO-1, PSMA, RANK, ROR1, TNFRSF4, CD40, CD137, TWEAK-R, HLA, tumor- or pathogen-associated peptide bound to HLA, hTERT peptide bound to HLA, tyrosinase peptide bound to HLA, LTβR, LRP5, MUC1, OSMRβ, TCRα, TCRβ, CD19, CD20, CD22, CD25, CD28, CD30, CD33, CD52, CD56, CD79a, CD79b, CD80, CD81, CD86, CD123, CD171, CD276, B7H4, TLR7, TLR9, PTCH1, WT-1, HA1-H, Robol, α-fetoprotein (AFP), Frizzled, OX40, PRAME, and SSX-2, or the like). For example, a unit dose or therapeutic regimen can comprise modified CD4+ T cells expressing a binding protein that specifically binds to a Msln antigen:HLA complex and modified CD4+ T cells (and/or modified CD8+ T cells) expressing a binding protein (e.g., a TCR or a CAR) that specifically binds to a CA19-9 antigen.

In any of the embodiments described herein, a unit dose comprises equal, or approximately equal, numbers of engineered CD45RA– CD3+CD8+ and modified CD45RA– CD3+CD4+ TM cells.

The pharmaceutical compositions described herein may be presented in unit-dose or multi-dose containers, such as sealed ampoules or vials. Such containers may be frozen to preserve the stability of the formulation until infusion into the patient.

As used herein, administration of a composition refers to delivering the same to a subject, regardless of the route or mode of delivery, such as, for example, intravenous, oral vaginal, rectal, subcutaneous, or the like. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., recombinant host cells with one or more cytokines; immunosuppressive therapy such as calcineurin inhibitors, corticosteroids, microtubule inhibitors, low dose of a mycophenolic acid prodrug, or any combination thereof).

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol, or polyethylene glycols in mixtures with water. Aqueous solutions or suspensions may further include one or more buffering agents, such as sodium acetate, sodium citrate, sodium borate, or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In certain embodiments, a plurality of doses of a composition described herein (e.g., a recombinant host cell) is administered to the subject, which may be administered at intervals between administrations of about two to about four weeks.

Treatment or prevention methods of this disclosure may be administered to a subject as part of a treatment course or regimen, which may comprise additional treatments prior to, or after, administration of the instantly disclosed unit doses, cells, or compositions. For example, in certain embodiments, a subject receiving a unit dose of the (e.g., a recombinant host cell is receiving or had previously received a hematopoietic cell transplant (HCT; including myeloablative and non-myeloablative HCT). Techniques and regimens for performing HCT are known in the art and can comprise transplantation of any suitable donor cell, such as a cell derived from umbilical cord blood, bone marrow, or peripheral blood, a hematopoietic stem cell, a mobilized stem cell, or a cell from amniotic fluid. Accordingly, in certain embodiments, a recombinant host cell of the present disclosure can be administered with or shortly after hematopoietic stem cells in a modified HCT therapy. In some embodiments, the HCT comprises a donor hematopoietic cell comprising a chromosomal knockout of a gene that encodes an HLA component, a chromosomal knockout of a gene that encodes a TCR component, or both.

The level of a CTL immune response may be determined by any one of numerous immunological methods described herein and routinely practiced in the art. The level of a CTL immune response may be determined prior to and following administration of any one of the herein described Msln-specific binding proteins (or a host cell encoding and/or expressing the same) or immunogenic compositions. Cytotoxicity assays for determining CTL activity may be performed using any one of several techniques and methods routinely practiced in the art (see, e.g., Henkart, et al., "Cytotoxic T-Lymphocytes" in Fundamental Immunology, Paul (ed.) (2003 Lippincott Williams & Wilkins, Philadelphia, PA), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a Msln peptide as described herein. A "biological sample" as used herein may be a blood sample (from which serum or plasma may be prepared), biopsy specimen, body fluids (e.g., lung lavage, ascites, mucosal washings, synovial fluid, etc.), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

In some embodiments, the subject receiving the subject composition has previously received chemotherapy, such as a lymphodepleting chemotherapy. In further embodiments, the lymphodepleting chemotherapy comprises cyclophosphamide, fludarabine, anti-thymocyte globulin, oxaliplatin, or a combination thereof. In some embodiments, the subject composition has previously received radiation therapy, immunotherapy comprising a cytokine, an antibody, an antibody-drug conjugate, or Fc fusion protein, antisense nucleotide therapy, gene therapy, a vaccine, or surgery, or any combination thereof.

Methods and uses according to this disclosure may further include administering one or more additional agents to treat the disease or disorder in a combination therapy. For example, in certain embodiments, a combination therapy comprises administering a composition (e.g., any one or more binding protein, modified host cell encoding and/or expressing the same, polynucleotide, vector) with (concurrently, simultaneously, or sequentially) an immune checkpoint inhibitor. In some embodiments, a combination therapy comprises administering a composition of the present disclosure with an agonist of a stimulatory immune checkpoint agent. In further embodiments, a combination therapy comprises administering a composition of the present disclosure with a secondary therapy, such as chemotherapeutic agent, a radiation therapy, a surgery, an antibody, antibody drug conjugate, a cytokine, an antisense therapy, a gene therapy, a vaccine, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/2B4, HVEM, BTLA, CD160, TIM3, GALS, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise a composition of the present disclosure with one or more inhibitor of any one of the following immune suppression components, singly or in any combination.

Accordingly, in certain embodiments, treatment methods according to the present disclosure may further include administering a PD-1 inhibitor to the subject. The PD-1 inhibitor may include nivolumab (OPDIVO®); pembrolizumab (KEYTRUDA®); ipilimumab+nivolumab (YER-VOY®+OPDIVO®); cemiplimab; IBI-308; nivolumab+relatlimab; BCD-100; camrelizumab; JS-001; spartalizumab; tislelizumab; AGEN-2034; BGBA-333+tislelizumab; CBT-501; dostarlimab; durvalumab+MEDI-0680; JNJ-3283; pazopanib hydrochloride+pembrolizumab; pidilizumab; REGN-1979+cemiplimab; ABBV-181; ADUS-100+spartalizumab; AK-104; AK-105; AMP-224; BAT-1306; BI-754091; CC-90006; cemiplimab+REGN-3767; CS-1003; GLS-010; LZM-009; MEDI-5752; MGD-013; PF-06801591; Sym-021; tislelizumab+pamiparib; XmAb-20717; AK-112; ALPN-202; AM-0001; an antibody to antagonize PD-1 for Alzheimer's disease; BH-2922; BH-2941; BH-2950; BH-2954; a biologic to antagonize CTLA-4 and PD-1 for solid tumor; a bispecific monoclonal antibody to target PD-1 and LAG-3 for oncology; BLSM-101; CB-201; CB-213; CBT-103; CBT-107; a cellular immunotherapy+PD-1 inhibitor; CX-188; HAB-21; HEIS-COIII-003; IKT-202; JTX-4014; MCLA-134; MD-402; mDX-400; MGD-019; a monoclonal antibody to antagonize PDCD1 for oncology; a monoclonal antibody to antagonize PD-1 for oncology; an oncolytic virus to inhibit PD-1 for oncology; OT-2; PD-1 antagonist+ropeginterferon alfa-2b; PEGMP-7; PRS-332; RXI-762; STIR-1110; TSR-075; a vaccine to target HER2 and PD-1 for oncology; a vaccine to target PD-1 for oncology and autoimmune disorders; XmAb-23104; an antisense oligonucleotide to inhibit PD-1 for oncology; AT-16201; a bispecific monoclonal antibody to inhibit PD-1 for oncology; IMM-1802; monoclonal antibodies to antagonize PD-1 and CTLA-4 for solid tumor and hematological tumor; nivolumab biosimilar; a recombinant protein to agonize CD278 and CD28 and antagonize PD-1 for oncology; a recombinant protein to agonize PD-1 for autoimmune disorders and inflammatory disorders; SNA-01; SSI-361; YBL-006; AK-103; JY-034; AUR-012; BGB-108; drug to inhibit PD-1, Gal-9, and TIM-3 for solid tumor; ENUM-244C8; ENUM-388D4; MEDI-0680; monoclonal antibodies to antagonize PD-1 for metastatic melanoma and metastatic lung cancer; a monoclonal antibody to inhibit PD-1 for oncology; monoclonal antibodies to target CTLA-4 and PD-1 for oncology; a monoclonal antibody to antagonize PD-1 for NSCLC; monoclonal antibodies to inhibit PD-1 and TIM-3 for oncology; a monoclonal antibody to inhibit PD-1 for oncology; a recombinant protein to inhibit PD-1 and VEGF-A for hematological malignancies and solid tumor; a small molecule to antagonize PD-1 for oncology; Sym-016; inebilizumab+MEDI-0680; a vaccine to target PDL-1 and IDO for metastatic melanoma; an anti-PD-1 monoclonal antibody+a cellular immunotherapy for glioblastoma; an antibody to antagonize PD-1 for oncology; monoclonal antibodies to inhibit PD-1/PD-L1 for hematological malignancies and bacterial infections; a monoclonal antibody to inhibit PD-1 for HIV; and/or a small molecule to inhibit PD-1 for solid tumor.

In certain embodiments, a composition of the present disclosure is used in combination with a LAG3 inhibitor, such as LAG525, IMP321, IMP701, 9H12, BMS-986016, or any combination thereof.

In certain embodiments, a composition of the present disclosure is used in combination with an inhibitor of CTLA4. In particular embodiments, a composition is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a composition of the present disclosure is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., Cancer Res. 73:4820, 2013, as well as those described in U.S. Pat. No. 9,574,000 and PCT Patent Publication Nos. WO/201640724A1 and WO 2013/025779A1.

In certain embodiments, a composition of the present disclosure is used in combination with an inhibitor of CD244.

In certain embodiments, a composition of the present disclosure is used in combination with an inhibitor of BLTA, HVEM, CD160, or any combination thereof. Anti CD-160 antibodies are described in, for example, PCT Publication No. WO 2010/084158.

In certain embodiments, a composition of the present disclosure is used in combination with an inhibitor of TIM3.

In certain embodiments, a composition of the present disclosure is used in combination with an inhibitor of Gal9.

In certain embodiments, a composition of the present disclosure is used in combination with an inhibitor of adenosine signaling, such as a decoy adenosine receptor.

In certain embodiments, a composition of the present disclosure is used in combination with an inhibitor of A2aR.

In certain embodiments, a composition of the present disclosure is used in combination with an inhibitor of KIR, such as lirilumab (BMS-986015).

In certain embodiments, a composition of the present disclosure is used in combination with an inhibitor of an inhibitory cytokine (typically, a cytokine other than TGFβ) or Treg development or activity.

In certain embodiments, a composition of the present disclosure is used in combination with an IDO inhibitor, such as levo-1-methyl tryptophan, epacadostat (INCB024360; Liu et al., Blood 115:3520-30, 2010), ebselen (Terentis et al., Biochem. 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a composition of the present disclosure is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, a composition of the present disclosure is used in combination with an inhibitor of VISTA, such as CA-170 (Curis, Lexington, Mass.).

In certain embodiments, a composition of the present disclosure is used in combination with an inhibitor of TIGIT such as, for example, COM902 (Compugen, Toronto, Ontario Canada), an inhibitor of CD155, such as, for example, COM701 (Compugen), or both.

In certain embodiments, a composition of the present disclosure is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, a composition of the present disclosure is used in combination with a LAIR1 inhibitor.

In certain embodiments, a composition of the present disclosure n is used in combination with an inhibitor of CEACAM-1, CEACAM-3, CEACAM-5, or any combination thereof.

In certain embodiments, a composition of the present disclosure is used in combination with an agent that increases the activity (i.e., is an agonist) of a stimulatory immune checkpoint molecule. For example a composition can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a composition of the present disclosure with one or more agonist of a stimulatory immune checkpoint molecule, including any of the foregoing, singly or in any combination.

In certain embodiments, a combination therapy comprises a composition of the present disclosure and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a composition of the present disclosure and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art.

Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with a composition of the present disclosure. In further embodiments, a cytokine is administered sequentially, provided that the subject was administered the Msln-specific composition at least three or four times before cytokine administration. In certain embodiments, the cytokine is administered subcutaneously. In some embodiments, the subject may have received or is further receiving an immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

In certain embodiments, a combination therapy method comprises administering a composition of the present disclosure according to the present disclosure and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups:

anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, Pseudomonas exotoxin, Bordetella pertussis adenylate cyclase toxin, or diphtheria toxin, and caspase activators; and chromatin disruptors.

In some embodiments, therapy further comprises administering a T cell based vaccine may be used (see, e.g., PCT Publication No. WO 2017/192924, of which the T cell vaccines, immunogenicity enhancers, transposon expression constructs, and related methods are incorporated by reference in their entireties entirety). In certain embodiments, a vaccine compoistion comprises a liposomal RNA preparation (see, e.g., Kreiter, et al, Nature 520: 692, 2015, which preparations and methods of making the same are incorporated by reference herein in their entireties). In certain embodiments, an vaccine composition is used to prepare a peptide-pulsed dendritic cell or other antigen-presenting cell, which may be performed ex vivo, in vitro, or in vivo.

The present disclosure also provides a method for preparing antigen-pulsed antigen-presenting cells. In some embodiments, the methods comprise contacting in vitro, under conditions and for a time sufficient for antigen processing and presentation by antigen-presenting cells to take place, (i) a population of antigen-presenting cells that are immunocompatible with a subject, and (ii) a polynucleotide, peptide, immunogenic composition, and/or an expression vector as described herein, thereby obtaining antigen-pulsed antigen-presenting cells capable of eliciting an antigen-specific T-cell response to a Msln peptide as described herein. The method may further include contacting the antigen-pulsed antigen-presenting cells with one or a plurality of immunocompatible T cells under conditions and for a time sufficient to generate Msln-specific T cells.

In certain embodiments, the method further comprises transfecting or transducing a population of immune cells in vitro or ex vivo with a polynucleotide comprising the binding protein-encoding nucleic acid sequence so-determined, thereby obtaining a population of engineered Msln-specific immune cells, optionally in an amount effective to adoptively transfer or confer an antigen-specific T-cell response to a Msln antigen when the cells are administered to a subject.

In some embodiments, immune cell lines may be generated as described by Ho, et al. (see 2006 J Immunol Methods 310 (1-2):40-52)). For example, dendritic cells (DCs) may be derived from a plastic adherent fraction of PBMCs by culture over two days (days −2 to 0) in DC media (CELLGENIX™, Freiburg, Germany) supplemented with GM-CSF (800 U/ml) and IL-4 (1000 U/ml). On day −1, maturation cytokines TNFα (1100 U/ml), IL-1β (2000 U/ml), IL-6 (1000 U/ml) and PGE2 (1 μg/ml) can be added. On day 0, DCs can be harvested, washed, and pulsed with peptide (single peptides at 10 μg/ml or peptide pools at 2 μg/ml) over 2 to 4 hours in serum-free DC media. CD8 T cells can be isolated from PBMCs using anti-CD8 microbeads (MILTENYI BIOTEC™, Auburn, Calif.) and stimulated with DCs at an effector target (E:T) ratio of 1:5 to 1:10 in the presence of IL-21 (30 ng/ml). On day 3, IL-2 (12.5 U/ml), IL-7 (5 ng/ml), and IL-15 (5 ng/ml) can be added. Cells may be restimulated between days 10 and 14 using the plastic adherent faction of irradiated autologous PBMCs as antigen presenting cells (APCs) after being peptide-pulsed for two hours and in the presence of IL-21. After restimulation, cells can be supplemented from day 1 on with IL-2 (25 U/ml), IL-7 (5 ng/ml), and IL-15 (5 ng/ml). T-cell clones can be generated by plating cells at limiting dilution and expanding with TM-LCLs coated with OKT3 (ORTHO BIOTECH™, Bridgewater, N.J.) and allogeneic PBMCs as feeders (REP protocol) as described (see Ho, et al., 2006 J Immunol Methods 310 (1-2):40-52).

The present disclosure provides, among other embodiments, the following embodiments.

In one embodiment, there is a binding protein comprising a T cell receptor (TCR) α-chain variable domain ($V_\alpha$) and a TCR β-chain variable domain ($V_\beta$), wherein: (a) the $V_\alpha$ comprises the CDR3 amino acid sequence set forth in SEQ ID NO:39 or 37, and the $V_\beta$ optionally comprises an amino acid sequence having at least about 85% identity to the amino acid sequence set forth in SEQ ID NO:101 or 99; (b) the V_β comprises the CDR3 amino acid sequence set forth in SEQ ID NO:40 or SEQ ID NO:38, and the V_α optionally comprises an amino acid sequence having at least about 85% identity to the amino acid sequence set forth in SEQ ID NO:102 or 100; and/or (c) the V_α comprises the CDR3 amino acid sequence set forth in SEQ ID NO:39 or 37, and the V_β comprises the CDR3 amino acid sequence set forth in SEQ ID NO:40 or 38, wherein the binding protein is capable of specifically binding to a mesothelin (Msln) peptide:HLA complex. In an embodiment, (i) the V_α of (a), (b), and/or (c) of a binding protein as disclosed herein comprises an amino acid sequence having at least about 85% identity to the amino acid sequence set forth in SEQ ID NO:102 or 100, provided that at least three or four of the CDRs have no change in sequence, wherein the CDRs that do have sequence changes have only up to two amino acid substitutions, up to a contiguous five amino acid deletion, or a combination thereof; and/or (ii) the V_β of (a), (b), and/or (c) of a binding protein as disclosed herein comprises an amino acid sequence having at least about 85% identity to the amino acid sequence set forth in SEQ ID NO:101 or 99, provided that at least three or four of the CDRs have no change in sequence, wherein the CDRs that do have sequence changes have only up to two amino acid substitutions, up to a contiguous five amino acid deletion, or a combination thereof. Further, the binding protein referred to with respect to an embodiment may comprise: (a) the CDR1α amino acid sequence set forth in SEQ ID NO:93; (b) the CDR2α amino acid sequence set forth in SEQ ID NO:94; (c) the CDR3α amino acid sequence set forth in SEQ ID NO:39; (d) a CDR1β amino acid sequence set forth in SEQ ID NO:83, optionally as set forth in SEQ ID NO:84, further optionally as set forth in SEQ ID NO:91; (e) the CDR2β amino acid sequence set forth in SEQ ID NO:92; and (f) the CDR3β amino acid sequence set forth in SEQ ID NO:40. Still further, the binding protein referred to with respect to an embodiment may comprise an amino acid sequence having at least 85% identity to an amino acid sequence encoded by: (a) TRBJ2-3*01; (b) TRAV21*01 or TRAV21*02; (c) TRBV5-4*01; (d) TRAJ57*01; and/or (e) TRBD1*01 or TRBD2*02. Still further, the binding protein referred to with respect to an embodiment may comprise a V_α comprising an amino acid sequence having at least about 85% identity to the amino acid sequence set forth in SEQ ID NO:102, and a V_β comprising an amino acid sequence having at least about 85% identity to the amino acid sequence set forth in SEQ ID NO:101. In some instances, an embodiment may comprise a binding protein wherein the V_α comprises or consists of the amino acid sequence set forth in SEQ ID NO:102, and wherein the V_β comprises or consists of the amino acid sequence set forth in SEQ ID NO:101. Still further, the binding protein in an embodiment may comprise a TCR α chain (TCRα) and a TCR chain (TCRβ), wherein the TCRα comprises or consists of an amino acid sequence having at least about 85% identity to the amino acid sequence set forth in SEQ ID NO:110 or 29, and/or wherein the TCRβ comprises or consists of an amino acid sequence having at least about 85% identity to the amino acid sequence set forth in SEQ ID NO:109 or 28. Some embodiments may comprise a binding protein wherein the TCRα comprises or consists of the amino acid sequence set forth in SEQ ID NO:110 or 29, and wherein the TCRβ comprises or consists of the amino acid sequence set forth in SEQ ID NO:109 or 28. In further embodiments, the binding protein comprises: (a) a CDR1α amino acid sequence as set forth in SEQ ID NO:89; (b) a CDR2α amino acid sequence as set forth in SEQ ID NO:90; (c) a CDR3α amino acid sequence as set forth in SEQ ID NO:37; (d) a CDR1β amino acid sequence as set forth in SEQ ID NO:83, optionally as set forth in SEQ ID NO:87; (e) a CDR2β amino acid sequence as set forth in SEQ ID NO:88; and (f) a CDR3β amino acid sequence as set forth in SEQ ID NO:38. In an embodiment, the binding protein may comprise an amino acid sequence having at least 85% identity to an amino acid sequence encoded by: (a) TRBJ1-1*01 or TRBJ2-3*01; (b) TRAV4-1*01; (c) TRAJ18*01; and/or (d) TRBD1*01 or TRBD2*02. In an embodiment, the binding protein may comprise a Vα that comprises an amino acid sequence having at least about 85% identity to the amino acid sequence set forth in SEQ ID NO:100 and the Vβ comprises an amino acid sequence having at least about 85% identity to the amino acid sequence set forth in SEQ ID NO:99. In an embodiment, the binding protein may comprise a Vα that comprises or consists of the amino acid sequence set forth in SEQ ID NO:100, and wherein the Vβ comprises or consists of the amino acid sequence set forth in SEQ ID NO:99. In some embodiments the binding protein comprises a TCR α chain (TCRα) and a TCR β chain (TCRβ), wherein the TCRα comprises or consists of an amino acid sequence having at least about 85% identity to the amino acid sequence set forth in SEQ ID NO:108 or 23, and/or wherein the TCRβ comprises or consists of an amino acid sequence having at least about 85% identity to the amino acid sequence set forth in SEQ ID NO:107 or 22. In some embodiments the binding protein comprises a TCRα that comprises or consists of the amino acid sequence set forth in SEQ ID NO:108 or 23, and wherein the TCRβ comprises or consists of the amino acid sequence set forth in SEQ ID NO:107 or 22. In some embodiments, the binding protein comprises a binding protein that is capable specifically binding to a SEQ ID NO:32:human leukocyte antigen (HLA) complex, and in some such instances the HLA comprises HLA-A*201. In some embodiments, alanine mutagenesis of any one or more of residues 3, 5, 6, or 9 of SEQ ID NO:32 does not abrogate or does not substantially impair binding by the binding protein to the Msln peptide:HLA complex. In some embodiments the binding protein is capable of binding to a peptide:HLA complex wherein the peptide comprises or consists of the consensus amino acid sequence set forth in SEQ ID NO:61. In some embodiments, alanine mutagenesis of any one or more of residues 1, 5, or 9 of SEQ ID NO:32 does not abrogate or does not substantially impair binding by the binding protein to the Msln peptide:HLA complex. In some embodiments, the binding protein is capable of binding to a peptide:HLA complex wherein the peptide comprises or consists of the consensus amino acid sequence set forth in SEQ ID NO:62. In some embodiments, the binding protein does not bind to, or does not specifically bind to, a peptide:HLA complex, wherein the peptide comprises or consists of the amino acid sequence set forth in any one or more of SEQ ID NOs:63-77, and wherein the HLA is optionally HLA-A:02*01.

In an embodiment, a binding protein comprises a T cell receptor (TCR) α-chain variable domain (V_α) and a TCR β-chain variable domain (V_β), wherein: (a) the V_α comprises the CDR3 amino acid sequence set forth in SEQ ID NO:33 or 35, and the V_β optionally comprises an amino acid sequence having at least about 85% identity to the amino acid sequence set forth in SEQ ID NO:95 or 97; (b) the V_β comprises the CDR3 amino acid sequence set forth in SEQ ID NO: 34 or 36, and the V_α optionally comprises an amino acid sequence having at least about 85% identity to the amino acid sequence set forth in SEQ ID NO:96 or 98;

and/or (c) the $V_\alpha$ comprises the CDR3 amino acid sequence shown in SEQ ID NO:33 or 35, and the $V_\beta$ comprises the CDR3 amino acid sequence shown in SEQ ID NO:40 or 38, wherein the binding protein is capable of specifically binding to a mesothelin (Msln) peptide:HLA complex. In an embodiment, (i) the $V_\alpha$ of (a), (b), and/or (c) comprises an amino acid sequence having at least about 85% identity to the amino acid sequence set forth in SEQ ID NO:96 or 98, provided that at least three or four of the CDRs have no change in sequence, wherein the CDRs that do have sequence changes have only up to two amino acid substitutions, up to a contiguous five amino acid deletion, or a combination thereof; and/or (ii) the $V_\beta$ of (a), (b), and/or (c) comprises an amino acid sequence having at least about 85% identity to the amino acid sequence set forth in SEQ ID NO:95 or 97, provided that at least three or four of the CDRs have no change in sequence, wherein the CDRs that do have sequence changes have only up to two amino acid substitutions, up to a contiguous five amino acid deletion, or a combination thereof. In an embodiment, the binding protein comprises: (a) the CDR1α amino acid sequence set forth in SEQ ID NO:80; (b) the CDR2α amino acid sequence set forth in SEQ ID NO:81 or 118; (c) the CDR3α amino acid sequence set forth in SEQ ID NO:33; (d) a CDR1β amino acid sequence as set forth in SEQ ID NO:83, optionally as set forth in SEQ ID NO:84, further optionally as set forth in SEQ ID NO:78; (e) the CDR2β amino acid sequence set forth in SEQ ID NO:79; and (f) the CDR3β amino acid sequence set forth in SEQ ID NO:34. In an embodiment, the binding protein comprises an amino acid sequence having at least 85% identity to an amino acid sequence encoded by: (a) TRBJ2-7*01 or TRBJ2-3*01; (b) TRAV1-1*01; (c) TRBV12-4*01; (d) TRAJ3*01; and/or (e) TRBD1*01 or TRBD2*02. In an embodiment, the binding protein comprises a Vα that comprises an amino acid sequence having at least about 85% identity to the amino acid sequence set forth in SEQ ID NO:96, and a Vβ that comprises an amino acid sequence having at least about 85% identity to the amino acid sequence set forth in SEQ ID NO:95. In an embodiment, the binding protein comprises a Vα that comprises or consists of the amino acid sequence set forth in SEQ ID NO:96, and a Vβ that comprises or consists of the amino acid sequence set forth in SEQ ID NO:95. In an embodiment, the binding protein comprises a TCR α chain (TCRα) and a TCR β chain (TCRβ), wherein the TCRα comprises or consists of an amino acid sequence having at least about 85% identity to the amino acid sequence set forth in SEQ ID NO:104 or 7, and/or wherein the TCRβ comprises or consists of an amino acid sequence having at least about 85% identity to the amino acid sequence set forth in SEQ ID NO:103 or 6. In an embodiment, the binding protein comprises a TCRα that comprises or consists of the amino acid sequence set forth in SEQ ID NO:104 or 7, and wherein the TCRβ comprises or consists of the amino acid sequence set forth in SEQ ID NO:103 or 106. In an embodiment, the binding protein comprises: (a) the CDR1α amino acid sequence set forth in SEQ ID NO:85; (b) the CDR2α amino acid sequence set forth in SEQ ID NO:86 or 119; (c) the CDR3α amino acid sequence set forth in SEQ ID NO:35; (d) a CDR1β amino acid sequence set forth in SEQ ID NO:83, optionally as set forth in SEQ ID NO:84, further optionally as set forth in SEQ ID NO:82; (e) the CDR2β amino acid sequence set forth in SEQ ID NO:79; and (f) the CDR3β amino acid sequence set forth in SEQ ID NO:36. In an embodiment, the binding protein comprises an amino acid sequence having at least 85% identity to an amino acid sequence encoded by: (a) TRBJ2-3*01; (b) TRAV12-3*01;

(c) TRBV12-3*01; (d) TRAJ29*01; and/or (e) TRBD1*01 or TRBD2*02. In an embodiment, the binding protein comprises a Vα that comprises an amino acid sequence having at least about 85% identity to the amino acid sequence set forth in SEQ ID NO:98 and a Vβ that comprises an amino acid sequence having at least about 85% identity to the amino acid sequence set forth in SEQ ID NO:97. In an embodiment, the binding protein comprises a Vα that comprises or consists the amino acid sequence set forth in SEQ ID NO:98, and a Vβ that comprises or consists the amino acid sequence set forth in SEQ ID NO:97. In an embodiment, the binding protein comprises a TCR α chain (TCRα) and a TCR β chain (TCRβ), wherein the TCRα comprises or consists of an amino acid sequence having at least about 85% identity to the amino acid sequence set forth in SEQ ID NO:106 or 15, and/or wherein the TCRβ comprises or consists of an amino acid sequence having at least about 85% identity to the amino acid sequence set forth in SEQ ID NO:105 or 14. In an embodiment, the binding protein comprises a TCRα that comprises or consists the amino acid sequence set forth in SEQ ID NO:106 or 15, and a TCRβ that comprises or consists of the amino acid sequence set forth in SEQ ID NO:105 or 14. In an embodiment, the binding protein is capable of binding to a SEQ ID NO:31: human leukocyte antigen (HLA) complex, and wherein the HLA is optionally HLA-A*201. In an embodiment, the binding protein is or comprises a TCR, wherein the TCR is optionally soluble, an antigen-binding fragment of a TCR, a scTCR, or CAR. In an embodiment, the binding protein is human, humanized, or chimeric. In an embodiment, the binding protein is capable of binding to the mesothelin:HLA complex in the absence of, or independent of, CD8.

In an embodiment, the binding protein has a Msln peptide EC50 of about 9 μM, about 8 μM, about 7 μM, about 6 μM, about 5 μM, about 4 μM, about 3 μM, about 2 μM, about 1 μM, about 0.9 μM, about 0.8 μM, about 0.7 μM, about 0.6 μM, about 0.5 μM, about 0.4 μM, about 0.3 μM, about 0.2 μM, or less.

In an embodiment, a composition is provided that comprises a binding protein described herein and a pharmaceutically acceptable carrier, diluent, or excipient.

In an embodiment, a polynucleotide encodes a binding protein described herein. In some embodiments, the polynucleotide is codon optimized for expression in a host cell, wherein the host cell is optionally a human immune system cell, preferably a T cell. Also, in some embodiments, the polynucleotide has at least about 50% identity to the polynucleotide sequence set forth in any one of SEQ ID NOs: 1-4, 9-12, 17-20, 25, and 26. In some embodiments, the polynucleotide comprises a TCRα chain-encoding polynucleotide and a TCRβ chain-encoding polynucleotide that have at least about 50% identity to the polynucleotide sequences set forth in SEQ ID NOs: (i) 1 and 3, respectively; (ii) 2 and 4, respectively; (iii) 9 and 11, respectively; (iv) 10 and 12, respectively; (v) 17 and 19, respectively; (vi) 18 and 20, respectively; or (vii) 25 and 26, respectively. In some embodiments, the polynucleotide comprises a polynucleotide that encodes a self-cleaving peptide disposed between a TCRβ chain-encoding polynucleotide and a TCRα chain-encoding polynucleotide. In some embodiments, the encoded polypeptide comprises the amino acid sequence as set forth in any one of SEQ ID NOs:8, 16, 24, and 30. In some embodiments, the polynucleotide encoding the binding protein has at least about 50% identity to the polynucleotide sequence as set forth in any one of SEQ ID NOs:5, 13, 21, 27, and 120. In particular embodiments, a polynucleotide encoding a binding protein comprises or consists of the polynucleotide sequence set forth in SEQ ID NO:120.

In some embodiments, an expression vector is provided that comprises a polynucleotide described herein operably linked to an expression control sequence. In some embodiments, the expression vector is capable of delivering the polynucleotide to a host cell. In some embodiments, the host cell is a hematopoietic progenitor cell or a human immune system cell. In some embodiments, the immune system cell is a CD4+ T cell, a CD8+ T cell, a CD4− CD8− double negative T cell, a γδ T cell, a natural killer cell, a natural killer T cell, a macrophage, a dendritic cell, or any combination thereof. In some embodiments, the immune system cell is a naïve T cell, a central memory T cell, a stem cell memory T cell, an effector memory T cell, or any combination thereof. In some embodiments, the expression vector, is a viral vector. In some embodiments, the viral vector is a lentiviral vector or a γ-retroviral vector.

In an embodiment, a recombinant host cell comprises a heterologous polynucleotide encoding a binding protein as described herein and/or an expression vector as described herein, wherein the recombinant host cell is capable of expressing on its cell surface the encoded binding protein. In some embodiments, the recombinant host cell is a hematopoietic progenitor cell or a human immune system cell. In some embodiments, the recombinant host cell is a CD4+ T cell, a CD8+ T cell, a CD4− CD8− double negative T cell, a γδ T cell, a natural killer cell, a natural killer T cell, a macrophage, a dendritic cell, or any combination thereof. In some embodiments, the recombinant host cell is a T cell. In some embodiments, the recombinant host cell is a naïve T cell, a central memory T cell, a stem cell memory T cell, an effector memory T cell, or any combination thereof. In some embodiments, the recombinant host cell is a T cell or a NK-T cell encoding an endogenous TCR, and wherein the mesothelin-specific binding protein encoded by the heterologous polynucleotide is capable of more efficiently associating with a CD3 protein as compared to the endogenous TCR. In some embodiments, Nur77 expression is increased in the recombinant host cell when the host cell is in the presence of the Msln peptide bound by the encoded binding protein at a concentration of about $10^{-2}$ µM peptide, about $10^{-1}$ µM peptide, about 1 µM peptide, or about $10^{1}$ µM peptide, wherein the peptide is optionally presented to the host cell by an antigen presenting cell. In some embodiments, the recombinant host cell is one wherein the recombinant host cell does not produce IFN-γ and/or does not exhibit activation and/or cytotoxic activity when contacted with a cell expressing: (i) HLA-C6:02:01; (ii) HLA-B13:01:01 without HLA-B13:02:01; (iii) HLA-A3; (iv) HLA-A29; (v) HLA-B40; (vi) HLA-B44; (vii) HLA-C3; (viii) HLA-C16; (ix) HLA-A1; (x) HLA-24; (xi) HLA-B7; (xii) HLA-B57; (xiii) HLA-C7; (xiv) HLA-A11; (xv) HLA-B15; (xvi) HLA-C4; (xvii) HLA-C12; (xviii) HLA-B8; (xix) HLA-B49; (xx) HLA-B51; (xxi) HLA-C15; (xxii) HLA-A30; (xxiii) HLA-A68; (xxiv) HLA-C2; (xxv) HLA-A32; (xxvi) HLA-A33; (xxvii) HLA-B55; (xxviii) HLA-C1; (xxvix) HLA-C5; (xxix) HLA-B8; (xxx) HLA-B35; or (xxxi) any combination of (i)-(xxx), provided that the mesothelin peptide bound by the encoded binding protein is not present. In some embodiments, the recombinant host cell comprises T cell or a NK-T cell encoding an endogenous TCR, wherein the binding protein encoded by the heterologous polynucleotide has higher cell surface expression as compared to the endogenous TCR.

In an embodiment, a cell composition is provided that comprises a recombinant host cell described herein and a pharmaceutically acceptable carrier, excipient, or diluent.

In an embodiment, a unit dose is provided that comprises an effective amount of a recombinant host cell or a cell composition described herein.

In an embodiment, a method of treating a disease or disorder associated with mesothelin expression and/or activity in a subject is provided, wherein the method comprises: administering to the subject an effective amount of the binding protein described herein, the recombinant host cell described herein, the composition described herein, or the unit dose of described herein. In an embodiment, the method comprises a method of treating a disease or disorder associated with mesothelin expression and/or activity in a subject, wherein the disease or disorder is a hyperproliferative disease or a proliferative disease. In an embodiment, the method comprises a method of treating a disease or disorder associated with mesothelin expression and/or activity in a subject, wherein the disease or disorder is a cancer and, optionally, the cancer is a solid cancer or a hematological malignancy. In an embodiment, the method comprises a method of treating a disease or disorder associated with mesothelin expression and/or activity in a subject, wherein the disease or disorder is one of biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer. In an embodiment, the method comprises a method of treating a disease or disorder associated with mesothelin expression and/or activity in a subject, wherein the disease or disorder is one of pancreatic cancer, ovarian cancer, breast cancer, gastric cancer, colorectal cancer, mesothelioma, or lung cancer. In an embodiment, the binding protein, host cell, composition, or unit dose is administered parenterally or intravenously. In an embodiment, the method comprises administering a plurality of doses of the binding protein, host cell, composition, or unit dose to the subject and, optionally, the plurality of doses are administered at intervals between administrations of about two to about four weeks. In an embodiment, method further comprises administering a cytokine to the subject. In an embodiment, the method comprises administering IL-2, IL-15, IL-21, or any combination thereof. In an embodiment, the method comprises a subject that is further receiving or has received an immune checkpoint inhibitor, an agonist of a stimulatory immune checkpoint agent, radiation therapy, an antibody, an antibody-drug conjugate, an Fc fusion protein, an antisense nucleotide therapy, a gene therapy, a vaccine, a surgery, a chemotherapy, or any combination thereof.

In an embodiment, the binding protein described herein, the composition described herein, the polynucleotide described herein, the expression vector described herein, the recombinant host cell described herein, the cell composition described herein, or the unit dose described herein, is for use in the treatment of a disease or disorder characterized by mesothelin expression and/or activity.

In an embodiment, the binding protein described herein, the composition described herein, the polynucleotide described herein, the expression vector described herein, the recombinant host cell described herein, the cell composition described herein, or the unit dose described herein, is for use in adoptive immunotherapy of a disease or disorder characterized by mesothelin expression and/or activity.

In an embodiment, the binding protein described herein, the composition described herein, the polynucleotide described herein, the expression vector described herein, the recombinant host cell described herein, the cell composition described herein, or the unit dose described herein, is for use in the manufacture of a medicament for treating a disease or disorder characterized by mesothelin expression and/or activity.

In an embodiment, the binding protein, composition, polynucleotide, expression vector, recombinant host cell, cell composition, or unit dose for use described herein, wherein the disease or disorder characterized by mesothelin expression and/or activity is mesothelioma, pancreatic cancer, ovarian cancer, lung cancer, a cancer wherein an $Msln_{20-28}$ peptide is expressed on a tumor cell of the cancer, or a cancer wherein an $Msln_{530-538}$ peptide is expressed on a tumor cell of the cancer.

In an embodiment, the binding protein, composition, polynucleotide, expression vector, recombinant host cell, cell composition, or unit dose for use described herein, wherein the disease or disorder characterized by mesothelin expression and/or activity is pancreatic cancer, ovarian cancer, breast cancer, gastric cancer, colorectal cancer, mesothelioma, or lung cancer.

In an embodiment, an isolated polynucleotide is provided that encodes a binding protein that is capable of specifically binding to a SEQ ID NO:32:HLA-A:02*01 complex, wherein the polynucleotide comprises or consists of the polynucleotide sequence set forth in SEQ ID NO:120. In an embodiment, an expression vector comprising the polynucleotide that encodes a binding protein that is capable of specifically binding to a SEQ ID NO:32:HLA-A:02*01 complex is provided, wherein the polynucleotide comprises or consists of the polynucleotide sequence set forth in SEQ ID NO:120 operably linked to an expression control sequence. In such an embodiment, the expression vector, the expression vector is capable of delivering the polynucleotide to a host cell. In such an embodiment, the host cell is a hematopoietic progenitor cell or a human immune system cell. In such an embodiment, the expression vector immune system cell is a CD4+ T cell, a CD8+ T cell, a CD4– CD8– double negative T cell, a γδ T cell, a natural killer cell, a natural killer T cell, a macrophage, a dendritic cell, or any combination thereof. In such an embodiment, the expression vector immune system cell is a naïve T cell, a central memory T cell, a stem cell memory T cell, an effector memory T cell, or any combination thereof. In some embodiments, the expression vector is a viral vector. In such an embodiment, the expression vector is a viral vector that is a lentiviral vector or a γ-retroviral vector.

In an embodiment, is a recombinant host cell comprising the polynucleotide described herein and/or the expression vector described herein, wherein the recombinant host cell is capable of expressing on its cell surface the encoded binding protein. In such an embodiment, the recombinant host cell is a hematopoietic progenitor cell or a human immune system cell. In such an embodiment, recombinant host cell is an immune system cell is a CD4+ T cell, a CD8+ T cell, a CD4– CD8– double negative T cell, a γδ T cell, a natural killer cell, a natural killer T cell, a macrophage, a dendritic cell, or any combination thereof. In such an embodiment, the recombinant host cell is a T cell. In such an embodiment, the recombinant host cell is a naïve T cell, a central memory T cell, a stem cell memory T cell, an effector memory T cell, or any combination thereof.

EXAMPLES

Example 1

Identification and Selection of TCRs Specific for $Msln_{20}$ or $Msln_{530}$

Figure 1B:
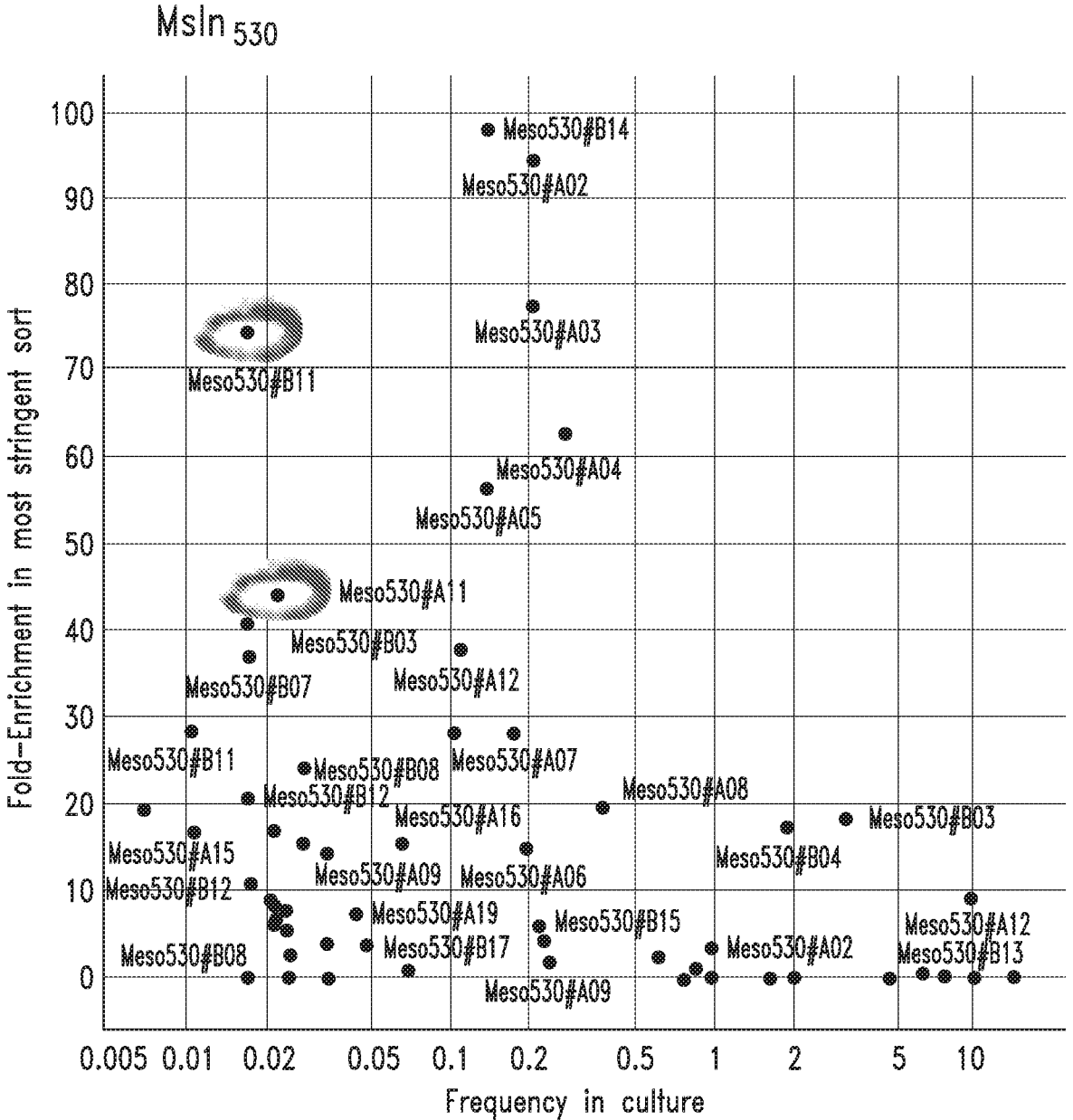
FIG. 1B depicts identification and selection of TCRs specific for $Msln_{530}$ (SEQ ID NO:32) based on the fold-enrichment of tetramer from a pool of TCRs with binding to a $Msln_{530}$:HLA tetramer. TCRs that were selected for further studies are circled.

Exemplary TCR clones specific for $Msln_{20}$ or $Msln_{530}$ are shown in FIGS. 1A and 1B, respectively, and the enrichment score of each TCR clonotype in the next-generation sequencing (NGS) based method for TCR isolation presented herein is compared to T cell frequency. The enrichment score on the y-axis correlates with the magnitude of binding to peptide:HLA tetramer. All TCRs were synthesized and tested for function when expressed in reporter T cell lines and primary CD8+ PBMCs. The TCRs with the highest functional avidity when transferred into recipient CD8+ T cells are encircled. These data show that the TCRs identified as having the highest functional activity did not have the highest magnitude of tetramer binding and were rare in the peptide-expanded T cell populations. Without being bound by theory, this may be due in part to decreased TCR surface expression by these highly avid clonotypes. More than 100 TCR constructs were synthesized and evaluated ($Msln_{20}$=60 TCRs synthesized; $Msln_{530}$=42 TCRs synthesized). Mesothelin-specific T cell lines were generated from 18 donors. Cells were stained with titrated concentrations of tetramer, sorted, and analyzed by single-cell TCR sequencing (~8 sorting experiments in total).

Example 2

Figure 2:
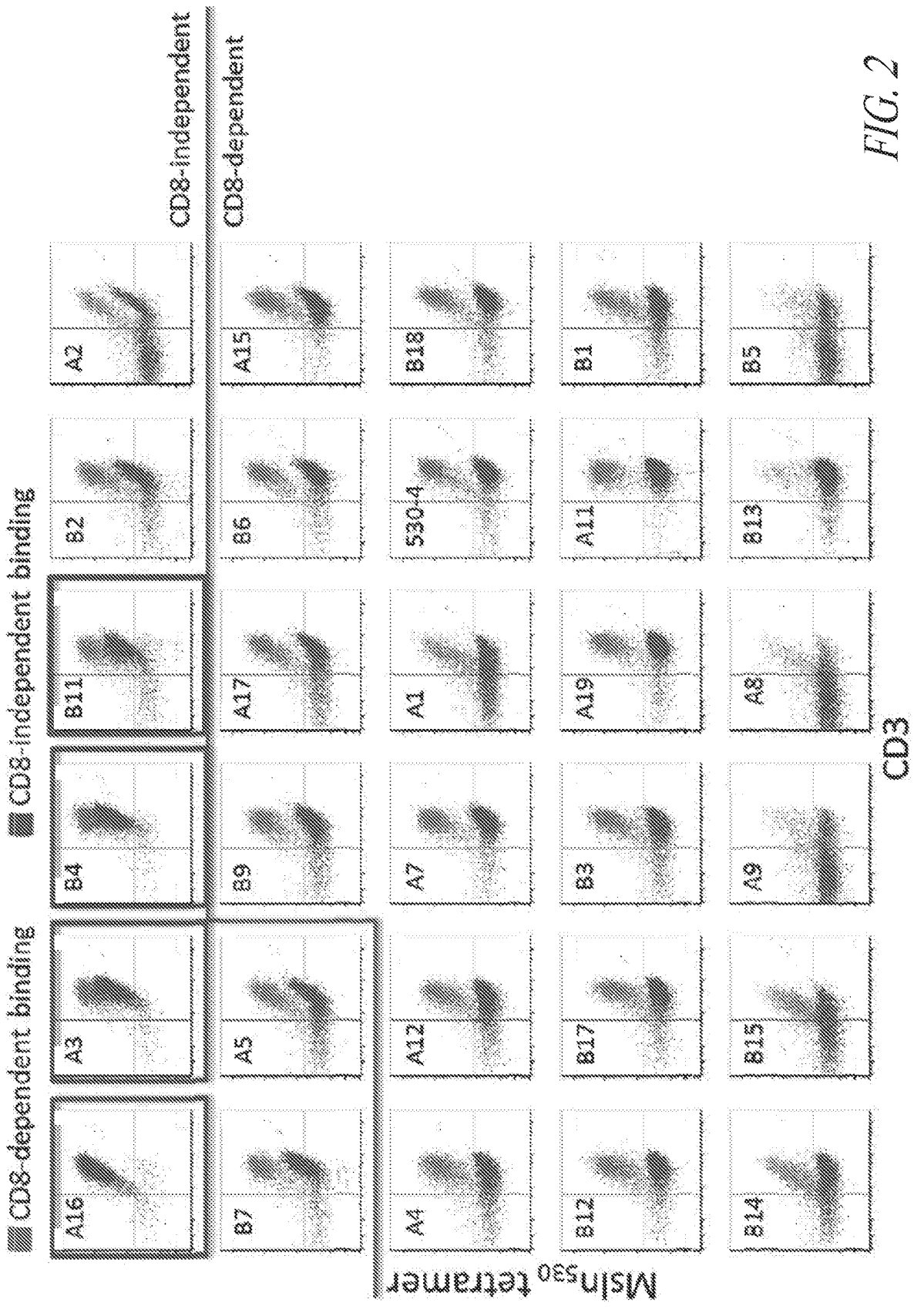
FIG. 2 depicts tetramer binding by $Msln_{530}$-specific TCRs (ranked by affinity, based on tetramer binding) in assays to determine whether or not cell-expressed TCR was able to detect the $Msln_{530}$ peptide:HLA complex in the presence or absence of the CD8 co-receptor. CD8-independent binding correlates with high affinity of the respective T cell clone.

Tetramer Binding by $Msln_{530}$ TCRs $Msln_{530}$-specific TCR coding constructs were lentivirally transduced into CD8– Jurkat T cells that lack endogenous TCR α/β chains (Jurkat76—dark gray plots) or Jurkat76 cells transduced to express CD8αβ (Jurkat76-CD8αβ—light gray plots) (see FIG. 2). In the absence of TCRα/β chains, CD3 cannot be expressed at the cell surface. Therefore, CD3 expression is a proxy for TCR surface expression in these cells, allowing tetramer binding to be assessed relative to TCR surface expression. With reference to FIG. 2, TCRs are presented in order of tetramer binding relative to CD3 expression, and TCRs above the indicated line are considered to be CD8-independent, characteristic of high affinity.

Example 3

Evaluation of Antigen-Specific T Cell Responses

Figure 3A:
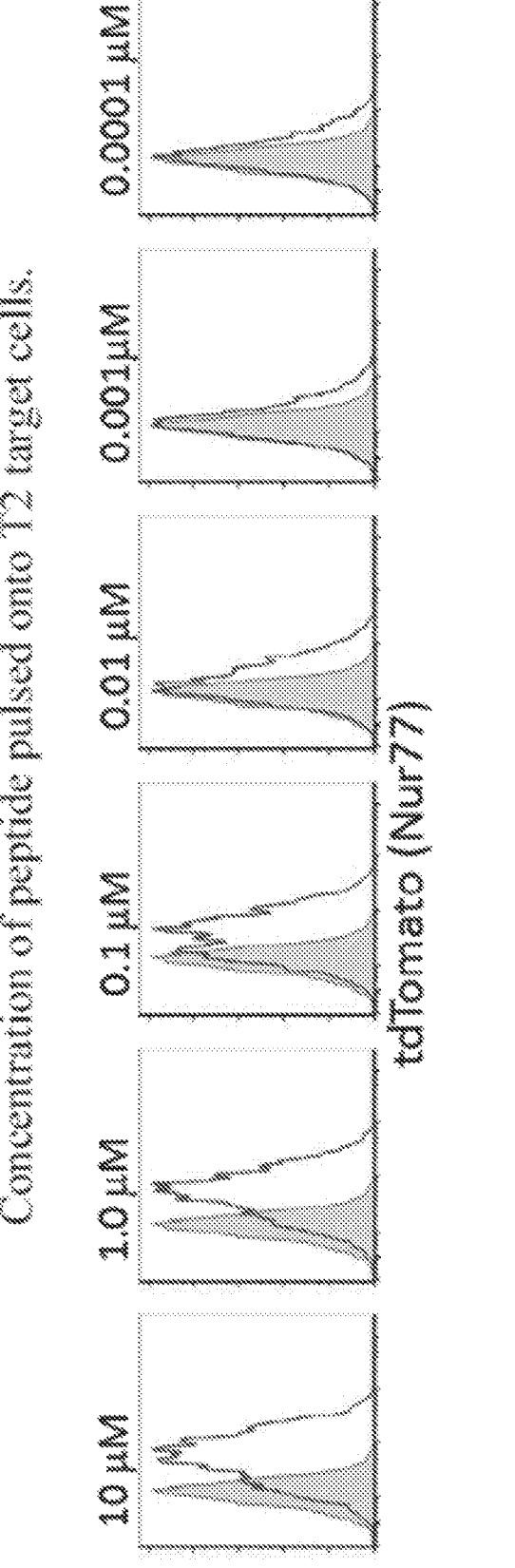
FIGS. 3A-3C show further functional testing of Msln-specific TCRs. (A) Representative data of a T cell clone evaluated for antigen-driven activation based on a reporter cell line expressing the Nur77-tdTomato transgene, as measured by flow cytometry. Nur77 is an indicator of antigen receptor signaling in human T cells (see, e.g., Ashouri and Weiss, J. Immunol. 198(2):657-658 (2017)). In this assay, the T cell clone was incubated with T2 target cells that were pulsed with increasing concentrations of peptide, as indicated. (B) Nur77 reporter activity of TCRs, as ranked according to sensitivity to T2 cells pulsed with peptide at the indicated concentration. (C) Avidity ranking of TCRs, based on the EC50 of peptide for Nur77 reporter activity. "B11" (also referred-to herein as 11B) had the lowest EC50 of the tested TCR clones.

The four TCRs that exhibited the highest level of tetramer binding were evaluated for antigen-specific function using a reporter Jurkat T cell line that has a tdTomato transgene knocked into the Nur77 locus. T2 target cells were pulsed with titrated concentrations of peptide and TCR-expressing T cells were assessed for tdTomato expression, as indicated in FIG. 3A. The percentage of tdTomato-positive cells detected at each peptide concentration was plotted and fit to a dose-response curve by non-linear regression (FIG. 3B).

Figures 3B, 3C:
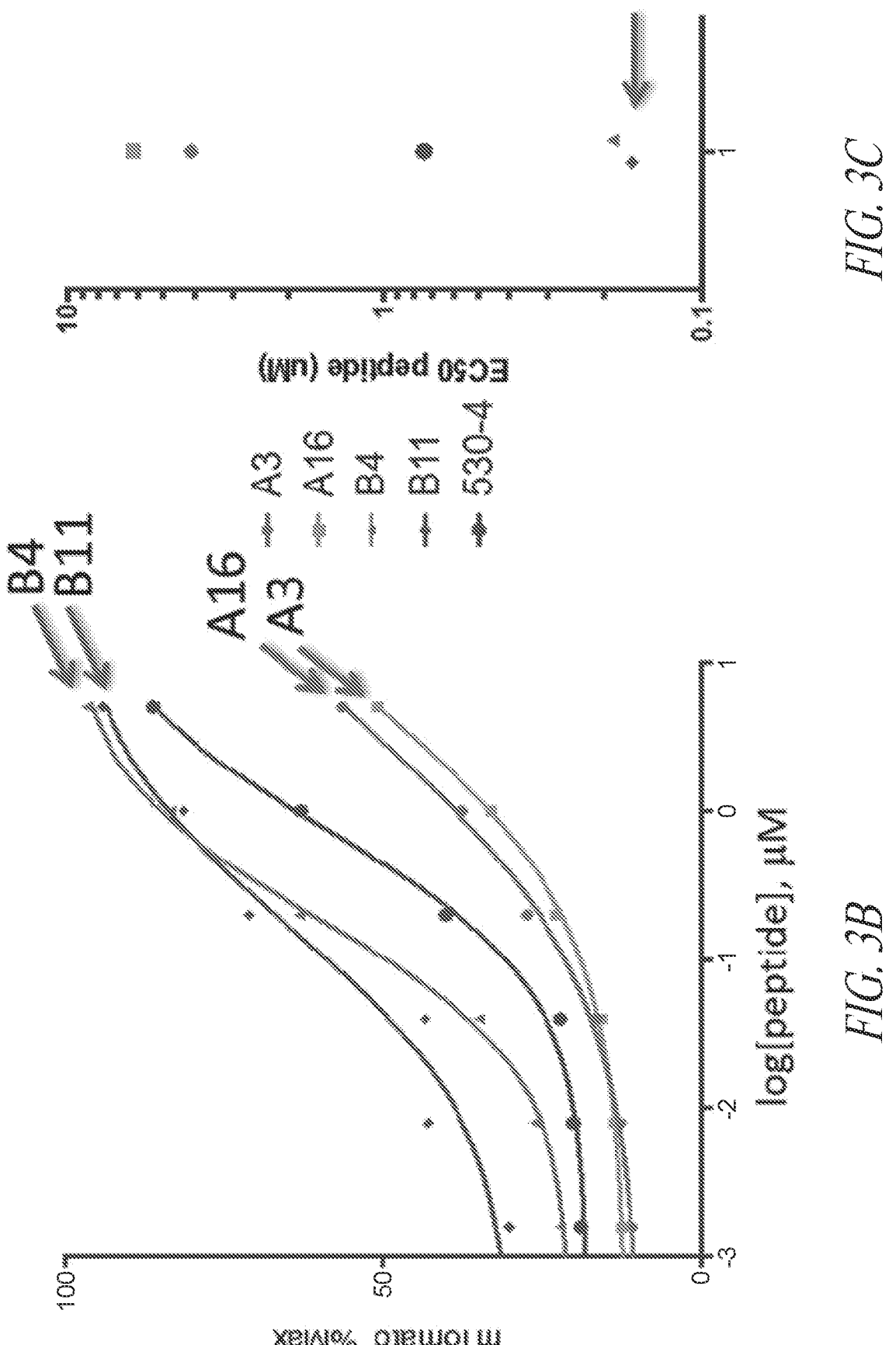

The calculated EC50 for each TCR was plotted and TCR B11 (also referred to herein as 11B) was identified as the most-avid TCR (see arrows in FIGS. 3B and 3C). The two TCRs with the highest level of tetramer binding (A16 and A3, also referred to as 16A and 3A, respectively) were found to have lower antigen sensitivity, and are also indicated by arrows in FIG. 3B.

Example 4

Functional Evaluation of $Msln_{530}$-Specific TCRs

Figure 4:
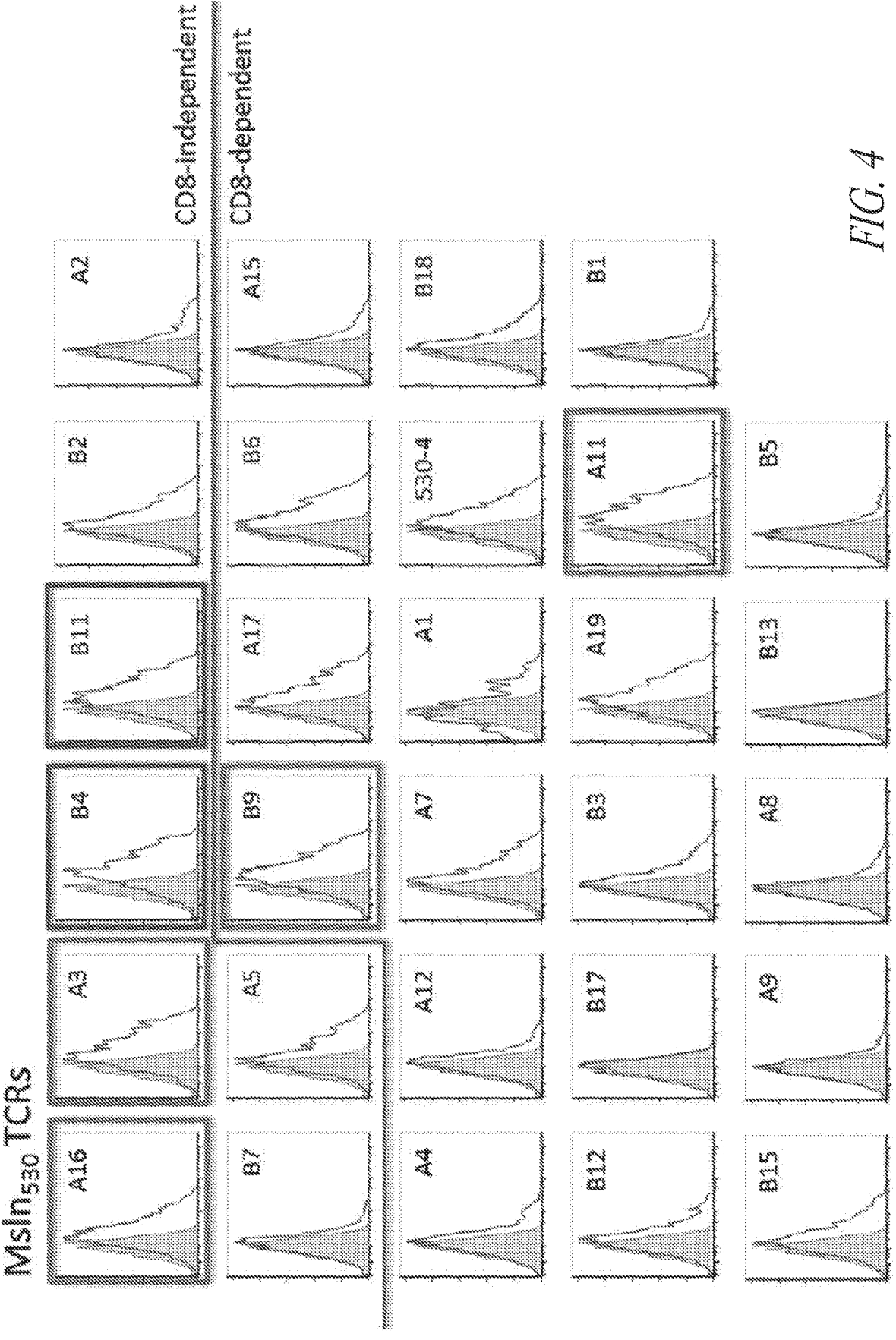
FIG. 4 shows functional evaluation of TCR clones in response to peptide, based on Nur77 tomato reporter activity. Several TCRs, including "B9" and "A11" (also referred to herein as "11A"), confer high antigen specificity despite exhibiting lower tetramer binding. TCRs are ranked (left-to right and top-to-bottom) according to tetramer binding.

Since function did not correlate with tetramer binding for the top four tetramer binders, all selected $Msln_{530}$-specific TCRs were assessed for tdTomato expression in response to a lower concentration of peptide (0.1 μm) as a proxy for antigen sensitivity (see FIG. 4). Two TCRs that bound tetramer at lower levels (B9 and A11) were found to mediate high-level tdTomato expression in response to antigen. Data from these and other TCRs is shown in boxes in FIG. 4; these were included in the set of TCRs for further study. Several TCRs, including B9 and A11, confer high antigen-specific activity despite lower tetramer binding. In FIG. 4, the TCRs are presented in rank order of tetramer binding.

Example 5

Functional Evaluation of Selected TCRs

Figure 5A:
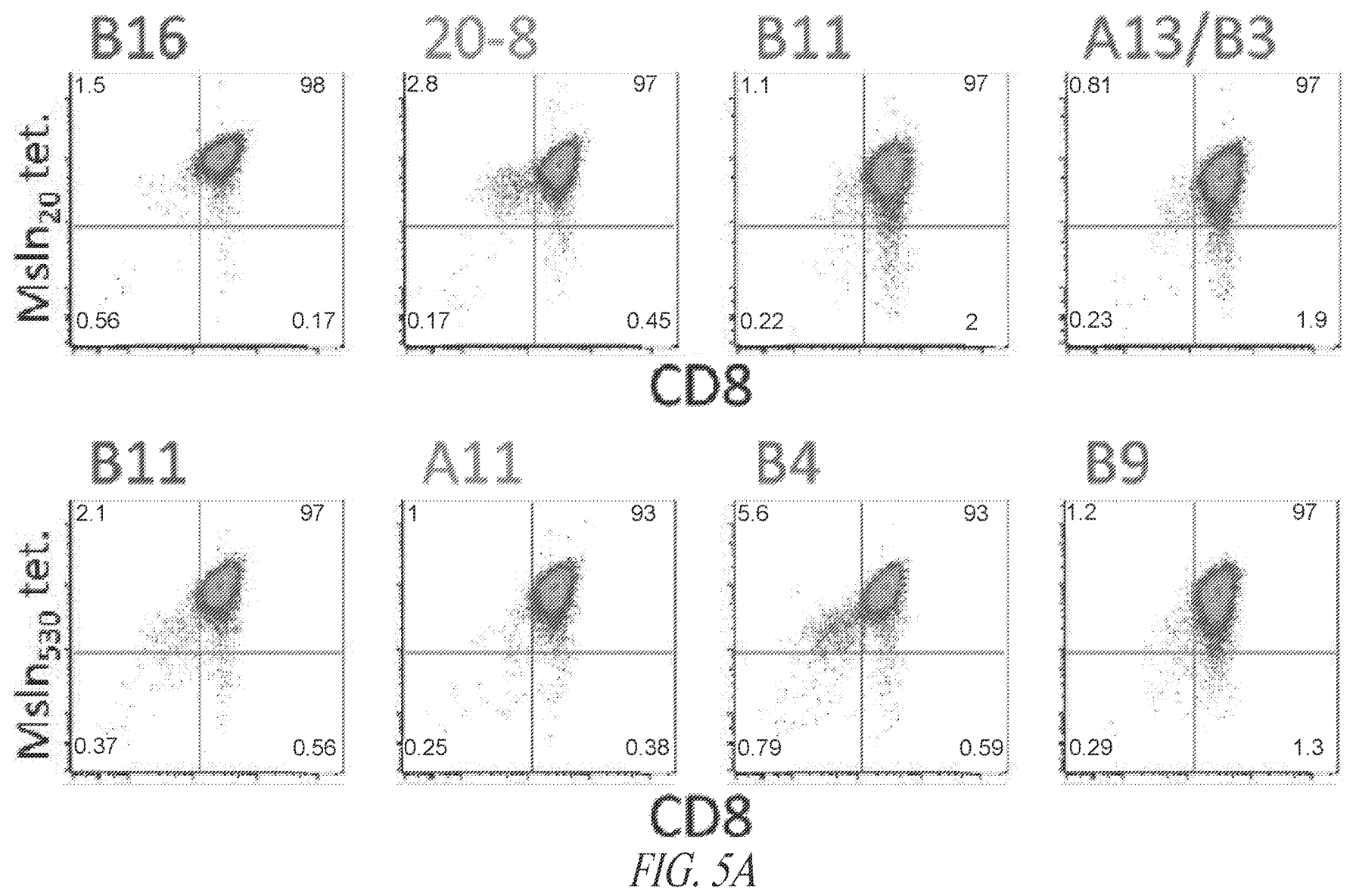
Figure 5B:
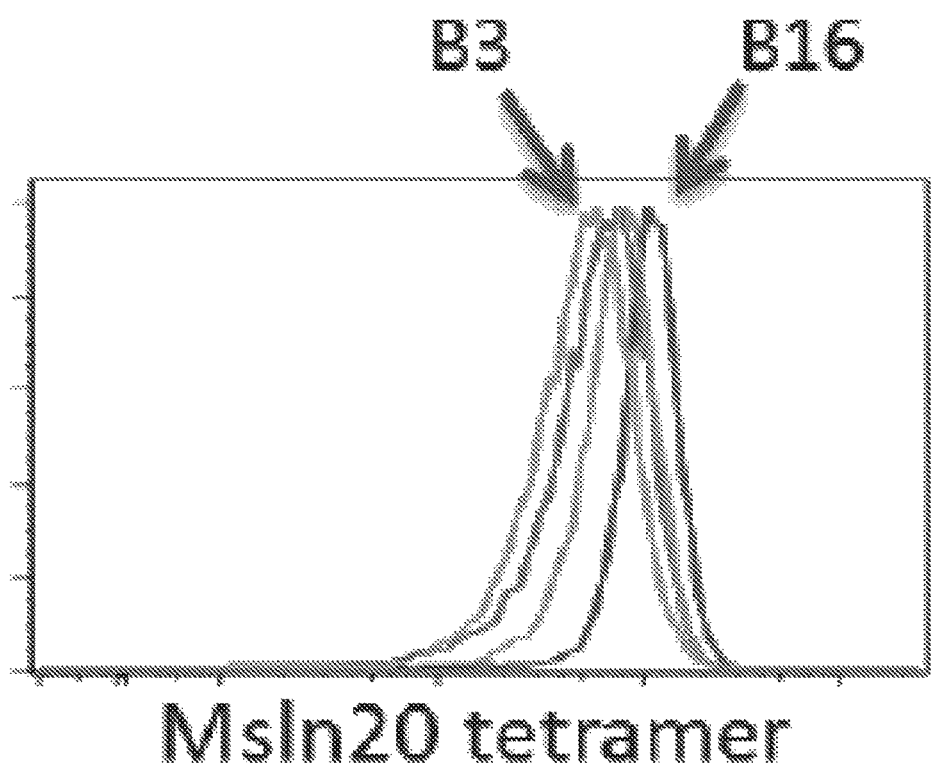
Figure 5C:
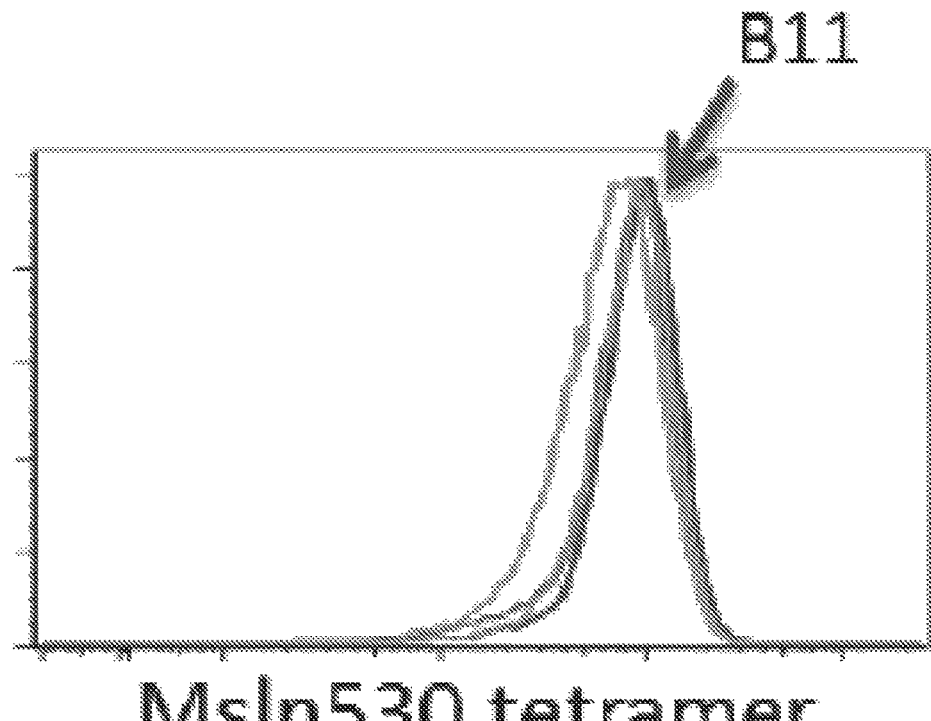

With reference to FIGS. 5A-5C, CD8+ T cells were purified from donor PBMCs and lentivirally transduced with TCRs specific for $Msln_{530}$ or $Msln_{20}$ (which were selected through a similar process to that described in Examples 3 and 4). After 8 days, tetramer$^{hi}$ cells were sorted and further expanded for 8-10 days. Transduced T cells were stained with tetramer and CD8 to confirm purity and uniform high level CD8 expression.

Figures 6A, 6B:
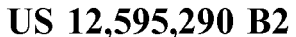
FIGS. 6A-6C show characterization of primary CD8+ T cells that were transduced with the indicated Msln-specific TCR and assessed for functional activity upon incubation with peptide-pulsed T2 cells, as measured by interferon-gamma production (A, B). TCRs were ranked by the EC50, based on the amount of peptide pulsed into T2 cells (C).
Figure 6C:
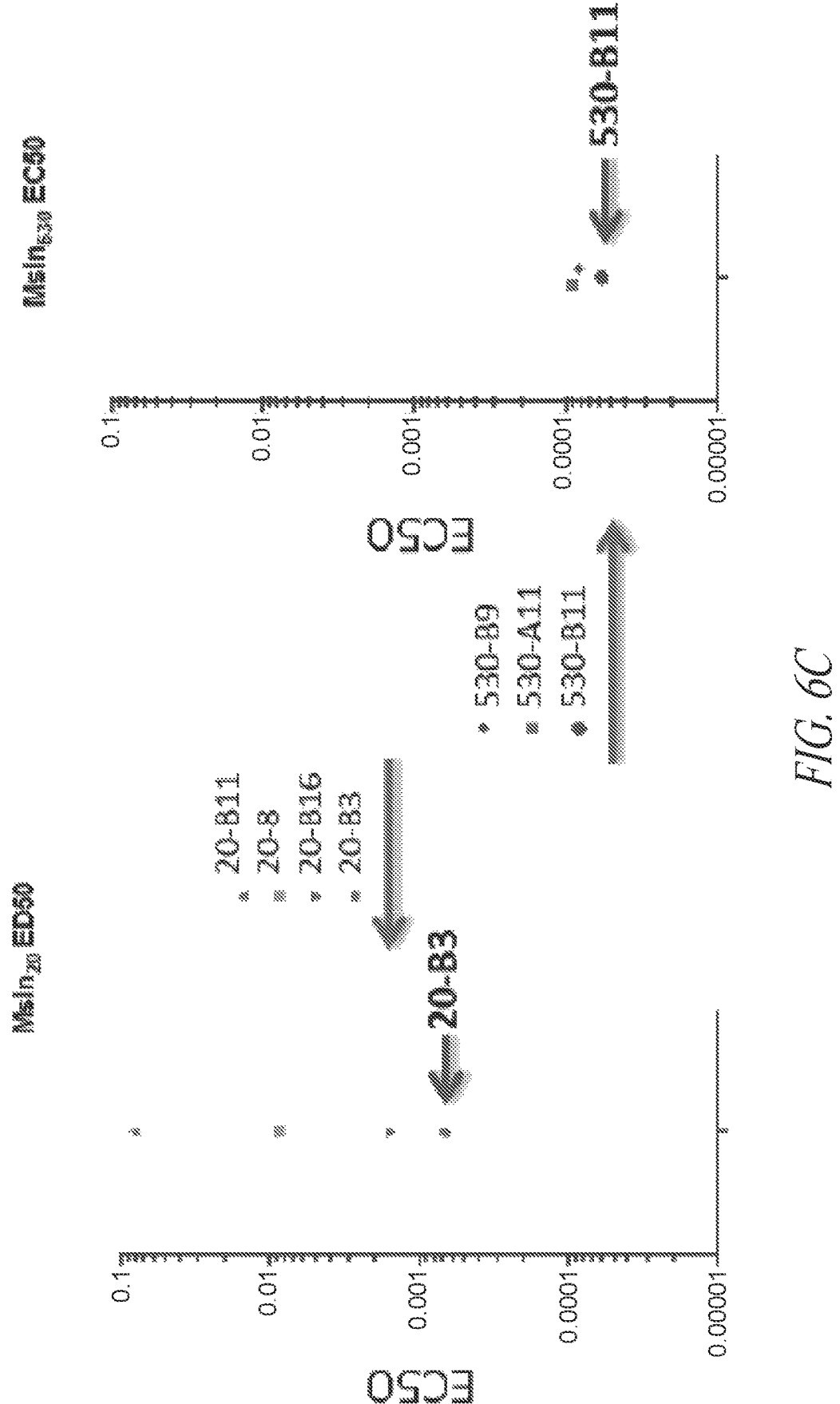

As shown in FIGS. 6A-6C, TCR-transduced effector CD8+ T cells specific for $Msln_{20}$ (A) or $Msln_{530}$ (B) were incubated with peptide-pulsed T2 target cells and dose-dependent IFN-γ production was assessed by flow cytometric analysis of intracellular IFN-γ (effector cells=TCR-transduced primary CD8+ T cells (sorted); targets=peptide-pulsed T2 cells). The percentage of IFN-γ-positive cells detected at each peptide concentration was plotted and fit to a dose-response curve by non-linear regression. The calculated EC50 for each TCR was plotted. In FIG. 6C, the most avid TCR specific for each epitope ("20-B3" and "530-B11", respectively) is indicated with an arrow.

Example 6

Tumor Cell Killing by TCR-Transduced CD8+ T Cells

Figures 7A, 7B:
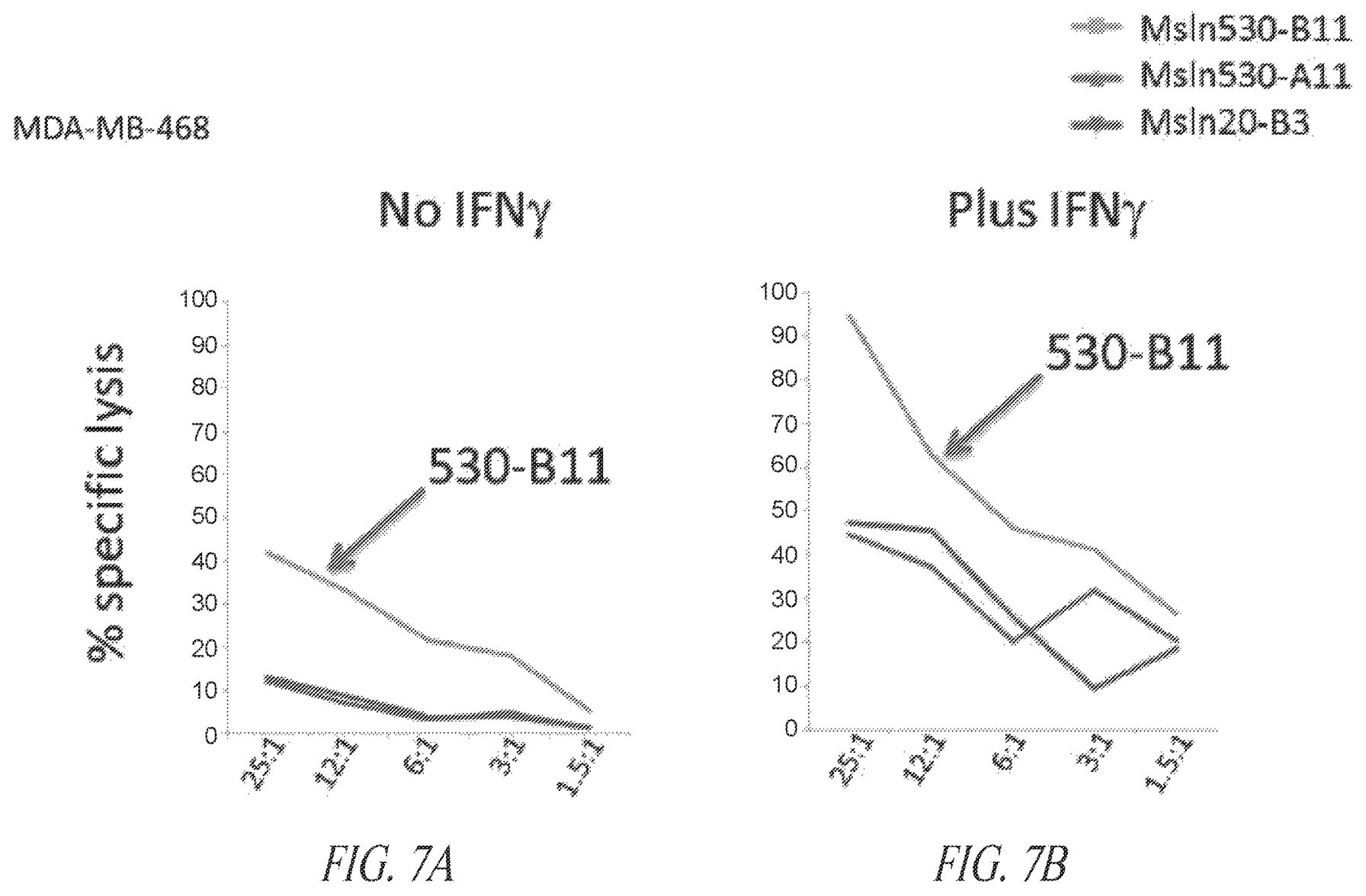

Two tumor cell lines that express Msln, MDA-MB-231 and MDA-MB-468, were targeted by titrated ratios of sort-purified Msln-specific TCR-transduced CD8+ T cells using a chromium release assay measuring specific tumor cell lysis (see FIGS. 7A-7C). Results for TCR $Msln_{530}$-B11, the highest avidity TCR identified, are indicated with an arrow.

Example 7

Figure 8:
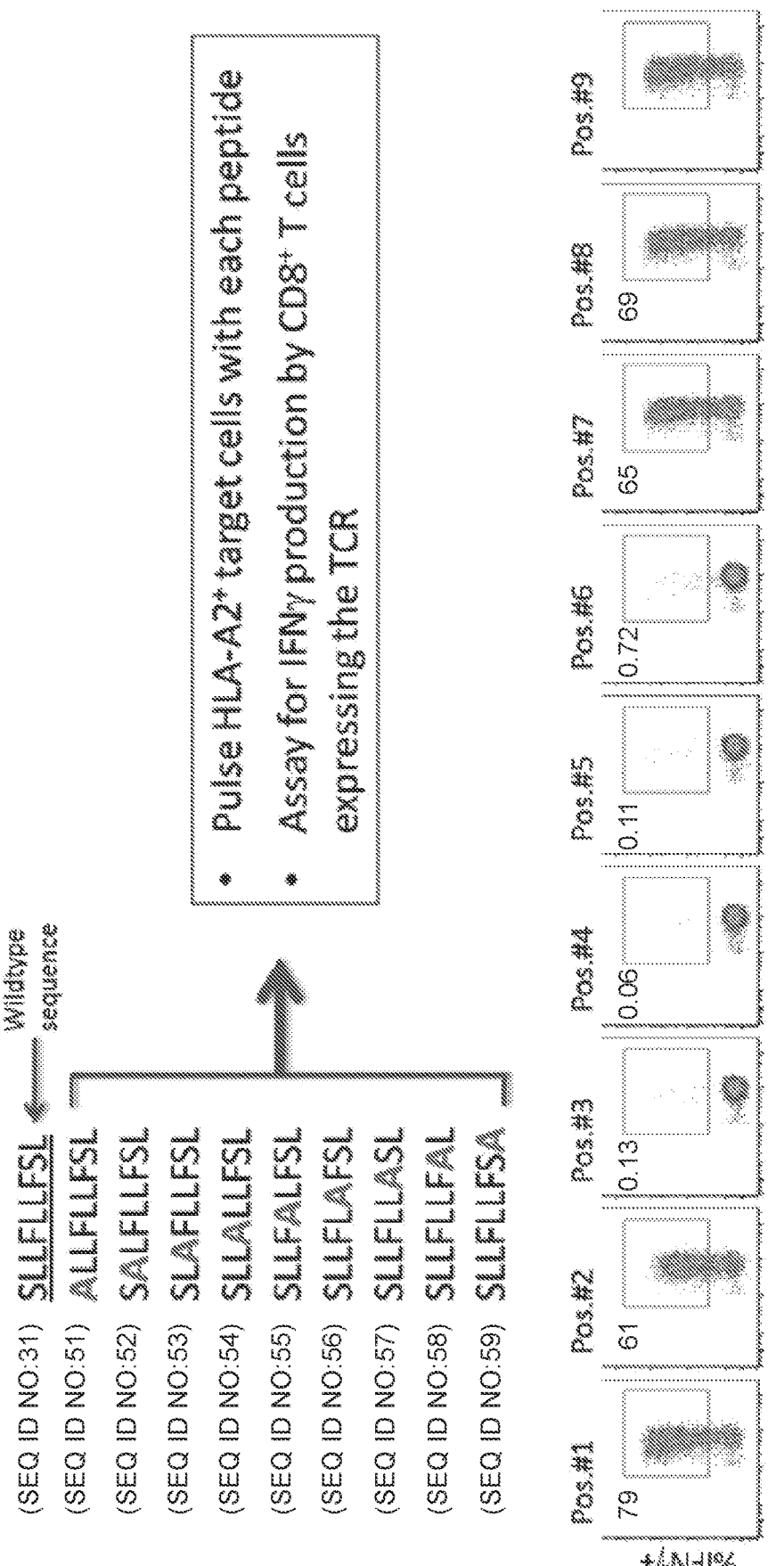
FIG. 8 relates to an alanine mutagenesis scanning experiment to assess which amino acids of the target $Msln_{20}$ peptide (SEQ ID NO:31) are essential for effective binding and killing by exemplary $Msln_{20}$-specific TCRs. A series of variant peptides were generated in which an alanine was substituted for each successive position along the peptide of SEQ ID NO:31, and each variant peptide was assessed for IFN-γ production by CD8+ T cells expressing the indicated $Msln_{20}$-specific TCR. These data show that positions 3-6 of SEQ ID NO:31 are essential for TCR binding. In the consensus sequence SEQ ID NO:60, an "X" indicates that a substitution mutation of the indicated residue in SEQ ID NO:31 to alanine does not impact or substantially impact functional binding of the TCR to its cognate peptide target.

Epitope Analysis by Alanine Scanning of $Msln_{20}$ and $Msln_{530}$ Peptides FIG. 8 demonstrates an epitope analysis assay in which each successive amino acid of the Mlsn target peptide sequence was replaced by an alanine and TCR-transduced T cells were incubated with HLA-A2+ target cells pulsed with the variant peptide. Representative data of IFN-γ production in response to each variant peptide by a $Msln_{20}$-specific TCR is shown at the bottom of the figure.

Results of the alanine scan assay, showing the percent IFN-γ+ T cells in response to each alanine-substituted peptide for each of the four tested TCRs are shown in FIGS. 9A-9D. The essential residues are identified by their one-letter amino acid code and the non-essential residues are indicated by an X.

Example 8

Analysis for Epitopes Homologous to $Msln_{530}$ in the Human Proteome

Human peptides predicted to have potential cross-reactivity with Msln-specific TCRs were identified using the ScanProsite tool by searching the human proteome for the indicated consensus epitope motif of each of the indicated $Msln_{530}$-specific TCRs (A11 and B11), as illustrated in FIG. 10. Resulting peptides were analyzed for HLA-A2 binding using three different prediction algorithms: SITHPATHI, PanMHCnet, and IEDB. The recommended cutoff for each approach is listed in parenthesis next to the name of the algorithm. Potential cross-reacting peptides are as indicated in the figure key, and were synthesized for further analysis.

Example 9

Figure 11A:
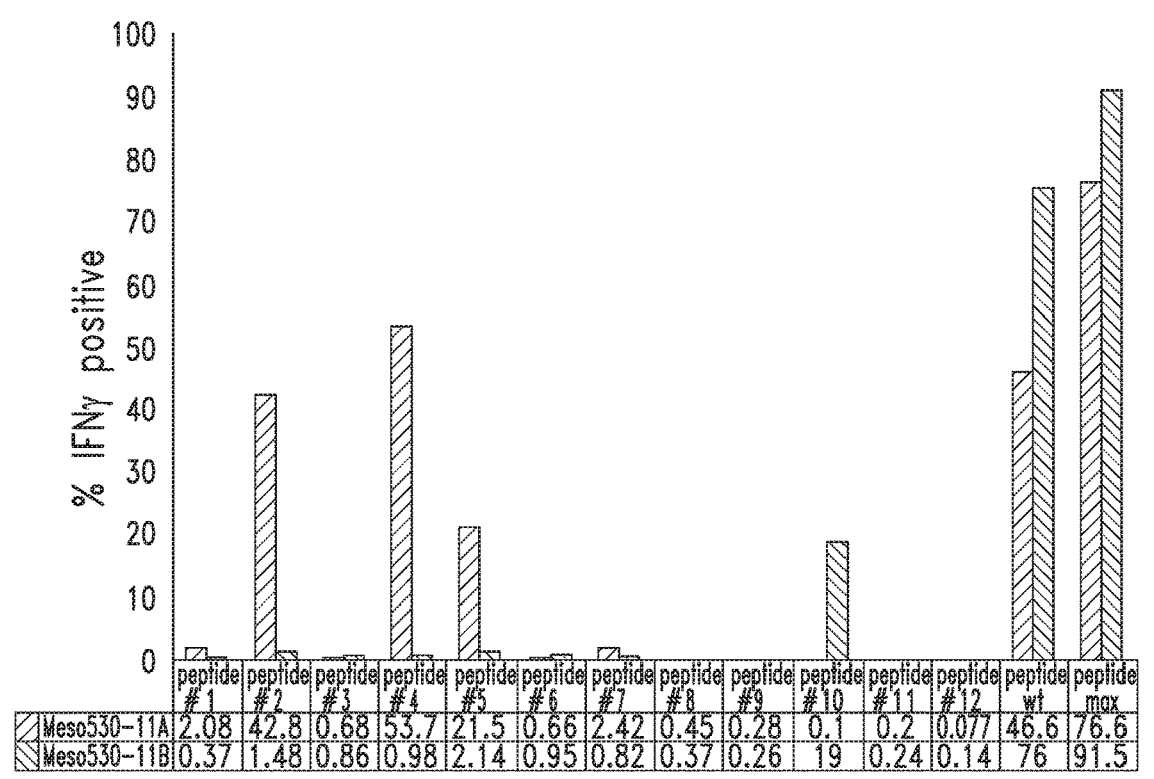
FIGS. 11A and 11B depict analysis of synthesized peptides with potential homology to $Msln_{530}$ in the human proteome. As described in Example 9, the functional activity of two $Msln_{530}$-specific TCRs (FIG. 11A, FIG. 11B) upon incubation with T2 cells pulsed with a high dose (10 μM) of peptide was measured by IFN-γ. (B) For peptides that showed cross-reactivity with a tested TCR, a dose-dependent titration was performed to determine the EC50. TCRs were ranked by the EC50 based on the amount of peptide pulsed into T2 cells. Peptide #10 is from a gene called EHF. This gene encodes a protein that belongs to an ETS transcription factor subfamily characterized by epithelial-specific expression. ETS acts as a transcriptional repressor, and may be involved in epithelial differentiation and carcinogenesis.
Figure 11B:
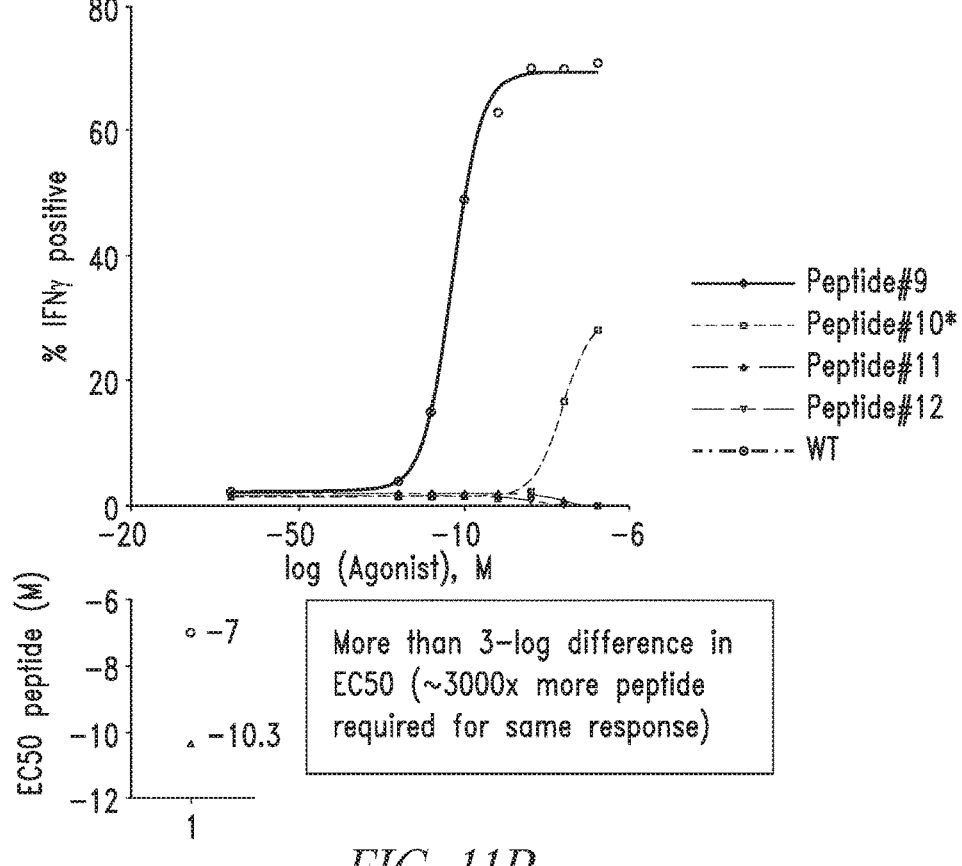

Analysis of Synthesized Peptides with Potential Homology to $Msln_{530}$ in the Human Proteome T2 target cells were pulsed with peptides with potential for cross-reactivity with $Msln_{530}$-A11 and -B11 TCRs, and were incubated with T cells that were transduced to express those TCRs and sorted for purity (see FIGS. 11A-11B; effector T cells=tetramer-sorted TCR-transduced CD8+ T cells; target cells=T2 cells pulsed with 10 μM peptide). A high dose of peptide (10 μM) was used in order to detect potential reactivities. The percentage of IFN-γ-positive TCR-transduced T cells is shown in FIG. 11A for $Msln_{530}$-11A and $Msln_{530}$-11B. The response with 10 μM of the wildtype $Msln_{530}$ peptide, and the maximal response obtained with a non-specific T cell activation cocktail are shown on the right side of the graph. Only one peptide (#10) elicited a low level (<20%) response from TCR $Msln_{530}$-11B-transduced T cells at 10 μM peptide. The graph in FIG. 11B shows a dose-response curve for $Msln_{530}$-11B transduced T cell reactivity to the $Msln_{530}$ peptide versus several potential cross-reactive peptides, including peptide #10, to determine reactivity at physiological levels. The percent IFN-γ+ data was fit to dose-response curves by non-linear regression, and EC50 values were calculated and are shown below the graph. These data show that the $Msln_{530}$-11B EC50 for peptide #10 is more than 3000× higher than for that of $Msln_{530}$; therefore, $Msln_{530}$-11B has much greater specificity for $Msln_{530}$ than for peptide #10.

Example 10

Analysis of Alloreactivity by Targeting Diverse Donor-Derived LCLs

Figure 12D:
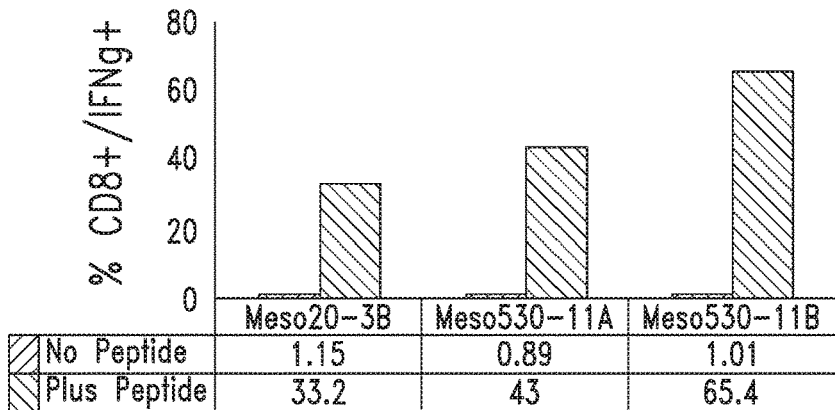
Figure 12E:
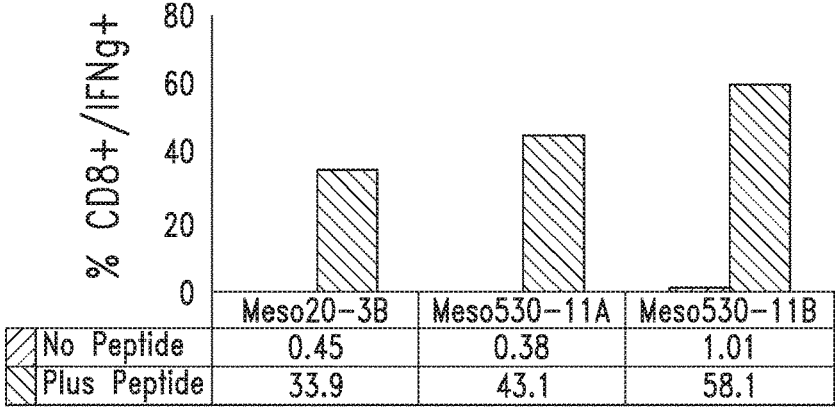
Figure 12F:
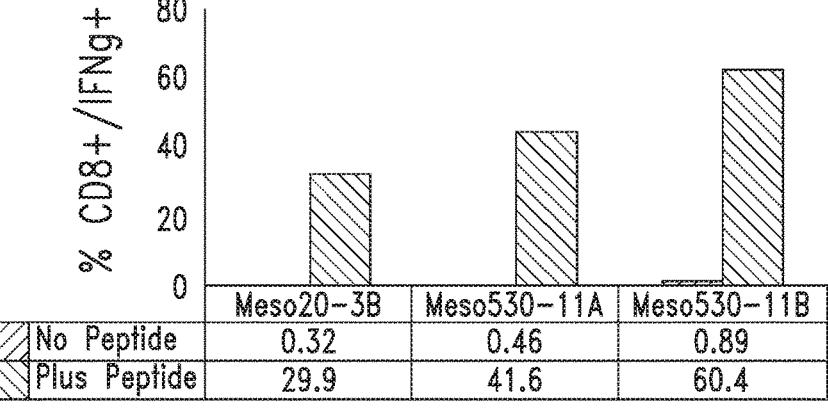
Figure 12G:
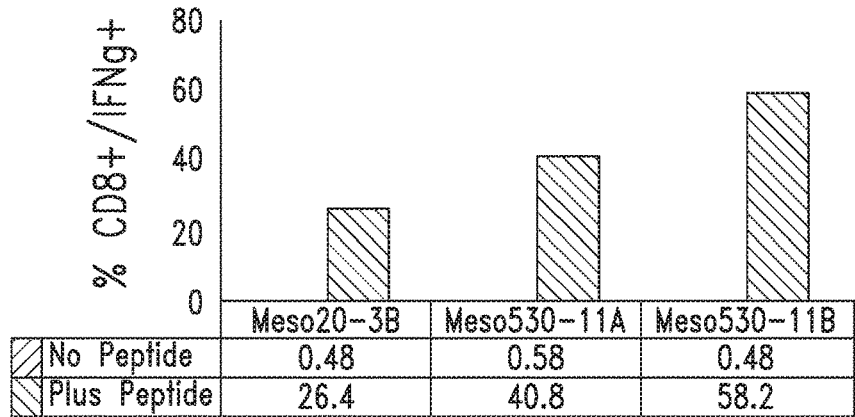
Figure 12H:
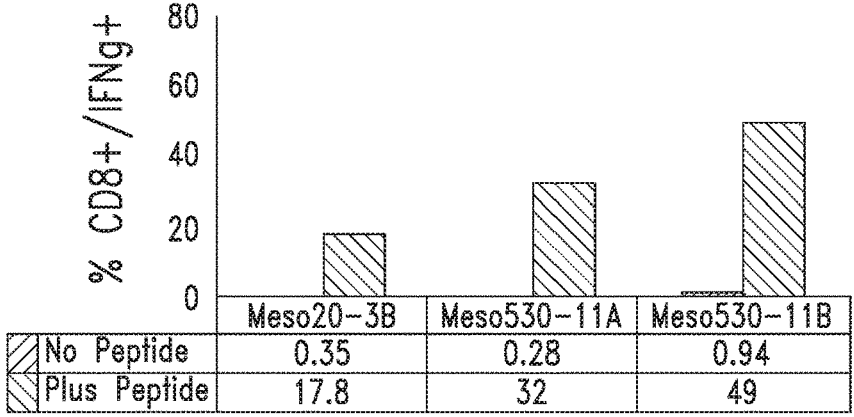
Figure 12I:
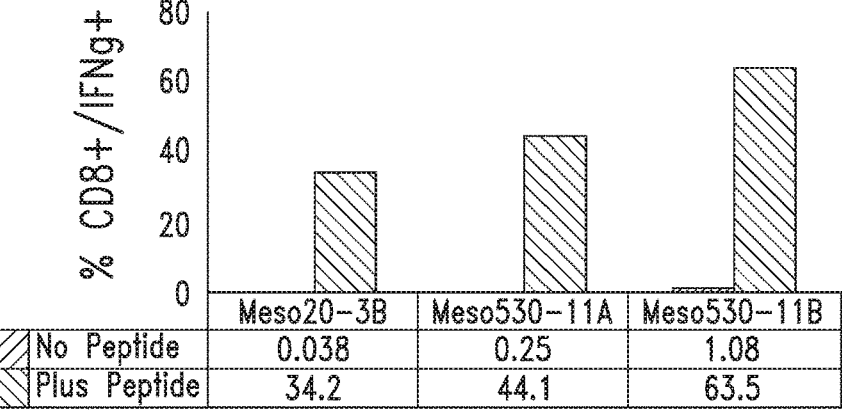
Figure 13B:
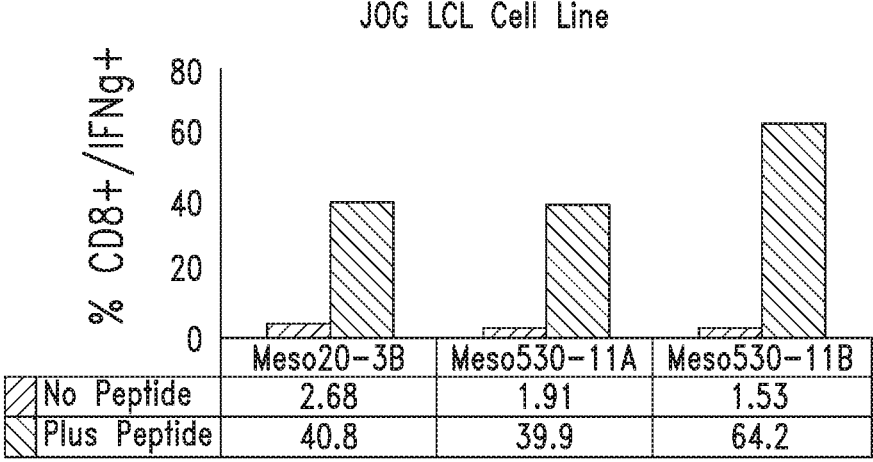
Figure 13C:
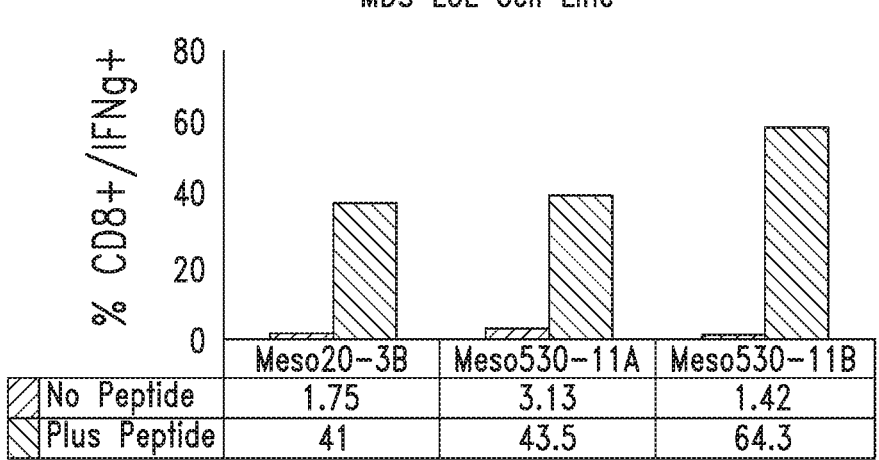
Figure 13D:
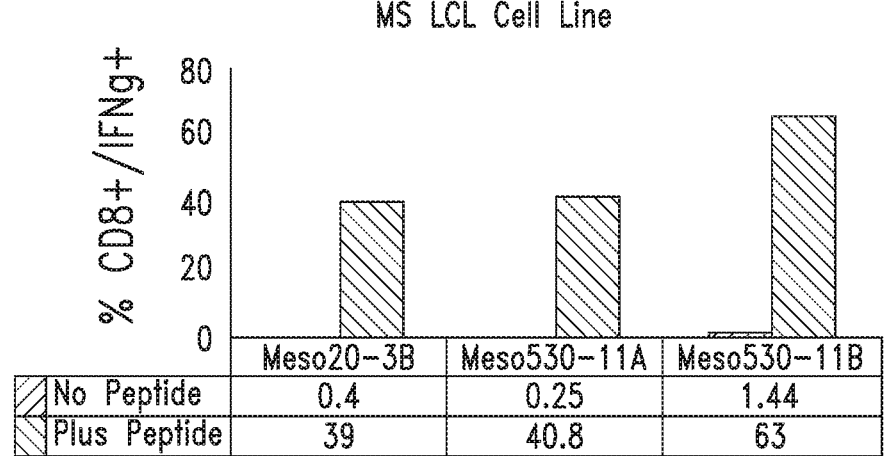
Figure 13E:
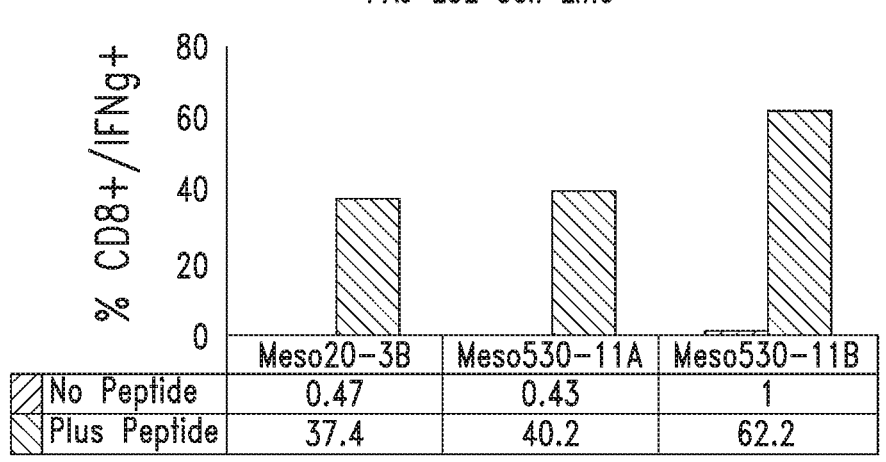
Figure 13F:
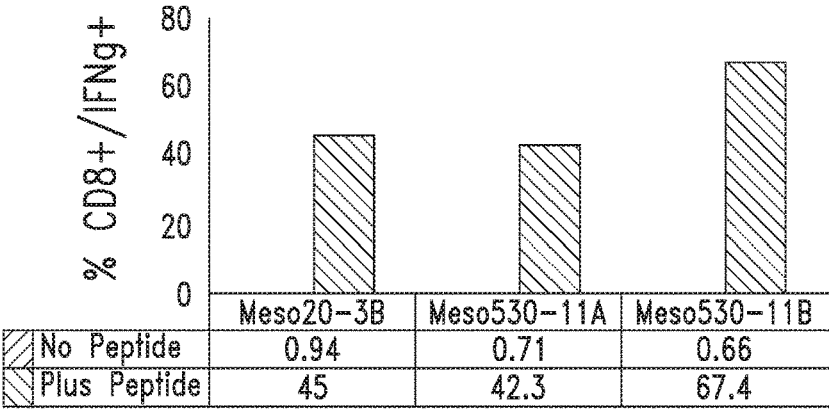
Figure 13G:
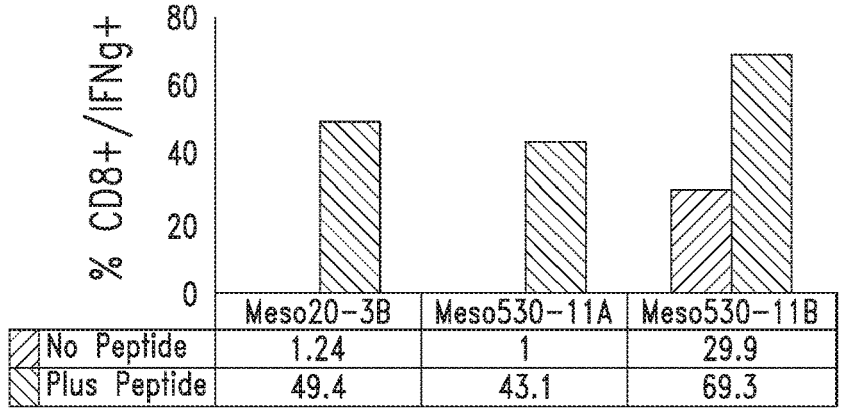
Figure 13H:
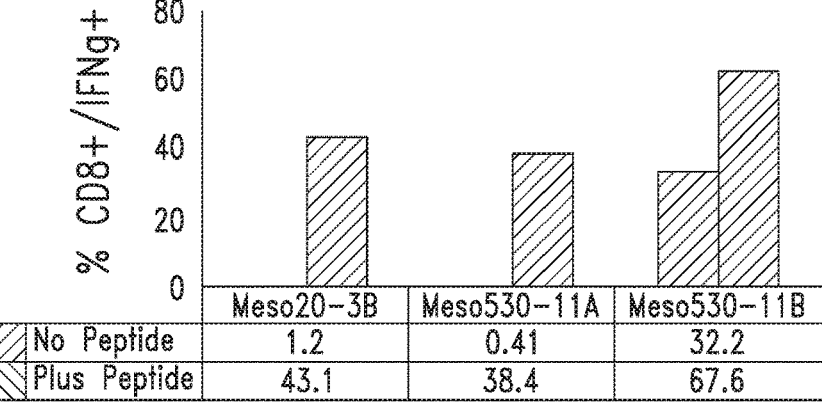

In order to determine potential alloreactivity of T cells expressing $Msln_{20}$-3B or $Msln_{530}$-11A or -11B, TCR-transduced T cells were cultured with allogeneic LCLs that naturally express diverse HLA alleles, including many of the more common alleles. The LCL lines and corresponding HLA allele expression are listed in the table in FIG. 12A. For each cell line (FIGS. 12B-12I), the percentage of IFN-γ expression is shown when the T cells and LCL cells were co-cultured in the presence or absence of added $Msln_{530}$ peptide (which is presented by the transduced T cells when the LCL cell line lacks HLA-A2 expression).

Further analysis of T cell targeting of diverse LCL cell lines is shown in FIGS. 13A-13H. In order to determine potential alloreactivity of T cells expressing $Msln_{20}$-3B or $Msln_{530}$-11A or -11B, TCR-transduced T cells were cultured with allogeneic LCLs that naturally express diverse HLA alleles, including many of the more common alleles. The LCL lines and corresponding HLA allele expression are listed in the table in FIG. 13A. For each cell line, the percentage IFN-γ expression is shown following co-culture of target and effector cells in the presence or absence of added $Msln_{530}$ peptide (which is presented by the transduced T cells when the LCL cell lines lack HLA-A2 expression). This second set of LCLs include several lines that express HLA-C6 and HLA-B13, which exhibit linkage disequilibrium and are commonly found together. Several of these LCLs elicited a response from $Msln_{530}$-11B-transduced T cells. These data show that HLA-B13:02:01 is the alloreactive allele, since only cells that express HLA-B13:02:01 elicit a response, while cells expressing HLA-C6:02:01 or HLA-B13:01:01 without HLA-B13:02:01 do not elicit a response.

Table 1 shows the frequency of HLA-B13:02:01 and HLA-A2:01:01 co-expression in different populations.

Some alloreactivity specific to HLA-B13:02:01 was detected. However, given the small haplotype frequency within the population, it is a rare event for a patient to present with an allele that is cross-reactive.

TABLE 1

| HLA A2:01/B13:02 Haplotype Frequencies | | |
|---|---|---|
| European Americans | 0.845% (B13:02) | (29.6% A2:01) |
| African Americans | 0.177% (B13:02) | (12.5% A2:01) |
| Asians and Pacific Islanders | 0.110% (B13:02) | (9.5% A2:01) |
| Hispanics | 0.129% (B13:02) | (19.4% A2:01) |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/758,397, filed Nov. 9, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A binding protein comprising a T cell receptor (TCR) α-chain variable domain (Vα) and a TCR β-chain variable domain (Vβ), wherein:

(a) the Vα comprises the complementarity determining region (CDR)1α, CDR2α, and CDR3α amino acid sequences set forth in SEQ ID NOs: 93, 94, and 39, respectively and the Vβ comprises the CDR1β, CDR2β, and CDR3β amino acid sequences set forth in SEQ ID NOs: 91, 92, and 40, respectively; or (b) the Vα comprises the CDR1α, CDR2α, and CDR3α amino acid sequences set forth in SEQ ID NOs: 89, 90, and 37, respectively and the Vβ comprises the CDR1β, CDR2β, and CDR3β amino acid sequences set forth in SEQ ID NOs: 87, 88, and 38, respectively wherein the binding protein is capable of specifically binding to a SEQ ID NO:32:HLA-A: 0201 complex, wherein the binding protein comprises:

(i) a TCR α-chain constant domain and a TCR β-chain constant domain, wherein the TCR α-chain constant domain, the TCR β-chain constant domain, or both comprise a non-native cysteine residue; and/or (ii) a single chain TCR (scTCR) or a CAR.

2. The binding protein of claim 1, comprising:

(a) the CDR1α amino acid sequence set forth in SEQ ID NO: 93;

(b) the CDR2α amino acid sequence set forth in SEQ ID NO: 94;

(c) the CDR3α amino acid sequence set forth in SEQ ID NO: 39;

(d) the CDR1β amino acid sequence set forth in SEQ ID NO: 91;

(e) the CDR2β amino acid sequence set forth in SEQ ID NO: 92; and (f) the CDR3β amino acid sequence set forth in SEQ ID NO: 40.

3. The binding protein of claim 2, wherein the Vα comprises an amino acid sequence having at least about 85% identity to the amino acid sequence set forth in SEQ ID NO: 102, and wherein the Vβ comprises an amino acid sequence having at least about 85% identity to the amino acid sequence set forth in SEQ ID NO: 101.

4. The binding protein of claim 2, comprising a TCR α chain (TCRα) and a TCR β chain (TCRβ), wherein the TCRα comprises or consists of an amino acid sequence having at least about 85% identity to the amino acid sequence set forth in SEQ ID NO: 110 or 29, and/or wherein the TCRβ comprises or consists of an amino acid sequence having at least about 85% identity to the amino acid sequence set forth in SEQ ID NO: 109 or 28.

5. The binding protein of claim 1, comprising:

(a) the CDR1α amino acid sequence set forth in SEQ ID NO: 89;

(b) the CDR2α amino acid sequence set forth in SEQ ID NO: 90;

(c) the CDR3α amino acid sequence set forth in SEQ ID NO: 37;

(d) the CDR1β amino acid sequence as set forth in SEQ ID NO: 87;

(e) the CDR2β amino acid sequence set forth in SEQ ID NO: 88; and (f) the CDR3β amino acid sequence set forth in SEQ ID NO: 38.

6. The binding protein of claim 5, wherein the Vα comprises an amino acid sequence having at least about 85% identity to the amino acid sequence set forth in SEQ ID NO:100 and the Vβ comprises an amino acid sequence having at least about 85% identity to the amino acid sequence set forth in SEQ ID NO:99.

7. The binding protein of claim 5, comprising a TCR α chain (TCRα) and a TCR β chain (TCRβ), wherein the TCRα comprises or consists of an amino acid sequence having at least about 85% identity to the amino acid sequence set forth in SEQ ID NO: 108 or 23, and/or wherein the TCRβ comprises or consists of an amino acid sequence having at least about 85% identity to the amino acid sequence set forth in SEQ ID NO: 107 or 22.

8. The binding protein of claim 1, wherein:

the Vα comprises or consists of the amino acid sequence set forth in SEQ ID NO: 102 and the Vβ comprises or consists of the amino acid sequence set forth in SEQ ID NO: 101; or the Vα comprises or consists of the amino acid sequence set forth in SEQ ID NO: 100 and the Vβ comprises or consists of the amino acid sequence set forth in SEQ ID NO: 99.

9. The binding protein of claim 1, wherein the binding protein comprises a TCR Cβ and a TCR Cα, wherein the TCR Cβ comprises a cysteine amino acid in place of a native serine at amino acid position 57 and the TCR Cα comprises a cysteine amino acid in place of a native threonine at amino acid position 48.

10. A binding protein comprising a T cell receptor (TCR) α-chain variable domain (Vα) and a TCR β-chain variable domain (Vβ), wherein:

(a) the Vα comprises the CDR1α amino acid sequence set forth in SEQ ID NO: 80, the CDR2α amino acid sequence set forth in SEQ ID NO: 81 or 118, and CDR3α amino acid sequence set forth in SEQ ID NO: 33 and the Vβ comprises the CDR1β, CDR2β, and CDR3β amino acid sequences set forth in SEQ ID NOs: 78, 79, and 34, respectively; or (b) the Vα comprises the CDR1α amino acid sequence set forth in SEQ ID NO: 85, the CDR2α amino acid sequence set forth in SEQ ID NO: 86 or 119, and CDR3α amino acid sequence set forth in SEQ ID NO: 35 and the Vβ comprises the CDR1β, CDR2β, and CDR3β amino acid sequences set forth in SEQ ID NOs: 82, 79, and 36, respectively, wherein the binding protein is capable of specifically binding to a SEQ ID NO:31:HLA-A: 0201 complex, wherein the binding protein comprises:

(i) a TCR α-chain constant domain and a TCR β-chain constant domain, wherein the TCR α-chain constant domain, the TCR β-chain constant domain, or both comprise a non-native cysteine residue; and/or (ii) a scTCR or a CAR.

11. The binding protein of claim 10, comprising:

(a) the CDR1α amino acid sequence set forth in SEQ ID NO: 80;

(b) the CDR2α amino acid sequence set forth in SEQ ID NO: 81 or 118;

(c) the CDR3α amino acid sequence set forth in SEQ ID NO: 33;

(d) the CDR1β amino acid sequence as set forth in SEQ ID NO: 78;

(e) the CDR2β amino acid sequence set forth in SEQ ID NO: 79; and (f) the CDR3β amino acid sequence set forth in SEQ ID NO: 34.

12. The binding protein of claim 11, wherein the Vα comprises an amino acid sequence having at least about 85% identity to the amino acid sequence set forth in SEQ ID NO: 96, and wherein the Vβ comprises an amino acid sequence having at least about 85% identity to the amino acid sequence set forth in SEQ ID NO: 95.

13. The binding protein of claim 11, comprising a TCR α chain (TCRα) and a TCR β chain (TCRβ), wherein the TCRα comprises or consists of an amino acid sequence having at least about 85% identity to the amino acid sequence set forth in SEQ ID NO: 104 or 7, and/or wherein the TCRβ comprises or consists of an amino acid sequence having at least about 85% identity to the amino acid sequence set forth in SEQ ID NO: 103 or 6; or (ii) wherein the TCRα comprises or consists of an amino acid sequence having at least about 85% identity to the amino acid sequence set forth in SEQ ID NO: 106 or 15, and/or wherein the TCR β comprises or consists of an amino acid sequence having at least about 85% identity to the amino acid sequence set forth in SEQ ID NO: 105 or 14.

14. The binding protein of claim 10, comprising:
(a) the CDR1α amino acid sequence set forth in SEQ ID NO: 85;
(b) the CDR2α amino acid sequence set forth in SEQ ID NO: 86 or 119;
(c) the CDR3α amino acid sequence set forth in SEQ ID NO: 35;
(d) the CDR1β amino acid sequence set forth in SEQ ID NO: 82;
(e) the CDR2β amino acid sequence set forth in SEQ ID NO: 79; and
(f) the CDR3β amino acid sequence set forth in SEQ ID NO: 36.

15. The binding protein of claim 10, wherein:
the Vα comprises or consists of the amino acid sequence set forth in SEQ ID NO: 96 and the Vβ comprises or consists of the amino acid sequence set forth in SEQ ID NO: 95; or
the Vα comprises or consists of the amino acid sequence set forth in SEQ ID NO: 98 and the Vβ comprises or consists of the amino acid sequence set forth in SEQ ID NO: 97.

16. A polynucleotide encoding the binding protein of claim 1.

17. A polynucleotide encoding the binding protein of claim 10.

18. A recombinant expression vector comprising the polynucleotide of claim 16 operably linked to an expression control sequence.

19. A recombinant expression vector comprising the polynucleotide of claim 17 operably linked to an expression control sequence.

20. A recombinant host cell comprising a heterologous polynucleotide of claim 16, wherein the recombinant host cell is capable of expressing on its cell surface the encoded binding protein.

21. A recombinant host cell comprising a heterologous polynucleotide of claim 17, wherein the recombinant host cell is capable of expressing on its cell surface the encoded binding protein.

22. A method of treating a disease or disorder associated with mesothelin expression and/or activity in a subject, the method comprising:
administering to the subject an effective amount of a composition comprising (a) the recombinant host cell of claim 20 and (b) a pharmaceutically acceptable carrier, excipient, or diluent.

23. The method of claim 22, wherein the disease or disorder associated with mesothelin expression and/or activity is a cancer.

24. The method of claim 23, wherein the cancer is a solid cancer or a hematological malignancy.

25. The method of claim 23, wherein the cancer comprises biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

26. A method of treating a disease or disorder associated with mesothelin expression and/or activity in a subject, the method comprising:
administering to the subject an effective amount of a composition comprising (a) the recombinant host cell of claim 21 and (b) a pharmaceutically acceptable carrier, excipient, or diluent.

27. The method of claim 26, wherein the disease or disorder associated with mesothelin expression and/or activity is a cancer.

28. The method of claim 27, wherein the cancer is a solid cancer or a hematological malignancy.

29. The method of claim 27, wherein the cancer comprises biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, oVαrian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

30. An isolated polynucleotide that encodes a binding protein that is capable of specifically binding to a SEQ ID NO:32:HLA-A: 02*01 complex, wherein the polynucleotide comprises or consists of the polynucleotide sequence set forth in SEQ ID NO: 120.

31. An expression vector comprising the polynucleotide of claim 30 operably linked to an expression control sequence.

32. A recombinant host cell comprising the polynucleotide of claim 30, wherein the recombinant host cell is capable of expressing on its cell surface the encoded binding protein.

33. A method of making the recombinant host cell of claim 20, the method comprising transfecting or transducing the host cell in vitro or ex vivo with the polynucleotide encoding the binding protein.

34. A method of making the recombinant host cell of claim 21, the method comprising transfecting or transducing the host cell in vitro or ex vivo with the polynucleotide encoding the binding protein.

35. A T cell receptor (TCR) comprising an alpha-chain (TCRα) and a beta-chain (TCRβ), wherein the TCRα and the TCRβ comprise the amino acid sequences set forth in SEQ ID NOs:
(i) 110 and 109, respectively;
(ii) 108 and 107, respectively;
(iii) 104 and 103, respectively; or
(v) 106 and 105, respectively.

36. A polynucleotide encoding a T cell receptor (TCR), wherein the encoded TCR comprises an alpha-chain (TCRα) and a beta-chain (TCRβ), wherein the TCRα and the TCRβ comprise the CDR1α, CDR2α, CDR3α, CDR1β, CDR2β, and CDR3β amino acid sequences set forth in:
(i) 93, 94, 39, 91, 92, and 40, respectively, wherein the binding protein is capable of specifically binding to a SEQ ID NO:32:HLA-A: 0201 complex;

(ii) 89, 90, 37, 87, 88, and 38, respectively, wherein the binding protein is capable of specifically binding to a SEQ ID NO:32:HLA-A: 0201 complex;

(iii) 80, 81 or 118, 33, 78, 79, and 34, respectively, wherein the binding protein is capable of specifically binding to a SEQ ID NO:31:HLA-A: 0201 complex; or (iv) 85, 86 or 119, 35, 82, 79, and 36, respectively, wherein the binding protein is capable of specifically binding to a SEQ ID NO:31:HLA-A: 0201 complex; and wherein:

(1) the polynucleotide comprises a sequence encoding a viral 2A peptide, an internal ribosome entry site (IRES), a furin cleavage site, or any combination thereof, disposed between a sequence encoding the TCRβ and a sequence encoding the TCRα; and/or (2) the polynucleotide further encodes a CD8 co-receptor α-chain and a CD8 co-receptor β-chain; and/or (3) the polynucleotide is comprised in a viral vector.

37. The polynucleotide of claim 36, wherein:

(a) the TCRα and the TCRβ comprise the Vα and Vβ amino acid sequences set forth in SEQ ID NOs: 102 and 101, respectively; 100 and 99, respectively; 96 and 95, respectively; or 98 and 97, respectively; and/or

(b) the polynucleotide comprises a sequence encoding the amino acid sequence set forth in any one of SEQ ID NOs: 113-117, disposed between a sequence encoding the TCRβ and a sequence encoding the TCRα; and/or (c) the polynucleotide encodes the amino acid sequence set forth in any one of SEQ ID NOs: 8, 16, 24, and 30.

38. A method of treating a cancer associated with meso-thelin expression and/or activity in a subject, the method comprising administering to the subject an effective amount of T cells comprising CD8+ T cells, wherein (1) cells of the cancer express a SEQ ID NO:32:HLA-A: 0201 complex, and the T cells express an αβ T cell receptor (TCR) comprising the CDR1α, CDR2α, CDR3α, CDR1β, CDR2β, and CDR3β amino acid sequences set forth in SEQ ID NOs: 93, 94, 39, 91, 92, and 40, respectively, or set forth in SEQ ID NOs: 89, 90, 37, 87, 88, and 38, respectively; or (2) cells of the cancer express a SEQ ID NO:31:HLA-A: 0201 complex, and the T cells express an αβ T cell receptor (TCR) comprising the CDR1α, CDR2α, CDR3α, CDR1β, CDR2β, and CDR3β amino acid sequences set forth in 80, 81 or 118, 33, 78, 79, and 34, respectively, or set forth in SEQ ID NOs: 85, 86 or 119, 35, 82, 79, and 36, respectively.

* * * * *